United States Patent
Tsuruda et al.

(10) Patent No.: US 11,632,955 B2
(45) Date of Patent: *Apr. 25, 2023

(54) HETEROCYCLIC COMPOUND AND HARMFUL ARTHROPODS CONTROL AGENT COMPRISING THE SAME

(71) Applicant: Sumitomo Chemical Company, Limited, Tokyo (JP)

(72) Inventors: Takeshi Tsuruda, Takarazuka (JP); Takamasa Tanabe, Takarazuka (JP); Masaru Shimomura, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 741 days.

This patent is subject to a terminal disclaimer.

(21) Appl. No.: 16/465,747

(22) PCT Filed: Nov. 30, 2017

(86) PCT No.: PCT/JP2017/043121
§ 371 (c)(1),
(2) Date: May 31, 2019

(87) PCT Pub. No.: WO2018/101424
PCT Pub. Date: Jun. 7, 2018

(65) Prior Publication Data
US 2019/0380345 A1 Dec. 19, 2019

(30) Foreign Application Priority Data

Dec. 1, 2016 (JP) .............................. JP2016-233934
Apr. 19, 2017 (JP) .............................. JP2017-082677

(51) Int. Cl.
*A01N 43/60* (2006.01)
*A01N 43/58* (2006.01)
*C07D 401/04* (2006.01)
*C07D 401/14* (2006.01)

(52) U.S. Cl.
CPC ............. *A01N 43/60* (2013.01); *A01N 43/58* (2013.01); *C07D 401/04* (2013.01); *C07D 401/14* (2013.01)

(58) Field of Classification Search
None
See application file for complete search history.

(56) References Cited

U.S. PATENT DOCUMENTS

| | | | | |
|---|---|---|---|---|
| 10,273,210 B2* | 4/2019 | Tsuruda | ................ | A01N 43/647 |
| 10,645,929 B2* | 5/2020 | Orimoto | .............. | C07D 239/34 |
| 11,149,027 B2* | 10/2021 | Orimoto | .............. | C07D 401/14 |
| 2004/0077641 A1* | 4/2004 | Bretschneider | ........ | A01N 47/24 544/122 |
| 2017/0295787 A1 | 10/2017 | Tanabe et al. | | |
| 2018/0009778 A1 | 1/2018 | Tanabe et al. | | |
| 2018/0297953 A1 | 10/2018 | Tsuruda et al. | | |
| 2018/0297978 A1 | 10/2018 | Orimoto et al. | | |
| 2018/0310559 A1 | 11/2018 | Tanabe et al. | | |
| 2018/0317485 A1 | 11/2018 | Orimoto et al. | | |
| 2019/0040038 A1 | 2/2019 | Tanabe et al. | | |
| 2019/0045786 A1 | 2/2019 | Matsuo et al. | | |

FOREIGN PATENT DOCUMENTS

| | | | | |
|---|---|---|---|---|
| CN | 104334551 A | 2/2015 | | |
| EP | 2857397 A1 | 4/2015 | | |
| EP | 3252041 A1 | 12/2017 | | |
| EP | 3444239 A1 | 2/2019 | | |
| EP | 3444245 A1 | 2/2019 | | |
| EP | 3366674 B1 * | 12/2020 | ............. | A01N 43/40 |
| EP | 3372588 B1 * | 5/2021 | ............. | A01N 43/54 |
| JP | 2017075161 A | 4/2017 | | |
| JP | 2017178820 A | 10/2017 | | |
| JP | 2018012664 A | 1/2018 | | |
| JP | 2018052816 A | 4/2018 | | |
| WO | 2016052455 A1 | 4/2016 | | |
| WO | 2016104746 A1 | 6/2016 | | |

(Continued)

OTHER PUBLICATIONS

Tanaji T. Talele, The "Cyclopropyl Fragment" is a Versatile Player that Frequently Appears in Preclinical/Clinical Drug Molecules, Jun. 14, 2016, J. Med. Chem, 59, 8712-8756 (Year: 2016).*

Office Action dated Nov. 24, 2021 in CN Application No. 201780074220.0.

International Preliminary Report on Patentability dated Jun. 4, 2019 in International Application No. PCT/JP2017/043121.

International Search Report dated Feb. 13, 2018 in International Patent Application No. PCT/JP2017/043121.

(Continued)

*Primary Examiner* — Abigail Vanhorn
*Assistant Examiner* — Ali S Saeed
(74) *Attorney, Agent, or Firm* — Panitch Schwarze Belisario & Nadel LLP

(57) ABSTRACT

A compound which has a superior control effect on arthropod pests is provided. In particular, a compound represented by formula (I) is provided, wherein the variable groups are as defined in the specification. Also provided is a composition containing the compound represented by formula (I), and uses thereof for controlling harmful arthropods.

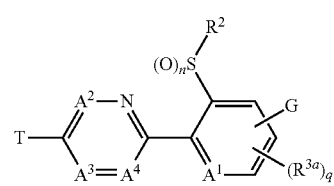

(I)

13 Claims, No Drawings

(56) References Cited

FOREIGN PATENT DOCUMENTS

| WO | 2016121969 A1 | 8/2016 |
|---|---|---|
| WO | 2016121970 A1 | 8/2016 |
| WO | 2017065228 A1 | 4/2017 |
| WO | 2017069105 A1 | 4/2017 |
| WO | 2017073733 A1 | 5/2017 |
| WO | 2017077911 A1 | 5/2017 |
| WO | 2017090655 A1 | 6/2017 |
| WO | 20170146226 A1 | 8/2017 |
| WO | 2017150209 A1 | 9/2017 |
| WO | 2017169894 A1 | 10/2017 |
| WO | 2017175613 A1 | 10/2017 |

OTHER PUBLICATIONS

Extended European Search Report dated Jun. 17, 2020 in EP Application No. 17875978.3.
Office Action dated Dec. 8, 2020 in IN Application No. 201947025318.

* cited by examiner

HETEROCYCLIC COMPOUND AND HARMFUL ARTHROPODS CONTROL AGENT COMPRISING THE SAME

CROSS-REFERENCE TO RELATED APPLICATION

This application is a Section 371 of International Application No. PCT/JP2017/043121, filed Nov. 30, 2017, which was published in the Japanese language on Jun. 7, 2018, under International Publication No. WO 2018/101424 A1, which claims priority under 35 U.S.C. § 119(b) to Japanese Application No. 2016-233934 filed on Dec. 1, 2016 and Japanese Application No. 2017-082677 filed on Apr. 19, 2017, the disclosures of which are incorporated herein by reference in their entireties.

TECHNICAL FIELD

The present invention is related to a heterocyclic compound and a composition for controlling harmful arthropods comprising the same.

BACKGROUND ART

To date, in order to control harmful arthropods, various compounds have been studied and come into practical use.

Also, a certain class of compound has been known to have an effect on controlling pests (see Patent Document 1 and Document 2).

CITATION LIST

Patent Document

Patent Document 1: WO 2016/052455
Patent Document 2: WO 2016/121969

SUMMARY OF THE INVENTION

Problems to be Solved by Invention

An object of the present invention is to provide a compound including an excellent efficacy for controlling harmful arthropods.

Means to Solve Problems

The present inventors have intensively studied to find compounds including an excellent efficacy for controlling harmful arthropods, and as a result, found that a compound represented by the below-mentioned formula (I) has an excellent efficacy for controlling harmful arthropods.

That is, the present invention is as follows.

[1] A compound represented by formula (I):

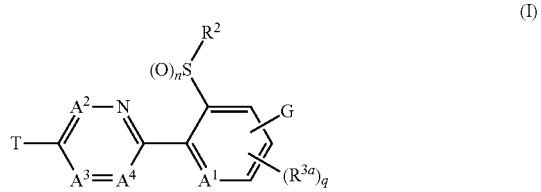

(I)

wherein $A^1$ represents a nitrogen atom or $CR^{3b}$,
n is 0, 1 or 2,
q is 0, 1 or 2,
G represents a C3-C8 alicyclic hydrocarbon group optionally having one or more substituents selected from Group E, or $-L^1-G^2$,
$L^1$ represents an oxygen atom or a sulfur atom,
$G^2$ represents a five to ten membered heterocyclic group optionally having one or more substituents selected from Group D,
$R^{3a}$ represents each independently a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, $OR^{12}$, $NR^{11}R^{12}$, $NR^{11a}R^{12a}$, $NH^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{15}R^{16}$, $NR^{24}NR^{11}C(O)NR^{15}R^{16}$, $N=CHNR^{15}R^{16}$, $N=S(O)_xR^{15}R^{16}$, $C(O)OR^{17}$, a cyano group, a nitro group, or a halogen atom,
$R^{3b}$ represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{15}R^{16}$, $NR^{24}NR^{11}C(O)NR^{15}R^{16}$, $N=CHNR^{15}R^{16}$, $N=S(O)_xR^{15}R^{16}$, $C(O)OR^{17}$, a cyano group, a nitro group, a hydrogen atom, or a halogen atom,
x is 0 or 1,
$A^2$ represents a nitrogen atom or $CR^{4a}$,
$A^3$ represents a nitrogen atom or $CR^{4b}$,
$A^4$ represents a nitrogen atom or $CR^{4c}$,
$R^{4a}$, $R^{4b}$ and $R^{4c}$ each independently represents a hydrogen atom, a C1-C6 chain hydrocarbon group optionally having one or more halogen atoms, a nitro group, $OR^{18}$, $NR^{18}R^{19}$, a cyano group, or a halogen atom,
T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12,

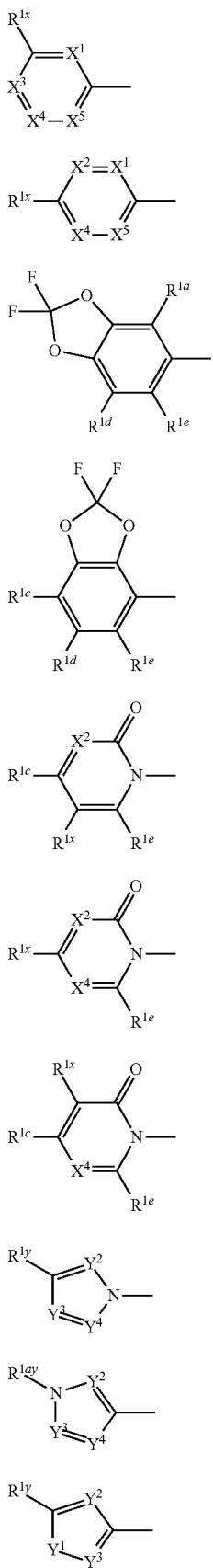

X¹ represents a nitrogen atom, or CR$^{1a}$,
X² represents a nitrogen atom, or CR$^{1b}$,
X³ represents a nitrogen atom, or CR$^{1c}$,
X⁴ represents a nitrogen atom, or CR$^{1d}$,
X⁵ represents a nitrogen atom, or CR$^{1e}$,
R$^{1a}$, R$^{1b}$, R$^{1c}$, R$^{1d}$ and R$^{1e}$ each independently represents a hydrogen atom, a C1-C6 chain hydrocarbon group optionally having one or more halogen atoms, a C3-C7 cycloalkyl group optionally having one or more halogen atoms, or a halogen atom,
R$^{1x}$ represents OR$^7$, OS(O)$_2$R$^7$, S(O)$_m$R$^7$, NR$^1$R$^{29}$, NR$^8$S(O)$_2$R$^7$, a C1-C5 chain hydrocarbon group having one or more halogen atoms, a cyano group, or a halogen atom,
Y¹ represents NR$^{25}$, an oxygen atom, or a sulfur atom,
Y² represents a nitrogen atom, or CR$^{26}$,
Y³ represents a nitrogen atom, or CR$^{27}$,
Y⁴ represents a nitrogen atom, or CR$^{28}$,
R$^{25}$ represents a hydrogen atom, a C1-C6 chain hydrocarbon group optionally having one or more halogen atoms, a C1-C6 alkoxy group optionally having one or more halogen atoms, a C3-C7 cycloalkyl group optionally having one or more halogen atoms, or a (C3-C7 cycloalkyl)C1-C6 alkyl group optionally having one or more halogen atoms,
R$^{26}$, R$^{27}$, and R$^{28}$ each independently represents a hydrogen atom, a C1-C6 chain hydrocarbon group optionally having one or more halogen atoms, a C3-C7 cycloalkyl group optionally having one or more halogen atoms, or a halogen atom,
R$^{1y}$ represents OR$^7$, OS(O)$_2$R$^7$, S(O)$_n$R$^7$, NR$^8$S(O)$_2$R$^7$, a cyano group, a C1-C5 chain hydrocarbon group having one or more halogen atoms, or a halogen atom,
R$^{1ay}$ and R$^{17}$ each independently represents a C1-C6 chain hydrocarbon group having one or more halogen atoms,
R$^8$ represents a hydrogen atom, or a C1-C6 chain hydrocarbon group optionally having one or more halogen atoms,
m is 0, 1, or 2,
R$^1$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G,
R$^2$ represents a cyclopropyl group, a cyclopropylmethyl group, or a C1-C6 alkyl group optionally having one or more halogen atoms,
R$^{11}$, R$^{17}$, R$^{19}$, R$^{24}$ and R$^{29}$ each independently represents a hydrogen atom, or a C1-C6 chain hydrocarbon group optionally having one or more halogen atoms, $R^{30}$ represents a hydrogen atom, a halogen atom, $OR^{31}$, $NR^{32}R^{33}$, or a C1-C6 chain hydrocarbon group optionally having one or more halogen atoms, $R^{18}$ and $R^{31}$ each independently represents a hydrogen atom, or a C1-C6 chain hydrocarbon group optionally having one or more halogen atoms, $R^{32}$ and $R^{33}$ each independently represents a hydrogen atom, or a C1-C6 chain hydrocarbon group optionally having one or more halogen atoms, $R^{12}$ represents a hydrogen atom, $S(O)_2R^{23}$, a C1-C6 chain hydrocarbon group optionally having one or more halogen atoms, or a C1-C6 alkyl group having one or more substituents selected from Group F, $R^{23}$ represents a C1-C6 chain hydrocarbon group optionally having one or more halogen atoms, or a phenyl group optionally having one or more substituents selected from Group D, $R^{11a}$ and $R^{12a}$, and the nitrogen atom to which they are attached are taken together to form a three to seven membered nonaromatic heterocyclic group optionally having one or more substituents selected from Group E, $R^{13}$ represents a hydrogen atom, a C1-C6 chain hydrocarbon group optionally having one or more halogen atoms, a C3-C7 cycloalkyl group optionally having one or more halogen atoms, a (C3-C7 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D, $R^{14}$ represents a C1-C6 chain hydrocarbon group optionally having one or more halogen atoms, a C3-C7 cycloalkyl group optionally having one or more halogen atoms, a (C3-C7 cycloalkyl)C1-C3 alkyl group optionally having one or more halogen atoms, or a phenyl C1-C3 alkyl group {the phenyl moiety in the phenyl C1-C3 alkyl group may optionally have one or more substituents selected from Group D}, $R^{15}$ and $R^{16}$ each independently represents a C1-C6 alkyl group optionally having one or more halogen atoms, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C7 cycloalkyl group optionally having one or more halogen atoms, a cyano group, a hydroxy group, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom ($R^{21}$ and $R^{22}$ each independently represents a C1-C6 alkyl group optionally having one or more halogen atoms);

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, an amino group, $NR^9R^{10}$, $C(O)R^{10}$, $C(O)NR^9R^{10}$, $OC(O)R^9$, $OC(O)R^9$, $NR^{10}C(O)R^9$, $NR^{10}C(O)OR^9$, $C(O)OR^{10}$, a C3-C7 cycloalkyl group optionally having one or more halogen atoms, a phenyl group optionally having one or more substituents selected from Group H, a five or six membered aromatic heterocyclic group optionally having one or more substituents selected from Group H, a halogen atom, an oxo group, a thioxo group, a hydroxy group, a cyano group, and a nitro group {$R^9$ represents a C1-C6 alkyl group optionally having one or more halogen atoms, or a C3-C7 cycloalkyl group optionally having one or more halogen atoms, and $R^{10}$ represents a hydrogen atom, a C1-C6 alkyl group optionally having one or more halogen atoms, or a C3-C7 cycloalkyl group optionally having one or more halogen atoms};

Group F: a group consisting of a C1-C6 alkoxy group optionally having one or more halogen atoms, an amino group, $NHR^{21}$, $NR^{21}R^{22}$, a cyano group, a phenyl group optionally having one or more substituents selected from Group D, a five or six membered aromatic heterocyclic group optionally having one or more substituents selected from Group D, a C3-C7 cycloalkyl group optionally having one or more halogen atoms, and a three to seven nonaromatic heterocyclic group optionally having one or more substituents selected from Group C {the $R^{21}$ and $R^{22}$ each independently represents a C1-C6 alkyl group optionally having one or more halogen atoms};

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group G: a group consisting of a halogen atom, and a C1-C6 haloalkyl group;

Group H: a group consisting of a halogen atom, a nitro group, a cyano group, an amino group, a five or six membered aromatic heterocyclic group optionally having one or more halogen atoms, a C1-C6 alkyl group optionally having one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, and $C(O)OR^{10}$ {the $R^9$ represents a C1-C6 alkyl group optionally having one or more halogen atoms, or a C3-C7 cycloalkyl group optionally having one or more halogen atoms, and $R^{10}$ represents a hydrogen atom, a C1-C6 alkyl group optionally having one or more halogen atoms, or a C3-C7 cycloalkyl group optionally having one or more halogen atoms}] (hereinafter, a compound represented by formula (I) is referred to as "Present compound" or "Compound of the present invention").

[2] The compound described in (1) wherein $L^1$ represents an oxygen atom.

[3] The compound described in [1] or [2] wherein $G^2$ represents a pyridyl group, a pyrimidinyl group, a pyrazinyl group, a pyridazinyl group, a pyrazolyl group, an imidazolyl group, a triazolyl group, an oxazolyl group, a thiazolyl group, a thiadiazolyl group, or an isoxazolyl group {the pyridyl group, the pyrimidinyl group, the pyrazinyl group, the pyridazinyl group, the pyrazolyl group, the imidazolyl group, the triazolyl group, the oxazolyl group, the thiazolyl group, the thiadiazolyl group, or the isoxazolyl group each independently may optionally have one or more substituents selected from Group D}.

The compound described in [1] wherein G represents a C3-C8 alicyclic hydrocarbon group optionally having one or more substituents selected from Group E (hereinafter, which is referred to as "Present compound A" or "Compound A of the present invention").

[5] The compound described in any one of (1 to [4] wherein $A^3$ represents $CR^{4b}$ and $A^4$ represents $CR^{4c}$.

[6] The compound described in any one of [1] to [4] wherein $A^2$ represents $CR^{4a}$, $A^3$ represents a nitrogen atom and $A^4$ represents $CR^{4c}$, alternatively, $A^2$ represents $CR^{4a}$, $A^3$ represents $CR^{4b}$ and $A^4$ represents a nitrogen atom.

[7] The compound described in any one of [1] to [6] wherein T represents a C1-C10 chain hydrocarbon group having one or more halogen atoms, a (C1-C5 alkoxy)C2-C5 alkyl group having one or more halogen atoms, a (C1-C5 alkylsulfanyl) C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl) C1-C3 alkyl group having one or more substituents selected from Group G, or a C3-C7 cycloalkyl group having one or more substituents selected from Group G, $OR^1$, $S(O)_m R^1$, $OS(O)_2 R^1$ or $NR^1 R^{29}$.

[8] The compound described in any one of [1] to [7] wherein T represents $OR^1$ and $R^1$ represents a C1-C5 alkyl group having three or more fluorine atoms.

[9] The compound described in any one of [1] to [8] wherein $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may be optionally having one or more substituents selected from Group H}, $OR^{12}$, $NR^{11}R^{12}$, $NR^{11}C(O)R^{13}$, or a halogen atom.

[10] The compound described in any one of [1] to (9) wherein $R^2$ represents an ethyl group.

[11] A composition for controlling harmful arthropod comprising the compound described in any one of [1] to [10] and an inert carrier.

[12] A method for controlling harmful arthropod which comprises applying an effective amount of the compound according to any one of [1] to [10] to a harmful arthropod or a habitat where a harmful arthropod lives.

[13] A composition comprising the compound according to any one of [1] to [10], and one or more ingredients selected from the group consisting of the following Group (a), Group (b), Group (c), Group (d) and Group (e), Group (a): a group consisting of insecticidal ingredients, miticidal ingredients, and nematicidal ingredients;
Group (b): fungicidal ingredients;
Group (c): plant growth modulating ingredients;
Group (d): phytotoxicity-reducing ingredients; and
Group (e): synergist ingredients
(hereinafter, which is referred to as "Present composition" or "Composition of the present invention").

Effect of Invention

The present invention can control harmful arthropod.

MODE FOR CARRYING OUT THE INVENTION

The substituent(s) as described herein is/are explained.
The term "halogen atom" represents fluorine atom, chlorine atom, bromine atom, or iodine atom.

When the substituent has two or more halogen atoms, these halogen atoms may be identical to or different from each other.

The expression of "CX-CY" as used herein represents that the number of carbon atom is from X to Y. For example, the expression of "C1-C6" represents that the number of carbon atom is from 1 to 6.

The term of "chain hydrocarbon group" represents an alkyl group, an alkenyl group, or an alkynyl group.

Examples of the term of "alkyl group" include methyl group, ethyl group, propyl group, isopropyl group, 1,1-dimethylpropyl group, 1,2-dimethylpropyl group, 1-ethylpropyl group, butyl group, tert-butyl group, pentyl group, hexyl group, and octyl group.

Examples of the term of "alkenyl group" include vinyl group, 1-propenyl group, 2-propenyl group, 1-methyl-1-propenyl group, 1-methyl-2-propenyl group, 1,2-dimethyl-2-propenyl group, 1-ethyl-2-propenyl group, 3-butenyl group, 4-pentenyl group, 5-hexenyl group, and 7-octenyl group.

Examples of the term of "alkynyl group" includes ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, 5-hexynyl group, and 7-octynyl group.

Examples of the term of "C1-C6 haloalkyl group" include trifluoromethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, and perfluorohexyl group.

Examples of the term of "C3-C8 alicyclic hydrocarbon group" include cyclopropyl, cyclobutyl, cyclopentyl, cyclohexyl, cycloheptyl, cyclooctyl, cyclohexenyl, cycloctenyl, bicyclo[2.2.1]heptyl, and bicyclo[3.3.0]octyl.

Examples of the term of "cycloalkyl group" include cyclopropyl group, cyclobutyl group, cyclopentyl group, cyclohexyl group, and cycloheptyl group.

Examples of the term of "alkoxy group" include methoxy group, ethoxy group, propoxy group, butoxy group, pentoxy group, and hexyloxy group The term of "C1-C6 alkoxy group optionally having one or more halogen atoms" represents a C1-C6 alkoxy group wherein one or more hydrogen atoms are substituted with a halogen atom, and includes, for example, trifluoromethoxy group, difluoromethoxy group, 2,2,2-trichloroethoxy group, and 2,2,2-trifluoroethoxy group.

The term of "C3-C6 alkenyloxy group optionally having one or more halogen atoms" represents a C3-C6 alkenyloxy group wherein one or more hydrogen atoms are substituted with a halogen atom, and includes, for example, 3,3,3-trifluoro-1-propenyloxy group, a 3,3,3-trichloro-1-propenyloxy group, a 3,3,3-trichloro-1-propenyloxy group, and 2,3,3,3-tetrafluoro-1-propenyloxy group.

The term of "C3-C6 alkynyloxy group optionally having one or more halogen atoms" represents a C3-C6 alkynyloxy group wherein one or more hydrogen atoms are substituted with a halogen atom, and includes, for example, a 3,3,3-trifluoro-1-propenyloxy group, and 3,3,3-trichloro-1-propinyloxy group.

The term of "alkylsulfanyl group", "alkylsulfinyl group", and "alkylsulfonyl group" represent an alkyl group including an $S(O)_z$ moiety, respectively.

For example, examples of the "alkylsulfanyl group" when z is 0 include methylsulfanyl group, ethylsulfanyl group, propylsulfanyl group, and isopropylsulfanyl group.

For example, examples of the "alkylsulfinyl group" when z is 1 include methylsulfinyl group, ethylsulfinyl group, propylsulfinyl group, and isopropylsulfinyl group.

For example, examples of the "alkylsulfonyl group" when z is 2 include methylsulfonyl group, ethylsulfonyl group, propylsulfonyl group, and isopropylsulfonyl group.

Examples of the term of "three (3) to seven (7) membered nonaromatic heterocyclic group" include aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiazinane ring, thiomorpholine ring, and 1,4-thiazepane ring. Examples of the three to seven membered nonaromatic heterocyclic group optionally having one or more substituents selected from Group E include the followings:

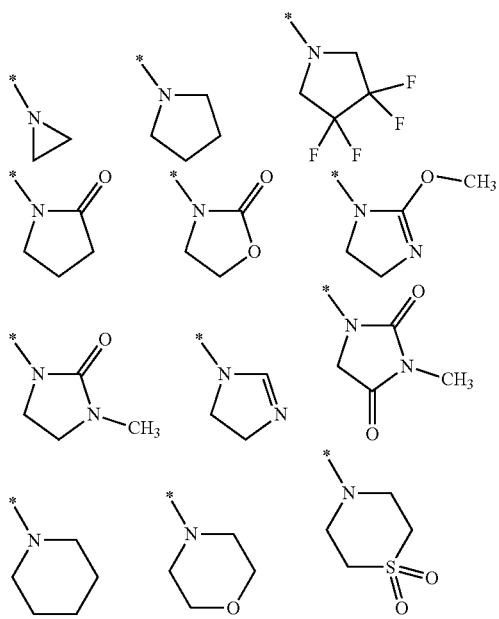

The term of "(C1-C5 alkoxy)C2-C5 alkyl group having one or more halogen atoms" represents a group wherein the (C1-C5 alkoxy) and/or the (C2-C5 alkyl) has/have one or more halogen atoms, and includes, for example, 2-(trifluoromethoxy)ethyl group, 2,2-difluoro-3-methoxypropyl group, 2,2-difluoro-3-(2,2,2-trifluoroethoxy)propyl group, and 3-(2-chloroethoxy)propyl group.

The term of "(C1-C5 alkylsulfanyl)C2-C5 alkyl group having one or more halogen atoms" represents a group wherein the (C1-C5 alkylsulfanyl) and/or the (C2-C5 alkyl) has/have one or more halogen atoms, and includes, for example, 2,2-difluoro-2-(trifluoromethylthio)ethyl group.

The term of "(C1-C5 alkylsulfinyl)C2-C5 alkyl group having one or more halogen atoms" represents a group wherein the (C1-C5 alkylsulfinyl) and/or the (C2-C5 alkyl) has/have one or more halogen atoms, and includes, for example, 2,2-difluoro-2-(trifluoromethansulfinyl)ethyl group.

The term of "(C1-C5 alkylsulfonyl)C2-C5 alkyl group having one or more halogen atoms" represents a group wherein the (C1-C5 alkylsulfonyl) and/or the (C2-C5 alkyl) has/have one or more halogen atoms, and includes, for example, 2,2-difluoro-2-(trifluoromethansulfonyl)ethyl group.

The term of "(C3-C7 cycloalkyl)C1-C3 alkyl group optionally having one or more halogen atoms" represents a group wherein the (C3-C7 cycloalkyl) and/or the (C1-C3 alkyl) has/have one or more halogen atoms, and includes, for example, (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The term of "(C3-C7 cycloalkyl)C1-C3 alkyl group having one or more substituents selected from Group G" represents a group wherein the (C3-C7 cycloalkyl) and/or the (C1-C3 alkyl) has/have one or more substituents selected from Group G, and includes, for example, (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2-tetrafluoroethyl group, 2-cyclopropyl-3,3,3-trifluoropropyl group, and 1,1,2,2-tetrafluoro-2-[2-(trifluoromethyl)cyclopropyl]ethyl group.

Examples of the term of "C3-C7 cycloalkyl)C1-C3 alkyl group having one or more substituents selected from Group G" include 2,2-difluorocyclopropyl group, 1-(2,2,2-trifluoroethyl)cyclopropyl group, and 4-(trifluoromethyl)cyclohexyl group.

Examples of the term of "phenyl C1-C3 alkyl group {the phenyl moiety in the phenyl C1-C3 alkyl group may optionally have one or more substituents selected from Group D}" include benzyl group, 2-fluorobenzyl group, 4-chlorobenzyl group, 4-(trifluoromethyl)benzyl group, and 2-[4-(trifluoromethyl)phenyl]ethyl group.

The term of "five (5) or six (6) membered aromatic heterocyclic group" represents a five membered aromatic heterocyclic group or a six membered aromatic heterocyclic group, and examples of the five membered aromatic heterocyclic group include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group. As the five membered aromatic heterocyclic group, a five membered aromatic heterocyclic group including 1 to 4 nitrogen atoms, that is, pyrrolyl group, pyrazolyl group, imidazolyl group, 1,2,4-triazolyl group, 1,2,3-triazolyl group, or tetrazolyl group is preferably included. Examples of the six membered aromatic heterocyclic group include pyridyl group, pyridazinyl group, pyrimidinyl group, and pyrazinyl group.

The term of "five (5) or ten (10) membered heterocyclic group" represents aromatic heterocyclic group or nonaromatic heterocyclic group. Examples of the aromatic heterocyclic group include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, thiadiazolyl group, pyridyl group, pyridazinyl group, pyrimidinyl group, pyrazinyl group, and quinolyl group. Examples of the nonaromatic heterocyclic group include pyrrolidinyl group, imidazolyl group, imidazolidinyl group, piperidyl group, tetrahydro pyrimidinyl group, hexahydro pyrimidinyl group, piperazinil group, azepanyl group, oxazolidinyl group, isoxazolidinyl group, 1,3-oxazinanyl group, morpholinyl group, 1,4-oxazepanyl group, thiazolidinyl group, isothiazolidinyl group, 1,3-thiadinanyl group, thiomorpholinyl group, and 1,4-thiazepanyl group.

Examples of the embodiment of the compound of the present invention include the following compounds.

Embodiment 1

A compound of the present invention wherein $G^2$ represents a pyridyl group, a pyrimidinyl group, a pyrazinyl group, a pyridazinyl group, a pyrazolyl group, an imidazolyl group, a triazolyl group, an oxazolyl group, a thiazolyl group, a thiadiazolyl group, or an isoxazolyl group {the pyridyl group, the pyrimidinyl group, the pyrazinyl group, the pyridazinyl group, the pyrazolyl group, the imidazolyl group, the triazolyl group, the oxazolyl group, the thiazolyl group, the thiadiazolyl group, and the isoxazolyl group each independently may optionally have one or more substituents selected from Group D}.

Embodiment 2

The compound of the present invention wherein $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 3

The compound described in Embodiment 1 wherein $L^1$ represents an oxygen atom.

Embodiment 4

The compound described in Embodiment 2 wherein $L^1$ represents an oxygen atom.

Embodiment 5

A compound of the present invention wherein $A^2$ represents $CR^{4a}$, and $A^4$ represents $CR^{4c}$.

Embodiment 6

The compound described in Embodiment 5 wherein $R^2$ represents a C1-C6 alkyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{12}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and G represents -$L^1$-$G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group represents each independently may optionally have one or more substituents selected from Group D}.

Embodiment 7

The compound described in Embodiment 5 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4a}$, $R^{4b}$, and $R^{4c}$ each independently represents a hydrogen atom, or a halogen atom, and G represents -$L^1$-$G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group represents each independently may optionally have one or more substituents selected from Group D}.

Embodiment 8

The compound described in Embodiment 5 wherein $R^2$ represents a C1-C6 alkyl group, and $R^{3a}$ represents a C1-C6 alkyl group optionally having one or more halogen atoms, $OR^{12}$, or a halogen atom, and $R^{4a}$, $R^{4b}$ and $R^{4c}$ each independently represents a hydrogen atom or a halogen atom, and G represents -$L^1$-$G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the a thiazolyl group represents each independently may optionally have one or more substituents selected from Group D} and $A^1$ represents a nitrogen atom.

Embodiment 9

The compound described in Embodiment 5 wherein $R^2$ represents an ethyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{12}R^{12}$, $NR^{13}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{4a}$, $R^{4b}$ and $R^{4c}$ each represents a hydrogen atom, and G represents -$L^1$-$G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 10

The compound described in Embodiment 5 wherein $R^2$ represents an ethyl group, and $R^{3a}$ represents a C1-C6 alkyl group optionally having one or more halogen atoms, $OR^{12}$, or a halogen atom, and $R^{4a}$, $R^{4b}$ and $R^{4c}$ each represents a hydrogen atom, and G represents -$L^1$-$G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom, an oxo group and a cyano group, and $L^1$ represents an oxygen atom, and $A^1$ represents a nitrogen atom.

Embodiment 11

The compound described in Embodiment 5 wherein $R^2$ represents an ethyl group, and $R^{4a}$, $R^{4b}$ and $R^{4c}$ each represents a hydrogen atom, and G represents -$L^1$-$G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom and a cyano group, $L^1$ represents an oxygen atom, and $A^1$ represents a nitrogen atom, and q is 0.

Embodiment 12

A compound of the present invention wherein $A^2$ represents $CR^{4a}$, and $A^3$ represents $CR^{4b}$, and $A^4$ represents $CR^{4c}$.

Embodiment 13

The compound described in Embodiment 12 wherein $R^2$ represents a C1-C6 alkyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{12}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and G represents -L1-G2, and L1 represents an oxygen atom, and G2 represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 14

The compound described in Embodiment 12 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4a}$, $R^{4b}$ and $R^{4c}$ each independently represents a hydrogen atom or a halogen atom, G represents -$L^1$-$G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 15

The compound described in Embodiment 12 wherein $R^2$ represents a C1-C6 alkyl group, and G-represents a C1-C6 alkyl group optionally having one or more halogen atoms, $OR^{12}$, or a halogen atom, and $R^{4a}$, $R^{4b}$ and $R^{4c}$ each independently represents a hydrogen atom or a halogen atom, and G represents -$L^1$-$G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}, and $A^1$ represents a nitrogen atom.

Embodiment 16

The compound described in Embodiment 12 wherein $R^2$ represents an ethyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{4a}$, $R^{4b}$ and $R^{4c}$ each represents a hydrogen atom, and G represents -$L^1$-$G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 17

The compound described in Embodiment 12 wherein $R^2$ represents an ethyl group, and $R^{3a}$ represents a C1-C6 alkyl group optionally having one or more halogen atoms, $OR^{12}$, or a halogen atom, and $R^{4a}$, $R^{4b}$ and $R^{4c}$ each represents a hydrogen atom, and G represents -$L^1$-$G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom, an oxo group, and a cyano group, and $L^1$ represents an oxygen atom, and $A^1$ represents a nitrogen atom.

Embodiment 18

The compound described in Embodiment 12 wherein $R^2$ represents an ethyl group, and $R^{4a}$, $R^{4b}$ and $R^{4c}$ each represents a hydrogen atom, and G represents -$L^1$-$G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom and a cyano group, and $L^1$ represents an oxygen atom, and $A^1$ represents a nitrogen atom, and q is 0.

Embodiment 19

A compound of the present invention wherein $A^2$ represents a nitrogen atom, and $A^3$ represents $CR^{4b}$ and $A^4$ represents $CR^{4c}$.

Embodiment 20

The compound descried in Embodiment 19 wherein $R^2$ represents a C1-C6 alkyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 21

The compound described in Embodiment 19 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4b}$ and $R^{4c}$ each independently represents a hydrogen atom or a halogen atom, and G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 22

The compound described in Embodiment 19 wherein $R^2$ represents a C1-C6 alkyl group, and $R^{3a}$ represents a C1-C6 alkyl group optionally having one or more halogen atoms, $OR^{12}$, or a halogen atom, and $R^{4b}$ and $R^{4c}$ each independently represents a hydrogen atom or a halogen atom, and G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}, and $A^1$ represents a nitrogen atom.

Embodiment 23

The compound described in Embodiment 19 wherein $R^2$ represents an ethyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{4b}$ and $R^{4c}$ each represents a hydrogen atom, and G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 24

The compound described in Embodiment 19 wherein $R^2$ represents an ethyl group, and $R^{3a}$ represents a C1-C6 alkyl group optionally having one or more halogen atoms, $OR^{12}$, or a halogen atom, and $R^{4b}$ and $R^{4c}$ each represents a hydrogen atom, and G represents $-L^1-G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom, an oxo group, and a cyano group, and $L^1$ represents an oxygen atom, and $A^1$ represents a nitrogen atom.

Embodiment 24

The compound described in Embodiment 19 wherein $R^2$ represents an ethyl group, and $R^{4b}$ and $R^{4c}$ each represents a hydrogen atom, and G represents $-L^1-G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom and a cyano group, and $L^1$ represents an oxygen atom, and $A^1$ represents a nitrogen atom, and q is 0.

Embodiment 26

A compound of the present invention wherein $A^2$ represents $CR^{4a}$, and $A^3$ represents a nitrogen atom, and $A^4$ represents $CR^{4c}$.

Embodiment 27

The compound described in Embodiment 26 wherein $R^2$ represents a C1-C6 alkyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and R3b represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 28

The compound described in Embodiment 26 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4a}$ and $R^{4c}$ each independently represents a hydrogen atom or a halogen atom, G represents $-L^1-G^2$, and $L^1$ represents an oxygen atom, and $G^1$ represents, a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 29

The compound described in Embodiment 26 wherein $R^2$ represents a C1-C6 alkyl group, and $R^{3a}$ represents a C1-C6 alkyl group optionally having one or more halogen atoms, $OR^{12}$, or a halogen atom, and $R^{4a}$ and $R^{4c}$ each independently represents a hydrogen atom or a halogen atom, and G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}, and $A^1$ represents a nitrogen atom.

Embodiment 30

The compound described in Embodiment 26 wherein $R^2$ represents an ethyl group, and $R^{3e}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{4a}$ and $R^{4c}$ each represents a hydrogen atom, and G represents $-L^1-G^2$, and $L^1$ represents an oxygen atom, and $G^2$ represents a pyridyl group, a pyrimidinyl group, a pyrazolyl group or a thiazolyl group {the pyridyl group, the pyrimidinyl group, the pyrazolyl group, and the thiazolyl group each independently may optionally have one or more substituents selected from Group D}.

Embodiment 31

The compound described in Embodiment 26 wherein $R^2$ represents an ethyl group, and $R^{3a}$ represents a C1-C6 alkyl group optionally having one or more halogen atoms, $OR^{12}$, or a halogen atom, and $R^{4a}$ and $R^{4c}$ each represents a hydrogen atom, and G represents $-L^1-G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom, an oxo group, and a cyano group, and $L^1$ represents an oxygen atom, and $A^1$ represents a nitrogen atom.

Embodiment 32

The compound described in Embodiment 26 wherein $R^2$ represents an ethyl group, and $R^{4a}$ and $R^{4c}$ each represents a hydrogen atom, and G represents $-L^1-G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom and a cyano group, and $L^1$ represents an oxygen atom, and $A^1$ represents a nitrogen atom, and q is 0.

Embodiment 33

A compound of the present invention wherein $A^2$ represents $CR^{4a}$, and $A^3$ represents $CR^{4b}$ and $A^4$ represents a nitrogen atom.

Embodiment 34

The compound described in Embodiment 33 wherein $R^2$ represents a C1-C6 alkyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group,

Embodiment 35

The compound described in Embodiment 33 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4a}$ and $R^{4b}$ each independently represents a hydrogen atom or a halogen atom, G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 36

The compound described in Embodiment 33 wherein $R^2$ represents a C1-C6 alkyl group, and $R^{3a}$ represents a C1-C6 alkyl group optionally having one or more halogen atoms, $OR^{12}$, or a halogen atom, $R^{4a}$ and $R^{4b}$ each independently represents a hydrogen atom or a halogen atom, G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}, and $A^1$ represents a nitrogen atom.

Embodiment 37

The compound described in Embodiment 33 wherein $R^2$ represents an ethyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O))OR^{14}$, or a halogen atom, and $R^{4a}$ and $R^{4b}$ each represents a hydrogen atom, G represents $-L^1-G^2$, and $L^1$ represents an oxygen atom, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}.

Embodiment 38

The compound described in Embodiment 33 wherein $R^2$ represents an ethyl group, and R3a represents a C1-C6 alkyl group optionally having one or more halogen atoms, $OR^{12}$, or a halogen atom, and $R^{4a}$ and $R^{4b}$ each represents a hydrogen atom, and G represents $-L^1-G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom, an oxo group, and a cyano group, and $L^1$ represents an oxygen atom, and $A^1$ represents a nitrogen atom.

Embodiment 39

The compound described in Embodiment 33 wherein $R^2$ represents an ethyl group, and $R^{4a}$ and $R^{4b}$ each represents a hydrogen atom, and G represents $-L^1-G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom and a cyano group, and $L^1$ represents an oxygen atom, and $A^1$ represents a nitrogen atom, and q is 0.

Embodiment 40

A compound A of the present invention wherein $R^{3a}$ represents a phenyl group optionally having one or more substituents selected from Group H, any one six membered aromatic heterocyclic group selected from Group V (the six membered aromatic heterocyclic group may optionally have one or more substituents selected from Group H), or any one five membered aromatic heterocyclic group selected from Group W (the five membered aromatic heterocyclic group may optionally have one or more substituents selected from Group H):

Group V:

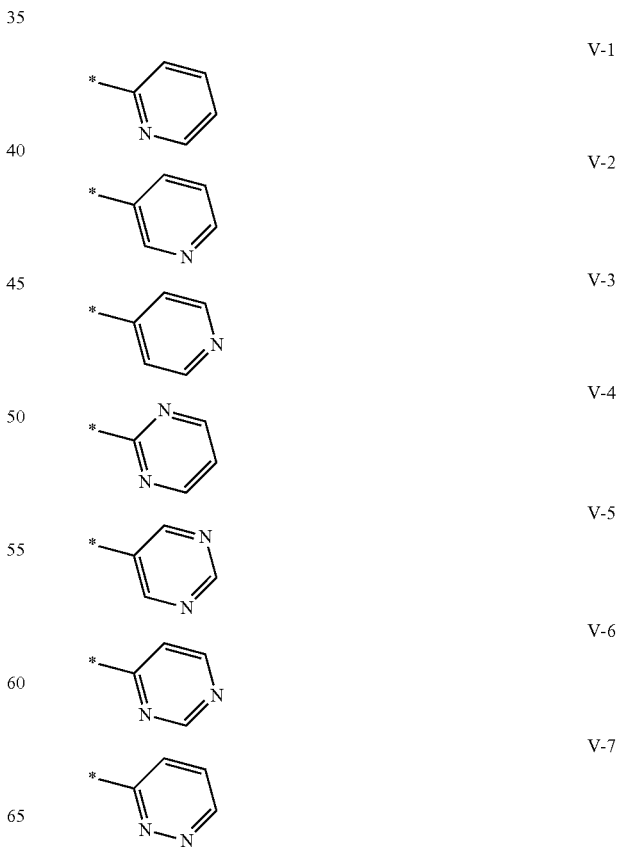

-continued

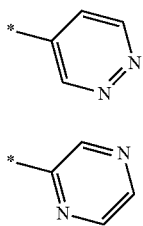

Group W:

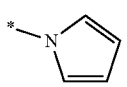 W-1

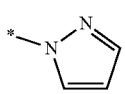 W-2

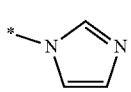 W-3

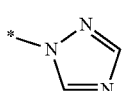 W-4

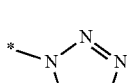 W-5

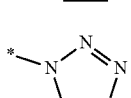 W-6

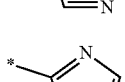 W-7

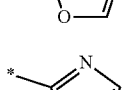 W-8

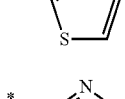 W-9

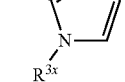 W-10

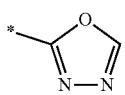 W-11

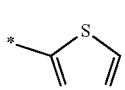 W-12

-continued

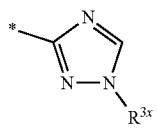 W-13

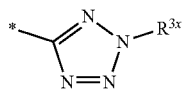 W-14

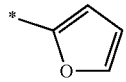 W-15

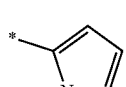 W-16

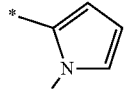 W-17

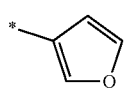 W-18

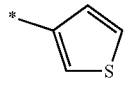 W-19

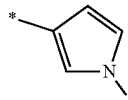 W-20

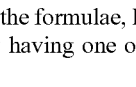

{in the formulae, $R^{3x}$ represents a C1-C6 alkyl group optionally having one or more halogen atoms};

Embodiment 41

The compound A of the present invention wherein $A^2$ represents $CR^{4a}$, and $A^4$ represents $CR^{4c}$.

Embodiment 42

The compound A described in Embodiment 41 wherein $R^2$ represents a C1-C6 alkyl group, and R3a represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and G represents a C3-C6 cycloalkyl group optionally having one or more substituents selected from Group E.

Embodiment 43

The compound A described in Embodiment 41 wherein $R^2$ represents a C1-C6 alkyl group, $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4a}$, $R^{4b}$ and $R^{4c}$ each independently represents a hydrogen atom or a halogen atom, and G represents a C3-C8 cycloalkyl group optionally having one or more substituents selected from Group E.

Embodiment 44

The compound A described in Embodiment 41 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4a}$, $R^{4b}$ and $R^{4c}$ each independently represents a hydrogen atom or a halogen atom, and G represents a C3-C8 cycloalkyl group optionally having one or more substituents selected from Group E, and $A^1$ represents a nitrogen atom.

Embodiment 45

The compound A described in Embodiment 41 wherein $R^2$ represents an ethyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{4a}$, $R^{4b}$ and $R^{4c}$ each represents a hydrogen atom, and G represents a C3-C8 cycloalkyl group optionally having one or more substituents selected from Group E.

Embodiment 46

The compound A described in Embodiment 41 wherein $R^2$ represents an ethyl group, and $R^{3a}$ represents a C1-C6 alkyl group optionally having one or more halogen atoms, $OR^{12}$, or a halogen atom, and $R^{4a}$, $R^{4b}$ and $R^{4c}$ each represents a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom.

Embodiment 47

The compound A described in Embodiment 41 wherein $R^2$ represents an ethyl group, and $R^{4a}$, $R^{4b}$ and $R^{4c}$ each represent a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom, and q is 0.

Embodiment 48

A compound A of the present invention wherein $A^2$ represents $CR^{4a}$, and $A^3$ represents $CR^{4b}$, and $A^4$ represents $CR^{4c}$.

Embodiment 49

The compound A described in Embodiment 48 wherein $R^2$ represents a C1-C6 alkyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and G represents a C3-C8 cycloalkyl group optionally having one or more substituents selected from Group E.

Embodiment 50

The compound A described in Embodiment 48 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4a}$, $R^{4b}$ and $R^{4c}$ each independently represents a hydrogen atom or a halogen atom, and G represents a C3-C8 cycloalkyl group optionally having one or more substituents selected from Group E.

Embodiment 51

The compound A described in Embodiment 48 wherein $R^2$ represents a C1-C6 alkyl group, and $R^{3a}$ represents a C1-C6 alkyl group optionally having one or more halogen atoms, $OR^{12}$, or a halogen atom, and $R^{4a}$, $R^{4b}$ and $R^{4c}$ each independently represents a hydrogen atom or a halogen atom, and G represents a C3-C8 cycloalkyl group optionally having one or more substituents selected from Group E, and $A^1$ represents a nitrogen atom.

Embodiment 52

The compound A described in Embodiment 48 wherein $R^2$ represents an ethyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{4a}$, $R^{4b}$ and $R^{4c}$ each represents a hydrogen atom, and G represents a C3-C8 cycloalkyl group optionally having one or more substituents selected from Group E.

Embodiment 53

The compound A described in Embodiment 48 wherein $R^2$ represents an ethyl group, and $R^{3a}$ represents a C1-C6 alkyl group optionally having one or more halogen atoms, $OR^{12}$, or a halogen atom, and $R^{4a}$, $R^{4b}$ and $R^{4c}$ each represents a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom.

Embodiment 54

The compound A described in Embodiment 48 wherein $R^2$ represents an ethyl group, and $R^{4a}$, $R^{4b}$ and $R^{4c}$ each represents a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom, and q is 0.

Embodiment 55

A compound A of the present invention wherein $A^2$ represents a nitrogen atom, and $A^3$ represents $CR^{4b}$, and $A^4$ represents $CR^{4c}$.

Embodiment 56

The compound A described in Embodiment 55 wherein $R^2$ represents a C1-C6 alkyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and G repre-sents a C3-C8 cycloalkyl group optionally having one or more substituents selected from Group E.

Embodiment 57

The compound A described in Embodiment 55 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4b}$ and $R^{4c}$ each independently represents a hydrogen atom or a halogen atom, and G represents a C3-C8 cycloalkyl group optionally having one or more substituents selected from Group E.

Embodiment 58

The compound A described in Embodiment 55 wherein $R^2$ represents a C1-C6 alkyl group, and $R^{3a}$ represents a C1-C6 alkyl group optionally having one or more halogen atoms, $OR^{12}$, or a halogen atom, and $R^{4b}$ and $R^{4c}$ each independently represents a hydrogen atom or a halogen atom, and G represents a C3-C8 cycloalkyl group optionally having one or more substituents selected from Group E, and $A^1$ represents a nitrogen atom.

Embodiment 59

The compound A described in Embodiment 55 wherein $R^2$ represents an ethyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{12}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{4b}$ and $R^{4c}$ each represents a hydrogen atom, and G represents a C3-C8 cycloalkyl group optionally having one or more substituents selected from Group E.

Embodiment 60

The compound A described in Embodiment 55 wherein $R^2$ represents an ethyl group, and $R^{3a}$ represents a C1-C6 alkyl group optionally having one or more halogen atoms, $OR^{12}$, or a halogen atom, and $R^{4b}$ and $R^{4c}$ each represents a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom.

Embodiment 61

The compound A described in Embodiment 55 wherein $R^2$ represents an ethyl group, and $R^{4b}$ and $R^{4c}$ each represents a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom, and q is 0.

Embodiment 62

A compound A of the present invention wherein $A^2$ represents $CR^{4a}$, and $A^3$ represents a nitrogen atom, and $A^4$ represents $CR^{4c}$.

Embodiment 63

The compound A described in Embodiment 62 wherein $R^2$ represents a C1-C6 alkyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and G represents a C3-C8 cycloalkyl group optionally having one or more substituents selected from Group E.

Embodiment 64

The compound A described in Embodiment 62 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4a}$ and $R^{4c}$ each independently represents a hydrogen atom or a halogen atom, and G represents a C3-C8 cycloalkyl group optionally having one or more substituents selected from Group E.

Embodiment 65

The compound A described in Embodiment 62 wherein $R^2$ represents a C1-C6 alkyl group, and $R^{3a}$ represents a C1-C6 alkyl group optionally having one or more halogen atoms, $OR^{12}$, or a halogen atom, and $R^{4a}$ and $R^{4c}$ each independently represents a hydrogen atom or a halogen atom, and G represents a C3-C8 cycloalkyl group optionally having one or more substituents selected from Group E, and $A^1$ represents a nitrogen atom.

Embodiment 66

The compound A described in Embodiment 62 wherein $R^2$ represents an ethyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{4a}$ and $R^{4c}$ each represents a hydrogen atom, and G represents a C3-C8 cycloalkyl group optionally having one or more substituents selected from Group E.

Embodiment 67

The compound A described in Embodiment 62 wherein $R^2$ represents an ethyl group, and $R^{3a}$ represents a C1-C6 alkyl group optionally having one or more halogen atoms, $OR^{12}$, or a halogen atom, and $R^{4a}$ and $R^{4c}$ each represents a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom.

Embodiment 68

The compound A described in Embodiment 62 wherein $R^2$ represents an ethyl group, and $R^{4a}$ and $R^{4c}$ each represents a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom, and q is 0.

Embodiment 69

A compound A of the present invention wherein $A^2$ represents $CR^{4a}$, and $A^3$ represents $CR^{4b}$, and $A^4$ represents a nitrogen atom.

Embodiment 70

The compound A described in Embodiment 69 wherein $R^2$ represents a C1-C6 alkyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and R3b represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and G repre-

Embodiment 71

The compound A described in Embodiment 69 wherein $R^2$ represents a C1-C6 alkyl group, and $R^{3a}$ represents a C1-C6 alkyl group optionally having one or more halogen atoms, $OR^{12}$, or a halogen atom, and $R^{3b}$ represents a hydrogen atom, a C1-C6 alkyl group optionally having one or more halogen atoms, $OR^{12}$, or a halogen atom, and $R^{4a}$ and $R^{4b}$ each independently represents a hydrogen atom, or a halogen atom, and G represents a C3-C8 cycloalkyl group optionally having one or more substituents selected from Group E.

Embodiment 72

The compound A described in Embodiment 69 wherein $R^2$ represents a C1-C6 alkyl group, and $R^{3a}$ represents a C1-C6 alkyl group optionally having one or more halogen atoms, $OR^{12}$, or a halogen atom, and $R^{4a}$ and $R^{4b}$ each independently represents a hydrogen atom or a halogen atom, and G represents a C3-C8 cycloalkyl group optionally having one or more substituents selected from Group E, and $A^1$ represents a nitrogen atom.

Embodiment 73

The compound A described in Embodiment 69 wherein $R^2$ represents an ethyl group, and $R^{3a}$ represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{3b}$ represents a hydrogen atom, a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, or a halogen atom, and $R^{4a}$ and $R^{4b}$ each represents a hydrogen atom, and G represents a C3-C8 cycloalkyl group optionally having one or more substituents selected from Group E.

Embodiment 74

The compound A described in Embodiment 69 wherein $R^2$ represents an ethyl group, and $R^{3a}$ represents a C1-C6 alkyl group optionally having one or more halogen atoms, $OR^{12}$, or a halogen atom, and $R^{4a}$ and $R^{4b}$ each represents a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom.

Embodiment 75

The compound A described in Embodiment 69 wherein $R^2$ represents an ethyl group, and $R^{4a}$ and $R^{4b}$ each represents a hydrogen atom, and G represents a C1-C6 chain hydrocarbon group optionally having one or more halogen atoms, a C1-C6 alkoxy group optionally having one or more halogen atoms, or a C3-C8 cycloalkyl group optionally having one or more substituents selected from a group consisting of a halogen atom, an oxo group, and a cyano group, and $A^1$ represents a nitrogen atom, and q is 0.

Embodiment 76

A compound A of the present invention wherein T represents a C1-C10 chain hydrocarbon group having one or more halogen atoms, a (C1-C5 alkoxy)C2-C5 alkyl group having one or more halogen atoms, a (C1-C5 alkylsulfanyl) C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, $NR^1R^{29}$, a group represented by formula T-1, a group represented by formula T-2, a group represented by formula T-3, a group represented by formula T-4, a group represented by formula T-5, a group represented by formula T-6, a group represented by formula T-7, or a group represented by formula T-8, and $R^1$, $R^{1x}$ and $R^{1y}$ each independently represents a C1-C5 chain hydrocarbon group having one or more halogen atoms.

Embodiment 77

The compound described in Embodiment 76 wherein $R^1$, $R^{1x}$ and $R^{1y}$ each independently represents a C1-C5 alkyl group including three or more fluorine atoms.

Embodiment 78

A compound A of the present invention wherein T represents a C1-C10 chain hydrocarbon group having one or more halogen atoms, a (C1-C5 alkoxy)C2-C5 alkyl group having one or more halogen atoms, a (C1-C5 alkylsulfanyl) C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{29}$.

Embodiment 79

A compound of the present invention wherein A1 represents a nitrogen atom, and $A^2$ represents $CR^{4a}$, $A^4$ represents $CR^{4c}$, and $R^{4a}$, $R^{4b}$ and $R^{4c}$ each represents a hydrogen atom, and $R^2$ represents a C1-C6 alkyl group optionally having one or more halogen atoms, and q is 0, and G represents —O-G2, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}, and T represents a C1-C6 alkyl group having one or more fluorine atoms, $OR^1$, $S(O)_mR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a phenyl group having one or more substituents selected from Group Z, a pyridyl group having one or more substituents selected from Group Z, a pyrazolyl group having one or more substituents selected from Group Z, an imidazolyl group having one or more substituents selected from Group Z, or a triazolyl group having one or more substituents selected from Group Z, and $R^1$ represents a C1-C6 alkyl group having one or more halogen atoms, and $R^{29}$ and $R^{30}$ each independently represents a C1-C6 alkyl group, and Group Z represents a C1-C6 alkyl group having one or more halogen atoms or a halogen atom.

Embodiment 80

A compound of the present invention wherein $A^1$ represents a nitrogen atom, and $A^2$ represents $CR^{4a}$, and $A^3$ represents $CR^{4b}$, and $A^4$ represents $CR^{4c}$, $R^{4a}$, $R^{4b}$ and $R^{4c}$ each represents a hydrogen atom, and $R^2$ represents a C1-C6 alkyl group optionally having one or more halogen atoms, q is 0, G represents —O-G2, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom and a cyano group, and T represents $OR^1$, and $R^1$ represents a C1-C6 alkyl group having one or more halogen atoms.

Embodiment 81

A compound A of the present invention wherein T represents a group represented by formula T-1, a group represented by formula T-2, a group represented by formula T-3, a group represented by formula T-4, a group represented by formula T-5, a group represented by formula T-6, a group represented by formula T-7, or a group represented by formula T-8, and $R^1$, $R^{1x}$ and $R^{1y}$ each independently represents a C1-C5 alkyl group including three or more fluorine atoms.

Embodiment 82

A compound A of the present invention wherein T represents $OR^1$.

Embodiment 83

The compound A described in Embodiment 82 wherein $R^1$ represents a C1-C5 chain hydrocarbon group having one or more halogen atoms.

Embodiment 84

The compound A described in Embodiment 82 wherein $R^1$ represents a C1-C5 alkyl group including three or more fluorine atoms.

Embodiment 85

A compound of the present invention wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, $NR^1R^{29}$, a group represented by formula T-1, a group represented by formula T-2, a group represented by formula T-3, a group represented by formula T-4, a group represented by formula T-5, a group represented by formula T-6, a group represented by formula T-7, or a group represented by formula T-8, and $R^1$, $R^{1x}$ and $R^{1y}$ each independently represents a C1-C5 chain hydrocarbon group having one or more halogen atoms.

Embodiment 86

The compound of the present invention described in Embodiment 85 wherein $R^1$, $R^{1x}$, $R^{1y}$ and $R^{a1y}$ each independently represents a C1-C5 alkyl group including three or more fluorine atoms.

Embodiment 87

A compound of the present invention wherein T represents a C1-C10 chain hydrocarbon group having one or more halogen atoms, a (C1-C5 alkoxy)C2-C5 alkyl group having one or more halogen atoms, a (C1-C5 alkylsulfanyl) C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{29}$.

Embodiment 88

The compound of the present invention described in Embodiment 87 wherein $R^1$, $R^{1x}$ and $R^{1y}$ each independently represents a C1-C5 chain hydrocarbon group having one or more halogen atoms.

Embodiment 89

The compound of the present invention described in Embodiment 87 wherein $R^1$, $R^{1x}$ and $R^{1y}$ each independently represents a C1-C5 alkyl group including three or more fluorine atoms.

Embodiment 90

A compound of the present invention wherein T represents a group represented by formula T-1, a group represented by formula T-2, a group represented by formula T-3, a group represented by formula T-4, a group represented by formula T-5, a group represented by formula T-6, a group represented by formula T-7, or a group represented by formula T-8, and $R^1$, $R^{1x}$ and $R^{1y}$ each independently represents a C1-C5 alkyl group including three or more fluorine atoms.

Embodiment 91

A compound of the present invention wherein T1 represents $OR^1$.

Embodiment 92

The compound of the present invention described in Embodiment 91 wherein $R^1$ represents a C1-C5 chain hydrocarbon group having one or more halogen atoms.

Embodiment 93

The compound of the present invention described in Embodiment 91 wherein $R^1$ represents a C1-C5 alkyl group including three or more fluorine atoms.

Embodiment 94

The compound of the present invention described in any one of Embodiments 2 to 75 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, $NR^1R^{29}$, a group represented by formula T-1, a group represented by formula T-2, a group represented by formula T-3, a group represented by formula T-4, a group represented by formula T-5, a group represented by formula T-6, a group represented by formula T-7, or a group represented by formula T-8, and $R^1$, $R^{1x}$ and $R^{1y}$ each independently represents a C1-C5 chain hydrocarbon group having one or more halogen atoms.

Embodiment 95

The compound of the present invention described in any one of Embodiments 2 to 75 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, $NR^1R^{29}$, a group represented by formula T-1, a group represented by formula T-2, a group represented by formula T-3, a group represented by formula T-4, a group represented by formula T-5, a group represented by formula T-6, a group represented by formula T-7, or a group represented by formula T-8, and $R^1$, $R^{1x}$ and $R^{1y}$ each independently represents a C1-C5 alkyl group including three or more fluorine atoms.

Embodiment 96

The compound of the present invention described in any one of Embodiments 2 to 75 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{29}$.

Embodiment 97

The compound of the present invention described in any one of Embodiments 2 to 75 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{29}$, and $R^1$ represents a C1-C5 chain hydrocarbon group having one or more halogen atoms.

Embodiment 98

The compound of the present invention described in any one of Embodiments 2 to 75 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{29}$, and $R^1$ represents a C1-C5 alkyl group including three or more fluorine atoms.

Embodiment 99

The compound of the present invention described in any one of Embodiments 2 to 75 wherein T represents a group represented by formula T-1, a group represented by formula T-2, a group represented by formula T-3, a group represented by formula T-4, a group represented by formula T-5, a group represented by formula T-6, a group represented by formula T-7, or a group represented by formula T-8, and $R^{1x}$ and $R^{1y}$ each independently represents a C1-C5 alkyl group including three or more fluorine atoms.

Embodiment 100

The compound of the present invention described in any one of Embodiments 1 to 75 wherein T represents $OR^1$.

Embodiment 101

The compound of the present invention described in any one of Embodiments 2 to 75 wherein T represents $OR^1$, and $R^1$ represents a C1-C5 chain hydrocarbon group having one or more halogen atoms.

Embodiment 102

The compound of the present invention described in any one of Embodiments 2 to 75 wherein T represents $OR^1$, and $R^1$ represents a C1-C5 alkyl group including three or more fluorine atoms.

Embodiment 103

A compound A of the present invention wherein A1 represents a nitrogen atom, and $A^2$ represents $CR^{4a}$, and $A^4$ represents $CR^{4c}$, and $R^{4a}$, $R^{4b}$ and $R^{4c}$ each represents a hydrogen atom, and $R^2$ represents a C1-C6 alkyl group optionally having one or more halogen atoms, and q is 0, and G represents a C1-C6 alkyl group optionally having one or more halogen atoms, or a C3-C6 cycloalkyl group optionally having one or more substituents selected from the group consisting of a halogen atom and a cyano group, and T represents a C1-C6 alkyl group having one or more fluorine atoms, $OR^1$, $S(O)_mR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a phenyl group having one or more substituents selected from Group Z, a pyridyl group having one or more substituents selected from Group Z, a pyrazolyl group having one or more substituents selected from Group Z, an imidazolyl group having one or more substituents selected from Group Z, or a triazolyl group having one or more substituents selected from Group Z, and $R^1$ represents a C1-C6 alkyl group having one or more halogen atoms, and $R^{29}$ and $R^{30}$ each independently represents a C1-C6 alkyl group, and Group Z represents a group consisting of a C1-C6 alkyl group having one or more halogen atoms and a halogen atom.

Embodiment 104

A compound A of the present invention wherein $A^1$ represents a nitrogen atom, $A^2$ represents $CR^{4a}$, and $A^1$ represents $CR^{4c}$, and $R^{4a}$, $R^{4b}$ and $R^{4c}$ each represents a hydrogen atom, and $R^2$ represents a C1-C6 alkyl group optionally having one or more halogen atoms, and q is 0, and G represents a C1-C6 alkyl group optionally having one or more halogen atoms, or a C3-C6 cycloalkyl group optionally having one or more substituents selected from the group consisting of a halogen atom and a cyano group, and T represents $OR^1$, and $R^1$ represents a C1-C6 alkyl group having one or more halogen atoms.

Embodiment 105

A compound of the present invention wherein $A^1$ represents a nitrogen atom, and $A^2$ represents $CR^{4a}$, and $A^4$ represents $CR^{4c}$, and $R^{4a}$, $R^{4b}$ and $R^{4c}$ each represents a hydrogen atom, and $R^2$ represents a C1-C6 alkyl group optionally having one or more halogen atoms, and q is 0, and G represents a C1-C6 alkyl group optionally having one or more halogen atoms, a phenyl group optionally having one or more halogen atoms, a C3-C6 cycloalkyl group optionally having one or more substituents selected from the group consisting of a halogen atom and a cyano group, or —O-$G^2$, and $G^2$ represents a pyridyl group, a pyrimidinyl group, a pyrazolyl group, or a thiazolyl group {the pyridyl group, the pyrimidinyl group, the pyrazolyl group, and the thiazolyl group each independently may optionally have one or more substituents selected from Group D}, and T represents a C1-C6 alkyl group having one or more fluorine atoms, $OR^1$, $S(O)_mR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a phenyl group having one or more substituents selected from Group Z, a pyridyl group having one or more substituents selected from Group Z, a pyrazolyl group having one or more substituents selected from Group Z, an imidazolyl group having one or more substituents selected from Group Z, or a triazolyl group having one or more substituents selected from Group Z, and $R^1$ represents a C1-C6 alkyl group having one or more halogen atoms, and $R^{29}$ and $R^{30}$ each independently represents a C1-C6 alkyl group, and Group Z represents a C1-C6 alkyl group having one or more halogen atoms or a halogen atom.

Embodiment 106

A compound of the present invention wherein A1 represents a nitrogen atom, and $A^2$ represents $CR^{4a}$, and $A^3$ represents $CR^{4b}$, and $A^4$ represents $CR^{4c}$, and $R^{4a}$, $R^{4b}$ and $R^{4c}$ each represents a hydrogen atom, and $R^2$ represents a C1-C6 alkyl group optionally having one or more halogen atoms, and q is 0, and G represents a C1-C6 alkyl group optionally having one or more halogen atoms, a C3-C6 cycloalkyl group optionally having one or more substituents selected from the group consisting of a halogen atom and a cyano group and —O-$G^2$, and $G^2$ represents a C1-C6 chain hydrocarbon group optionally having one or more halogen atoms, a C1-C6 alkoxy group optionally having one or more halogen atoms, or a pyridyl group optionally having one or more substituents selected from a group consisting of a halogen atom and a cyano group, and T represents $OR^1$, and $R^1$ represents a C1-C6 alkyl group having one or more halogen atoms.

Next, a process for preparing the compound of the present invention is explained.

Process 1

A compound represented by formula (IA) of the present invention can be prepared by reacting a compound represented by formula (M-1) (hereinafter, referred to as Compound (M-1)) with a compound represented by formula (R-1) (hereinafter, referred to as Compound (R-1)) in the presence of a metal catalyst.

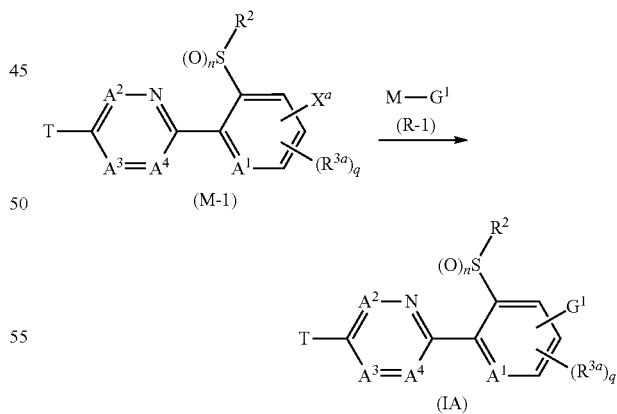

[wherein $G^1$ represents a C3-C8 alicyclic hydrocarbon group optionally having one or more substituents selected from Group E, $X^a$ represents a chlorine atom, a bromine atom, an iodine atom, or a trifluoromethansulfonyloxy group, M represents a 9-borabiclo[3.3.1]nonan-9-yl group, B(OH)₂, or BF₃K, and the other symbols are the same as defined above.]

The reaction is usually carried out in a solvent. Examples of the solvent to be used in the reaction include ethers such as dimethoxyethane, 1,4-dioxane, tetrahydrofuran (hereinafter, referred to as THF), aromatic hydrocarbons such as toluene and xylene, polar aprotic solvents such as N,N-dimethylformamide (hereinafter, referred to as DMF), N-methyl pyrrolidone (hereinafter, referred to as NMP), dimethyl sulfoxide (hereinafter, referred to as DMSO), and mixed solvents thereof.

Examples of the metal catalyst to be used in the reaction include palladium catalysts such as tetrakis(triphenylphosphine)palladium(0), [1,1'-bis(diphenylphosphino)ferrocene]palladium(II) dichloride, tris(dibenzylideneacetncetone)dipalladium(0), palladium(II) acetate (hereinafter, referred to as palladium catalysts).

A ligand, a base and/or an inorganic halogenated compound may be added to the reaction as needed.

Examples of the ligand to be used in the reaction include phosphine ligands such as triphenylphosphine, Xantphos, 2,2'-bis(diphenylphoshino)-1,1'-binaphthyl, 1,1'-bis(diphenylphoshino)ferrocene, 2-(dicyclohexylphosphino)-2',4',6'-triisopropyl-1,1'-biphenyl, 2-dicyclohexylphosphino-2',6'-dimethoxybiphenyl, 1,2-bis(diphenylphosphino)ethane (hereinafter, referred to as phosphine ligands).

Examples of the base to be used in the reaction include alkali metal hydrides such as sodium hydride (hereinafter, referred to as alkali metal hydrides), alkali metal carbonates such as potassium carbonate (hereinafter, referred to as alkali metal carbonates), and organic bases such as triethylamine, diisopropylethylamine, pyridine, and 4-(dimethylamino)pyridine (hereinafter, referred to as organic bases).

In the reaction, the compound (R-1) is usually used within a range of 1 to 10 molar ratio(s), the metal catalyst is usually used within a range of 0.01 to 0.5 molar ratio(s), the ligand is usually used within a range of 0.01 to 1 molar ratio(s), and the base is usually used within a range of 0.1 to 5 molar ratio(s), as opposed to 1 mole of the compound (M-1).

The reaction temperature is usually within a range of −20 to 200° C. The reaction period of the reaction is usually within a range of 0.1 to 24 hours.

The compound (R-1) is a commercially available compound, or can be prepared according to a known method.

When the reaction is completed, water is added to the reaction mixtures, and the reaction mixtures are extracted with organic solvent(s), and the organic layers are worked up (such as drying and concentration) to obtain the compound of the present invention.

Process 2

The compound A of the present invention can be prepared by reacting a compound represented by formula (M-2) (hereinafter, referred to as Compound (M-2)) with a compound represented by formula (R-2) (hereinafter, referred to as Compound (R-2)) in the presence of a metal catalyst.

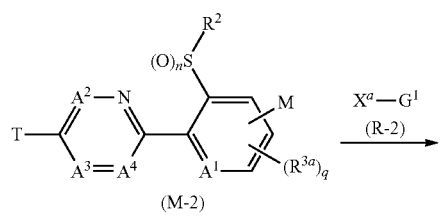

(M-2)

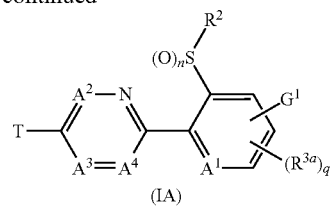

(IA)

[wherein the symbols are the same as defined above.]

The compound A of the present invention can be prepared by using the compound (R-2) instead of the compound (M-1) and the compound (M-2) instead of the compound (R-1), according to a method described in the Process 1.

The compound (R-2) is commercially available compound, or can be prepared according to a known method.

Process 3

Among the compounds of the present invention, a compound represented by formula (Ib) (hereinafter, referred to as Compound (Ib)) and a compound represented by formula (Ic) (hereinafter, referred to as Compound (Ic)) can be prepared by oxidizing a compound represented by formula (Ia) (hereinafter, referred to as Compound (Ia)).

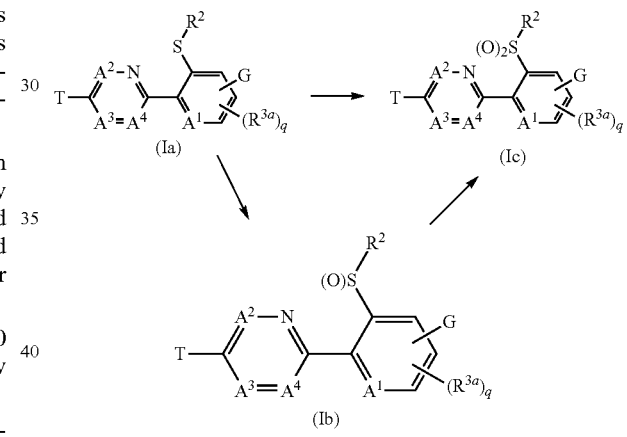

[wherein the symbols are the same as defined above.]

Firstly, a process for preparing the compound (Ib) from the compound (Ia) is described.

The reaction is usually carried out in a solvent. Examples of the solvents to be used in the reaction include halogenated hydrocarbons such as dichloromethane and chloroform (hereinafter, referred, to as halogenated hydrocarbons), nitriles such as acetonitrile (hereinafter, referred to as nitriles), and alcohols such as methanol and ethanol (hereinafter, referred to as alcohols), acetic acid, water, and mixed solvents thereof.

Examples of the oxidizing agent to be used in the reaction include sodium periodate, m-chloroperoxybenzoic acid (hereinafter, referred to as mCPBA), and hydrogen peroxide. When hydrogen peroxide is used as an oxidizing agent, sodium carbonate or a catalyst may be added as needed.

Examples of the catalyst to be used in the reaction include tungstic acid, and sodium tungstate.

In the reaction, the oxidizing agent is usually used within a range of 1 to 1.2 molar ratio(s), the sodium carbonate is usually used within a range of 0.01 to 1 molar ratio(s), and the catalyst is usually used within a range of 0.01 to 0.5 molar ratios, as opposed to 1 mole of the compound (Ia).

The reaction temperature of the reaction is usually within a range of −20 to 80° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to obtain the compound (Ib).

Next, a process for preparing the compound (Ic) from the compound (Ib) is described.

Examples of the solvent to be used in the reaction include halogenated hydrocarbons, nitriles, alcohols, acetic acid, water, and mixed solvents thereof.

Examples of the oxidizing agent to be used in the reaction include mCPBA and peroxide hydrogen. When peroxide hydrogen is used as an oxidizing agent, a base or a catalyst may be added as needed.

Examples of the catalyst to be used in the reaction include sodium tungstate.

In the reaction, the oxidizing agent is usually used within a range of 1 to 2 molar ratio(s), the sodium carbonate is usually used within a range of 0.01 to 1 molar ratio(s), and the catalyst is usually used within a range of 0.01 to 0.5 molar ratios, as opposed to 1 mole of the compound (Ib).

The reaction temperature of the reaction is usually within a range of −20 to 120° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to obtain the compound (Ic).

Also, the compound (Ic) can be prepared by reacting the compound (Ia) with an oxidizing agent in one step (one-pot). The reaction can be carried out by using the oxidizing agent in a ratio of usually 2 to 5 molar ratios as opposed to 1 mole of the compound (Ia), according to the method for preparing the compound (Ic) from the compound (Ib).

Process 4

A compound represented by formula (Id) (hereinafter, referred to as Compound (Id)) according to the following scheme.

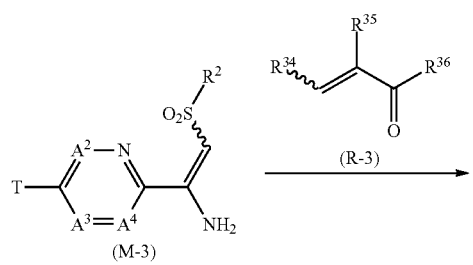

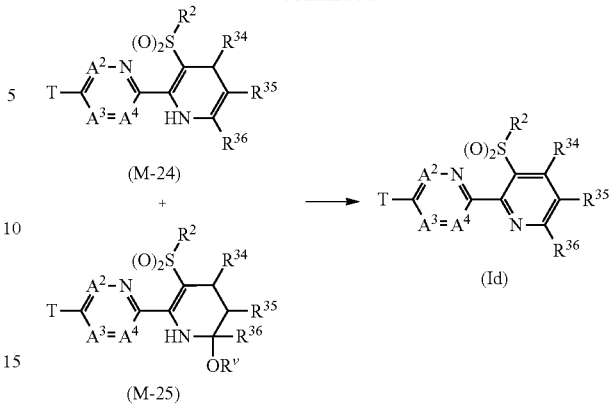

[wherein, when methanol is used as a solvent, $R^v$ represents a methyl group, or when ethanol is used as a solvent, $R^v$ represents an ethyl group, or when propanol is used as a solvent, $R^v$ represents a propyl group, or when butanol is used as a solvent, $R^v$ represents a butyl group, or when the other solvent is used, $R^v$ represents a hydrogen atom. Also, any one of $R^{34}$, $R^{35}$ and $R^{36}$ represents G, and the remaining groups each independently represents a hydrogen atom, a C1-C6 alkyl group optionally having one or more halogen atoms, a phenyl group optionally having one or more substituents selected from Group H, or a five or six membered aromatic heterocyclic group optionally having one or more substituents selected from Group H, and the other symbols are the same as defined above.]

The Firstly step is described, in which a compound represented by formula (M-3) (hereinafter, referred to as compound (M-3)) and a compound represented by formula (R-3) (hereinafter, referred to as compound (R-3)) are reacted to obtain a compound represented by formula (M-24) (hereinafter, referred to as Compound (M-24)) or a compound represented by formula (M-25) (hereinafter, referred to as Compound (M-25)), respectively, or a mixture thereof.

The reaction is usually carried out in a solvent. Examples of the solvent to be used in the reaction include methanol, ethanol, propanol, butanol, ethers, aliphatic hydrocarbons such as pentane and hexane (hereinafter, referred to as aliphatic hydrocarbons), aromatic hydrocarbons, aliphatic halogenated hydrocarbons such as chloroform and dichloromethane (hereinafter, referred to as aliphatic halogenated hydrocarbons), esters such as ethyl acetate (hereinafter, referred to as ethers), nitriles, polar aprotic solvents, and nitrogen-containing aromatic compounds such as pyridine and 2,6-lutidine (hereinafter, referred to as nitrogen-containing aromatic compounds) and mixture thereof.

An acid or a base may be added to the reaction as needed. Examples of the acid to be used in the reaction include carboxylic acids such as acetic acid, and sulfonic acids such as methane sulfonic acid and p-toluene sulfonic acid, and examples of the base include alkali metal carbonates, alkali metal hydrides, and organic bases.

In the reaction, the compound (R-3) is usually used within a range of 1 to 10 molar ratio(s), and the base is usually used within a range of 0.1 to 10 molar ratio(s), and the acid is usually used within a range of 0.1 to 10 molar ratio(s), as opposed to 1 mole of the compound (M-3).

The reaction temperature of the reaction is usually within a range of 0 to 200° C. The reaction period of the reaction is usually within a range of 0.1 to 24 hours.

The compound (R-3) is a commercially available compound, or can be prepared according to a known method.

When the reaction is completed, water is added to reaction mixtures, and the reaction mixtures are extracted with organic solvent(s), and the organic layers are worked up (for example, drying and concentration) to obtain the compound (M-24) or the compound (M-25) respectively, or a mixture thereof.

Next, the second step is described, in which the compound (M-24), the compound (M-25), or a mixture thereof is reacted with an oxidizing agent to prepare the compound (Id).

The reaction is usually carried out in a solvent. Examples of the solvent to be used in the reaction include ethers, aliphatic hydrocarbons, aromatic hydrocarbons, aliphatic halogenated hydrocarbons, nitriles, polar aprotic solvents, nitrogen-containing aromatic compounds, and mixed solvents thereof.

Examples of the oxidizing agent to be used in the reaction include manganese dioxide.

Instead of reacting with the oxidizing agent, methane sulfonylchloride and triethylamine are mixed with each other, or each of them is reacted successively to the compound (M-24), the compound (M-25), or mixtures of thereof.

Alternatively, instead of reacting with the oxidizing agent, Pd—C and olefins such as vinyl acetate are mixed with each other, or each of them is reacted successively to the compound (M-24), the compound (M-25), or mixtures of thereof.

In the reaction, the oxidizing agent is usually used within a range of 1 to 10 molar ratio(s), as opposed to 1 mole of the compound (M-24) and/or the compound (M-25).

In the reaction, when methanesulfonyl chloride and triethylamine are used instead of the oxidizing agent, the methanesulfonyl chloride is usually used within a range of 1 to 10 molar ratio(s), and the triethylamine is usually used within a range of 1 to 10 molar ratio(s), as opposed to 1 mole of the compound (M-24) or the compound (M-25).

In the reaction, when Pd—C and olefins are used instead of the oxidizing agent, the Pd—C is usually used within a range of 0.001 to 1 molar ratio(s), and the olefins are usually used within a range of 1 to 10 molar ratio(s), as opposed to 1 mole of the compound (M-24) or the compound (M-25).

The reaction temperature of the reaction is usually within a range of 0 to 200° C. The reaction period of the reaction is usually within a range of 0.1 to 24 hours.

When the reaction is completed, water is added to reaction mixtures, and the reaction mixtures are extracted with organic solvent(s), and the organic layers are worked up (such as drying and concentration) to isolate the compound (Id).

Process 5

A compound represented by formula (Ie) (hereinafter, referred to as Compound (Ie)) can be prepared according to the below-mentioned method.

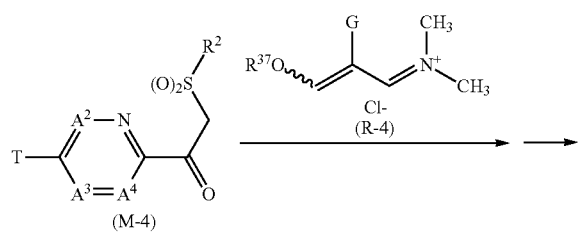

(M-4)

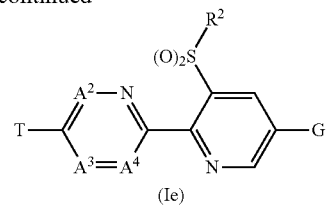

(Ie)

[wherein $R^{37}$ represents a C1-C6 alkyl group, and the other symbols are the same as defined above.]

The Firstly step is described, in which a compound represented by formula (M-4) (hereinafter, referred to as Compound (M-4)) and a compound represented by formula (R-4) (hereinafter, referred to as Compound (R-4)) are reacted.

The compound (R-4) can be prepared according to the method described in WO 2009/054742.

The reaction is usually carried out in a solvent. Examples of the solvents to be used in the reaction include ethers, aliphatic hydrocarbons, aromatic hydrocarbons, aliphatic halogenated hydrocarbons, alcohols, esters, nitriles, polar aprotic solvents, nitrogen-containing aromatic compounds, and mixed solvents thereof.

A base may be added to the reaction as needed, and examples of the base include organic bases.

In the reaction, the compound (R-4) is usually used within a range of 1 to 10 molar ratio(s), and the base is usually used within a range of 1 to 10 molar ratio(s), as opposed to 1 mole of the compound (M-4).

The reaction temperature of the reaction is usually within a range of −50 to 200° C. The reaction period of the reaction is usually within a range of 0.1 to 24 hours.

When the reaction is completed, the reaction mixtures are concentrated to give a residue, and the resulting residue is used as it is in the second step, alternatively, water is added to the reaction mixtures, and the reaction mixtures are extracted with organic solvent(s), and the organic layers are worked up (such as drying and concentration) to give the residue, and the resulting residue is used in the second step.

Next, the second step is described, in which the residue obtained in the Firstly step and ammonia or a salt thereof are reacted to prepare the compound (Ie).

The reaction is usually carried out in a solvent. Examples of the solvent to be used in the reaction include ethers, nitriles, alcohols, polar aprotic solvents, nitrogen-containing aromatic compounds, water, and mixed solvents thereof.

Examples of the ammonia or the salt thereof to be used in the reaction include an aqueous ammonia solution, an ammonia alcoholic solution, ammonium carboxylate salts such as ammonium acetate, and ammonium halide salts such as ammonium chloride.

In the reaction, the ammonia or the salt thereof is usually used within a range of 1 to 100 molar ratio(s), as opposed to 1 mole of the compound (M-4).

The reaction temperature of the reaction is usually within a range of 0 to 100° C. The reaction period of the reaction is usually within a range of 0.1 to 24 hours.

When the reaction is completed, water is added to the reaction mixtures, and the reaction mixtures are extracted with organic solvent(s), and the organic layers are worked up (such as drying and concentration) to obtain the compound (Ie).

Process 6

The compound (Id) can be prepared by reacting the compound (M-3) with a compound represented by formula (R-5) (hereinafter, referred to as Compound (R-5)).

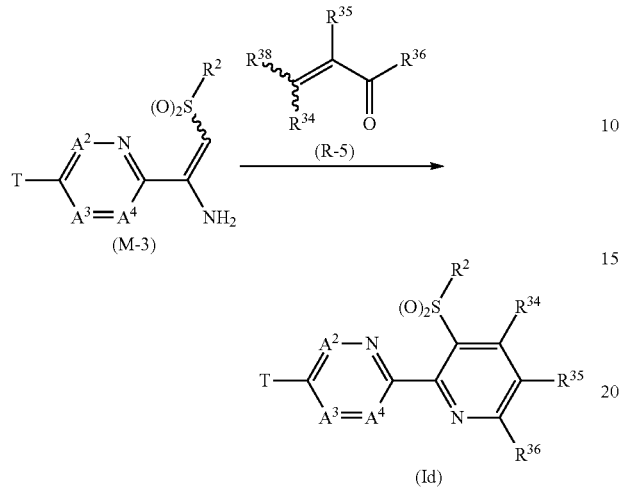

[wherein $R^{38}$ represents $OR^{37}$, a halogen atom, a C1-C3 alkylsulfonyloxy group optionally having one or more halogen atoms, or a p-toluenesulfonyloxy group, and the other symbols are the same as defined above.]

The reaction is usually carried out in a solvent. Examples of the solvent to be used in the reaction include ethers, aliphatic hydrocarbons, aromatic hydrocarbons, aliphatic halogenated hydrocarbons, nitriles, alcohols, polar aprotic solvents, nitrogen-containing aromatic compounds, and mixed solvents thereof.

In the reaction, the compound (R-5) is usually used within a range of 1 to 10 molar ratio(s), as opposed to 1 mole of the compound (M-3).

The reaction temperature of the reaction is usually within a range of 0 to 200° C. The reaction period of the reaction is usually within a range of 0.1 to 24 hours.

The compound (R-5) is a commercially available compound, or can be prepared according to a known method.

When the reaction is completed, water is added to the reaction mixtures, and the reaction mixtures are extracted with organic solvent(s), and the organic layers are worked up (such as drying and concentration) to isolate the compound (Id).

Process 7

The compound (Ia) can be prepared by reacting a compound represented by formula (M-9) (hereinafter, referred to as Compound (M-9)) with a compound represented by formula (R-6) (hereinafter, referred to as Compound (R-6)) in the presence of a base.

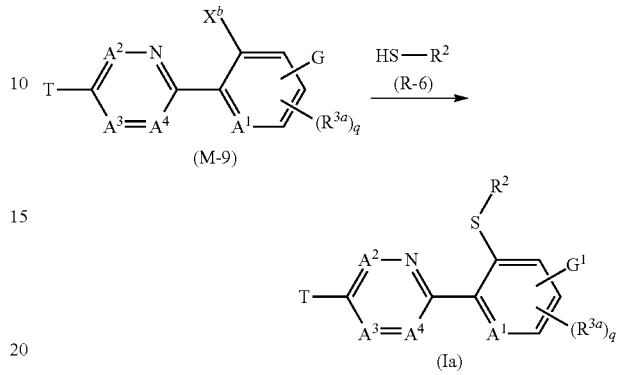

[wherein $X^b$ represents a fluorine atom or a chlorine atom, and the other symbols are the same as defined above.]

The reaction is usually carried out in a solvent. Examples of the solvent to be used in the reaction include ethers, aromatic hydrocarbons, nitriles, polar aprotic solvents, and mixed solvents thereof.

Examples of the base to be used in the reaction include alkali metal carbonates, and alkali metal hydrides.

In the reaction, the compound (R-6) is usually used within a range of 1 to 10 molar ratio(s), and the base is usually used within a range of 1 to 10 molar ratio(s), as opposed to 1 mole of the compound (M-9).

The reaction temperature of the reaction is usually within a range of –20 to 150° C. The reaction period of the reaction is usually within a range of 0.5 to 24 hours.

The compound (R-6) is a commercially available compound, or can be prepared according to a known method.

When the reaction is completed, water is added to reaction mixtures, and the reaction mixtures are extracted with organic solvent(s), and the organic layers are worked up (such as drying and concentration) to obtain the compound (Ia).

Process 8

A compound represented by formula (If) (hereinafter, referred to as Compound (If)) can be prepared according to the below-mentioned scheme.

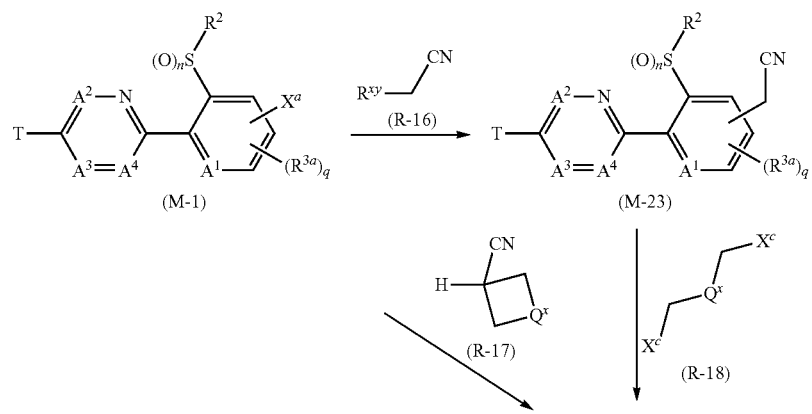

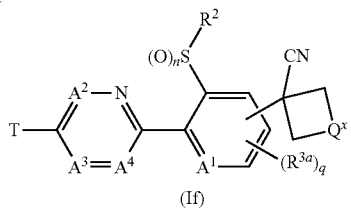

(If)

[wherein $R^{xy}$ represents a carboxy group or a trimethylsilyl group, $Q^x$ represents a single bond, a C1-C5 alkylene group optionally having one or more substituents selected from group E, or a C2-C5 alkenylene group optionally having one or more substituents selected from group E, $X^c$ represents a halogen atom, a trifluoromethansulfonyloxy group, or a p-toluenesulfonyloxy group, and the other symbols are the same as defined above.]

Firstly, a process for preparing a compound represented by formula (M-23) (hereinafter, referred to as Compound (M-23)) is described.

The compound (M-23) can be prepared by reacting the compound (M-1) with a compound represented by formula (R-16) (hereinafter, referred to as Compound (R-16)) in the presence of a metal catalyst.

The reaction is usually carried out in a solvent. Examples of the solvent to be used in the reaction include ethers, aromatic hydrocarbons, polar aprotic solvents, water, and mixed solvents thereof.

Examples of the metal catalyst include palladium catalysts, nickel catalysts, and copper catalyst.

A ligand, a base, or an inorganic halogenated compound may be added to the reaction as needed.

Examples of the ligand to be used in the reaction include phosphine ligands, 2,2'-bipyridine, 2-aminoethanol, 8-hydroquinoline, and 1,10-phenanthroline.

Examples of the base to be used in the reaction include alkali metal hydrides, alkali metal carbonates, and organic bases.

Examples of the inorganic halogenated compound to be used in the reaction include metal fluorides such as potassium fluoride, cesium fluoride, and zinc fluoride, and alkali metal chlorides such as lithium chloride and sodium chloride.

In the reaction, the compound (R-16) is usually used within a range of 1 to 10 molar ratio(s), the metal catalyst is usually used within a range of 0.01 to 0.5 molar ratio(s), the ligand is usually used within a range of 0.01 to 1 molar ratio(s), the base is usually used within a range of 0.1 to 5 molar ratio(s), and the inorganic halogenated compound is usually used within a range of 0.1 to 5 molar ratio(s), as opposed to 1 mole of the compound (M-1).

The reaction temperature is usually within a range of −20 to 200° C. The reaction period of the reaction is usually within a range of 0.1 to 24 hours.

The compound (R-16) is a commercially available compound, or can be prepared according to a known method.

When the reaction is completed, water is added to reaction mixtures, and the reaction mixtures are extracted with organic solvent(s), and the organic layers are worked up (such as drying and concentration) to obtain the compound (M-23).

Next, the process for preparing the compound (If) is described.

The compound (If) can be prepared by reacting the compound (M-23) with a compound represented by formula (R-18) (hereinafter, referred to as Compound (R-18)) in the presence of a base.

The reaction is usually carried out in a solvent. Examples of the solvent to be used in the reaction include ethers, aromatic hydrocarbons, nitriles, polar aprotic solvents, and mixed solvents thereof.

Examples of the base to be used in the reaction include alkali metal carbonates, and alkali metal hydrides.

In the reaction, the compound (R-19) is used within a range of 1 to 2 molar ratio(s), and the base is usually used within a range of 1 to 10 molar ratio(s), as opposed to 1 mole of the compound (M-23).

The reaction temperature is usually within a range of −20 to 150° C. The reaction period of the reaction is usually within a range of 0.5 to 24 hours.

When the reaction is completed, water is added to reaction mixtures, and the resulting mixtures are extracted with organic solvent(s), and the organic layers are worked up (such as drying and concentration) to obtain the compound (If).

The compound (R-18) is a commercially available compound, or can be prepared by using a known method.

Also, the compound (If) can be prepared by reacting the compound (M-1) with a compound represented by formula (R-17) (hereinafter, referred to as Compound (R-17)) in the presence of a metal catalyst.

The reaction is usually carried in a solvent. Examples of the solvent to be used in the reaction include ethers, aromatic hydrocarbons, polar aprotic solvents, water, and mixed solvents thereof.

Examples of the metal catalyst to be used in the reaction include palladium catalysts, nickel catalysts, and copper catalysts.

A ligand, or a base may be added to the reaction as needed.

Examples of the ligand to be used in the reaction include phosphine ligands, 2,2'-bipyridine, 2-aminoethanol, 8-hydroquinoline, and 1,10-phenanthroline.

Examples of the base to be used in the reaction include lithium bis(trimethylsilyl) amide, lithium diisopropylamide, alkali metal hydrides, alkali metal carbonates, and organic bases.

In the reaction, the compound (R-17) is usually used within a range of 1 to 10 molar ratio(s), the metal catalyst is usually used within a range of 0.01 to 0.5 molar ratios, the ligand is usually used within a range of 0.01 to 1 molar ratio(s), and the base is usually used within a range of 0.1 to 5 molar ratio(s), as opposed to 1 mole of the compound (M-1).

The reaction temperature of the reaction is usually within a range of −20 to 200° C. The reaction period of the reaction is usually within a range of 0.1 to 24 hours.

The compound (R-17) is a commercially available compound, or can be prepared according to the known method.

When the reaction is completed, water is added to reaction mixtures, and the resulting mixtures are extracted with organic solvent(s), and the organic layers are worked up (such as drying and concentration) to obtain the compound (If).

Process 9

A compound represented by formula (Ig) (hereinafter, referred to as Compound (Ig)) and a compound represented by formula (Ih) (hereinafter, referred to as Compound (Ih)) can be prepared according to the below-mentioned scheme.

The reaction is usually carried out in a solvent. Examples of the solvents to be used in the reaction include aliphatic halogenated hydrocarbons, aromatic hydrocarbons, and mixed solvents thereof.

Examples of the fluorinating agent to be used in the reaction include sulfur tetrafluoride, and 4-tert-butyl-2,6-dimethylphenylsulfur trifluoride.

Hydrofluoric acid, or pyridinium poly(hydrogenfluoride) may be added to the reaction as needed.

In the reaction, the fluorinating agent is usually used within a range of 3 to 10 molar ratio(s), or when the hydrofluoric acid or pyridinium poly(hydrogenfluoride) is

[wherein the symbols are the same as defined above.]

Firstly, a process for preparing the compound (Ig) from the compound (If) is described.

The compound (Ig) can be prepared by hydrolyzing the compound (If) in the presence of a base or an acid.

The reaction is usually carried out in a solvent. Examples of the solvent to be used in the reaction include aliphatic halogenated hydrocarbons, aromatic hydrocarbons, alcohols, acetic acid, water, and mixed solvents thereof.

Examples of the base to be used in the reaction include alkali metal hydroxides such as sodium hydroxide and lithium hydroxide.

Examples of the acid to be used in the reaction include mineral acids such as hydrochloric acid.

In the reaction, when the base is used, the base is usually used within a range of 2 to 10 molar ratio(s), and when the acid is used, the acid is usually used within a range of 0.1 to 10 molar ratio(s), as opposed to 1 mole of the compound (If). When the mineral acids are used as an acid, the mineral acids may be used also as a solvent.

The reaction temperature of the reaction is usually within a range of –20 to 150° C. The reaction period of the reaction is usually within a range of 0.1 to 24 hours.

When the reaction is completed, water is added to reaction mixtures, and the reaction mixtures are extracted with organic solvent(s), and the organic layers are worked up (such as drying and concentration) to obtain the compound (Ig).

Next, the process for preparing the compound (Ih) is described.

The compound (Ih) can be prepared by reacting the compound (Ig) with a fluorinating agent.

added, within a range of 0.01 to 0.5 molar ratios, as opposed to 1 mole of the compound (Ig).

The reaction temperature of the reaction is usually within a range of –20 to 200° C. The reaction period of the reaction is usually within a range of 0.1 to 24 hours.

When the reaction is completed, water is added to reaction mixtures, and the reaction mixtures are extracted with organic solvent(s), and the organic layers are worked up (such as drying and concentration) to obtain the compound (Ih).

Process 10

A compound represented by formula (M-1b) (hereinafter, referred to as Compound (M-1b)) and a compound represented by formula (M-1c) (hereinafter, referred to as Compound (M-1c)) can be prepared by oxidizing a compound represented by formula (M-1a) (hereinafter, referred to as Compound (M-1a)).

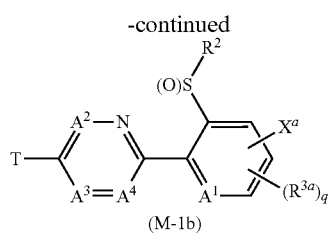

(M-1b)

[wherein the symbols are the same as defined above.]

The compound (M-1b) and the compound (M-1c) can be prepared by using the compound (M-1a) instead of the compound (Ia) according to the method described in the process 3.

Process 11

The compound (M-2) can be prepared from the compound (M-1).

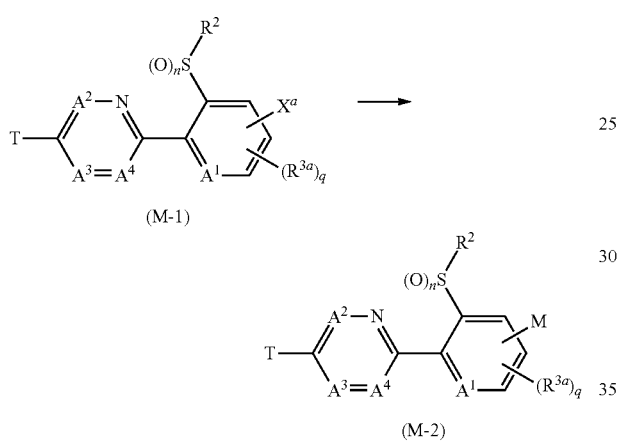

[wherein the symbols are the same as defined above.]

The reaction is carried out according to the method described in Angew. Chem. Int. Ed., 2007, 5359, or Eur. J. Org. Chem., 2003, 4313.

Process 12

The compound (M-3) can be prepared by reacting the compound (M-4) with ammonia or the salt thereof.

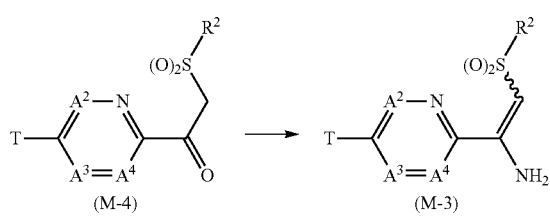

[wherein the symbols are the same as defined above.]

The reaction is usually carried out in a solvent. Examples of the solvent to be used in the reaction include ethers, aromatic hydrocarbons, nitriles, alcohols, polar aprotic solvents, water, and mixed solvents thereof.

Examples of the ammonia or the salt thereof to be used in the reaction include an aqueous ammonia solution, or an ammonia alcoholic solution, ammonium carboxylate salts such as ammonium acetate, and ammonium halide salts such as ammonium chloride.

In the reaction, the ammonia or the salt thereof is usually used within a range of 1 to 100 molar ratio(s), as opposed to 1 mole of the compound (M-4).

The reaction temperature of the reaction is usually within a range of 0 to 200° C. The reaction period of the reaction is usually within a range of 0.5 to 24 hours.

When the reaction is completed, water is added to reaction mixtures, and the reaction mixtures are extracted with organic solvent(s), and the organic layers are worked up (such as drying and concentration) to obtain the compound (M-3).

Process 13

The compound (M-3) can be prepared by reacting a compound represented by formula (M-5) (hereinafter, referred to as Compound (M-5)) with a compound represented by formula (R-19) (hereinafter, referred to as Compound (R-19)) in the presence of a base.

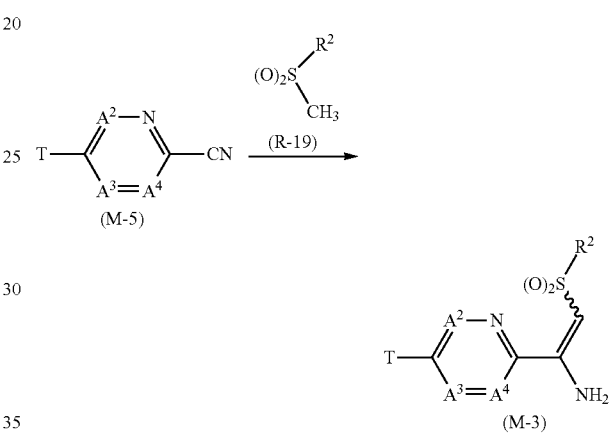

[wherein the symbols are the same as defined above.]

The compound (R-19) is a commercially available compound, or can be prepared by the method described in Journal of Molecular Catalysis A: Chemical, 2011, 341(1-2), 57.

The reaction is usually carried out in a solvent. Examples of the solvent to be used in the reaction include alcohols, ethers, aromatic hydrocarbons, polar aprotic solvents, and mixed solvents thereof.

Examples of the base to be used in the reaction include butyl lithium, sec-butyl lithium, tert-butyl lithium, lithium diisopropylamide, sodium bis(trimethylsilyl)amide, potassium bis(trimethylsilyl)amide, potassium tert-butoxide, sodium methoxide, sodium ethoxide, and alkali metal hydrides.

In the reaction, the compound (R-19) is usually used within a range of 1 to 5 molar ratio(s), and the base is usually used within a range of 1 to 5 molar ratio(s), as opposed to 1 mole of the compound (M-5). Preferably, the compound (R-19) is used within a range of 1.0 to 1.1 molar ratio(s), and the base is used within a range of 1 to 2 molar ratio(s), as opposed to 1 mole of the compound (M-5).

The reaction temperature of the reaction is usually within a range of −78 to 100° C. The reaction period of the reaction is usually within a range of 0.5 to 12 hours.

When the reaction is completed, water is added to reaction mixtures, and the reaction mixtures are extracted with organic solvent(s), and the organic layers are worked up (such as drying and concentration) to obtain the compound (M-3).

Process 14

A compound represented by formula (M-5) (hereinafter, referred to as Compound (M-5)) can be prepared by reacting a compound represented by formula (M-6) (hereinafter, referred to as Compound (M-6)) with a cyanide compound in the presence of a metal catalyst.

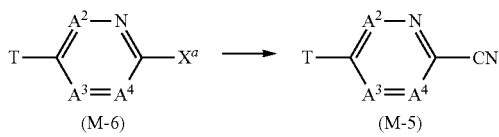

[wherein the symbols are the same as defined above.]

The reaction is usually carried out in a solvent. Examples of the solvent to be used in the reaction include ethers, aromatic hydrocarbons, polar aprotic solvents, water, and mixed solvents thereof.

Examples of the cyanide compound to be used in the reaction include sodium cyanide and zinc cyanide.

Examples of the metal catalyst to be used in the reaction include palladium catalysts, nickel catalysts, and copper catalysts.

A ligand may be added to the reaction as needed.

Examples of the ligand to be used in the reaction include phosphine ligands, 2,2'-bipyridine, 2-aminoethanol, 8-hydroquinoline, and 1,10-phenanthroline.

In the reaction, the cyanide compound is usually used within a range of 1 to 10 molar ratio(s), the metal catalyst is usually used within a range of 0.01 to 0.5 molar ratios, and the ligand is usually used within a range of 0.01 to 1 molar ratio(s), as opposed to 1 mole of the compound (M-6).

The reaction temperature of the reaction is usually within a range of −20 to 200° C. The reaction period of the reaction is usually within a range of 0.1 to 24 hours.

When the reaction is completed, water is added to reaction mixtures, and the reaction mixtures are extracted with organic solvent(s), and the organic layers are worked up (such as drying and concentration) to obtain the compound (M-5).

Process 15

A compound represented by formula (M-7) (hereinafter, referred to as Compound (M-7)) can be prepared by reacting the compound (M-5) with a compound represented by formula (R-22) (hereinafter, referred to as Compound (R-22)) in the presence of an acid.

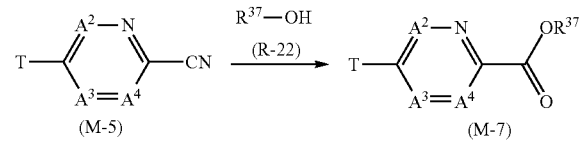

[wherein the symbols are the same as defined above.]

The reaction is usually carried out in a solvent. Examples of the solvent to be used in the reaction include ethers, aromatic hydrocarbons, polar aprotic solvents, and mixed solvents thereof.

Examples of the acid to be used in the reaction include mineral acids such as hydrochloric acid and sulfuric acid, sulfonic acids such as p-toluenesulfonic acid, and Lewis acids such as aluminum chloride.

In the reaction, the compound (R-22) is usually used within a range of 1 to 100 molar ratio(s), and the acid is usually used within a range of 0.01 to 10 molar ratio(s), as opposed to 1 mole of the compound (M-5). The compound (R-22) may be used also as a solvent.

The reaction temperature of the reaction is usually within a range of −20 to 200° C. The reaction period of the reaction is usually within a range of 0.1 to 24 hours.

The compound (R-22) is a commercially available compound, or can be prepared according to a known method.

When the reaction is completed, water is added to reaction mixtures, and the resulting reaction mixtures are extracted with organic solvent(s), and the organic layers are worked up (such as drying and concentration) to obtain the compound (M-7).

Process 16

The compound (M-7) can be prepared by reacting the compound (M-6) with the compound (R-22) in the presence of carbon monoxide and a metal catalyst.

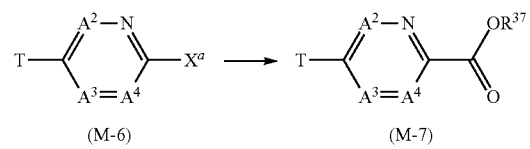

[wherein the symbols are the same as defined above.]

The reaction is usually carried out in a solvent. Examples of the solvent to be used in the reaction include ethers, aromatic hydrocarbons, polar aprotic solvents, and mixed solvents thereof.

Examples of the metal catalyst to be used in the reaction include palladium catalysts, nickel catalysts, and copper catalysts.

A ligand or a base may be added to the reaction as needed.

Examples of the ligand to be used in the reaction include phosphine catalysts, 2,2'-bipyridine, 2-aminoethanol, 8-hydroquinoline, and 1,10-phenanthroline.

Examples of the base to be used in the reaction include alkali metal carboxylates such as sodium acetate and potassium acetate, alkali metal hydrides, alkali metal carbonates, and organic bases.

In the reaction, carbon monoxide is usually used within a range of 1 to 10000 molar ratio(s), a base is usually used within a range of 1 to 10 molar ratio(s), the metal catalyst is usually used within a range of 0.01 to 0.5 molar ratios, and the ligand is usually used within a range of 0.01 to 1 molar ratio(s), as opposed to 1 mole of the compound (M-6). The reaction may be also carried out under carbon monoxide atmosphere.

The reaction temperature of the reaction is usually within a range of −20 to 200° C. The reaction period of the reaction is usually within a range of 0.1 to 24 hours.

When the reaction is completed, water is added to reaction mixtures, and the resulting reaction mixtures are extracted with organic solvent(s), and the organic layers are worked up (such as drying and concentration) to obtain the compound (M-7).

Process 17

The compound (1-4) can be prepared by reacting the compound (M-7) with the compound (R-19) in the presence of a base.

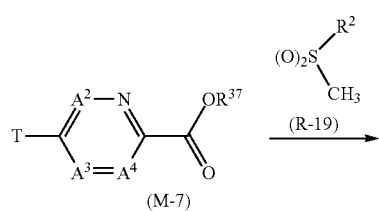

(M-7)

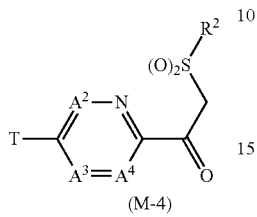

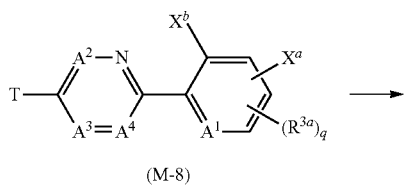

(M-9A)

[wherein the symbols are the same as defined above.]

The compound (M-9A) can be prepared by using the compound (M-10) instead of the compound (M-2) according to the method described in the process 2.

Process 20

The compound (M-10) can be prepared from the compound (M-8).

[wherein the symbols are the same as defined above.]

The compound (M-4) can be prepared by using the compound (M-7) instead of the compound (M-5) according to the method described in the process 13.

Process 18

A compound represented by formula (M-9A) (hereinafter, referred to as Compound (M-9A)) can be prepared by reacting a compound represented by formula (M-8) (hereinafter, referred to as Compound (M-8)) with the compound (R-1).

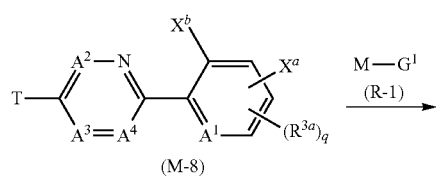

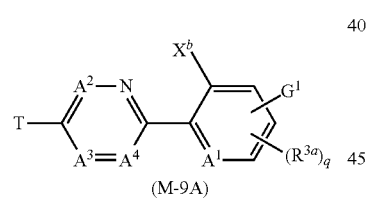

(M-9A)

[wherein the symbols are the same as defined above.]

The compound (M-9A) can be prepared by using the compound (M-8) instead of the compound (M-1) according to the method described in the process 1.

Process 19

The compound (M-9A) can be prepared by reacting a compound represented by formula (M-10) (hereinafter, referred to as compound (M-10)) with the compound (R-2).

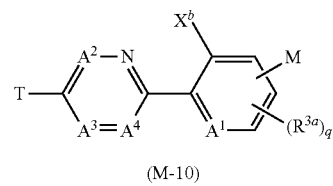

(M-10)

[wherein the symbols are the same as defined above.]

The compound (M-10) can be prepared by using the compound (M-8) instead of the compound (M-1) according to the method described in the process 11.

Process 21

The compound (M-1a) can be prepared by reacting the compound (M-8) with the compound (R-6) in the presence of a base.

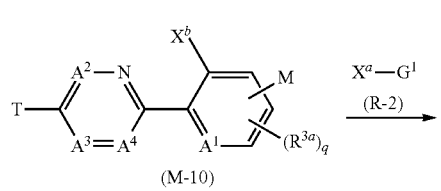

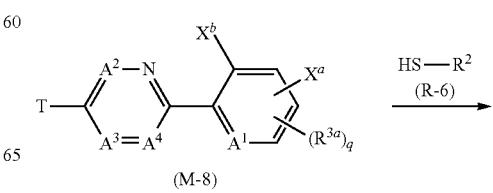

-continued

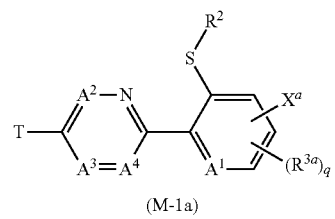

(M-1a)

[wherein the symbols are the same as defined above.]

The compound (M-1a) can be prepared by using the compound (M-8) instead of the compound (M-9) according to the method described in the process 7.

Process 22

A compound represented by formula (M-1d) (hereinafter, referred to as Compound (M-1d)) can be prepared by reacting a compound represented by formula (M-11) (hereinafter, referred to as Compound (M-11)) with phosphorus oxychloride or phosphorus oxybromide.

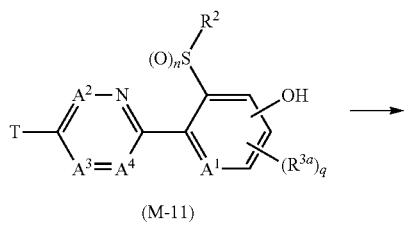

(M-11)

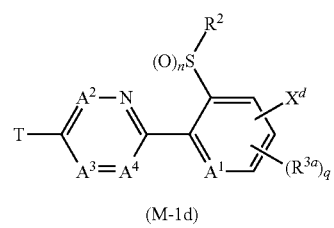

(M-1d)

[wherein $X^d$ represents a chlorine atom, or a bromine atom, and the other symbols are the same as defined above.]

The reaction is usually carried out in a solvent. Examples of the solvent to be used in the reaction include aromatic hydrocarbons.

When phosphorus oxychloride is used, the phosphorus oxychloride may be used also as a solvent.

In the reaction, the phosphorus oxychloride or phosphorus oxybromide is usually used within a range of 1 to 10 molar ratio(s), as opposed to 1 sole of the compound (M-11).

The reaction temperature of the reaction is usually within a range of 0 to 150° C. The reaction period of the reaction is usually within a range of 0.5 to 24 hours.

When the reaction is completed, water is added to reaction mixtures, and the resulting reaction mixtures are extracted with organic solvent(s), and the organic layers are worked up (such as drying and concentration) to obtain the compound (M-1d).

Process 23

The compound (M-11) can be prepared by reacting a compound represented by formula (M-12) (hereinafter, referred to as Compound (M-12)) with an acid.

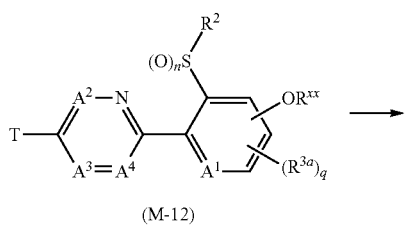

(M-12)

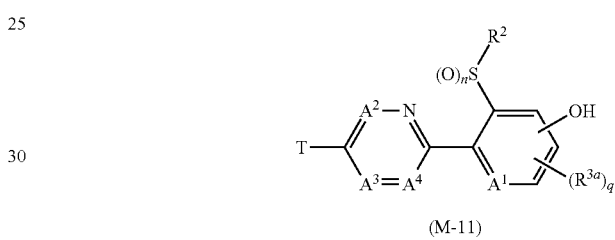

(M-11)

[wherein $R^{xx}$ represents a methyl group or an ethyl group, and the other symbols are the same as defined above.]

The reaction is usually carried out in a solvent. Examples of the solvent to be used in the reaction include aliphatic halogenated hydrocarbons, aromatic hydrocarbons, nitriles, alcohols, acetic acid, and mixed solvents thereof.

Examples of the acid to be used in the reaction include mineral acids such as hydrochloric acid, boron halides such as boron trichloride and boron tribromide, titanium(IV) chlorides, and aluminum chloride.

In the reaction, the acid is usually used within a range of 0.1 to 10 molar ratio(s), as opposed to 1 mole of the compound (M-12). When the mineral acids are used as an acid, the mineral acids may be used also as a solvent.

The reaction temperature of the reaction is usually within a range of −20 to 150° C. The reaction period of the reaction is usually within a range of 0.1 to 24 hours.

When the reaction is completed, water is added to reaction mixtures, and the resulting mixtures are extracted with organic solvent(s), and the organic layers are worked up (such as drying and concentration) to obtain the compound (M-11).

Process 24

A compound represented by formula (M-12a) (hereinafter, referred to as Compound (M-12a)), a compound represented by formula (M-12b) (hereinafter, referred to as Compound (M-12b)), and a compound represented by formula (M-12c) (hereinafter, referred to as Compound (M-12c)) can be prepared according to the below-mentioned scheme.

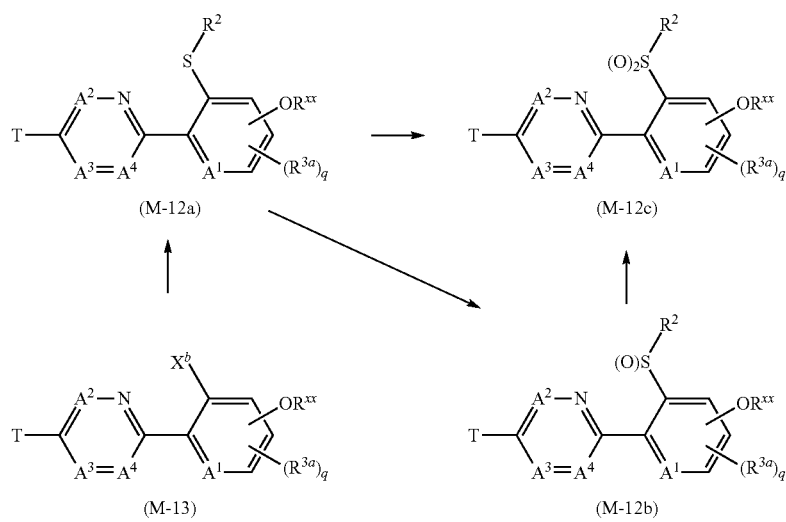

[wherein the symbols are the same as defined above.]

The compound (M-12a) can be prepared by using the compound (M-13) (hereinafter, referred to as Compound (M-13)) instead of the compound (M-9) according to the method described in the process 7.

The compound (M-12b) and the compound (M-12c) can be prepared by using the compound (M-12a) instead of the compound (Ia) according to the method described in the process 3.

Process 25

The compound (M-13) can be prepared by reacting the compound (M-6) with a compound represented by formula (M-15) (hereinafter, referred to as Compound (M-15)) in the presence of a metal catalyst.

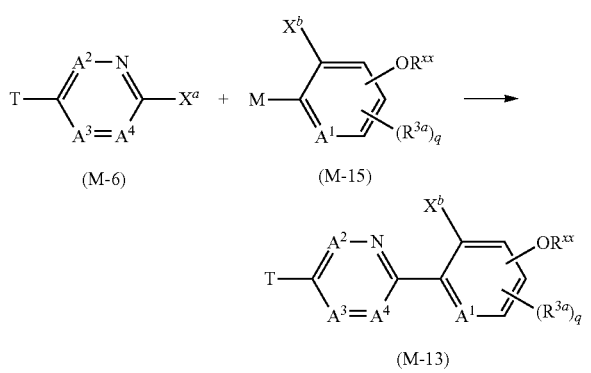

[wherein the symbols are the same as defined above.]

The compound (M-13) can be prepared by using the compound (M-6) instead of the compound (M-1) and the compound (M-15) instead of the compound (R-1) according to the method described in the process 1.

The compound (M-15) is a commercially available compound, or can be prepared according to a known method.

Process 26

The compound (M-13) can be prepared by reacting a compound represented by formula (4-16) (hereinafter, referred to as Compound (M-16)) with a compound represented by formula (M-17) (hereinafter, referred to as Compound (M-17)) in the presence of a metal catalyst.

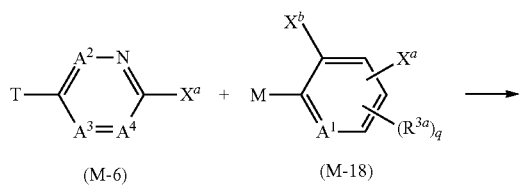

[wherein the symbols are the same as defined above.]

The compound (M-13) can be prepared by using the compound (M-16) instead of the compound (M-2) and the compound (M-17) instead of the compound (R-2) according to the method described in the process 2.

The compound (M-16) and the compound (M-17) are commercially available compounds, or can be prepared according to a known method.

Process 27

The compound (M-8) can be prepared by reacting the compound (M-6) with a compound represented by formula (M-18) (hereinafter, referred to as Compound (M-18)) in the presence of a metal catalyst.

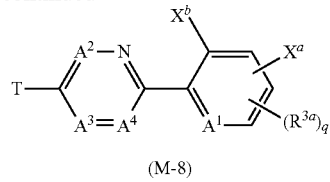

(M-8)

[wherein the symbols are the same as defined above.]

The compound (M-8) can be prepared by using the compound (M-6) instead of the compound (M-1) and the compound (M-18) instead of the compound (R-1) according to the method described in the process 1.

The compound (M-18) is a commercially available compound, or can be prepared according to a known method.

Process 28

The compound (M-8) can be prepared by reacting the compound (M-16) with a compound represented by formula (M-19) (hereinafter, referred to as Compound (M-19)) in the presence of a metal catalyst.

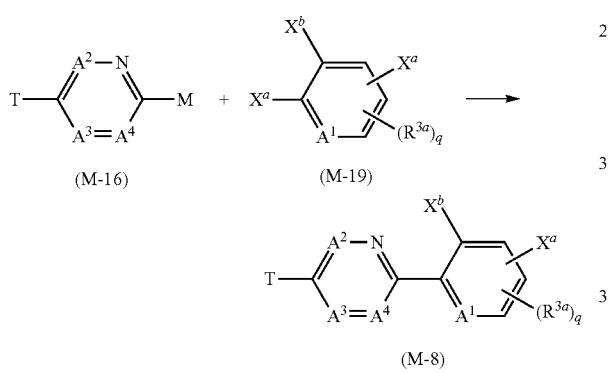

[wherein the symbols are the same as defined above.]

The compound (M-8) can be prepared by using the compound (M-16) instead of the compound (M-1) and the compound (M-19) instead of the compound (R-1) according to the method described in the process 1.

The compound (M-19) is a commercially available compound, or can be prepared according to a known method.

Process 29

A compound represented by formula (M-6a) (hereinafter, referred to as Compound (M-6a)) can be prepared by reacting a compound represented by formula (M-20a) (hereinafter, referred to as Compound (M-20a)) with a compound represented by formula (R-7) (hereinafter, referred to as Compound (R-7)) in the presence of a base.

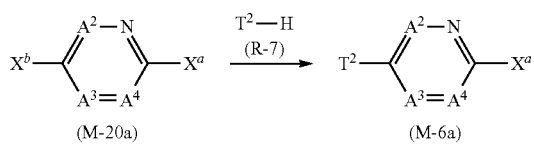

[wherein $T^2$ represents $OR^1$, $NR^1R^{29}$, a group represented by formula T-5, a group represented by formula T-6, a group represented by formula T-7, or a group represented by formula T-8, and the other symbols are the same as defined above.]

The reaction is usually carried out in a solvent. Examples of the solvent to be used in the reaction include ethers, aromatic hydrocarbons, nitriles, polar aprotic solvents, and mixed solvents thereof.

Examples of the base to be used in the reaction include alkali metal carbonates and alkali metal hydrides.

In the reaction, the compound (R-7) is usually used within a range of 1 to 2 molar ratio(s), and the base is usually used within a range of 1 to 10 molar ratio(s), as opposed to 1 mole of the compound (M-20a).

The reaction temperature of the reaction is usually within a range of −20 to 150° C. The reaction period of the reaction is usually within a range of 0.5 to 24 hours.

When the reaction is completed, water is added to reaction mixtures, and the resulting reaction mixtures are extracted with organic solvent(s), and the organic layers are worked up (such as drying and concentration) to obtain the compound (M-6a).

The compound (R-7) and the compound (M-20a) are commercially available compounds, or can be prepared by a known method.

Process 30

A compound represented by formula (M-6b) (hereinafter, referred to as Compound (M-6b)) can be prepared by reacting a compound represented by formula (M-20b) (hereinafter, referred to as Compound (M-20b)) with a compound represented by formula (R-8) (hereinafter, referred to as Compound (R-8)).

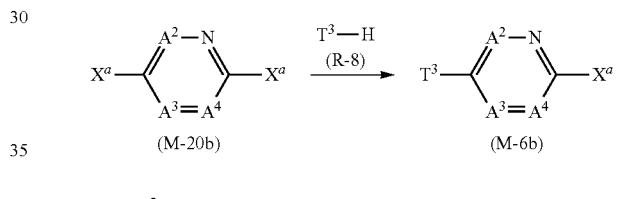

[wherein $T^3$ represents a group represented by formula T-1, a group represented by formula T-2, a group represented by formula T-3, a group represented by formula T-4, a group represented by formula T-9, a group represented by formula T-10, a group represented by formula T-11, or a group represented by formula T-12, and the other symbols are the same as defined above.]

The compound (M-6b) can be prepared by using the compound (M-20b) instead of the compound (1-1) and the compound (M-8) instead of the compound (R-1) according to the method described in the process 1.

The compound (R-8) and the compound (R-20b) are commercially available compounds, or can be prepared by a known method.

Process 31

A compound represented by formula (M-6c) (hereinafter, referred to as Compound (M-6c)) can be prepared by reacting a compound represented by formula (M-20c) (hereinafter, referred to as Compound (M-20c)) with a compound represented by formula (R-9) (hereinafter, referred to as Compound (R-9)).

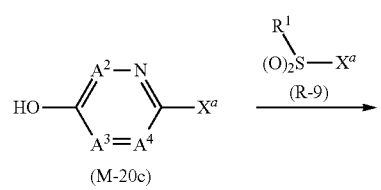

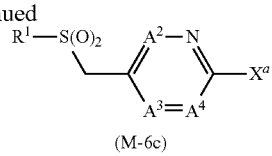

(M-6c)

[wherein the symbols are the same as defined above.]

The reaction is carried out according to the method described in NO 2016/121969.

The compound (R-9) and the compound (M-20c) are commercially available compounds, or prepared by using a known method.

Process 32

A compound represented by formula (M-6d) (hereinafter, referred to as Present compound (M-6d)) can be prepared reacting the compound (M-20b) with a compound represented by formula (R-10) (hereinafter, referred to as Compound (R-10)) in the presence of a copper.

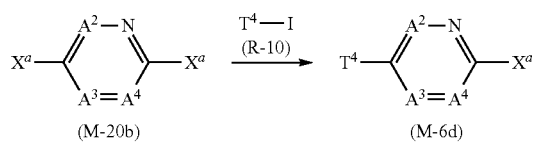

[wherein $T^4$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G, and the other symbols are the same as defined above.]

The compound (R-10) is a commercially available compound, or can be prepared according to a known method.

The reaction is usually carried out in a solvent. Examples of the solvent to be used in the reaction include aromatic hydrocarbons, polar aprotic solvents, and mixed solvents thereof.

In the reaction, the compound (R-10) is used usually within a range of 1 to 10 molar ratio(s), and the copper is usually used within a range of 1 to 10 molar ratio(s), as opposed to 1 mole of the compound (M-20b).

The reaction temperature of the reaction is usually within a range of 40 to 200° C. The reaction period of the reaction is usually within a range of 0.1 to 24 hours.

When the reaction is completed, water is added to reaction mixtures, and the reaction mixtures are extracted with organic solvent(s), and the organic layers are worked up (such as drying and concentration) to obtain the compound (M-6d).

Process 33

A compound represented by formula (M-6e) (hereinafter, referred to as Compound (M-6e)) can be prepared by reacting a compound represented by formula (M-20d) (hereinafter, referred to as Compound (M-20d)) with a compound represented by formula (R-11) (hereinafter, referred to as Compound (R-11)) in the presence of a condensing agent.

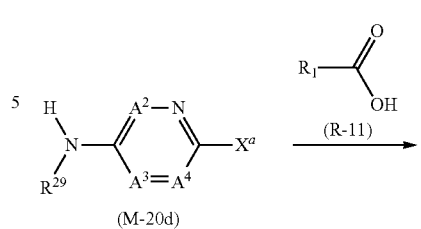

[wherein the symbols are the same as defined above.]

The reaction can be carried out according to the method described in WO 2014/021468.

The compound (R-11) is a commercially available compound, or can be prepared according to a known method.

Process 34

A compound represented by formula (M-6f) (hereinafter, referred to as Compound (M-6f)) can be prepared by reacting the compound (M-20b) with a compound represented by formula (R-12) (hereinafter, referred to as Compound (R-12)) in the presence of a base.

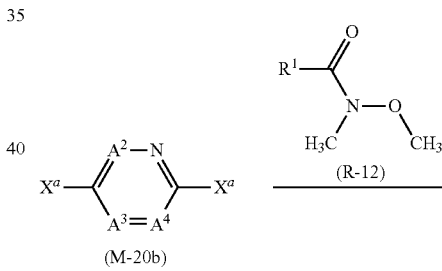

[wherein the symbols are the same as defined above.]

The reaction can be carried out according to the method described in Synthesis, 2000, 23, 3707.

The compound (R-12) is a commercially available compound, or can be prepared according to a known method.

Process 35

A compound represented by formula (M-6g) (hereinafter, referred to as compound (M-6g)) can be prepared by reacting a compound represented by formula (M-20e) (hereinafter, referred to as Compound (M-20e)) with a compound represented by formula (R-13) (hereinafter, referred to as Compound (R-13)) in the presence of a condensing agent.

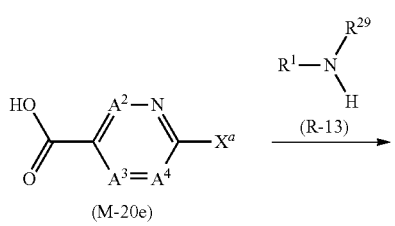

(M-20e)

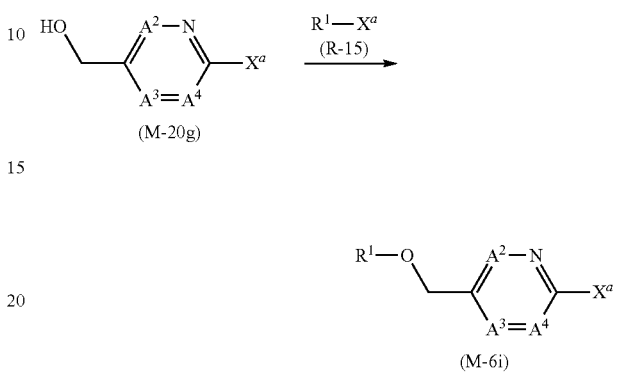

Process 37

A compound represented by formula (M-6i) (hereinafter, referred to as Compound (M-6i)) can be prepared by reacting a compound represented by formula (M-20g) (hereinafter, referred to as Compound (M-20g)) with a compound represented by formula (R-15) (hereinafter, referred to as Compound (R-15)) in the presence of a base.

[wherein the symbols are the same as defined above.]

The reaction can be carried out according to the method described in WO 2014/021468.

The compound (R-13) is a commercially available compound, or can be prepared according to a known method.

Process 36

A compound represented by formula (M-6h) (hereinafter, referred to as Compound (M-6h)) can be prepared by reacting a compound represented by formula (M-20f) (hereinafter, referred to as Compound (M-20f) with a compound represented by formula (R-14) (hereinafter, referred to as Compound (R-14)).

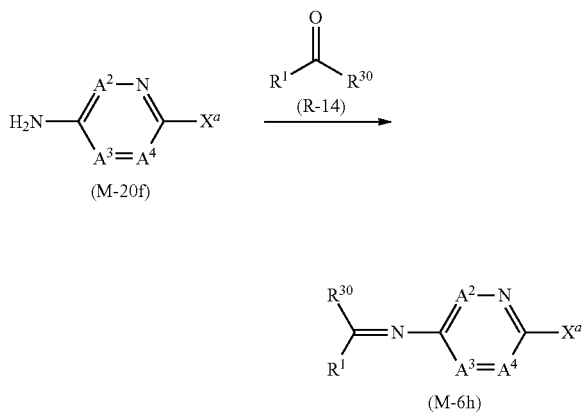

[wherein the symbols are the same as defined above.]

The compound (R-15) and the compound (R-20g) are commercially available compounds, or can be prepared according to a known method.

The reaction is usually carried in a solvent. Examples of the solvent to be used in the reaction include ethers, aromatic hydrocarbons, polar aprotic solvents, and mixed solvents thereof.

Examples of the base to be used in the reaction include organic bases, alkali metal hydrides, and alkali metal carbonates.

In the reaction, the compound (R-15) is usually used within a range of 1 to 10 molar ratio(s), and the base is usually used within a range of 0.1 to 5 molar ratio(s), as opposed to 1 mole of the compound (M-20g).

The reaction temperature of the reaction is usually within a range of −20 to 120° C. The reaction period of the reaction is usually within a range of 0.1 to 24 hours.

When the reaction is completed, water is added to reaction mixtures, and the resulting reaction mixtures are extracted with organic solvent(s), and the organic layers are worked up (such as drying and concentration) to obtain the compound (M-6i).

Process 38

A compound represented by formula (M-6j) (hereinafter, referred to as Compound (M-6i)), a compound represented by formula (M-6k) (hereinafter, referred to as Compound (M-6k)), and a compound represented by formula (M-6m) (hereinafter, referred to as Compound (M-6m)) can be prepared according to the below-mentioned methods.

[wherein the symbols are the same as defined above.]

The reaction can be carried out according to the method described in Journal of Heterocyclic Chemistry, 2000, 1309.

The compound (R-14) is a commercially available compound, or can be prepared according to a known method.

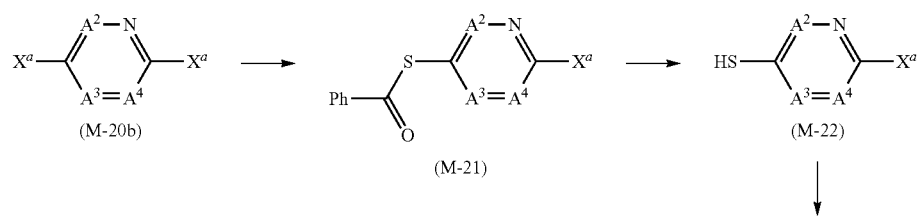

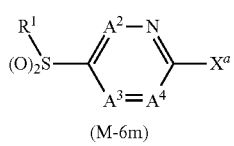 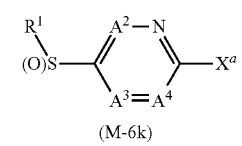 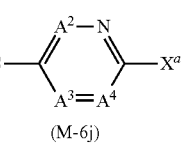

(M-6m)   (M-6k)   (M-6j)

[wherein the symbols are the same as defined above.]

Firstly, a process for preparing a compound represented by formula (M-21) (hereinafter, referred to as Compound (M-21)) is described.

The compound (M-21) can be prepared by reacting the compound (M-20b) with a thiobenzoic acid in the presence of a copper catalyst and a base.

The reaction is usually carried out in a solvent. Examples of the solvent to be used in the reaction include ethers, aromatic hydrocarbons, polar aprotic solvents, water, and mixed solvents thereof.

Examples of the copper catalyst to be used in the reaction include copper chloride, copper bromide, and copper iodide.

Examples of the base to be used in the reaction include alkali metal hydrides, alkali metal carbonates, and organic bases.

A ligand may be added to the reaction as needed.

Examples of the ligand to be used in the reaction include 2,2'-bipyridine, 2-aminoethanol, 8-hydroquinoline, and 1,10-phenanthroline.

In the reaction, a thiobenzoic acid is within usually within a range of 1 to 10 molar ratio(s), the copper catalyst is usually used within a range of 0.01 to 0.5 molar ratios, the ligand is usually used within a range of 0.01 to 1 molar ratio(s), and the base is used usually within a range of 0.1 to 5 molar ratio(s), as opposed to 1 mole of the compound (M-20b).

The reaction temperature of the reaction is usually within a range of −20 to 200° C. The reaction period of the reaction is usually within a range of 0.1 to 24 hours.

When the reaction is completed, water is added to reaction mixtures, and the resulting reaction mixtures are extracted with organic bases, and the organic layers are worked up (such as drying and concentration) to obtain the compound (M-21).

Next, a process for preparing a compound represented by formula (M-22) (hereinafter, referred to as Compound (M-22)) is described.

The compound (M-22) can be prepared, for example, according to the method described in NO 2011/068171 or Journal of Organic Chemistry, 1978, 43(6), 1190-1192.

Further, a process for preparing the compound (M-6j) is described.

The compound (M-6j) can be prepared by using the compound (M-22) instead of the compound (M-20g) according to the method described in the process 37.

Further, a process for preparing the compound (M-6k) is described.

The compound (M-6k) can be prepared by using the compound (M-6j) instead of the compound (1a) according to the method described in the process 3.

Further, a process for preparing the compound (M-6m) is described.

The compound (M-6m) can be prepared by using the compound (M-6k) instead of the compound (Ib) according to the method described in the process 3.

Process 39

A compound represented by formula (IB) (hereinafter, referred to as Present compound B) can be prepared by reacting the compound (M-1) with a compound represented by formula (R-20) (hereinafter, referred to as Compound (R-20) in the presence of a copper catalyst and a base.

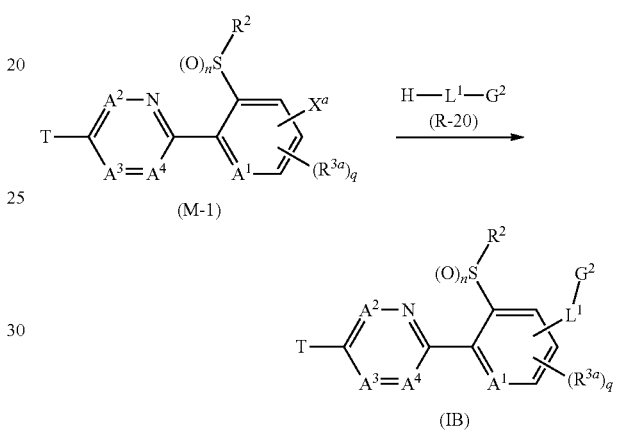

[wherein the symbols are the same as defined above.]

The reaction is carried out in a solvent. Examples of the solvent to be used in the reaction include ethers, aromatic hydrocarbons, polar aprotic solvents, and mixed solvents thereof.

Examples of the copper catalyst to be used in the reaction include copper chloride (I), copper bromide (I), and copper iodide (I).

Examples of the base to be used in the reaction include alkali metal hydrides, alkali metal carbonates, and organic bases.

A ligand may be added to the reaction as needed.

Examples of the ligand to be used in the reaction include 2,2'-bipyridine, 2-aminoethanol, 8-hydroquinoline, and, 1,10-phenanthroline.

In the reaction, the compound (R-20) is usually used within a range of 1 to 10 molar ratio(s), the copper catalyst is usually used within a range of 0.01 to 0.5 molar ratios, the ligand is usually used within a range of 0.01 to 1 molar ratio(s), and the base is used usually within a range of 0.1 to 5 molar ratio(s), as opposed to 1 mole of the compound (R-20).

The reaction temperature of the reaction is usually within a range of −20 to 200° C. The reaction period of the reaction is usually within a range of 0.1 to 24 hours.

The compound (R-20) is a commercially available compound, or can be prepared according to a known method.

When the reaction is completed, water is added to reaction mixtures, and the resulting reaction mixtures are extracted with organic solvent(s), and the organic layers are worked up (such as drying and concentration) to obtain the present compound (IB).

Process 40

The present compound B can be prepared by reacting the compound (M-11) with a compound represented by formula (R-21) (hereinafter, referred to as Compound (R-21)) in the presence of a copper catalyst and a base.

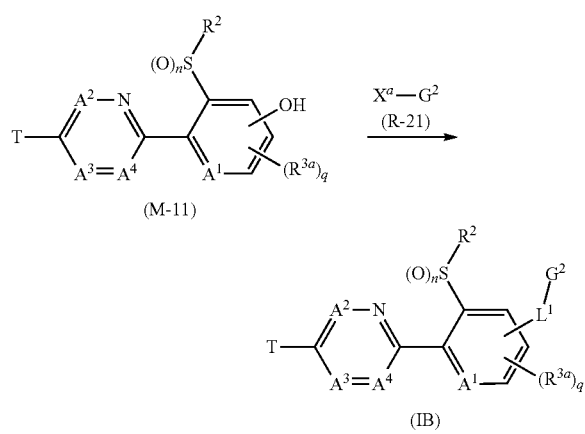

[wherein the symbols are the same as defined above.]

The reaction is usually carried out in a solvent. Examples of the solvent to be used in the reaction include ethers, aromatic hydrocarbons, polar aprotic solvents, and mixed solvents thereof.

Examples of the copper catalyst to be used in the reaction include copper chloride (I), copper bromide (I), and copper iodide (I).

Examples of the base to be used in the reaction include alkali metal hydrides, alkali metal carbonates, and organic bases.

A ligand may be added to the reaction as needed.

Examples of the ligand to be used in the reaction include 2,2'-bipyridine, 2-aminoethanol, 8-hydroquinoline, and 1,10-phenanthroline.

In the reaction, the compound (R-21) is usually used within a range of 1 to 10 molar ratio(s), the copper catalyst is used within a range of 0.01 to 0.5 molar ratios, the ligand is carried out within a range of 0.01 to 1 molar ratio(s), and the base is usually used within a range of 0.1 to 5 molar ratio(s), as opposed to 1 mole of the compound (M-11).

The reaction temperature of the reaction is usually within a range of −20 to 200° C. The reaction period of the reaction is usually within a range of 0.1 to 24 hours.

The compound (R-21) is a commercially available compound, or can be prepared according to a known method.

When the reaction is completed, water is added to reaction mixtures, and the resulting reaction mixtures are extracted with organic solvent(s), and the organic layers are worked up (such as drying and concentration) to obtain the present compound (IB).

Next, specific examples of the present compounds are shown below.

Herein, He represents a methyl group, Et represents an ethyl group, Ph represents a phenyl group, Py2 represents a 2-pyridyl group, Py3 represents a 3-pyridyl group, Py4 represents a 4-pyridyl group. When the Ph, Py2, Py3, and Py4 have any substituents, the substituents are described together with a substitution position before the symbol. For example, 4-$CF_3$—Py2 represents a 4-(trifluoromethyl)-2-pyridyl group, and 3,5-$(CF_3)_2$-Ph represents a 3,5-bis(trifluoromethyl)phenyl group.

a compound represented by formula (L-1):

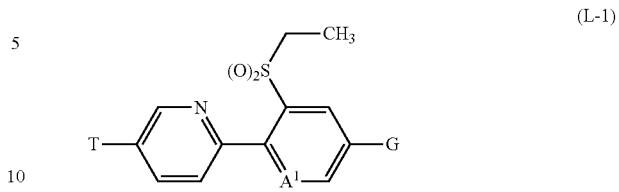

wherein $A^1$ represents a CH, G represents a cyclopropyl group, and T represents any substituents indicated in Table 1 to Table 6 (hereinafter, referred to as Compound Class SX1).

TABLE 1

| |
|---|
| $CF_3$ |
| $CHF_2$ |
| $CH_2CF_3$ |
| $CF_2CF_3$ |
| $CH_2CF_2CF_3$ |
| $CF_2CF_2CF_3$ |
| $CF_2CF_2CF_2CF_3$ |
| $CF_2CF_2CF_2CF_2CF_3$ |
| $OCF_3$ |
| $OCHF_2$ |
| $OCH_2CF_3$ |
| $OCH_2CHF_2$ |
| $OCF_2CF_3$ |
| $OCH(CH_3)CF_3$ |
| $OCH_2CF_2CHF_2$ |
| $OCH_2CF_2CF_3$ |
| $OCF_2CF_2CF_3$ |
| $OCH_2CF_2CHFCF_3$ |
| $OCH_2CF_2CF_2CF_3$ |
| $OCF_2CF_2CF_2CF_3$ |
| $OCH_2CF_2CF_2CF_2CF_3$ |

TABLE 2

| |
|---|
| $SCF_3$ |
| $SCH_2CF_3$ |
| $SCF_2CF_3$ |
| $SCH_2CF_2CF_3$ |
| $SCF_2CF_2CF_3$ |
| $SCH_2CF_2CF_2CF_3$ |
| $SCF_2CF_2CF_2CF_3$ |
| $S(O)CF_3$ |
| $S(O)CH_2CF_3$ |
| $S(O)CF_2CF_3$ |
| $S(O)CH_2CF_2CF_3$ |
| $S(O)CF_2CF_2CF_3$ |
| $S(O)CH_2CF_2CF_2CF_3$ |
| $S(O)CF_2CF_2CF_2CF_3$ |
| $S(O)_2CF_3$ |
| $S(O)_2CH_2CF_3$ |
| $S(O)_2CF_2CF_3$ |
| $S(O)_2CH_2CF_2CF_3$ |
| $S(O)_2CF_2CF_2CF_3$ |
| $S(O)_2CH_2CF_2CF_2CF_3$ |
| $S(O)_2CF_2CF_2CF_2CF_3$ |

TABLE 3

| |
|---|
| $NHCH_2CF_3$ |
| $NHCH_2CF_2CF_3$ |
| $NHCH_2CF_2CF_2CF_3$ |
| $NMeCH_2CF_3$ |
| $NMeCH_2CF_2CF_3$ |
| $NMeCH_2CF_2CF_2CF_3$ |
| $NEtCH_2CF_3$ |

TABLE 3-continued

NEtCH$_2$CF$_2$CF$_3$
NEtCH$_2$CF$_2$CF$_2$CF$_2$CF$_3$
OS(O)$_2$CF$_3$
OS(O)$_2$CF$_2$CF$_3$
OS(O)$_2$CF$_2$CF$_2$CF$_3$
CH$_2$OCF$_3$
CH$_2$OCH$_2$CF$_3$
CH$_2$OCF$_2$CF$_3$
C(O)CF$_3$
C(O)CF$_2$CF$_3$
C(O)CF$_2$CF$_2$CF$_3$
C(O)NMeCH$_2$CF$_3$
NMeC(O)CF$_3$
N=CEtCH$_2$CF$_3$

TABLE 4

3-CF$_3$—Ph
4-CF$_3$—Ph
3,5-(CF$_3$)$_2$—Ph
3-SCF$_3$—Ph
3-S(O)CF$_3$—Ph
3-S(O)$_2$CF$_3$—Ph
4-SCF$_3$—Ph
4-S(O)CF$_3$—Ph
4-S(O)$_2$CF$_3$—Ph

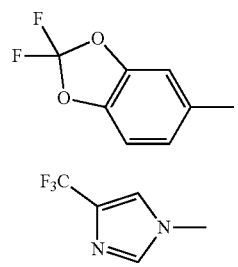

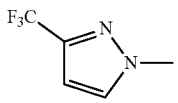

TABLE 5

4-CF$_3$—Py2
5-CF$_3$—Py2
4-SCF$_3$—Py2
4-S(O)CF$_3$—Py2
4-S(O)$_2$CF$_3$—Py2
5-SCF$_3$—Py2
5-S(O)CF$_3$—Py2
5-S(O)$_2$CF$_3$—Py2
5-NMeCH$_2$CF$_3$—Py2

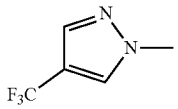

TABLE 5-continued

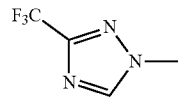

TABLE 6

5-CF$_3$—Py3
6-CF$_3$—Py3
5-SCF$_3$—Py3
5-S(O)CF$_3$—Py3
5-S(O)$_2$CF$_3$—Py3
6-SCF$_3$—Py3
6-S(O)CF$_3$—Py3
6-S(O)$_2$CF$_3$—Py3
6-NMeCH$_2$CF$_3$—Py3

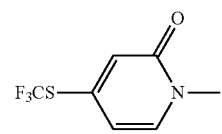

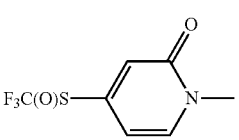

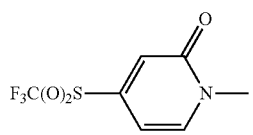

a compound (L-1) wherein A$^1$ represents CH, G represents a 1-(trifluoromethyl)cyclopropyl group, and T represents any substituents indicated in Table 1 to Table 6 (hereinafter, referred to as Compound Class SX2).

a compound (L-1) wherein A$^1$ represents CH, G represents a 1-cyanocyclopropyl group, and T represents any substituents indicated in Table 1 to Table 6 (hereinafter, referred to as Compound Class SX3).

a compound (L-1) wherein A$^1$ represents CH, G represents a 2,2-difluorocyclopropyl group, and T represents any substituents indicated in Table 1 to Table 6 (hereinafter, referred to as Compound Class SX4).

a compound (L-1) wherein A$^1$ represents CH, G represents a 2-(4-fluorophenyl)cyclopropyl group, and T represents any substituents indicated in Table 1 to Table 6 (hereinafter, referred to as Compound Class SX5).

a compound (L-1) wherein A$^1$ represents CH, G represents a cyclobutyl group, and T represents any substituents indicated in Table 1 to Table 6 (hereinafter, referred to as Compound Class SX6).

a compound (L-1) wherein A$^1$ represents CH, G represents a 1-cyanocyclobutyl group, and T represents any substituents indicated in Table 1 to Table 6 (hereinafter, referred to as Compound Class SX7).

a compound (L-1) wherein A$^1$ represents CH, G represents a cyclopentyl group, and T represents any substituents indicated in Table 1 to Table 6 (hereinafter, referred to as Compound Class SX8).

a compound (L-1) wherein A$^1$ represents CH, G represents a 1-cyanocyclopentyl group, and T represents any substituents indicated in Table 1 to Table 6 (hereinafter, referred to as Compound Class SX9).

a compound (L-1) wherein $A^1$ represents CH, G represents a cyclohexyl group, and T represents any substituents indicated in Table 1 to Table 6 (hereinafter, referred to as Compound Class SX10).

a compound (L-1) wherein $A^1$ represents CH, G represents a 1-cyanocyclohexyl group, and T represents any substituents indicated in Table 1 to Table 6 (hereinafter, referred to as Compound Class SX11).

a compound (L-1) wherein $A^1$ represents CH, G represents a 4,4-difluorocyclohexyl group, and T represents any substituents indicated in Table 1 to Table 6 (hereinafter, referred to as Compound Class SX12).

a compound (L-1) wherein $A^1$ represents a nitrogen atom, G represents a cyclopropyl group, and T represents any substituents indicated in Table 1 to Table 6 (hereinafter, referred to as Compound Class SX13).

a compound (L-1) wherein $A^1$ represents a nitrogen atom, G represents a 1-(trifluoromethyl)cyclopropyl group, and T represents any substituents indicated in Table 1 to Table 6 (hereinafter, referred to as Compound Class SX14).

a compound (L-1) wherein $A^1$ represents a nitrogen atom, G represents a 1-cyanocyclopropyl group, and T represents any substituents indicated in Table 1 to Table 6 (hereinafter, referred to as Compound Class SX15).

a compound (L-1) wherein $A^1$ represents a nitrogen atom, G represents a 2,2-difluorocyclopropyl group, and T represents any substituents indicated in Table 1 to Table 6 (hereinafter, referred to as Compound Class SX16).

a compound (L-1) wherein $A^1$ represents a nitrogen atom, G represents a 2-(4-fluorophenyl)cyclopropyl group, and T represents any substituents indicated in Table 1 to Table 6 (hereinafter, referred to as Compound Class SX17).

a compound (L-1) wherein $A^1$ represents a nitrogen atom, G represents a cyclobutyl group, and T represents any substituents indicated in Table 1 to Table 6 (hereinafter, referred to as Compound Class SX18).

a compound (L-1) wherein $A^3$ represents a nitrogen atom, A1 represents a 1-cyanocyclobutyl group, G represents a cyclobutyl group, and T represents any substituents indicated in Table 1 to Table 6 (hereinafter, referred to as Compound Class SX19).

a compound (L-1) wherein $A^1$ represents a nitrogen atom, G represents a cyclobutyl group, and T represents any substituents indicated in Table 1 to Table 6 (hereinafter, referred to as Compound Class SX20).

a compound (L-1) wherein $A^1$ represents a nitrogen atom, G represents a 1-cyanocyclopentyl group, and T represents any substituents indicated in Table 1 to Table 6 (hereinafter, referred to as Compound Class SX21).

a compound (L-1) wherein $A^1$ represents a nitrogen atom, G represents a cyclohexyl group, and T represents any substituents indicated in Table 1 to Table 6 (hereinafter, referred to as Compound Class SX22).

a compound (L-1) wherein $A^1$ represents a nitrogen atom, G represents a 1-cyanocyclohexyl group, and T represents any substituents indicated in Table 1 to Table 6 (hereinafter, referred to as Compound Class SX23).

a compound (L-1) wherein $A^1$ represents a nitrogen atom, G represents a 4,4-difluorocyclohexyl group, and T represents any substituents indicated in Table 1 to Table 6 (hereinafter, referred to as Compound Class SX24).

a compound represented by formula (L-2):

(L-2)

wherein $A^1$ represents CH, G represents a cyclopropyl group, and T represents any substituents indicated in Table 1 to Table 6 (hereinafter, referred to as Compound Class SX25).

a compound (L-2) wherein $A^1$ represents CH, G represents a 1-(trifluoromethyl)cyclopropyl group, and T represents any substituents indicated in Table 1 to Table 6 (hereinafter, referred to as Compound Class SX26).

a compound (L-2) wherein $A^1$ represents CH, G represents a 1-cyanocyclopropyl group, and T represents any substituents indicated in Table 1 to Table 6 (hereinafter, referred to as Compound Class SX27).

a compound (L-2) wherein $A^1$ represents CH, G represents a 2,2-difluorocyclopropyl group, and T represents any substituents indicated in Table 1 to Table 6 (hereinafter, referred to as Compound Class SX28).

a compound (L-2) wherein $A^1$ represents CH, G represents a 2-(4-fluorophenyl)cyclopropyl group, and T represents any substituents indicated in Table 1 to Table 6 (hereinafter, referred to as Compound Class SX29).

a compound (L-2) wherein $A^1$ represents CH, G represents a cyclobutyl group, and T represents any substituents indicated in Table 1 to Table 6 (hereinafter, referred to as Compound Class SX30).

a compound (L-2) wherein $A^1$ represents CH, G represents a 1-cyanocyclobutyl group, and T represents any substituents indicated in Table 1 to Table 6 (hereinafter, referred to as Compound Class SX31).

a compound (L-2) wherein $A^1$ represents CH, G represents a cyclopentyl group, and T represents any substituents indicated in Table 1 to Table 6 (hereinafter, referred to as Compound Class SX32).

a compound (L-2) wherein $A^1$ represents CH, G represents a 1-cyanocyclopentyl group, and T represents any substituents indicated in Table 1 to Table 6 (hereinafter, referred to as Compound Class SX33).

a compound (L-2) wherein $A^1$ represents CH, G represents a cyclohexyl group, and T represents any substituents indicated in Table 1 to Table 6 (hereinafter, referred to as Compound Class SX34).

a compound (L-2) wherein $A^1$ represents CH, G represents a 1-cyanocyclohexyl group, and T represents any substituents indicated in Table 1 to Table 6 (hereinafter, referred to as Compound Class SX35).

a compound (L-2) wherein $A^1$ represents CH, G represents a 4,4-difluorocyclohexyl group, and T represents any substituents indicated in Table 1 to Table 6 (hereinafter, referred to as Compound Class SX36).

a compound (L-2) wherein $A^1$ represents a nitrogen atom, G represents a cyclopropyl group, and T represents any substituents indicated in Table 1 to Table 6 (hereinafter, referred to as Compound Class SX37).

a compound (L-2) wherein $A^1$ represents a nitrogen atom, G represents a 1-(trifluoromethyl)cyclopropyl group, and T represents any substituents indicated in Table 1 to Table 6 (hereinafter, referred to as Compound Class SX38).

a compound (L-2) wherein $A^1$ represents a nitrogen atom, G represents a 1-cyanocyclopropyl group, and T represents any substituents indicated in Table 1 to Table 6 (hereinafter, referred to as Compound Class SX39).

a compound (L-2) wherein $A^1$ represents a nitrogen atom, G represents a 2,2-difluorocyclopropyl group, and T represents any substituents indicated in Table 1 to Table 6 (hereinafter, referred to as Compound Class SX40).

a compound (L-2) wherein $A^1$ represents a nitrogen atom, G represents a 2-(4-fluorophenyl)cyclopropyl group, and T represents any substituents indicated in Table 1 to Table 6 (hereinafter, referred to as Compound Class SX41).

a compound (L-2) wherein $A^1$ represents a nitrogen atom, G represents a cyclobutyl group, and T represents any substituents indicated in Table 1 to Table 6 (hereinafter, referred to as Compound Class SX42).

a compound (L-2) wherein $A^1$ represents a nitrogen atom, G represents a 1-cyanocyclobutyl group, and T represents any substituents indicated in Table 1 to Table 6 (hereinafter, referred to as Compound Class SX43).

a compound (L-2) wherein $A^1$ represents a nitrogen atom, G represents a cyclopentyl group, and T represents any substituents indicated in Table 1 to Table 6 (hereinafter, referred to as Compound Class SX44).

a compound (L-2) wherein $A^1$ represents a nitrogen atom, G represents a 1-cyanocyclopentyl group, and T represents any substituents indicated in Table 1 to Table 6 (hereinafter, referred to as Compound Class SX45).

a compound (L-2) wherein $A^1$ represents a nitrogen atom, G represents a cyclohexyl group, and T represents any substituents indicated in Table 1 to Table 6 (hereinafter, referred to as Compound Class SX46).

a compound (L-2) wherein $A^1$ represents a nitrogen atom, G represents a 1-cyanocyclohexyl group, and T represents any substituents indicated in Table 1 to Table 6 (hereinafter, referred to as Compound Class SX47).

a compound (L-2) wherein $A^1$ represents a nitrogen atom, G represents a 4,4-difluorocyclohexyl group, and T represents any substituents indicated in Table 1 to Table 6 (hereinafter, referred to as Compound Class SX48).

a compound represented by formula (L-3):

wherein $A^1$ represents CH, G represents a cyclopropyl group, and T represents any substituents indicated in Table 1 to Table 6 (hereinafter, referred to as Compound Class SX49).

a compound formula (L-3) wherein $A^1$ represents CH, G represents a 1-(trifluoromethyl)cyclopropyl group, and T represents any substituents indicated in Table 1 to Table 6 (hereinafter, referred to as Compound Class SX50).

a compound formula (L-3) wherein $A^1$ represents CH, G represents a 1-cyanocyclopropyl group, and T represents any substituents indicated in Table 1 to Table 6 (hereinafter, referred to as Compound Class SX51).

a compound formula (L-3) wherein $A^1$ represents CH, G represents a 2,2-difluorocyclopropyl group, and T represents any substituents indicated in Table 1 to Table 6 (hereinafter, referred to as Compound Class SX52).

a compound formula (L-3) wherein $A^1$ represents CH, G represents a 2-(4-fluorophenyl)cyclopropyl group, and T represents any substituents indicated in Table 1 to Table 6 (hereinafter, referred to as Compound Class SX53).

a compound formula (L-3) wherein $A^1$ represents CH, G represents a cyclobutyl group, and T represents any substituents indicated in Table 1 to Table 6 (hereinafter, referred to as Compound Class SX54).

a compound formula (L-3) wherein $A^1$ represents CH, G represents a 1-cyanocyclobutyl group, and T represents any substituents indicated in Table 1 to Table 6 (hereinafter, referred to as Compound Class SX55).

a compound formula (L-3) wherein $A^1$ represents CH, G represents a cyclopentyl group, and T represents any substituents indicated in Table 1 to Table 6 (hereinafter, referred to as Compound Class SX56).

a compound formula (L-3) wherein $A^1$ represents CH, G represents a 1-cyanocyclopentyl group, and T represents any substituents indicated in Table 1 to Table 6 (hereinafter, referred to as Compound Class SX57).

a compound formula (L-3) wherein $A^1$ represents CH, G represents a cyclohexyl group, and T represents any substituents indicated in Table 1 to Table 6 (hereinafter, referred to as Compound Class SX58).

a compound formula (L-3) wherein $A^1$ represents CH, G represents a 1-cyanocyclohexyl group, and T represents any substituents indicated in Table 1 to Table 6 (hereinafter, referred to as Compound Class SX59).

a compound formula (L-3) wherein $A^1$ represents CH, G represents a 4,4-difluorocyclohexyl group, and T represents any substituents indicated in Table 1 to Table 6 (hereinafter, referred to as Compound Class SX60).

a compound formula (L-3) wherein $A^1$ represents a nitrogen atom, G represents a cyclopropyl group, and T represents any substituents indicated in Table 1 to Table 6 (hereinafter, referred to as Compound Class SX61).

a compound formula (L-3) wherein $A^1$ represents a nitrogen atom, G represents a 1-(trifluoromethyl)cyclopropyl group, and T represents any substituents indicated in Table 1 to Table 6 (hereinafter, referred to as Compound Class SX62).

a compound formula (L-3) wherein $A^1$ represents a nitrogen atom, G represents a 1-cyanocyclopropyl group, and T represents any substituents indicated in Table 1 to Table 6 (hereinafter, referred to as Compound Class SX63).

a compound formula (L-3) wherein $A^1$ represents a nitrogen atom, G represents a 2,2-difluorocyclopropyl group, and T represents any substituents indicated in Table 1 to Table 6 (hereinafter, referred to as Compound Class SX64).

a compound formula (L-3) wherein $A^1$ represents a nitrogen atom, G represents a 2-(4-fluorophenyl)cyclopropyl group, and T represents any substituents indicated in Table 1 to Table 6 (hereinafter, referred to as Compound Class SX65).

a compound formula (L-3) wherein $A^1$ represents a nitrogen atom, G represents a cyclobutyl group, and T represents any substituents indicated in Table 1 to Table 6 (hereinafter, referred to as Compound Class SX66).

a compound formula (L-3) wherein $A^1$ represents a nitrogen atom, G represents a 1-cyanocyclobutyl group, and T represents any substituents indicated in Table 1 to Table 6 (hereinafter, referred to as Compound Class SX67).

a compound formula (L-3) wherein $A^1$ represents a nitrogen atom, G represents a cyclopentyl group, and T represents any substituents indicated in Table 1 to Table 6 (hereinafter, referred to as Compound Class SX68).

a compound formula (L-3) wherein $A^1$ represents a nitrogen atom, G represents a 1-cyanocyclopentyl group, and T represents any substituents indicated in Table 1 to Table 6 (hereinafter, referred to as Compound Class SX69).

a compound formula (L-3) wherein $A^1$ represents a nitrogen atom, G represents a cyclohexyl group, and T represents any substituents indicated in Table 1 to Table 6 (hereinafter, referred to as Compound Class SX70).

a compound formula (L-3) wherein $A^1$ represents a nitrogen atom, G represents a 1-cyanocyclohexyl group, and T represents any substituents indicated in Table 1 to Table 6 (hereinafter, referred to as Compound Class SX71).

a compound formula (L-3) wherein $A^1$ represents a nitrogen atom, G represents a 4,4-difluorocyclohexyl group, and T represents any substituents indicated in Table 1 to Table 6 (hereinafter, referred to as Compound Class SX72).

a compound represented by formula (L-4):

$$\text{(L-4)}$$

wherein $A^1$ represents CH, G represents a cyclopropyl group, and T represents any one of substituents indicated in Table 1 to Table 6 (hereinafter, referred to as Compound Class SX73).

a compound (L-4) wherein $A^1$ represents CH, G represents a 1-(trifluoromethyl)cyclopropyl group, and T represents any one of substituents indicated in Table 1 to Table 6 (hereinafter, referred to as Compound Class SX74).

a compound (L-4) wherein $A^1$ represents CH, G represents a 1-cyanocyclopropyl group, and T represents any one of substituents indicated in Table 1 to Table 6 (hereinafter, referred to as Compound Class SX75).

a compound (L-4) wherein $A^1$ represents CH, G represents a 2,2-difluorocyclopropyl group, and T represents any one of substituents indicated in Table 1 to Table 6 (hereinafter, referred to as Compound Class SX76).

a compound (L-4) wherein $A^1$ represents CH, G represents a 2-(4-fluorophenyl)cyclopropyl group, and T represents any one of substituents indicated in Table 1 to Table 6 (hereinafter, referred to as Compound Class SX77).

a compound (L-4) wherein $A^1$ represents CH, G represents a cyclobutyl group, and T represents any one of substituents indicated in Table 1 to Table 6 (hereinafter, referred to as Compound Class SX78).

a compound (L-4) wherein $A^1$ represents CH, G represents a 1-cyanocyclobutyl group, and T represents any one of substituents indicated in Table 1 to Table 6 (hereinafter, referred to as Compound Class SX79).

a compound (L-4) wherein $A^1$ represents CH, G represents a cyclopentyl group, and T represents any one of substituents indicated in Table 1 to Table 6 (hereinafter, referred to as Compound Class SX80).

a compound (L-4) wherein $A^1$ represents CH, G represents a 1-cyanocyclopentyl group, and T represents any one of substituents indicated in Table 1 to Table 6 (hereinafter, referred to as Compound Class SX81).

a compound (L-4) wherein $A^1$ represents CH, G represents a cyclohexyl group, and T represents any one of substituents indicated in Table 1 to Table 6 (hereinafter, referred to as Compound Class SX82).

a compound (L-4) wherein $A^1$ represents CH, G represents a 1-cyanocyclohexyl group, and T represents any one of substituents indicated in Table 1 to Table 6 (hereinafter, referred to as Compound Class SX83).

a compound (L-4) wherein $A^1$ represents CH, G represents a 4,4-difluorocyclohexyl group, and T represents any one of substituents indicated in Table 1 to Table 6 (hereinafter, referred to as Compound Class SX84).

a compound (L-4) wherein $A^1$ represents a nitrogen atom, G represents a cyclopropyl group, and T represents any one of substituents indicated in Table 1 to Table 6 (hereinafter, referred to as Compound Class SX85).

a compound (L-4) wherein $A^1$ represents a nitrogen atom, G represents a 1-(trifluoromethyl)cyclopropyl group, and T represents any one of substituents indicated in Table 1 to Table 6 (hereinafter, referred to as Compound Class SX86).

a compound (L-4) wherein $A^1$ represents a nitrogen atom, G represents a 1-cyanocyclopropyl group, and T represents any one of substituents indicated in Table 1 to Table 6 (hereinafter, referred to as Compound Class SX87).

a compound (L-4) wherein $A^1$ represents a nitrogen atom, G represents a 2,2-difluorocyclopropyl group, and T represents any one of substituents indicated in Table 1 to Table 6 (hereinafter, referred to as Compound Class SX88).

a compound (L-4) wherein $A^1$ represents a nitrogen atom, G represents a 2-(4-fluorophenyl)cyclopropyl group, and T represents any one of substituents indicated in Table 1 to Table 6 (hereinafter, referred to as Compound Class SX89).

a compound (L-4) wherein $A^1$ represents a nitrogen atom, G represents a cyclobutyl group, and T represents any one of substituents indicated in Table 1 to Table 6 (hereinafter, referred to as Compound Class SX90).

a compound (L-4) wherein $A^1$ represents a nitrogen atom, G represents a 1-cyanocyclobutyl group, and T represents any one of substituents indicated in Table 1 to Table 6 (hereinafter, referred to as Compound Class SX91).

a compound (L-4) wherein $A^1$ represents a nitrogen atom, G represents a cyclopentyl group, and T represents any one of substituents indicated in Table 1 to Table 6 (hereinafter, referred to as Compound Class SX92).

a compound (L-4) wherein $A^1$ represents a nitrogen atom, G represents a 1-cyanocyclopentyl group, and T represents any one of substituents indicated in Table 1 to Table 6 (hereinafter, referred to as Compound Class SX93).

a compound (L-4) wherein $A^1$ represents a nitrogen atom, G represents a cyclohexyl group, and T represents any one of substituents indicated in Table 1 to Table 6 (hereinafter, referred to as Compound Class SX94).

a compound (L-4) wherein $A^1$ represents a nitrogen atom, G represents a 1-cyanocyclohexyl group, and T represents any one of substituents indicated in Table 1 to Table 6 (hereinafter, referred to as Compound Class SX95).

a compound (L-4) wherein $A^1$ represents a nitrogen atom, G represents a 4,4-difluorocyclohexyl group, and T represents any one of substituents indicated in Table 1 to Table 6 (hereinafter, referred to as Compound Class SX96).

a compound (L-1) wherein $A^1$ represents CH, G represents —O—$G^2$, $G^2$ represents Py2, and T represents any one of substituents indicated in Table 1 to Table 6 (hereinafter, referred to as Compound Class SX97).

a compound (L-1) wherein $A^1$ represents CH, G represents —O-$G^2$, $G^2$ represents 3-Me-Py2, and T represents any one of substituents indicated in Table 1 to Table 6 (hereinafter, referred to as Compound Class SX98).

a compound (L-1) wherein $A^1$ represents CH, G represents —O-$G^2$, $G^2$ represents 4-Me-Py2, and T represents any one of substituents indicated in Table 1 to Table 6 (hereinafter, referred to as Compound Class SX99).

a compound (L-1) wherein $A^1$ represents CH, G represents —O-$G^2$, $G^2$ represents 5-Me-Py2, and T represents any one of substituents indicated in Table 1 to Table 6 (hereinafter, referred to as Compound Class SX100).

a compound (L-1) wherein $A^1$ represents CH, G represents —O-$G^2$, $G^2$ represents 6-Me-Py2, and T represents any one of substituents indicated in Table 1 to Table 6 (hereinafter, referred to as Compound Class SX101).

a compound (L-1) wherein $A^1$ represents CH, G represents —O-$G^2$, $G^2$ represents 3-Cl-Py2, and T represents any one of substituents indicated in Table 1 to Table 6 (hereinafter, referred to as Compound Class SX102).

a compound (L-1) wherein $A^1$ represents CH, G represents —O-$G^2$, $G^2$ represents 4-Cl-Py2, and T represents any one of substituents indicated in Table 1 to Table 6 (hereinafter, referred to as Compound Class SX103).

a compound (L-1) wherein $A^1$ represents CH, G represents —O-$G^2$, $G^2$ represents 5-Cl-Py2, and T represents any one of substituents indicated in Table 1 to Table 6 (hereinafter, referred to as Compound Class SX104).

a compound (L-1) wherein $A^1$ represents CH, G represents —O-$G^2$, $G^2$ represents 6-Cl-Py2, and T represents any one of substituents indicated in Table 1 to Table 6 (hereinafter, referred to as Compound Class SX105).

a compound (L-1) wherein $A^1$ represents CH, G represents —O-$G^2$, $G^2$ represents 3-$CF_3$-Py2, and T represents any one of substituents indicated in Table 1 to Table 6 (hereinafter, referred to as Compound Class SX106).

a compound (L-1) wherein $A^1$ represents CH, G represents —O-$G^2$, $G^2$ represents 4-$CF_3$-Py2, and T represents any one of substituents indicated in Table 1 to Table 6 (hereinafter, referred to as Compound Class SX107).

a compound (L-1) wherein $A^1$ represents CH, G represents —O-$G^2$, $G^2$ represents 5-$CF_3$-Py2, and T represents any one of substituents indicated in Table 1 to Table 6 (hereinafter, referred to as Compound Class SX108).

a compound (L-1) wherein $A^1$ represents CH, G represents —O-$G^2$, $G^2$ represents 6-$CF_3$-Py2, and T represents any one of substituents indicated in Table 1 to Table 6 (hereinafter, referred to as Compound Class SX109).

a compound (L-1) wherein $A^1$ represents CH, G represents —O-$G^2$, $G^2$ represents 3-OMe-Py2, and T represents any one of substituents indicated in Table 1 to Table 6 (hereinafter, referred to as Compound Class SX110).

a compound (L-1) wherein $A^1$ represents CH, G represents —O-$G^2$, $G^2$ represents 4-OMe-Py2, and T represents any one of substituents indicated in Table 1 to Table 6 (hereinafter, referred to as Compound Class SX111).

a compound (L-1) wherein $A^1$ represents CH, G represents —O-$G^2$, $G^2$ represents 5-OMe-Py2, and T represents any one of substituents indicated in Table 1 to Table 6 (hereinafter, referred to as Compound Class SX112).

a compound (L-1) wherein $A^1$ represents CH, G represents —O-$G^2$, $G^2$ represents 6-OMe-Py2, and T represents any one of substituents indicated in Table 1 to Table 6 (hereinafter, referred to as Compound Class SX113).

a compound (L-1) wherein $A^1$ represents CH, G represents —O-$G^2$, $G^2$ represents Py3, and T represents any one of substituents indicated in Table 1 to Table 6 (hereinafter, referred to as Compound Class SX114).

a compound (L-1) wherein $A^1$ represents CH, G represents —O-$G^2$, $G^2$ represents 2-Me-Py3, and T represents any one of substituents indicated in Table 1 to Table 6 (hereinafter, referred to as Compound Class SX115).

a compound (L-1) wherein $A^1$ represents CH, G represents —O-$G^2$, $G^2$ represents 4-Me-Py3, and T represents any one of substituents indicated in Table 1 to Table 6 (hereinafter, referred to as Compound Class SX116).

a compound (L-1) wherein $A^1$ represents CH, G represents —O-$G^2$, $G^2$ represents 5-Me-Py3, and T represents any one of substituents indicated in Table 1 to Table 6 (hereinafter, referred to as Compound Class SX117).

a compound (L-1) wherein $A^1$ represents CH, G represents —O-$G^2$, $G^2$ represents 6-Me-Py3, and T represents any one of substituents indicated in Table 1 to Table 6 (hereinafter, referred to as Compound Class SX118).

a compound (L-1) wherein $A^1$ represents CH, G represents —O-$G^2$, $G^2$ represents 2-Cl-Py3, and T represents any one of substituents indicated in Table 1 to Table 6 (hereinafter, referred to as Compound Class SX119).

a compound (L-1) wherein $A^1$ represents CH, G represents —O-$G^2$, $G^2$ represents 4-Cl-Py3, and T represents any one of substituents indicated in Table 1 to Table 6 (hereinafter, referred to as Compound Class SX120).

a compound (L-1) wherein $A^1$ represents CH, G represents —O-$G^2$, $G^2$ represents 5-Cl-Py3, and T represents any one of substituents indicated in Table 1 to Table 6 (hereinafter, referred to as Compound Class SX121).

a compound (L-1) wherein $A^1$ represents CH, G represents —O-$G^2$, $G^2$ represents 6-Cl-Py3, and T represents any one of substituents indicated in Table 1 to Table 6 (hereinafter, referred to as Compound Class SX122).

a compound (L-1) wherein $A^1$ represents CH, G represents —O-$G^2$, $G^2$ represents 2-$CF_3$-Py3, and T represents any one of substituents indicated in Table 1 to Table 6 (hereinafter, referred to as Compound Class SX123).

a compound (L-1) wherein $A^1$ represents CH, G represents —O-$G^2$, $G^2$ represents 4-$CF_3$-Py3, and T represents any one of substituents indicated in Table 1 to Table 6 (hereinafter, referred to as Compound Class SX124).

a compound (L-1) wherein $A^1$ represents CH, G represents —O-$G^2$, $G^2$ represents 5-$CF_3$-Py3, and T represents any one of substituents indicated in Table 1 to Table 6 (hereinafter, referred to as Compound Class SX125).

a compound (L-1) wherein $A^1$ represents CH, G represents —O-$G^2$, $G^2$ represents 6-$CF_3$-Py3, and T represents any one of substituents indicated in Table 1 to Table 6 (hereinafter, referred to as Compound Class SX126).

a compound (L-1) wherein $A^1$ represents CH, G represents —O-$G^2$, $G^2$ represents 2-OMe-Py3, and T represents any one of substituents indicated in Table 1 to Table 6 (hereinafter, referred to as Compound Class SX127).

a compound (L-1) wherein $A^1$ represents CH, G represents —O-$G^2$, $G^2$ represents 4-OMe-Py3, and T represents any one of substituents indicated in Table 1 to Table 6 (hereinafter, referred to as Compound Class SX128).

a compound (L-1) wherein $A^1$ represents CH, G represents —O-$G^2$, $G^2$ represents 5-OMe-Py3, and T represents any one of substituents indicated in Table 1 to Table 6 (hereinafter, referred to as Compound Class SX129).

a compound (L-1) wherein $A^1$ represents CH, G represents —O-$G^2$, $G^2$ represents 6-OMe-Py3, and T represents any one of substituents indicated in Table 1 to Table 6 (hereinafter, referred to as Compound Class SX130).

a compound (L-1) wherein $A^1$ represents CH, G represents —O-$G^2$, $G^2$ represents Py4, and T represents any one of substituents indicated in Table 1 to Table 6 (hereinafter, referred to as Compound Class SX131).

a compound (L-1) wherein $A^1$ represents CH, G represents —O-$G^2$, $G^2$ represents 3-Me-Py4, and T represents any one of substituents indicated in Table 1 to Table 6 (hereinafter, referred to as Compound Class SX132).

a compound (L-1) wherein $A^1$ represents CH, G represents —O-$G^2$, $G^2$ represents 2-Me-Py4, and T represents any one of substituents indicated in Table 1 to Table 6 (hereinafter, referred to as Compound Class SX133).

a compound (L-1) wherein $A^1$ represents CH, G represents —O-$G^2$, $G^2$ represents 3-Cl-Py4, and T represents any one of substituents indicated in Table 1 to Table 6 (hereinafter, referred to as Compound Class SX136).

a compound (L-1) wherein $A^1$ represents CH, G represents —O-$G^2$, $G^2$ represents 2-Cl-Py4, and T represents any one of substituents indicated in Table 1 to Table 6 (hereinafter, referred to as Compound Class SX137).

a compound (L-1) wherein $A^1$ represents CH, G represents —O-$G^2$, $G^2$ represents 3-$CF_3$-Py4, and T represents any one of substituents indicated in Table 1 to Table 6 (hereinafter, referred to as Compound Class SX140).

a compound (L-1) wherein $A^1$ represents CH, G represents —O-$G^2$, $G^2$ represents 2-$CF_3$-Py4, and T represents any one of substituents indicated in Table 1 to Table 6 (hereinafter, referred to as Compound Class SX141).

a compound (L-1) wherein $A^1$ represents CH, G represents —O-$G^2$, $G^2$ represents 3-OMe-Py4, and T represents any one of substituents indicated in Table 1 to Table 6 (hereinafter, referred to as Compound Class SX144).

a compound (L-1) wherein $A^1$ represents CH, G represents —O-$G^2$, $G^2$ represents 2-OMe-Py4, and T represents any one of substituents indicated in Table 1 to Table 6 (hereinafter, referred to as Compound Class SX145).

a compound (L-1) wherein $A^1$ represents a nitrogen atom, G represents —O-$G^2$, $G^2$ represents Py2, and T represents any one of substituents indicated in Table 1 to Table 6 (hereinafter, referred to as Compound Class SX148).

a compound (L-1) wherein $A^1$ represents a nitrogen atom, G represents —O-$G^2$, $G^2$ represents 3-Me-Py2, and T represents any one of substituents indicated in Table 1 to Table 6 (hereinafter, referred to as Compound Class SX149).

a compound (L-1) wherein $A^1$ represents a nitrogen atom, G represents —O-$G^2$, $G^2$ represents 4-Me-Py2, and T represents any one of substituents indicated in Table 1 to Table 6 (hereinafter, referred to as Compound Class SX150).

a compound (L-1) wherein $A^1$ represents a nitrogen atom, G represents —O-$G^2$, $G^2$ represents 5-Me-Py2, and T represents any one of substituents indicated in Table 1 to Table 6 (hereinafter, referred to as Compound Class SX151).

a compound (L-1) wherein $A^1$ represents a nitrogen atom, G represents —O-$G^2$, $G^2$ represents 6-Me-Py2, and T represents any one of substituents indicated in Table 1 to Table 6 (hereinafter, referred to as Compound Class SX152).

a compound (L-1) wherein $A^1$ represents a nitrogen atom, G represents —O-$G^2$, $G^2$ represents 3-Cl-Py2, and T represents any one of substituents indicated in Table 1 to Table 6 (hereinafter, referred to as Compound Class SX153).

a compound (L-1) wherein $A^1$ represents a nitrogen atom, G represents —O-$G^2$, $G^2$ represents 4-Cl-Py2, and T represents any one of substituents indicated in Table 1 to Table 6 (hereinafter, referred to as Compound Class SX154).

a compound (L-1) wherein AA represents a nitrogen atom, G represents —O-$G^2$, $G^2$ represents 5-Cl-Py2, and T represents any one of substituents indicated in Table 1 to Table 6 (hereinafter, referred to as Compound Class SX155).

a compound (L-1) wherein $A^1$ represents a nitrogen atom, G represents —O-$G^2$, $G^2$ represents 6-Cl-Py2, and T represents any one of substituents indicated in Table 1 to Table 6 (hereinafter, referred to as Compound Class SX156).

a compound (L-1) wherein $A^1$ represents a nitrogen atom, G represents —O-$G^2$, $G^2$ represents 3-$CF_3$-Py2, and T represents any one of substituents indicated in Table 1 to Table 6 (hereinafter, referred to as Compound Class SX157).

a compound (L-1) wherein $A^1$ represents a nitrogen atom, G represents —O-$G^2$, $G^2$ represents 4-$CF_3$-Py2, and T represents any one of substituents indicated in Table 1 to Table 6 (hereinafter, referred to as Compound Class SX158).

a compound (L-1) wherein $A^1$ represents a nitrogen atom, G represents —O-$G^2$, $G^2$ represents 5-$CF_3$-Py2, and T represents any one of substituents indicated in Table 1 to Table 6 (hereinafter, referred to as Compound Class SX159).

a compound (L-1) wherein $A^1$ represents a nitrogen atom, G represents —O-$G^2$, $G^2$ represents 6-$CF_3$-Py2, and T represents any one of substituents indicated in Table 1 to Table 6 (hereinafter, referred to as Compound Class SX160).

a compound (L-1) wherein $A^1$ represents a nitrogen atom, G represents —O-$G^2$, $G^2$ represents 3-OMe-Py2, and T represents any one of substituents indicated in Table 1 to Table 6 (hereinafter, referred to as Compound Class SX161).

a compound (L-1) wherein $A^1$ represents a nitrogen atom, G represents —O-$G^2$, $G^2$ represents 4-OMe-Py2, and T represents any one of substituents indicated in Table 1 to Table 6 (hereinafter, referred to as Compound Class SX162).

a compound (L-1) wherein $A^1$ represents a nitrogen atom, G represents —O-$G^2$, $G^2$ represents 5-OMe-Py2, and T represents any one of substituents indicated in Table 1 to Table 6 (hereinafter, referred to as Compound Class SX163).

a compound (L-1) wherein $A^1$ represents a nitrogen atom, G represents —O-$G^2$, $G^2$ represents 6-OMe-Py2, and T represents any one of substituents indicated in Table 1 to Table 6 (hereinafter, referred to as Compound Class SX164).

a compound (L-1) wherein $A^1$ represents a nitrogen atom, G represents —O-$G^2$, $G^2$ represents Py3, and T represents any one of substituents indicated in Table 1 to Table 6 (hereinafter, referred to as Compound Class SX165).

a compound (L-1) wherein $A^1$ represents a nitrogen atom, G represents —O-$G^2$, $G^2$ represents 2-Me-Py3, and T represents any one of substituents indicated in Table 1 to Table 6 (hereinafter, referred to as Compound Class SX166).

a compound (L-1) wherein $A^1$ represents a nitrogen atom, G represents —O-$G^2$, $G^2$ represents 4-Me-Py3, and T represents any one of substituents indicated in Table 1 to Table 6 (hereinafter, referred to as Compound Class SX167).

a compound (L-1) wherein $A^1$ represents a nitrogen atom, G represents —O-$G^2$, $G^2$ represents 5-Me-Py3, and T represents any one of substituents indicated in Table 1 to Table 6 (hereinafter, referred to as Compound Class SX168).

a compound (L-1) wherein $A^1$ represents a nitrogen atom, G represents —O-$G^2$, $G^2$ represents 6-Me-Py3, and T represents any one of substituents indicated in Table 1 to Table 6 (hereinafter, referred to as Compound Class SX169).

a compound (L-1) wherein $A^1$ represents a nitrogen atom, G represents —O-$G^2$, $G^2$ represents 2-Cl-Py3, and T represents any one of substituents indicated in Table 1 to Table 6 (hereinafter, referred to as Compound Class SX170).

a compound (L-1) wherein $A^1$ represents a nitrogen atom, G represents —O-$G^2$, $G^2$ represents 4-Cl-Py3, and T represents any one of substituents indicated in Table 1 to Table 6 (hereinafter, referred to as Compound Class SX171).

a compound (L-1) wherein $A^1$ represents a nitrogen atom, G represents —O-$G^2$, $G^2$ represents 5-Cl-Py3, and T represents any one of substituents indicated in Table 1 to Table 6 (hereinafter, referred to as Compound Class SX172).

a compound (L-1) wherein $A^1$ represents a nitrogen atom, G represents —O-$G^2$, $G^2$ represents 6-Cl-Py3, and T represents any one of substituents indicated in Table 1 to Table 6 (hereinafter, referred to as Compound Class SX173).

a compound (L-1) wherein $A^1$ represents a nitrogen atom, G represents —O-$G^2$, $G^2$ represents 2-$CF_3$-Py3, and T represents any one of substituents indicated in Table 1 to Table 6 (hereinafter, referred to as Compound Class SX174).

a compound (L-1) wherein $A^1$ represents a nitrogen atom, G represents —O-$G^2$, $G^2$ represents 4-$CF_3$-Py3, and T represents any one of substituents indicated in Table 1 to Table 6 (hereinafter, referred to as Compound Class SX17S).

a compound (L-1) wherein $A^1$ represents a nitrogen atom, G represents —O-$G^2$, $G^2$ represents 5-$CF_3$-Py3, and T represents any one of substituents indicated in Table 1 to Table 6 (hereinafter, referred to as Compound Class SX176).

a compound (L-1) wherein $A^1$ represents a nitrogen atom, G represents —O-$G_2$, $G_2$ represents 6-$CF_3$-Py3, and T represents any one of substituents indicated in Table 1 to Table 6 (hereinafter, referred to as Compound Class SX177).

a compound (L-1) wherein $A^1$ represents a nitrogen atom, G represents —O-$G_2$, $G_2$ represents 2-OMe-Py3, and T represents any one of substituents indicated in Table 1 to Table 6 (hereinafter, referred to as Compound Class SX178).

a compound (L-1) wherein $A^1$ represents a nitrogen atom, G represents —O-$G_2$, $G_2$ represents 4-OMe-Py3, and T represents any one of substituents indicated in Table 1 to Table 6 (hereinafter, referred to as Compound Class SX179).

a compound (L-1) wherein $A^1$ represents a nitrogen atom, G represents —O-$G_2$, $G_2$ represents 5-OMe-Py3, and T represents any one of substituents indicated in Table 1 to Table 6 (hereinafter, referred to as Compound Class SX180).

a compound (L-1) wherein $A^1$ represents a nitrogen atom, G represents —O-$G^2$, $G^2$ represents 6-OMe-Py3, and T represents any one of substituents indicated in Table 1 to Table 6 (hereinafter, referred to as Compound Class SX181).

a compound (L-1) wherein $A^1$ represents a nitrogen atom, G represents —O-$G^2$, $G^2$ represents Py4, and T represents any one of substituents indicated in Table 1 to Table 6 (hereinafter, referred to as Compound Class SX182).

a compound (L-1) wherein $A^1$ represents a nitrogen atom, G represents —O-$G^2$, $G^2$ represents 3-Me-Py4, and T represents any one of substituents indicated in Table 1 to Table 6 (hereinafter, referred to as Compound Class SX183).

a compound (L-1) wherein $A^1$ represents a nitrogen atom, G represents —O-$G^2$, $G^2$ represents 2-Me-Py4, and T represents any one of substituents indicated in Table 1 to Table 6 (hereinafter, referred to as Compound Class SX184).

a compound (L-1) wherein $A^1$ represents a nitrogen atom, G represents —O-$G^2$, $G^2$ represents 3-Cl-Py4, and T represents any one of substituents indicated in Table 1 to Table 6 (hereinafter, referred to as Compound Class SX187).

a compound (L-1) wherein $A^1$ represents a nitrogen atom, G represents —O-$G^2$, $G^2$ represents 2-Cl-Py4, and T represents any one of substituents indicated in Table 1 to Table 6 (hereinafter, referred to as Compound Class SX188).

a compound (L-1) wherein $A^1$ represents a nitrogen atom, G represents —O-$G^2$, $G^2$ represents 3-$CF_3$-Py4, and T represents any one of substituents indicated in Table 1 to Table 6 (hereinafter, referred to as Compound Class SX191).

a compound (L-1) wherein $A^1$ represents a nitrogen atom, G represents —O-$G^2$, $G^2$ represents 2-$CF_3$-Py4, and T represents any one of substituents indicated in Table 1 to Table 6 (hereinafter, referred to as Compound Class SX192).

a compound (L-1) wherein $A^1$ represents a nitrogen atom, G represents —O-$G^2$, $G^2$ represents 3-OMe-Py4, and T represents any one of substituents indicated in Table 1 to Table 6 (hereinafter, referred to as Compound Class SX195).

a compound (L-1) wherein $A^1$ represents a nitrogen atom, G represents —O-$G^2$, $G^2$ represents 2-OMe-Py4, and T represents any one of substituents indicated in Table 1 to Table 6 (hereinafter, referred to as Compound Class SX196).

a compound (L-2) wherein $A^1$ represents CH, G represents —O-$G^2$, $G^2$ represents Py2, and T represents any one of substituents indicated in Table 1 to Table 6 (hereinafter, referred to as Compound Class SX199).

a compound (L-2) wherein $A^1$ represents CH, G represents —O-$G^2$, $G^2$ represents 3-Me-Py2, and T represents any one of substituents indicated in Table 1 to Table 6 (hereinafter, referred to as Compound Class SX200).

a compound (L-2) wherein $A^1$ represents CH, G represents —O-$G^2$, $G^2$ represents 4-Me-Py2, and T represents any one of substituents indicated in Table 1 to Table 6 (hereinafter, referred to as Compound Class SX201).

a compound (L-2) wherein $A^1$ represents CH, G represents —O-$G^2$, $G^2$ represents 5-Me-Py2, and T represents any one of substituents indicated in Table 1 to Table 6 (hereinafter, referred to as Compound Class SX202).

a compound (L-2) wherein $A^1$ represents CH, G represents —O-$G^2$, $G^2$ represents 6-Me-Py2, and T represents any one of substituents indicated in Table 1 to Table 6 (hereinafter, referred to as Compound Class SX203).

a compound (L-2) wherein $A^1$ represents CH, G represents —O-$G^2$, $G^2$ represents 3-Cl-Py2, and T represents any one of substituents indicated in Table 1 to Table 6 (hereinafter, referred to as Compound Class SX204).

a compound (L-2) wherein $A^1$ represents CH, G represents —O-$G^2$, $G^2$ represents 4-Cl-Py2, and T represents any one of substituents indicated in Table 1 to Table 6 (hereinafter, referred to as Compound Class SX205).

a compound (L-2) wherein $A^1$ represents CH, G represents —O-$G^2$, $G^2$ represents 5-Cl-Py2, and T represents any one of substituents indicated in Table 1 to Table 6 (hereinafter, referred to as Compound Class SX206).

a compound (L-2) wherein $A^1$ represents CH, G represents —O-$G^2$, $G^2$ represents 6-Cl-Py2, and T represents any one of substituents indicated in Table 1 to Table 6 (hereinafter, referred to as Compound Class SX207).

a compound (L-2) wherein $A^1$ represents CH, G represents —O-$G^2$, $G^2$ represents 3-$CF_3$-Py2, and T represents any one of substituents indicated in Table 1 to Table 6 (hereinafter, referred to as Compound Class SX208).

a compound (L-2) wherein $A^1$ represents CH, G represents —O-$G^2$, $G^2$ represents 4-$CF_3$-Py2, and T represents any one of substituents indicated in Table 1 to Table 6 (hereinafter, referred to as Compound Class SX209).

a compound (L-2) wherein $A^1$ represents CH, G represents —O-$G^2$, $G^2$ represents 5-$CF_3$-Py2, and T represents any one of substituents indicated in Table 1 to Table 6 (hereinafter, referred to as Compound Class SX210).

a compound (L-2) wherein $A^1$ represents CH, G represents —O-$G^2$, $G^2$ represents 6-$CF_3$-Py2, and T represents any one of substituents indicated in Table 1 to Table 6 (hereinafter, referred to as Compound Class SX211).

a compound (L-2) wherein $A^1$ represents CH, G represents —O-$G^2$, $G^2$ represents 3-OMe-Py2, and T represents any one of substituents indicated in Table 1 to Table 6 (hereinafter, referred to as Compound Class SX212).

a compound (L-2) wherein $A^1$ represents CH, G represents —O-$G^2$, $G^2$ represents 4-OMe-Py2, and T represents any one of substituents indicated in Table 1 to Table 6 (hereinafter, referred to as Compound Class SX213).

a compound (L-2) wherein $A^1$ represents CH, G represents —O-$G^2$, $G^2$ represents 5-OMe-Py2, and T represents any one of substituents indicated in Table 1 to Table 6 (hereinafter, referred to as Compound Class SX214).

a compound (L-2) wherein $A^1$ represents CH, G represents —O-$G^2$, $G^2$ represents 6-OMe-Py2, and T represents any one of substituents indicated in Table 1 to Table 6 (hereinafter, referred to as Compound Class SX215).

a compound (L-2) wherein $A^1$ represents CH, G represents —O-$G^2$, $G^2$ represents Py3, and T represents any one of substituents indicated in Table 1 to Table 6 (hereinafter, referred to as Compound Class SX216).

a compound (L-2) wherein $A^1$ represents CH, G represents —O-$G^2$, $G^2$ represents 2-Me-Py3, and T represents any one of substituents indicated in Table 1 to Table 6 (hereinafter, referred to as Compound Class SX217).

a compound (L-2) wherein $A^1$ represents CH, G represents —O-$G^2$, $G^2$ represents 4-Me-Py3, and T represents any one of substituents indicated in Table 1 to Table 6 (hereinafter, referred to as Compound Class SX218).

a compound (L-2) wherein $A^1$ represents CH, G represents —O-$G^2$, $G^2$ represents 5-Me-Py3, and T represents any one of substituents indicated in Table 1 to Table 6 (hereinafter, referred to as Compound Class SX219).

a compound (L-2) wherein $A^1$ represents CH, G represents —O-$G^2$, $G^2$ represents 6-Me-Py3, and T represents any one of substituents indicated in Table 1 to Table 6 (hereinafter, referred to as Compound Class SX220).

a compound (L-2) wherein $A^1$ represents CH, G represents —O-$G^2$, $G^2$ represents 2-Cl-Py3, and T represents any one of substituents indicated in Table 1 to Table 6 (hereinafter, referred to as Compound Class SX221).

a compound (L-2) wherein $A^1$ represents CH, G represents —O-$G^2$, $G^2$ represents 4-Cl-Py3, and T represents any one of substituents indicated in Table 1 to Table 6 (hereinafter, referred to as Compound Class SX222).

a compound (L-2) wherein $A^1$ represents CH, G represents —O-$G^2$, $G^2$ represents 5-Cl-Py3, and T represents any one of substituents indicated in Table 1 to Table 6 (hereinafter, referred to as Compound Class SX223).

a compound (L-2) wherein $A^1$ represents CH, G represents —O-$G^2$, $G^2$ represents 6-Cl-Py3, and T represents any one of substituents indicated in Table 1 to Table 6 (hereinafter, referred to as Compound Class SX224).

a compound (L-2) wherein $A^1$ represents CH, G represents —O-$G^2$, $G^2$ represents 2-$CF_3$-Py3, and T represents any one of substituents indicated in Table 1 to Table 6 (hereinafter, referred to as Compound Class SX225).

a compound (L-2) wherein $A^1$ represents CH, G represents —O-$G^2$, $G^2$ represents 4-$CF_3$-Py3, and T represents any one of substituents indicated in Table 1 to Table 6 (hereinafter, referred to as Compound Class SX226).

a compound (L-2) wherein $A^1$ represents CH, G represents —O-$G^2$, $G^2$ represents 5-$CF_3$-Py3, and T represents any one of substituents indicated in Table 1 to Table 6 (hereinafter, referred to as Compound Class SX227).

a compound (L-2) wherein $A^1$ represents CH, G represents —O-$G^2$, $G^2$ represents 6-$CF_3$-Py3, and T represents any one of substituents indicated in Table 1 to Table 6 (hereinafter, referred to as Compound Class SX228).

a compound (L-2) wherein $A^1$ represents CH, G represents —O-$G^2$, $G^2$ represents 2-OMe-Py3, and T represents any one of substituents indicated in Table 1 to Table 6 (hereinafter, referred to as Compound Class SX229).

a compound (L-2) wherein $A^1$ represents CH, G represents —O-$G^2$, $G^2$ represents 4-OMe-Py3, and T represents any one of substituents indicated in Table 1 to Table 6 (hereinafter, referred to as Compound Class SX230).

a compound (L-2) wherein $A^1$ represents CH, G represents —O-$G^2$. $G^2$ represents 5-OMe-Py3, and T represents any one of substituents indicated in Table 1 to Table 6 (hereinafter, referred to as Compound Class SX231).

a compound (L-2) wherein $A^1$ represents CH, G represents —O-$G^2$, $G^2$ represents 6-OMe-Py3, and T represents any one of substituents indicated in Table 1 to Table 6 (hereinafter, referred to as Compound Class SX232).

a compound (L-2) wherein $A^1$ represents CH, G represents —O-$G^2$, $G^2$ represents Py4, and T represents any one of substituents indicated in Table 1 to Table 6 (hereinafter, referred to as Compound Class SX233).

a compound (L-2) wherein $A^1$ represents CH, G represents —O-$G^2$, $G^2$ represents 3-Me-Py4, and T represents any one of substituents indicated in Table 1 to Table 6 (hereinafter, referred to as Compound Class SX234).

a compound (L-2) wherein $A^1$ represents CH, G represents —O-$G^2$, $G^2$ represents 2-Me-Py4, and T represents any one of substituents indicated in Table 1 to Table 6 (hereinafter, referred to as Compound Class SX235).

a compound (L-2) wherein $A^1$ represents CH, G represents —O-$G^2$, $G^2$ represents 3-Cl-Py4, and T represents any one of substituents indicated in Table 1 to Table 6 (hereinafter, referred to as Compound Class SX238).

a compound (L-2) wherein $A^1$ represents CH, G represents —O-$G^2$, $G^2$ represents 2-Cl-Py4, and T represents any one of substituents indicated in Table 1 to Table 6 (hereinafter, referred to as Compound Class SX239).

a compound (L-2) wherein $A^1$ represents CH, G represents —O-$G^2$, $G^2$ represents 3-$CF_3$-Py4, and T represents any one of substituents indicated in Table 1 to Table 6 (hereinafter, referred to as Compound Class SX242).

a compound (L-2) wherein $A^1$ represents CH, G represents —O-$G^2$, $G^2$ represents 2-$CF_3$-Py4, and T represents any one of substituents indicated in Table 1 to Table 6 (hereinafter, referred to as Compound Class SX243).

a compound (L-2) wherein $A^1$ represents CH, G represents —O-$G^2$, $G^2$ represents 3-OMe-Py4, and T represents any one of substituents indicated in Table 1 to Table 6 (hereinafter, referred to as Compound Class SX246).

a compound (L-2) wherein $A^1$ represents CH, G represents —O-$G^2$, $G^2$ represents 2-OMe-Py4, and T represents any one of substituents indicated in Table 1 to Table 6 (hereinafter, referred to as Compound Class SX247).

a compound (L-2) wherein $A^1$ represents a nitrogen atom, G represents —O-$G^2$, $G^2$ represents Py2, and T represents any one of substituents indicated in Table 1 to Table 6 (hereinafter, referred to as Compound Class SX250).

a compound (L-2) wherein $A^1$ represents a nitrogen atom, G represents —O-$G^2$, $G^2$ represents 3-Me-Py2, and T represents any one of substituents indicated in Table 1 to Table 6 (hereinafter, referred to as Compound Class SX251).

a compound (L-2) wherein $A^1$ represents a nitrogen atom, G represents —O-$G^2$, $G^2$ represents 4-Me-Py2, and T represents any one of substituents indicated in Table 1 to Table 6 (hereinafter, referred to as Compound Class SX252).

a compound (L-2) wherein $A^1$ represents a nitrogen atom, G represents —O-$G^2$, $G^2$ represents 5-Me-Py2, and T represents any one of substituents indicated in Table 1 to Table 6 (hereinafter, referred to as Compound Class SX253).

a compound (L-2) wherein $A^1$ represents a nitrogen atom, G represents —O-$G^2$, $G^2$ represents 6-Me-Py2, and T represents any one of substituents indicated in Table 1 to Table 6 (hereinafter, referred to as Compound Class SX254).

a compound (L-2) wherein $A^1$ represents a nitrogen atom, G represents —O-$G^2$, $G^2$ represents 3-Cl-Py2, and T represents any one of substituents indicated in Table 1 to Table 6 (hereinafter, referred to as Compound Class SX255).

a compound (L-2) wherein $A^1$ represents a nitrogen atom, G represents —O-$G^2$, $G^2$ represents 4-Cl-Py2, and T represents any one of substituents indicated in Table 1 to Table 6 (hereinafter, referred to as Compound Class SX256).

a compound (L-2) wherein $A^1$ represents a nitrogen atom, G represents —O-$G^2$, $G^2$ represents 5-Cl-Py2, and T represents any one of substituents indicated in Table 1 to Table 6 (hereinafter, referred to as Compound Class SX257).

a compound (L-2) wherein $A^1$ represents a nitrogen atom, G represents —O-$G^2$, $G^2$ represents 6-Cl-Py2, and T represents any one of substituents indicated in Table 1 to Table 6 (hereinafter, referred to as Compound Class SX258).

a compound (L-2) wherein $A^1$ represents a nitrogen atom, G represents —O-$G^2$, $G^2$ represents 3-$CF_3$-Py2, and T represents any one of substituents indicated in Table 1 to Table 6 (hereinafter, referred to as Compound Class SX259).

a compound (L-2) wherein $A^L$ represents a nitrogen atom, G represents —O-$G^2$, $G^2$ represents 4-$CF_3$-Py2, and T represents any one of substituents indicated in Table 1 to Table 6 (hereinafter, referred to as Compound Class SX260).

a compound (L-2) wherein $A^1$ represents a nitrogen atom, G represents —O-$G^2$, $G^2$ represents 5-$CF_3$-Py2, and T represents any one of substituents indicated in Table 1 to Table 6 (hereinafter, referred to as Compound Class SX261).

a compound (L-2) wherein $A^1$ represents a nitrogen atom, G represents —O-$G^2$, $G^2$ represents 6-$CF_3$-Py2, and T represents any one of substituents indicated in Table 1 to Table 6 (hereinafter, referred to as Compound Class SX262).

a compound (L-2) wherein $A^1$ represents a nitrogen atom, G represents —O-$G^2$, $G^2$ represents 3-OMe-Py2, and T represents any one of substituents indicated in Table 1 to Table 6 (hereinafter, referred to as Compound Class SX263).

a compound (L-2) wherein $A^1$ represents a nitrogen atom, G represents —O-$G^2$, $G^2$ represents 4-OMe-Py2, and T represents any one of substituents indicated in Table 1 to Table 6 (hereinafter, referred to as Compound Class SX264).

a compound (L-2) wherein $A^1$ represents a nitrogen atom, G represents —O-$G^2$, $G^2$ represents 5-OMe-Py2, and T represents any one of substituents indicated in Table 1 to Table 6 (hereinafter, referred to as Compound Class SX265).

a compound (L-2) wherein $A^1$ represents a nitrogen atom, G represents —O-$G^2$, $G^2$ represents 6-OMe-Py2, and T represents any one of substituents indicated in Table 1 to Table 6 (hereinafter, referred to as Compound Class SX266).

a compound (L-2) wherein $A^1$ represents a nitrogen atom, G represents —O-$G^2$, $G^2$ represents Py3, and T represents any one of substituents indicated in Table 1 to Table 6 (hereinafter, referred to as Compound Class SX267).

a compound (L-2) wherein $A^1$ represents a nitrogen atom, G represents —O-$G^2$, $G^2$ represents 2-Me-Py3, and T represents any one of substituents indicated in Table 1 to Table 6 (hereinafter, referred to as Compound Class SX268).

a compound (L-2) wherein $A^1$ represents a nitrogen atom, G represents —O-$G^2$, $G^2$ represents 4-Me-Py3, and T represents any one of substituents indicated in Table 1 to Table 6 (hereinafter, referred to as Compound Class SX269).

a compound (L-2) wherein $A^1$ represents a nitrogen atom, G represents —O-$G^2$, $G^2$ represents 5-Me-Py3, and T represents any one of substituents indicated in Table 1 to Table 6 (hereinafter, referred to as Compound Class SX270).

a compound (L-2) wherein $A^1$ represents a nitrogen atom, G represents —O-$G^2$, $G^2$ represents 6-Me-Py3, and T represents any one of substituents indicated in Table 1 to Table 6 (hereinafter, referred to as Compound Class SX271).

a compound (L-2) wherein $A^1$ represents a nitrogen atom, G represents —O-$G^2$, $G^2$ represents 2-Cl-Py3, and T represents any one of substituents indicated in Table 1 to Table 6 (hereinafter, referred to as Compound Class SX272).

a compound (L-2) wherein $A^1$ represents a nitrogen atom, G represents —O-$G^2$, $G^2$ represents 4-Cl-Py3, and T represents any one of substituents indicated in Table 1 to Table 6 (hereinafter, referred to as Compound Class SX273).

a compound (L-2) wherein $A^1$ represents a nitrogen atom, G represents —O-$G^2$, $G^2$ represents 5-Cl-Py3, and T represents any one of substituents indicated in Table 1 to Table 6 (hereinafter, referred to as Compound Class SX274).

a compound (L-2) wherein $A^1$ represents a nitrogen atom, G represents —O-$G^2$, $G^2$ represents 6-Cl-Py3, and T represents any one of substituents indicated in Table 1 to Table 6 (hereinafter, referred to as Compound Class SX275).

a compound (L-2) wherein $A^1$ represents a nitrogen atom, G represents —O-$G^2$, $G^2$ represents 2-$CF_3$—Py3, and T represents any one of substituents indicated in Table 1 to Table 6 (hereinafter, referred to as Compound Class SX276).

a compound (L-2) wherein $A^1$ represents a nitrogen atom, G represents —O-$G^2$, $G^2$ represents 4-$CF_3$-Py3, and T represents any one of substituents indicated in Table 1 to Table 6 (hereinafter, referred to as Compound Class SX277).

a compound (L-2) wherein $A^1$ represents a nitrogen atom, G represents —O-$G^2$, $G^2$ represents 5-$CF_3$-Py3, and T represents any one of substituents indicated in Table 1 to Table 6 (hereinafter, referred to as Compound Class SX276).

a compound (L-2) wherein $A^1$ represents a nitrogen atom, G represents —O-$G^2$, $G^2$ represents 6-$CF_3$-Py3, and T represents any one of substituents indicated in Table 1 to Table 6 (hereinafter, referred to as Compound Class SX279).

a compound (L-2) wherein $A^1$ represents a nitrogen atom, G represents —O-$G^2$, $G^2$ represents 2-OMe-Py3, and T represents any one of substituents indicated in Table 1 to Table 6 (hereinafter, referred to as Compound Class SX280).

a compound (L-2) wherein $A^1$ represents a nitrogen atom, G represents —O-$G^2$, $G^2$ represents 4-OMe-Py3, and T represents any one of substituents indicated in Table 1 to Table 6 (hereinafter, referred to as Compound Class SX281).

a compound (L-2) wherein $A^1$ represents a nitrogen atom, G represents —O-$G^2$, $G^2$ represents 5-OMe-Py3, and T represents any one of substituents indicated in Table 1 to Table 6 (hereinafter, referred to as Compound Class SX282).

a compound (L-2) wherein $A^1$ represents a nitrogen atom, G represents —O-$G^2$, $G^2$ represents 6-OMe-Py3, and T represents any one of substituents indicated in Table 1 to Table 6 (hereinafter, referred to as Compound Class SX283).

a compound (L-2) wherein $A^1$ represents a nitrogen atom, G represents —O-$G^2$, $G^2$ represents Py4, and T represents any one of substituents indicated in Table 1 to Table 6 (hereinafter, referred to as Compound Class SX284).

a compound (L-2) wherein $A^1$ represents a nitrogen atom, G represents —O-$G^2$, $G^2$ represents 3-Me-Py4, and T represents any one of substituents indicated in Table 1 to Table 6 (hereinafter, referred to as Compound Class SX285).

a compound (L-2) wherein $A^1$ represents a nitrogen atom, G represents —O-$G^2$, $G^2$ represents 2-Me-Py4, and T represents any one of substituents indicated in Table 1 to Table 6 (hereinafter, referred to as Compound Class SX286).

a compound (L-2) wherein A¹ represents a nitrogen atom, G represents —O-G², G² represents 3-Cl-Py4, and T represents any one of substituents indicated in Table 1 to Table 6 (hereinafter, referred to as Compound Class SX289).

a compound (L-2) wherein A¹ represents a nitrogen atom, G represents —O-G², G² represents 2-CL-Py4, and T represents any one of substituents indicated in Table 1 to Table 6 (hereinafter, referred to as Compound Class SX290).

a compound (L-2) wherein A¹ represents a nitrogen atom, G represents —O-G², G² represents 3-CF$_3$-Py4, and T represents any one of substituents indicated in Table 1 to Table 6 (hereinafter, referred to as Compound Class SX293).

a compound (L-2) wherein A¹ represents a nitrogen atom, G represents —O-G², G² represents 2-CF$_3$-Py4, and T represents any one of substituents indicated in Table 1 to Table 6 (hereinafter, referred to as Compound Class SX294).

a compound (L-2) wherein A¹ represents a nitrogen atom, G represents —O-G², G² represents 3-OMe-Py4, and T represents any one of substituents indicated in Table 1 to Table 6 (hereinafter, referred to as Compound Class SX297).

a compound (L-2) wherein A¹ represents a nitrogen atom, G represents —O-G², G² represents 2-OMe-Py4, and T represents any one of substituents indicated in Table 1 to Table 6 (hereinafter, referred to as Compound Class SX298).

a compound (L-3) wherein A¹ represents CH, G represents —O-G², G² represents Py2, and T represents any one of substituents indicated in Table 1 to Table 6 (hereinafter, referred to as Compound Class SX301).

a compound (L-3) wherein A¹ represents CH, G represents —O-G², G² represents 3-Me-Py2, and T represents any one of substituents indicated in Table 1 to Table 6 (hereinafter, referred to as Compound Class SX302).

a compound (L-3) wherein A¹ represents CH, G represents —O-G², G² represents 4-Me-Py2, and T represents any one of substituents indicated in Table 1 to Table 6 (hereinafter, referred to as Compound Class SX303).

a compound (L-3) wherein A¹ represents CH, G represents —O-G², G² represents 5-Me-Py2, and T represents any one of substituents indicated in Table 1 to Table 6 (hereinafter, referred to as Compound Class SX304).

a compound (L-3) wherein A¹ represents CH, G represents —O-G², G² represents 6-Me-Py2, and T represents any one of substituents indicated in Table 1 to Table 6 (hereinafter, referred to as Compound Class SX305).

a compound (L-3) wherein A¹ represents CH, G represents —O-G², G² represents 3-Cl-Py2, and T represents any one of substituents indicated in Table 1 to Table 6 (hereinafter, referred to as Compound Class SX306).

a compound (L-3) wherein A¹ represents CH, G represents —O-G², G² represents 4-Cl-Py2, and T represents any one of substituents indicated in Table 1 to Table 6 (hereinafter, referred to as Compound Class SX307).

a compound (L-3) wherein A¹ represents CH, G represents —O-G², G² represents 5-Cl-Py2, and T represents any one of substituents indicated in Table 1 to Table 6 (hereinafter, referred to as Compound Class SX308).

a compound (L-3) wherein A¹ represents CH, G represents —O-G², G² represents 6-Cl-Py2, and T represents any one of substituents indicated in Table 1 to Table 6 (hereinafter, referred to as Compound Class SX309).

a compound (L-3) wherein A¹ represents CH, G represents —O-G², G² represents 3-CF$_3$-Py2, and T represents any one of substituents indicated in Table 1 to Table 6 (hereinafter, referred to as Compound Class SX310).

a compound (L-3) wherein A¹ represents CH, G represents —O-G², G² represents 4-CF$_3$-Py2, and T represents any one of substituents indicated in Table 1 to Table 6 (hereinafter, referred to as Compound Class SX311).

a compound (L-3) wherein A¹ represents CH, G represents —O-G², G² represents 5-CF$_3$-Py2, and T represents any one of substituents indicated in Table 1 to Table 6 (hereinafter, referred to as Compound Class SX312).

a compound (L-3) wherein A¹ represents CH, G represents —O-G², G² represents 6-CF$_3$-Py2, and T represents any one of substituents indicated in Table 1 to Table 6 (hereinafter, referred to as Compound Class SX313).

a compound (L-3) wherein A¹ represents CH, G represents —O-G², G² represents 3-OMe-Py2, and T represents any one of substituents indicated in Table 1 to Table 6 (hereinafter, referred to as Compound Class SX314).

a compound (L-3) wherein A¹ represents CH, G represents —O-G², G² represents 4-OMe-Py2, and T represents any one of substituents indicated in Table 1 to Table 6 (hereinafter, referred to as Compound Class SX315).

a compound (L-3) wherein A¹ represents CH, G represents —O-G², G² represents 5-OMe-Py2, and T represents any one of substituents indicated in Table 1 to Table 6 (hereinafter, referred to as Compound Class SX316).

a compound (L-3) wherein A¹ represents CH, G represents —O-G², G² represents 6-OMe-Py2, and T represents any one of substituents indicated in Table 1 to Table 6 (hereinafter, referred to as Compound Class SX317).

a compound (L-3) wherein A¹ represents CH, G represents —O-G², G² represents Py3, and T represents any one of substituents indicated in Table 1 to Table 6 (hereinafter, referred to as Compound Class SX318).

a compound (L-3) wherein A¹ represents CH, G represents —O-G², G² represents 2-Me-Py3, and T represents any one of substituents indicated in Table 1 to Table 6 (hereinafter, referred to as Compound Class SX318).

a compound (L-3) wherein A¹ represents CH, G represents —O-G², G² represents 4-Me-Py3, and T represents any one of substituents indicated in Table 1 to Table 6 (hereinafter, referred to as Compound Class SX319).

a compound (L-3) wherein A¹ represents CH, G represents —O-G², G² represents 4-Me-Py3, and T represents any one of substituents indicated in Table 1 to Table 6 (hereinafter, referred to as Compound Class SX319).

a compound (L-3) wherein A¹ represents CH, G represents —O-G², G² represents 5-Me-Py3, and T represents any one of substituents indicated in Table 1 to Table 6 (hereinafter, referred to as Compound Class SX320).

a compound (L-3) wherein A¹ represents CH, G represents —O-G², G² represents 6-Me-Py3, and T represents any one of substituents indicated in Table 1 to Table 6 (hereinafter, referred to as Compound Class SX321).

a compound (L-3) wherein A¹ represents CH, G represents —O-G², G² represents 2-Cl-Py3, and T represents any one of substituents indicated in Table 1 to Table 6 (hereinafter, referred to as Compound Class SX322).

a compound (L-3) wherein A¹ represents CH, G represents —O-G², G² represents 4-Cl-Py3, and T represents any one of substituents indicated in Table 1 to Table 6 (hereinafter, referred to as Compound Class SX323).

a compound (L-3) wherein A¹ represents CH, G represents —O-G², G² represents 5-Cl-Py3, and T represents any one of substituents indicated in Table 1 to Table 6 (hereinafter, referred to as Compound Class SX324).

a compound (L-3) wherein A¹ represents CH, G represents —O-G², G² represents 6-Cl-Py3, and T represents any one of substituents indicated in Table 1 to Table 6 (hereinafter, referred to as Compound Class SX325).

a compound (L-3) wherein $A^1$ represents CH, G represents —O-$G^2$, $G^2$ represents 2-CF$_3$-Py3, and T represents any one of substituents indicated in Table 1 to Table 6 (hereinafter, referred to as Compound Class SX326).

a compound (L-3) wherein $A^1$ represents CH, G represents —O-$G^2$, $G^2$ represents 4-CF$_3$-Py3, and T represents any one of substituents indicated in Table 1 to Table 6 (hereinafter, referred to as Compound Class SX327).

a compound (L-3) wherein $A^1$ represents CH, G represents —O-$G^2$, $G^2$ represents 5-CF$_3$-Py3, and T represents any one of substituents indicated in Table 1 to Table 6 (hereinafter, referred to as Compound Class SX328).

a compound (L-3) wherein $A^1$ represents CH, G represents —O-$G^2$, $G^2$ represents 6-CF$_3$-Py3, and T represents any one of substituents indicated in Table 1 to Table 6 (hereinafter, referred to as Compound Class SX329).

a compound (L-3) wherein $A^1$ represents CH, G represents —O-$G^2$, $G^2$ represents 2-OMe-Py3, and T represents any one of substituents indicated in Table 1 to Table 6 (hereinafter, referred to as Compound Class SX330).

a compound (L-3) wherein $A^1$ represents CH, G represents —O-$G^2$, $G^2$ represents 4-OMe-Py3, and T represents any one of substituents indicated in Table 1 to Table 6 (hereinafter, referred to as Compound Class SX331).

a compound (L-3) wherein $A^1$ represents CH, G represents —O-$G^2$, $G^2$ represents 5-OMe-Py3, and T represents any one of substituents indicated in Table 1 to Table 6 (hereinafter, referred to as Compound Class SX332).

a compound (L-3) wherein $A^1$ represents CH, G represents —O-$G^2$, $G^2$ represents 6-OMe-Py3, and T represents any one of substituents indicated in Table 1 to Table 6 (hereinafter, referred to as Compound Class SX333).

a compound (L-3) wherein $A^1$ represents CH, G represents —O-$G^2$, $G^2$ represents Py4, and T represents any one of substituents indicated in Table 1 to Table 6 (hereinafter, referred to as Compound Class SX334).

a compound (L-3) wherein $A^1$ represents CH, G represents —O-$G^2$, $G^2$ represents 3-Me-Py4, and T represents any one of substituents indicated in Table 1 to Table 6 (hereinafter, referred to as Compound Class SX335).

a compound (L-3) wherein $A^1$ represents CH, G represents —O-$G^2$, $G^2$ represents 2-Me-Py4, and T represents any one of substituents indicated in Table 1 to Table 6 (hereinafter, referred to as Compound Class SX336).

a compound (L-3) wherein $A^1$ represents CH, G represents —O-$G^2$, $G^2$ represents 3-Cl-Py4, and T represents any one of substituents indicated in Table 1 to Table 6 (hereinafter, referred to as Compound Class SX339).

a compound (L-3) wherein $A^1$ represents CH, G represents —O-$G^2$, $G^2$ represents 2-Cl-Py4, and T represents any one of substituents indicated in Table 1 to Table 6 (hereinafter, referred to as Compound Class SX340).

a compound (L-3) wherein $A^1$ represents CH, G represents —O-$G^2$, $G^2$ represents 3-CF$_3$-Py4, and T represents any one of substituents indicated in Table 1 to Table 6 (hereinafter, referred to as Compound Class SX343).

a compound (L-3) wherein $A^1$ represents CH, G represents —O-$G^2$, $G^2$ represents 2-CF$_3$-Py4, and T represents any one of substituents indicated in Table 1 to Table 6 (hereinafter, referred to as Compound Class SX344).

a compound (L-3) wherein $A^1$ represents CH, G represents —O-$G^2$, $G^2$ represents 3-OMe-Py4, and T represents any one of substituents indicated in Table 1 to Table 6 (hereinafter, referred to as Compound Class SX347).

a compound (L-3) wherein $A^1$ represents CH, G represents —O-$G^2$, $G^2$ represents 2-OMe-Py4, and T represents any one of substituents indicated in Table 1 to Table 6 (hereinafter, referred to as Compound Class SX348).

a compound (L-3) wherein $A^1$ represents a nitrogen atom, G represents —O-$G^2$, $G^2$ represents Py2, and T represents any one of substituents indicated in Table 1 to Table 6 (hereinafter, referred to as Compound Class SX351).

a compound (L-3) wherein $A^1$ represents a nitrogen atom, G represents —O-$G^2$, $G^2$ represents 3-Me-Py2, and T represents any one of substituents indicated in Table 1 to Table 6 (hereinafter, referred to as Compound Class SX352).

a compound (L-3) wherein $A^1$ represents a nitrogen atom, G represents —O-$G^2$, $G^2$ represents 4-Me-Py2, and T represents any one of substituents indicated in Table 1 to Table 6 (hereinafter, referred to as Compound Class SX353).

a compound (L-3) wherein $A^1$ represents a nitrogen atom, G represents —O-$G^2$, $G^2$ represents 5-Me-Py2, and T represents any one of substituents indicated in Table 1 to Table 6 (hereinafter, referred to as Compound Class SX354).

a compound (L-3) wherein $A^1$ represents a nitrogen atom, G represents —O-$G^2$, $G^2$ represents 6-Me-Py2, and T represents any one of substituents indicated in Table 1 to Table 6 (hereinafter, referred to as Compound Class SX355).

a compound (L-3) wherein $A^1$ represents a nitrogen atom, G represents —O-$G^2$, $G^2$ represents 3-Cl-Py2, and T represents any one of substituents indicated in Table 1 to Table 6 (hereinafter, referred to as Compound Class SX356).

a compound (L-3) wherein $A^1$ represents a nitrogen atom, G represents —O-$G^2$, $G^2$ represents 4-Cl-Py2, and T represents any one of substituents indicated in Table 1 to Table 6 (hereinafter, referred to as Compound Class SX357).

a compound (L-3) wherein $A^1$ represents a nitrogen atom, G represents —O-$G^2$, $G^2$ represents 5-Cl-Py2, and T represents any one of substituents indicated in Table 1 to Table 6 (hereinafter, referred to as Compound Class SX358).

a compound (L-3) wherein $A^1$ represents a nitrogen atom, G represents —O-$G^2$, $G^2$ represents 6-Cl-Py2, and T represents any one of substituents indicated in Table 1 to Table 6 (hereinafter, referred to as Compound Class SX359).

a compound (L-3) wherein $A^1$ represents a nitrogen atom, G represents —O-$G^2$, $G^2$ represents 3-CF$_3$-Py2, and T represents any one of substituents indicated in Table 1 to Table 6 (hereinafter, referred to as Compound Class SX360).

a compound (L-3) wherein $A^1$ represents a nitrogen atom, G represents —O-$G^2$, $G^2$ represents 4-CF$_3$-Py2, and T represents any one of substituents indicated in Table 1 to Table 6 (hereinafter, referred to as Compound Class SX361).

a compound (L-3) wherein $A^1$ represents a nitrogen atom, G represents —O-$G^2$, $G^2$ represents 5-CF$_3$-Py2, and T represents any one of substituents indicated in Table 1 to Table 6 (hereinafter, referred to as Compound Class SX362).

a compound (L-3) wherein $A^1$ represents a nitrogen atom, G represents —O-$G^2$, $G^2$ represents 6-CF$_3$-Py2, and T represents any one of substituents indicated in Table 1 to Table 6 (hereinafter, referred to as Compound Class SX363).

a compound (L-3) wherein $A^1$ represents a nitrogen atom, G represents —O-$G^2$, $G^2$ represents 3-OMe-Py2, and T represents any one of substituents indicated in Table 1 to Table 6 (hereinafter, referred to as Compound Class SX364).

a compound (L-3) wherein $A^1$ represents a nitrogen atom, G represents —O-$G^2$, $G^2$ represents 4-OMe-Py2, and T represents any one of substituents indicated in Table 1 to Table 6 (hereinafter, referred to as Compound Class SX365).

a compound (L-3) wherein $A^1$ represents a nitrogen atom, G represents —O-$G^2$, $G^2$ represents 5-OMe-Py2, and T represents any one of substituents indicated in Table 1 to Table 6 (hereinafter, referred to as Compound Class SX366).

a compound (L-3) wherein A$^1$ represents a nitrogen atom, G represents —O-G$^2$, G$^2$ represents 6-OMe-Py2, and T represents any one of substituents indicated in Table 1 to Table 6 (hereinafter, referred to as Compound Class SX367).

a compound (L-3) wherein A$^1$ represents a nitrogen atom, G represents —O-G$^2$, G$^2$ represents Py3, and T represents any one of substituents indicated in Table 1 to Table 6 (hereinafter, referred to as Compound Class SX368).

a compound (L-3) wherein A$^1$ represents a nitrogen atom, G represents —O-G$^2$, G$^2$ represents 2-Me-Py3, and T represents any one of substituents indicated in Table 1 to Table 6 (hereinafter, referred to as Compound Class SX369).

a compound (L-3) wherein A$^1$ represents a nitrogen atom, G represents —O-G$^2$, G$^2$ represents 4-Me-Py3, and T represents any one of substituents indicated in Table 1 to Table 6 (hereinafter, referred to as Compound Class SX370).

a compound (L-3) wherein A$^1$ represents a nitrogen atom, G represents —O-G$^2$, G$^2$ represents 5-Me-Py3, and T represents any one of substituents indicated in Table 1 to Table 6 (hereinafter, referred to as Compound Class SX371).

a compound (L-3) wherein A$^1$ represents a nitrogen atom, G represents —O-G$^2$, G$^2$ represents 6-Me-Py3, and T represents any one of substituents indicated in Table 1 to Table 6 (hereinafter, referred to as Compound Class SX372).

a compound (L-3) wherein A$^1$ represents a nitrogen atom, G represents —O-G$^2$, G$^2$ represents 2-Cl-Py3, and T represents any one of substituents indicated in Table 1 to Table 6 (hereinafter, referred to as Compound Class SX373).

a compound (L-3) wherein A$^1$ represents a nitrogen atom, G represents —O-G$^2$, G$^2$ represents 4-Cl-Py3, and T represents any one of substituents indicated in Table 1 to Table 6 (hereinafter, referred to as Compound Class SX374).

a compound (L-3) wherein A$^1$ represents a nitrogen atom, G represents —O-G$^2$, G$^2$ represents 5-Cl-Py3, and T represents any one of substituents indicated in Table 1 to Table 6 (hereinafter, referred to as Compound Class SX375).

a compound (L-3) wherein A$^1$ represents a nitrogen atom, G represents —O-G$^2$, G$^2$ represents 6-Cl-Py3, and T represents any one of substituents indicated in Table 1 to Table 6 (hereinafter, referred to as Compound Class SX376).

a compound (L-3) wherein A$^1$ represents a nitrogen atom, G represents —O-G$^2$, G$^2$ represents 2-CF$_3$-Py3, and T represents any one of substituents indicated in Table 1 to Table 6 (hereinafter, referred to as Compound Class SX377).

a compound (L-3) wherein A$^1$ represents a nitrogen atom, G represents —O-G$^2$, G$^2$ represents 4-CF$_3$-Py3, and T represents any one of substituents indicated in Table 1 to Table 6 (hereinafter, referred to as Compound Class SX378).

a compound (L-3) wherein A$^1$ represents a nitrogen atom, G represents —O-G$^2$, G$^2$ represents 5-CF$_3$-Py3, and T represents any one of substituents indicated in Table 1 to Table 6 (hereinafter, referred to as Compound Class SX379).

a compound (L-3) wherein A$^1$ represents a nitrogen atom, G represents —O-G$^2$, G$^2$ represents 6-CF$_3$-Py3, and T represents any one of substituents indicated in Table 1 to Table 6 (hereinafter, referred to as Compound Class SX380).

a compound (L-3) wherein A$^1$ represents a nitrogen atom, G represents —O-G$^2$, G$^2$ represents 2-OMe-Py3, and T represents any one of substituents indicated in Table 1 to Table 6 (hereinafter, referred to as Compound Class SX381.

a compound (L-3) wherein A$^1$ represents a nitrogen atom, G represents —O-G$^2$, G$^2$ represents 4-OMe-Py3, and T represents any one of substituents indicated in Table 1 to Table 6 (hereinafter, referred to as Compound Class SX382).

a compound (L-3) wherein A$^1$ represents a nitrogen atom, G represents —O-G$^2$, G$^2$ represents 5-OMe-Py3, and T represents any one of substituents indicated in Table 1 to Table 6 (hereinafter, referred to as Compound Class SX383).

a compound (L-3) wherein A$^1$ represents a nitrogen atom, G represents —O-G$^2$, G$^2$ represents 6-OMe-Py3, and T represents any one of substituents indicated in Table 1 to Table 6 (hereinafter, referred to as Compound Class SX384).

a compound (L-3) wherein A$^1$ represents a nitrogen atom, G represents —O-G$^2$, G$^2$ represents Py4, and T represents any one of substituents indicated in Table 1 to Table 6 (hereinafter, referred to as Compound Class SX385).

a compound (L-3) wherein A$^1$ represents a nitrogen atom, G represents —O-G$^2$, G$^2$ represents 3-Me-Py4, and T represents any one of substituents indicated in Table 1 to Table 6 (hereinafter, referred to as Compound Class SX386).

a compound (L-3) wherein A$^1$ represents a nitrogen atom, G represents —O-G$^2$, G$^2$ represents 2-Me-Py4, and T represents any one of substituents indicated in Table 1 to Table 6 (hereinafter, referred to as Compound Class SX387).

a compound (L-3) wherein A$^1$ represents a nitrogen atom, G represents —O-G$^2$, G$^2$ represents 3-Cl-Py4, and T represents any one of substituents indicated in Table 1 to Table 6 (hereinafter, referred to as Compound Class SX390).

a compound (L-3) wherein A$^1$ represents a nitrogen atom, G represents —O-G$^2$, G$^2$ represents 2-Cl-Py4, and T represents any one of substituents indicated in Table 1 to Table 6 (hereinafter, referred to as Compound Class SX391).

a compound (L-3) wherein A$^1$ represents a nitrogen atom, G represents —O-G$^2$, G$^2$ represents 3-CF$_3$-Py4, and T represents any one of substituents indicated in Table 1 to Table 6 (hereinafter, referred to as Compound Class SX394).

a compound (L-3) wherein A$^1$ represents a nitrogen atom, G represents —O-G$^2$, G$^2$ represents 2-CF$_3$-Py4, and T represents any one of substituents indicated in Table 1 to Table 6 (hereinafter, referred to as Compound Class SX395).

a compound (L-3) wherein A$^1$ represents a nitrogen atom, G represents —O-G$^2$, G$^2$ represents 3-OMe-Py4, and T represents any one of substituents indicated in Table 1 to Table 6 (hereinafter, referred to as Compound Class SX398).

a compound (L-3) wherein A$^1$ represents a nitrogen atom, G represents —O-G$^2$, G$^2$ represents 2-Me-Py4, and T represents any one of substituents indicated in Table 1 to Table 6 (hereinafter, referred to as Compound Class SX399).

a compound (L-4) wherein A$^1$ represents CH, G represents —O-G$^2$, G$^2$ represents Py2, and T represents any one of substituents indicated in Table 1 to Table 6 (hereinafter, referred to as Compound Class SX402).

a compound (L-4) wherein A$^1$ represents CH, G represents —O-G$^2$, G$^2$ represents 3-Me-Py2, and T represents any one of substituents indicated in Table 1 to Table 6 (hereinafter, referred to as Compound Class SX403).

a compound (L-4) wherein A$^1$ represents CH, G represents —O-G$^2$, G$^2$ represents 4-Me-Py2, and T represents any one of substituents indicated in Table 1 to Table 6 (hereinafter, referred to as Compound Class SX404).

a compound (L-4) wherein A$^1$ represents CH, G represents —O-G$^2$, G$^2$ represents 5-Me-Py2, and T represents any one of substituents indicated in Table 1 to Table 6 (hereinafter, referred to as Compound Class SX405).

a compound (L-4) wherein A$^1$ represents CH, G represents —O-G$^2$, G$^2$ represents 6-Me-Py2, and T represents any one of substituents indicated in Table 1 to Table 6 (hereinafter, referred to as Compound Class SX406).

a compound (L-4) wherein A$^1$ represents CH, G represents —O-G$^2$, G$^2$ represents 3-Cl-Py2, and T represents any one of substituents indicated in Table 1 to Table 6 (hereinafter, referred to as Compound Class SX407).

a compound (L-4) wherein $A^1$ represents CH, G represents —O-$G^2$, $G^2$ represents 4-Cl-Py2, and T represents any one of substituents indicated in Table 1 to Table 6 (hereinafter, referred to as Compound Class SX408).

a compound (L-4) wherein $A^1$ represents CH, G represents —O-$G^2$, $G^2$ represents 5-Cl-Py2, and T represents any one of substituents indicated in Table 1 to Table 6 (hereinafter, referred to as Compound Class SX409).

a compound (L-4) wherein $A^1$ represents CH, G represents —O-$G^2$, $G^2$ represents 6-Cl-Py2, and T represents any one of substituents indicated in Table 1 to Table 6 (hereinafter, referred to as Compound Class SX410).

a compound (L-4) wherein $A^1$ represents CH, G represents —O-$G^2$, $G^2$ represents 3-$CF_3$-Py2, and T represents any one of substituents indicated in Table 1 to Table 6 (hereinafter, referred to as Compound Class SX411).

a compound (L-4) wherein $A^1$ represents CH, G represents —O-$G^2$, $G^2$ represents 4-$CF_3$-Py2, and T represents any one of substituents indicated in Table 1 to Table 6 (hereinafter, referred to as Compound Class SX412).

a compound (L-4) wherein $A^1$ represents CH, G represents —O-$G^2$, $G^2$ represents 5-$CF_3$-Py2, and T represents any one of substituents indicated in Table 1 to Table 6 (hereinafter, referred to as Compound Class SX413).

a compound (L-4) wherein $A^1$ represents CH, G represents —O-$G^2$, $G^2$ represents 6-$CF_3$-Py2, and T represents any one of substituents indicated in Table 1 to Table 6 (hereinafter, referred to as Compound Class SX414).

a compound (L-4) wherein $A^1$ represents CH, G represents —O-$G^2$, $G^2$ represents 3-OMe-Py2, and T represents any one of substituents indicated in Table 1 to Table 6 (hereinafter, referred to as Compound Class SX415).

a compound (L-4) wherein $A^1$ represents CH, G represents —O-$G^2$, $G^2$ represents 4-OMe-Py2, and T represents any one of substituents indicated in Table 1 to Table 6 (hereinafter, referred to as Compound Class SX416).

a compound (L-4) wherein $A^1$ represents CH, G represents —O-$G^2$, $G^2$ represents 5-OMe-Py2, and T represents any one of substituents indicated in Table 1 to Table 6 (hereinafter, referred to as Compound Class SX417).

a compound (L-4) wherein $A^1$ represents CH, G represents —O-$G^2$, $G^2$ represents 6-OMe-Py2, and T represents any one of substituents indicated in Table 1 to Table 6 (hereinafter, referred to as Compound Class SX418).

a compound (L-4) wherein $A^1$ represents CH, G represents —O-$G^2$, $G^2$ represents Py3, and T represents any one of substituents indicated in Table 1 to Table 6 (hereinafter, referred to as Compound Class SX419).

a compound (L-4) wherein $A^1$ represents CH, G represents —O-$G^2$, $G^2$ represents 2-Me-Py3, and T represents any one of substituents indicated in Table 1 to Table 6 (hereinafter, referred to as Compound Class SX420).

a compound (L-4) wherein $A^1$ represents CH, G represents —O-$G^2$, $G^2$ represents 4-Me-Py3, and T represents any one of substituents indicated in Table 1 to Table 6 (hereinafter, referred to as Compound Class SX421).

a compound (L-4) wherein $A^1$ represents CH, G represents —O-$G^2$, $G^2$ represents 5-Me-Py3, and T represents any one of substituents indicated in Table 1 to Table 6 (hereinafter, referred to as Compound Class SX422).

a compound (L-4) wherein $A^1$ represents CH, G represents —O-$G^2$, $G^2$ represents 6-Me-Py3, and T represents any one of substituents indicated in Table 1 to Table 6 (hereinafter, referred to as Compound Class SX423).

a compound (L-4) wherein $A^1$ represents CH, G represents —O-$G^2$, $G^2$ represents 2-Cl-Py3, and T represents any one of substituents indicated in Table 1 to Table 6 (hereinafter, referred to as Compound Class SX424).

a compound (L-4) wherein $A^1$ represents CH, G represents —O-$G^2$, $G^2$ represents 4-Cl-Py3, and T represents any one of substituents indicated in Table 1 to Table 6 (hereinafter, referred to as Compound Class SX425).

a compound (L-4) wherein $A^1$ represents CH, G represents —O-$G^2$, $G^2$ represents 5-Cl-Py3, and T represents any one of substituents indicated in Table 1 to Table 6 (hereinafter, referred to as Compound Class SX426).

a compound (L-4) wherein $A^1$ represents CH, G represents —O-$G^2$, $G^2$ represents 6-Cl-Py3, and T represents any one of substituents indicated in Table 1 to Table 6 (hereinafter, referred to as Compound Class SX427).

a compound (L-4) wherein $A^1$ represents CH, G represents —O-$G^2$, $G^2$ represents 2-$CF_3$-Py3, and T represents any one of substituents indicated in Table 1 to Table 6 (hereinafter, referred to as Compound Class SX428).

a compound (L-4) wherein $A^1$ represents CH, G represents —O-$G^2$, $G^2$ represents 4-$CF_3$-Py3, and T represents any one of substituents indicated in Table 1 to Table 6 (hereinafter, referred to as Compound Class SX429).

a compound (L-4) wherein $A^1$ represents CH, G represents —O-$G^2$, $G^2$ represents 5-$CF_3$-Py3, and T represents any one of substituents indicated in Table 1 to Table 6 (hereinafter, referred to as Compound Class SX430).

a compound (L-4) wherein $A^1$ represents CH, G represents —O-$G^2$, $G^2$ represents 6-$CF_3$-Py3, and T represents any one of substituents indicated in Table 1 to Table 6 (hereinafter, referred to as Compound Class SX431).

a compound (L-4) wherein $A^1$ represents CH, G represents —O-$G^2$, $G^2$ represents 4-OMe-Py3, and T represents any one of substituents indicated in Table 1 to Table 6 (hereinafter, referred to as Compound Class SX432).

a compound (L-4) wherein $A^1$ represents CH, G represents —O-$G^2$, $G^2$ represents 2-OMe-Py3, and T represents any one of substituents indicated in Table 1 to Table 6 (hereinafter, referred to as Compound Class SX433).

a compound (L-4) wherein $A^1$ represents CH, G represents —O-$G^2$, $G^2$ represents 5-OMe-Py3, and T represents any one of substituents indicated in Table 1 to Table 6 (hereinafter, referred to as Compound Class SX434).

a compound (L-4) wherein $A^1$ represents CH, G represents —O-$G^2$, $G^2$ represents 6-OMe-Py3, and T represents any one of substituents indicated in Table 1 to Table 6 (hereinafter, referred to as Compound Class SX435).

a compound (L-4) wherein $A^1$ represents CH, G represents —O-$G^2$, $G^2$ represents Py4, and T represents any one of substituents indicated in Table 1 to Table 6 (hereinafter, referred to as Compound Class SX436).

a compound (L-4) wherein $A^1$ represents CH, G represents —O-$G^2$, $G^2$ represents 3-Me-Py4, and T represents any one of substituents indicated in Table 1 to Table 6 (hereinafter, referred to as Compound Class SX437).

a compound (L-4) wherein $A^1$ represents CH, G represents —O-$G^2$, $G^2$ represents 2-Me-Py4, and T represents any one of substituents indicated in Table 1 to Table 6 (hereinafter, referred to as Compound Class SX438).

a compound (L-4) wherein $A^1$ represents CH, G represents —O-$G^2$, $G^2$ represents 3-Cl-Py4, and T represents any one of substituents indicated in Table 1 to Table 6 (hereinafter, referred to as Compound Class SX441).

a compound (L-4) wherein $A^1$ represents CH, G represents —O-$G^2$, $G^2$ represents 2-Cl-Py4, and T represents any one of substituents indicated in Table 1 to Table 6 (hereinafter, referred to as Compound Class SX442).

a compound (L-4) wherein $A^1$ represents CH, G represents —O-$G^2$, $G^2$ represents 3-CF$_3$-Py4, and T represents any one of substituents indicated in Table 1 to Table 6 (hereinafter, referred to as Compound Class SX445).

a compound (L-4) wherein $A^1$ represents CH, G represents —O-$G^2$, $G^2$ represents 2-CF$_3$-Py4, and T represents any one of substituents indicated in Table 1 to Table 6 (hereinafter, referred to as Compound Class SX446).

a compound (L-4) wherein $A^1$ represents CH, G represents —O-$G^2$, $G^2$ represents 3-OMe-Py4, and T represents any one of substituents indicated in Table 1 to Table 6 (hereinafter, referred to as Compound Class SX449).

a compound (L-4) wherein $A^1$ represents CH, G represents —O-$G^2$, $G^2$ represents 2-OMe-Py4, and T represents any one of substituents indicated in Table 1 to Table 6 (hereinafter, referred to as Compound Class SX450).

a compound (L-4) wherein $A^1$ represents a nitrogen atom, G represents —O-$G^2$, $G^2$ represents Py2, and T represents any one of substituents indicated in Table 1 to Table 6 (hereinafter, referred to as Compound Class SX453).

a compound (L-4) wherein $A^1$ represents a nitrogen atom, G represents —O-$G^2$, $G^2$ represents 3-Me-Py2, and T represents any one of substituents indicated in Table 1 to Table 6 (hereinafter, referred to as Compound Class SX454).

a compound (L-4) wherein $A^1$ represents a nitrogen atom, G represents —O-$G^2$, $G^2$ represents 4-Me-Py2, and T represents any one of substituents indicated in Table 1 to Table 6 (hereinafter, referred to as Compound Class SX455).

a compound (L-4) wherein $A^1$ represents a nitrogen atom, G represents —O-$G^2$, $G^2$ represents 5-Me-Py2, and T represents any one of substituents indicated in Table 1 to Table 6 (hereinafter, referred to as Compound Class SX456).

a compound (L-4) wherein $A^1$ represents a nitrogen atom, G represents —O-$G^2$, $G^2$ represents 6-Me-Py2, and T represents any one of substituents indicated in Table 1 to Table 6 (hereinafter, referred to as Compound Class SX457).

a compound (L-4) wherein $A^1$ represents a nitrogen atom, G represents —O-$G^2$, $G^2$ represents 3-Cl-Py2, and T represents any one of substituents indicated in Table 1 to Table 6 (hereinafter, referred to as Compound Class SX458).

a compound (L-4) wherein $A^1$ represents a nitrogen atom, G represents —O-$G^2$, $G^2$ represents 4-Cl-Py2, and T represents any one of substituents indicated in Table 1 to Table 6 (hereinafter, referred to as Compound Class SX459).

a compound (L-4) wherein $A^1$ represents a nitrogen atom, G represents —O-$G^2$, $G^2$ represents 5-Cl-Py2, and T represents any one of substituents indicated in Table 1 to Table 6 (hereinafter, referred to as Compound Class SX460).

a compound (L-4) wherein $A^1$ represents a nitrogen atom, G represents —O-$G^2$, $G^2$ represents 6-Cl-Py2, and T represents any one of substituents indicated in Table 1 to Table 6 (hereinafter, referred to as Compound Class SX461).

a compound (L-4) wherein $A^1$ represents a nitrogen atom, G represents —O-$G^2$, $G^2$ represents 3-CF$_3$-Py2, and T Table 6 (hereinafter, referred to as Compound Class SX462).

a compound (L-4) wherein $A^1$ represents a nitrogen atom, G represents —O-$G^2$, $G^2$ represents 4-CF$_3$-Py2, and T represents any one of substituents indicated in Table 1 to Table 6 (hereinafter, referred to as Compound Class SX463).

a compound (L-4) wherein $A^1$ represents a nitrogen atom, G represents —O-$G^2$, $G^2$ represents 5-CF$_3$-Py2, and T represents any one of substituents indicated in Table 1 to Table 6 (hereinafter, referred to as Compound Class SX464).

a compound (L-4) wherein $A^1$ represents a nitrogen atom, G represents —O-$G^2$, $G^2$ represents 6-CF$_3$—Py2, and T represents any one of substituents indicated in Table 1 to Table 6 (hereinafter, referred to as Compound Class SX465).

a compound (L-4) wherein $A^1$ represents a nitrogen atom, G represents —O-$G^2$, $G^2$ represents 3-OMe-Py2, and T represents any one of substituents indicated in Table 1 to Table 6 (hereinafter, referred to as Compound Class SX466).

a compound (L-4) wherein $A^1$ represents a nitrogen atom, G represents —O-$G^2$, $G^2$ represents 4-OMe-Py2, and T represents any one of substituents indicated in Table 1 to Table 6 (hereinafter, referred to as Compound Class SX467).

a compound (L-4) wherein $A^1$ represents a nitrogen atom, G represents —O-$G^2$, $G^2$ represents 5-OMe-Py2, and T represents any one of substituents indicated in Table 1 to Table 6 (hereinafter, referred to as Compound Class SX468).

a compound (L-4) wherein $A^1$ represents a nitrogen atom, G represents —O-$G^2$, $G^2$ represents 6-OMe-Py2, and T represents any one of substituents indicated in Table 1 to Table 6 (hereinafter, referred to as Compound Class SX469).

a compound (L-4) wherein $A^1$ represents a nitrogen atom, G represents —O-$G^2$, $G^2$ represents Py3, and T represents any one of substituents indicated in Table 1 to Table 6 (hereinafter, referred to as Compound Class SX470).

a compound (L-4) wherein $A^1$ represents a nitrogen atom, G represents —O-$G^2$, $G^2$ represents 2-Me-Py3, and T represents any one of substituents indicated in Table 1 to Table 6 (hereinafter, referred to as Compound Class SX471).

a compound (L-4) wherein $A^1$ represents a nitrogen atom, G represents —O-$G^2$, $G^2$ represents 4-Me-Py3, and T represents any one of substituents indicated in Table 1 to Table 6 (hereinafter, referred to as Compound Class SX472).

a compound (L-4) wherein $A^1$ represents a nitrogen atom, G represents —O-$G^2$, $G^2$ represents 5-Me-Py3, and T represents any one of substituents indicated in Table 1 to Table 6 (hereinafter, referred to as Compound Class SX473).

a compound (L-4) wherein $A^1$ represents a nitrogen atom, G represents —O-$G^2$, $G^2$ represents 6-Me-Py3, and T represents any one of substituents indicated in Table 1 to Table 6 (hereinafter, referred to as Compound Class SX474).

a compound (L-4) wherein $A^1$ represents a nitrogen atom, G represents —O-$G^2$, $G^2$ represents 2-Cl-Py3, and T represents any one of substituents indicated in Table 1 to Table 6 (hereinafter, referred to as Compound Class SX475).

a compound (L-4) wherein $A^1$ represents a nitrogen atom, G represents —O-$G^2$, $G^2$ represents 4-Cl-Py3, and T represents any one of substituents indicated in Table 1 to Table 6 (hereinafter, referred to as Compound Class SX476).

a compound (L-4) wherein $A^1$ represents a nitrogen atom, G represents —O-$G^2$, $G^2$ represents 5-Cl-Py3, and T represents any one of substituents indicated in Table 1 to Table 6 (hereinafter, referred to as Compound Class SX477).

a compound (L-4) wherein $A^1$ represents a nitrogen atom, G represents —O-$G^2$, $G^2$ represents 6-Cl-Py3, and T represents any one of substituents indicated in Table 1 to Table 6 (hereinafter, referred to as Compound Class SX478).

a compound (L-4) wherein $A^1$ represents a nitrogen atom, G represents —O-$G^2$, $G^2$ represents 2-CF$_3$-Py3, and T represents any one of substituents indicated in Table 1 to Table 6 (hereinafter, referred to as Compound Class SX479).

a compound (L-4) wherein $A^1$ represents a nitrogen atom, G represents —O-$G^2$, $G^2$ represents 4-CF$_3$—Py3, and T represents any one of substituents indicated in Table 1 to Table 6 (hereinafter, referred to as Compound Class SX480).

a compound (L-4) wherein $A^1$ represents a nitrogen atom, G represents —O-$G^2$, $G^2$ represents 5-CF$_3$-Py3, and T represents any one of substituents indicated in Table 1 to Table 6 (hereinafter, referred to as Compound Class SX481).

a compound (L-4) wherein $A^1$ represents a nitrogen atom, G represents —O-$G^2$, $G^2$ represents 6-CF$_3$-Py3, and T represents any one of substituents indicated in Table 1 to Table 6 (hereinafter, referred to as Compound Class SX482).

a compound (L-4) wherein $A^1$ represents a nitrogen atom, G represents —O-$G^2$, $G^2$ represents 2-OMe-Py3, and T represents any one of substituents indicated in Table 1 to Table 6 (hereinafter, referred to as Compound Class SX483).

a compound (L-4) wherein $A^1$ represents a nitrogen atom, G represents —O-$G^2$, $G^2$ represents 4-OMe-Py3, and T represents any one of substituents indicated in Table 1 to Table 6 (hereinafter, referred to as Compound Class SX484).

a compound (L-4) wherein $A^1$ represents a nitrogen atom, G represents —O-$G^2$, $G^2$ represents 5-OMe-Py3, and T represents any one of substituents indicated in Table 1 to Table 6 (hereinafter, referred to as Compound Class SX485).

a compound (L-4) wherein $A^1$ represents a nitrogen atom, G represents —O-$G^2$, $G^2$ represents 6-OMe-Py3, and T represents any one of substituents indicated in Table 1 to Table 6 (hereinafter, referred to as Compound Class SX486).

a compound (L-4) wherein $A^1$ represents a nitrogen atom, G represents —O-$G^2$, $G^2$ represents Py4, and T represents any one of substituents indicated in Table 1 to Table 6 (hereinafter, referred to as Compound Class SX487).

a compound (L-4) wherein $A^1$ represents a nitrogen atom, G represents —O-$G^2$, $G^2$ represents 3-Me-Py4, and T represents any one of substituents indicated in Table 1 to Table 6 (hereinafter, referred to as Compound Class SX488).

a compound (L-4) wherein $A^1$ represents a nitrogen atom, G represents —O-$G^2$, $G^2$ represents 2-Me-Py4, and T represents any one of substituents indicated in Table 1 to Table 6 (hereinafter, referred to as Compound Class SX489).

a compound (L-4) wherein $A^1$ represents a nitrogen atom, G represents —O-$G^2$, $G^2$ represents 3-Cl-Py4, and T represents any one of substituents indicated in Table 1 to Table 6 (hereinafter, referred to as Compound Class SX492).

a compound (L-4) wherein $A^1$ represents a nitrogen atom, G represents —O-$G^2$, $G^2$ represents 2-Cl-Py4, and T represents any one of substituents indicated in Table 1 to Table 6 (hereinafter, referred to as Compound Class SX493).

a compound (L-4) wherein $A^1$ represents a nitrogen atom, G represents —O-$G^2$, $G^2$ represents 3-$CF_3$-Py4, and T represents any one of substituents indicated in Table 1 to Table 6 (hereinafter, referred to as Compound Class SX496).

a compound (L-4) wherein $A^1$ represents a nitrogen atom, G represents —O-$G^2$, $G^2$ represents 2-$CF_3$-Py4, and T represents any one of substituents indicated in Table 1 to Table 6 (hereinafter, referred to as Compound Class SX497).

a compound (L-4) wherein $A^1$ represents a nitrogen atom, G represents —O-$G^2$, $G^2$ represents 3-OMe-Py4, and T represents any one of substituents indicated in Table 1 to Table 6 (hereinafter, referred to as Compound Class SX500).

a compound (L-4) wherein $A^1$ represents a nitrogen atom, G represents —O-$G^2$, $G^2$ represents 2-OMe-Py4, and T represents any one of substituents indicated in Table 1 to Table 6 (hereinafter, referred to as Compound Class SX501).

Herein, the symbols of 1G to 39G represent the substituents indicated in Tables 7 to 9.

TABLE 7

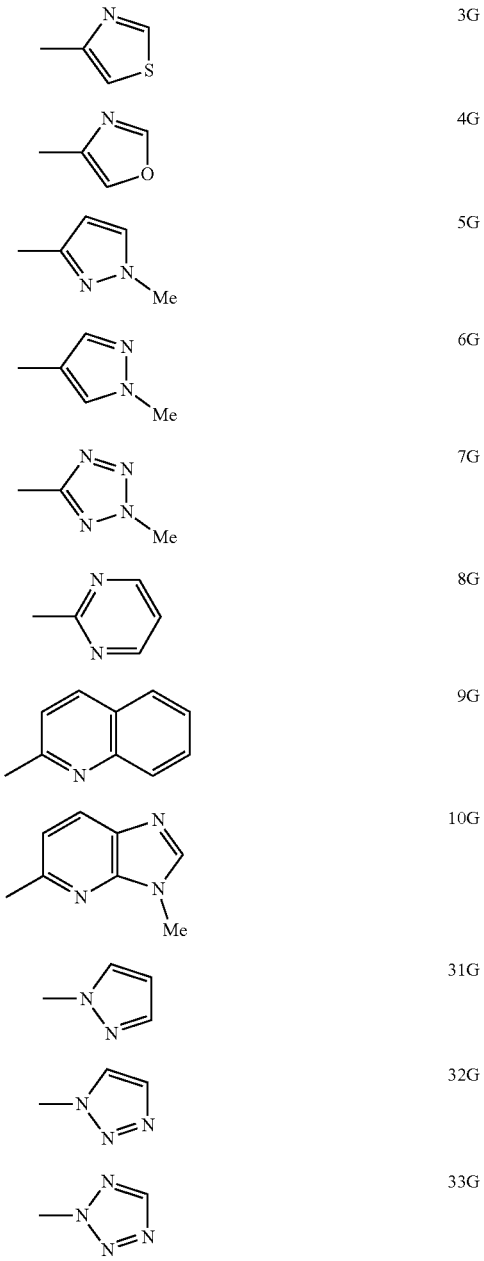

TABLE 8

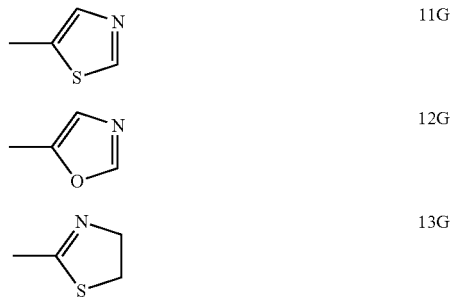

TABLE 8-continued

| | |
|---|---|
| 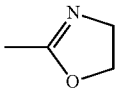 | 14G |
| 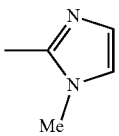 | 15G |
| 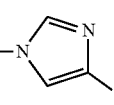 | 16G |
| 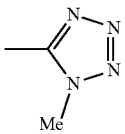 | 17G |
| 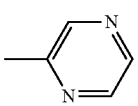 | 18G |
| 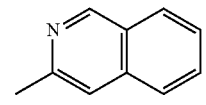 | 19G |
| 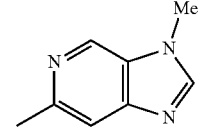 | 20G |
| 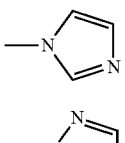 | 34G |
| 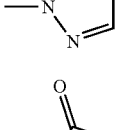 | 35G |
| 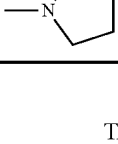 | 36G |

TABLE 9

| | |
|---|---|
| 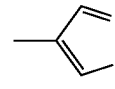 | 21G |
| 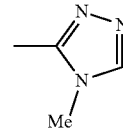 | 22G |
| 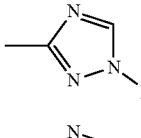 | 23G |

TABLE 9-continued

| | |
|---|---|
| 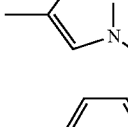 | 24G |
| 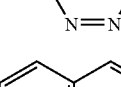 | 25G |
| 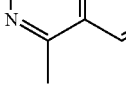 | 26G |
| 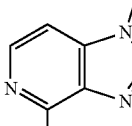 | 27G |
| 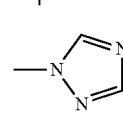 | 28G |
| 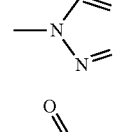 | 29G |
| 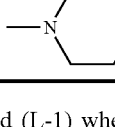 | 30G |
| 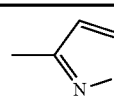 | 37G |
| 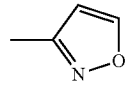 | 38G |
| 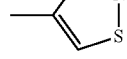 | 39G | a compound (L-1) wherein $A^1$ represents CH, G represents —O-$G^2$, $G^2$ represents 1G, and T represents any one of substituents indicated in Table 1 to Table 6 (hereinafter, referred to as Compound Class SX504).

a compound (L-1) wherein $A^1$ represents CH, G represents —O-$G^2$, $G^2$ represents 2G, and T represents any (hereinafter, referred to as Compound Class SX505).

a compound (L-1) wherein $A^1$ represents CH, G represents —O-$G^2$, $G^2$ represents 3G, and T represents any one of substituents indicated in Table 1 to Table 6 (hereinafter, referred to as Compound Class SX506).

a compound (L-1) wherein $A^1$ represents CH, G represents —O-$G^2$, $G^2$ represents 4G, and T represents any one of substituents indicated in Table 1 to Table 6 (hereinafter, referred to as Compound Class SX507).

a compound (L-1) wherein $A^1$ represents CH, G represents —O-$G^2$, $G^2$ represents 5G, and T represents any one of substituents indicated in Table 1 to Table 6 (hereinafter, referred to as Compound Class SX508).

a compound (L-1) wherein $A^1$ represents CH, G represents —O-$G^2$, $G^2$ represents 6G, and T represents any one of substituents indicated in Table 1 to Table 6 (hereinafter, referred to as Compound Class SX509).

a compound (L-1) wherein $A^1$ represents CH, G represents —O-$G^2$, $G^2$ represents 7G, and T represents any one of substituents indicated in Table 1 to Table 6 (hereinafter, referred to as Compound Class SX510).

a compound (L-1) wherein $A^1$ represents CH, G represents —O-$G^2$, $G^2$ represents 8G, and T represents any one of substituents indicated in Table 1 to Table 6 (hereinafter, referred to as Compound Class SX511).

a compound (L-1) wherein $A^1$ represents CH, G represents —O-$G^2$, $G^2$ represents 9G, and T represents any one of substituents indicated in Table 1 to Table 6 (hereinafter, referred to as Compound Class SX512).

a compound (L-1) wherein $A^1$ represents CH, G represents —O-$G^2$, $G^2$ represents 10G, and T represents any one of substituents indicated in Table 1 to Table 6 (hereinafter, referred to as Compound Class SX513).

a compound (L-1) wherein $A^1$ represents CH, G represents —O-$G^2$, $G^2$ represents 11G, and T represents any one of substituents indicated in Table 1 to Table 6 (hereinafter, referred to as Compound Class SX514).

a compound (L-1) wherein $A^1$ represents CH, G represents —O-$G^2$, $G^2$ represents 12G, and T represents any one of substituents indicated in Table 1 to Table 6 (hereinafter, referred to as Compound Class SX515).

a compound (L-1) wherein $A^1$ represents CH, G represents —O-$G^2$, $G^2$ represents 13G, and T represents any one of substituents indicated in Table 1 to Table 6 (hereinafter, referred to as Compound Class SX516).

a compound (L-1) wherein $A^1$ represents CH, G represents —O-$G^2$, $G^2$ represents 14G, and T represents any one of substituents indicated in Table 1 to Table 6 (hereinafter, referred to as Compound Class SX517).

a compound (L-1) wherein $A^1$ represents CH, G represents —O-$G^2$, $G^2$ represents 15G, and T represents any one of substituents indicated in Table 1 to Table 6 (hereinafter, referred to as Compound Class SX518).

a compound (L-1) wherein $A^1$ represents CH, G represents —O-$G^2$, $G^2$ represents 16G, and T represents any one of substituents indicated in Table 1 to Table 6 (hereinafter, referred to as Compound Class SX519).

a compound (L-1) wherein $A^1$ represents CH, G represents —O-$G^2$, $G^2$ represents 17G, and T represents any one of substituents indicated in Table 1 to Table 6 (hereinafter, referred to as Compound Class SX520).

a compound (L-1) wherein $A^1$ represents CH, G represents —O-$G^2$, $G^2$ represents 18G, and T represents any one of substituents indicated in Table 1 to Table 6 (hereinafter, referred to as Compound Class SX521).

a compound (L-1) wherein $A^1$ represents CH, G represents —O-$G^2$, $G^2$ represents 19G, and T represents any one of substituents indicated in Table 1 to Table 6 (hereinafter, referred to as Compound Class SX522).

a compound (L-1) wherein $A^1$ represents CH, G represents —O-$G^2$, $G^2$ represents 20G, and T represents any one of substituents indicated in Table 1 to Table 6 (hereinafter, referred to as Compound Class SX523).

a compound (L-1) wherein $A^1$ represents CH, G represents —O-$G^2$, $G^2$ represents 21G, and T represents any one of substituents indicated in Table 1 to Table 6 (hereinafter, referred to as Compound Class SX5241.

a compound (L-1) wherein $A^1$ represents CH, G represents —O-$G^2$, $G^2$ represents 22G, and T represents any one of substituents indicated in Table 1 to Table 6 (hereinafter, referred to as Compound Class SX525).

a compound (L-1) wherein $A^1$ represents CH, G represents —O-$G^2$, $G^2$ represents 23G, and T represents any one of substituents indicated in Table 1 to Table 6 (hereinafter, referred to as Compound Class SX526).

a compound (L-1) wherein $A^1$ represents CH, G represents —O-$G^2$, $G^2$ represents 24G, and T represents any one of substituents indicated in Table 1 to Table 6 (hereinafter, referred to as Compound Class SX527).

a compound (L-1) wherein $A^1$ represents CH, G represents —O-$G^2$, $G^2$ represents 25G, and T represents any one of substituents indicated in Table 1 to Table 6 (hereinafter, referred to as Compound Class SX528).

a compound (L-1) wherein $A^1$ represents CH, G represents —O-$G^2$, $G^2$ represents 26G, and T represents any one of substituents indicated in Table 1 to Table 6 (hereinafter, referred to as Compound Class SX529).

a compound (L-1) wherein $A^1$ represents CH, G represents —O-$G^2$, $G^2$ represents 27G, and T represents any one of substituents indicated in Table 1 to Table 6 (hereinafter, referred to as Compound Class SX530).

a compound (L-1) wherein $A^1$ represents CH, G represents —O-$G^2$, $G^2$ represents 28G, and T represents any one of substituents indicated in Table 1 to Table 6 (hereinafter, referred to as Compound Class SX531).

a compound (L-1) wherein $A^1$ represents CH, G represents —O-$G^2$, $G^2$ represents 29G, and T represents any one of substituents indicated in Table 1 to Table 6 (hereinafter, referred to as Compound Class SX532).

a compound (L-1) wherein $A^1$ represents CH, G represents —O-$G^2$, $G^2$ represents 30G, and T represents any one of substituents indicated in Table 1 to Table 6 (hereinafter, referred to as Compound Class SX533).

a compound (L-1) wherein $A^1$ represents CH, G represents —O-$G^2$, $G^2$ represents 31G, and T represents any one of substituents indicated in Table 1 to Table 6 (hereinafter, referred to as Compound Class SX534).

a compound (L-1) wherein $A^1$ represents CH, G represents —O-$G^2$, $G^2$ represents 32G, and T represents any one of substituents indicated in Table 1 to Table 6 (hereinafter, referred to as Compound Class SX535).

a compound (L-1) wherein $A^1$ represents CH, G represents —O-$G^2$, $G^2$ represents 33G, and T represents any one of substituents indicated in Table 1 to Table 6 (hereinafter, referred to as Compound Class SX536).

a compound (L-1) wherein $A^1$ represents CH, G represents —O-$G^2$, $G^2$ represents 34G, and T represents any one of substituents indicated in Table 1 to Table 6 (hereinafter, referred to as Compound Class SX537).

a compound (L-1) wherein $A^1$ represents CH, G represents —O-$G^2$, $G^2$ represents 35G, and T represents any one of substituents indicated in Table 1 to Table 6 (hereinafter, referred to as Compound Class SX538).

a compound (L-1) wherein $A^1$ represents CH, G represents —O-$G^2$, $G^2$ represents 36G, and T represents any one of substituents indicated in Table 1 to Table 6 (hereinafter, referred to as Compound Class SX539).

a compound (L-1) wherein $A^1$ represents CH, G represents —O-$G^2$, $G^2$ represents 37G, and T represents any one of substituents indicated in Table 1 to Table 6 (hereinafter, referred to as Compound Class SX540).

a compound (L-1) wherein $A^1$ represents CH, G represents —O-$G^2$, $G^2$ represents 38G, and T represents any one of substituents indicated in Table 1 to Table 6 (hereinafter, referred to as Compound Class SX541).

a compound (L-1) wherein $A^1$ represents CH, G represents —O-$G^2$, $G^2$ represents 39G, and T represents any one of substituents indicated in Table 1 to Table 6 (hereinafter, referred to as Compound Class SX542).

a compound (L-1) wherein $A^1$ represents a nitrogen atom, G represents —O-$G^2$, $G^2$ represents 1G, and T represents any one of substituents indicated in Table 1 to Table 6 (hereinafter, referred to as Compound Class SX543).

a compound (L-1) wherein $A^1$ represents a nitrogen atom, G represents —O-$G^2$, $G^2$ represents 2G, and T represents any one of substituents indicated in Table 1 to Table 6 (hereinafter, referred to as Compound Class SX544).

a compound (L-1) wherein $A^1$ represents a nitrogen atom, G represents —O-$G^2$, $G^2$ represents 3G, and T represents any one of substituents indicated in Table 1 to Table 6 (hereinafter, referred to as Compound Class SX545).

a compound (L-1) wherein $A^1$ represents a nitrogen atom, G represents —O-$G^2$, $G^2$ represents 4G, and T represents any one of substituents indicated in Table 1 to Table 6 (hereinafter, referred to as Compound Class SX546).

a compound (L-1) wherein $A^1$ represents a nitrogen atom, G represents —O-$G^2$, $G^2$ represents 5G, and T represents any one of substituents indicated in Table 1 to Table 6 (hereinafter, referred to as Compound Class SX547).

a compound (L-1) wherein $A^1$ represents a nitrogen atom, G represents —O-$G^2$, $G^2$ represents 6G, and T represents any one of substituents indicated in Table 1 to Table 6 (hereinafter, referred to as Compound Class SX540).

a compound (L-1) wherein $A^1$ represents a nitrogen atom, G represents —O-$G^2$, $G^2$ represents 7G, and T represents any one of substituents indicated in Table 1 to Table 6 (hereinafter, referred to as Compound Class SX549).

a compound (L-1) wherein $A^1$ represents a nitrogen atom, G represents —O-$G^2$, $G^2$ represents 8G, and T represents any one of substituents indicated in Table 1 to Table 6 (hereinafter, referred to as Compound Class SX550).

a compound (L-1) wherein $A^1$ represents a nitrogen atom, G represents —O-$G^2$, $G^2$ represents 9G, and T represents any one of substituents indicated in Table 1 to Table 6 (hereinafter, referred to as Compound Class SX551).

a compound (L-1) wherein $A^1$ represents a nitrogen atom, G represents —O-$G^2$, $G^2$ represents 10G, and T represents any one of substituents indicated in Table 1 to Table 6 (hereinafter, referred to as Compound Class SX552).

a compound (L-1) wherein $A^1$ represents a nitrogen atom, G represents —O-$G^2$, $G^2$ represents 11G, and T represents any one of substituents indicated in Table 1 to Table 6 (hereinafter, referred to as Compound Class SX553).

a compound (L-1) wherein $A^1$ represents a nitrogen atom, G represents —O-$G^2$, $G^2$ represents 12G, and T represents any one of substituents indicated in Table 1 to Table 6 (hereinafter, referred to as Compound Class SX554).

a compound (L-1) wherein $A^1$ represents a nitrogen atom, G represents —O-$G^2$, $G^2$ represents 13G, and T represents any one of substituents indicated in Table 1 to Table 6 (hereinafter, referred to as Compound Class SX555).

a compound (L-1) wherein $A^1$ represents a nitrogen atom, G represents —O-$G^2$, $G^2$ represents 14G, and T represents any one of substituents indicated in Table 1 to Table 6 (hereinafter, referred to as Compound Class SX556).

a compound (L-1) wherein $A^1$ represents a nitrogen atom, G represents —O-$G^2$, $G^2$ represents 15G, and T represents any one of substituents indicated in Table 1 to Table 6 (hereinafter, referred to as Compound Class SX557).

a compound (L-1) wherein $A^1$ represents a nitrogen atom, G represents —O-$G^2$, $G^2$ represents 16G, and T represents any one of substituents indicated in Table 1 to Table 6 (hereinafter, referred to as Compound Class SX558).

a compound (L-1) wherein $A^1$ represents a nitrogen atom, G represents —O-$G^2$, $G^2$ represents 17G, and T represents any one of substituents indicated in Table 1 to Table 6 (hereinafter, referred to as Compound Class SX559).

a compound (L-1) wherein $A^1$ represents a nitrogen atom, G represents —O-$G^2$, $G^2$ represents 18G, and T represents any one of substituents indicated in Table 1 to Table 6 (hereinafter, referred to as Compound Class SX560).

a compound (L-1) wherein $A^1$ represents a nitrogen atom, G represents —O-$G^2$, $G^2$ represents 19G, and T represents any one of substituents indicated in Table 1 to Table 6 (hereinafter, referred to as Compound Class SX561).

a compound (L-1) wherein $A^1$ represents a nitrogen atom, G represents —O-$G^2$, $G^2$ represents 20G, and T Table 6 (hereinafter, referred to as Compound Class SX562).

a compound (L-1) wherein $A^1$ represents a nitrogen atom, G represents —O-$G^2$, $G^2$ represents 21G, and T represents any one of substituents indicated in Table 1 to Table 6 (hereinafter, referred to as Compound Class SX563).

a compound (L-1) wherein $A^1$ represents a nitrogen atom, G represents —O-$G^2$, $G^2$ represents 22G, and T represents any one of substituents indicated in Table 1 to Table 6 (hereinafter, referred to as Compound Class SX564).

a compound (L-1) wherein $A^1$ represents a nitrogen atom, G represents —O-$G^2$, $G^2$ represents 23G, and T represents any one of substituents indicated in Table 1 to Table 6 (hereinafter, referred to as Compound Class SX565).

a compound (L-1) wherein $A^1$ represents a nitrogen atom, G represents —O-$G^2$, $G^2$ represents 24G, and T represents any one of substituents indicated in Table 1 to Table 6 (hereinafter, referred to as Compound Class SX566).

a compound (L-1) wherein $A^1$ represents a nitrogen atom, G represents —O-$G^2$, $G^2$ represents 25G, and T represents any one of substituents indicated in Table 1 to Table 6 (hereinafter, referred to as Compound Class SX567).

a compound (L-1) wherein $A^1$ represents a nitrogen atom, G represents —O-$G^2$, $G^2$ represents 26G, and T represents any one of substituents indicated in Table 1 to Table 6 (hereinafter, referred to as Compound Class SX568).

a compound (L-1) wherein $A^1$ represents a nitrogen atom, G represents —O-$G^2$, $G^2$ represents 27G, and T represents any one of substituents indicated in Table 1 to Table 6 (hereinafter, referred to as Compound Class SX569).

a compound (L-1) wherein $A^1$ represents a nitrogen atom, G represents —O-$G^2$, $G^2$ represents 28G, and T represents any one of substituents indicated in Table 1 to Table 6 (hereinafter, referred to as Compound Class SX570).

a compound (L-1) wherein $A^1$ represents a nitrogen atom, G represents —O-$G^2$, $G^2$ represents 29G, and T represents any one of substituents indicated in Table 1 to Table 6 (hereinafter, referred to as Compound Class SX571).

a compound (L-1) wherein $A^1$ represents a nitrogen atom, G represents —O-$G^2$, $G^2$ represents 30G, and T represents any one of substituents indicated in Table 1 to Table 6 (hereinafter, referred to as Compound Class SX572).

a compound (L-1) wherein $A^1$ represents a nitrogen atom, G represents —O-$G^2$, $G^2$ represents 31G, and T represents any one of substituents indicated in Table 1 to Table 6 (hereinafter, referred to as Compound Class SX573).

a compound (L-1) wherein $A^1$ represents a nitrogen atom, G represents —O-$G^2$, $G^2$ represents 32G, and T represents any one of substituents indicated in Table 1 to Table 6 (hereinafter, referred to as Compound Class SX574).

a compound (L-1) wherein $A^1$ represents a nitrogen atom, G represents —O-$G^2$, $G^2$ represents 33G, and T represents any one of substituents indicated in Table 1 to Table 6 (hereinafter, referred to as Compound Class SX575).

a compound (L-1) wherein $A^1$ represents a nitrogen atom, G represents —O-$G^2$, $G^2$ represents 34G, and T represents any one of substituents indicated in Table 1 to Table 6 (hereinafter, referred to as Compound Class SX576).

a compound (L-1) wherein $A^1$ represents a nitrogen atom, G represents —O-$G^2$, $G^2$ represents 35G, and T represents any one of substituents indicated in Table 1 to Table 6 (hereinafter, referred to as Compound Class SX577).

a compound (L-1) wherein $A^1$ represents a nitrogen atom, G represents —O-$G^2$, $G^2$ represents 36G, and T represents any one of substituents indicated in Table 1 to Table 6 (hereinafter, referred to as Compound Class SX578).

a compound (L-1) wherein $A^1$ represents a nitrogen atom, G represents —O-$G^2$, $G^2$ represents 37G, and T represents any one of substituents indicated in Table 1 to Table 6 (hereinafter, referred to as Compound Class SX579).

a compound (L-1) wherein $A^1$ represents a nitrogen atom, G represents —O-$G^2$, $G^2$ represents 38G, and T represents any one of substituents indicated in Table 1 to Table 6 (hereinafter, referred to as Compound Class SX580).

a compound (L-1) wherein $A^1$ represents a nitrogen atom, G represents —O-$G^2$, $G^2$ represents 39G, and T represents any one of substituents indicated in Table 1 to Table 6 (hereinafter, referred to as Compound Class SX581).

a compound (L-2) wherein $A^1$ represents a nitrogen atom, G represents —O-$G^2$, $G^2$ represents 1G, and T represents any one of substituents indicated in Table 1 to Table 6 (hereinafter, referred to as Compound Class SX582).

a compound (L-2) wherein $A^1$ represents a nitrogen atom, G represents —O-$G^2$, $G^2$ represents 2G, and T represents any one of substituents indicated in Table 1 to Table 6 (hereinafter, referred to as Compound Class SX583).

a compound (L-2) wherein $A^1$ represents a nitrogen atom, G represents —O-$G^2$, $G^2$ represents 3G, and T represents any one of substituents indicated in Table 1 to Table 6 (hereinafter, referred to as Compound Class SX584).

a compound (L-2) wherein $A^1$ represents a nitrogen atom, G represents —O-$G^2$, $G^2$ represents 4G, and T represents any one of substituents indicated in Table 1 to Table 6 (hereinafter, referred to as Compound Class SX585).

a compound (L-2) wherein $A^1$ represents a nitrogen atom, G represents —O-$G^2$, $G^2$ represents 5G, and T represents any one of substituents indicated in Table 1 to Table 6 (hereinafter, referred to as Compound Class SX586).

a compound (L-2) wherein $A^1$ represents a nitrogen atom, G represents —O-$G^2$, $G^2$ represents 6G, and T represents any one of substituents indicated in Table 1 to Table 6 (hereinafter, referred to as Compound Class SX587).

a compound (L-2) wherein $A^1$ represents a nitrogen atom, G represents —O-$G^2$, $G^2$ represents 7G, and T represents any one of substituents indicated in Table 1 to Table 6 (hereinafter, referred to as Compound Class SX588).

a compound (L-2) wherein $A^1$ represents a nitrogen atom, G represents —O-$G^2$, $G^2$ represents 8G, and T represents any one of substituents indicated in Table 1 to Table 6 (hereinafter, referred to as Compound Class SX589).

a compound (L-2) wherein $A^1$ represents a nitrogen atom, G represents —O-$G^2$, $G^2$ represents 9G, and T represents any one of substituents indicated in Table 1 to Table 6 (hereinafter, referred to as Compound Class SX590).

a compound (L-2) wherein $A^1$ represents a nitrogen atom, G represents —O-$G^2$, $G^2$ represents 10G, and T represents any one of substituents indicated in Table 1 to Table 6 (hereinafter, referred to as Compound Class SX591).

a compound (L-2) wherein $A^1$ represents a nitrogen atom, G represents —O-$G^2$, $G^2$ represents 11G, and T represents any one of substituents indicated in Table 1 to Table 6 (hereinafter, referred to as Compound Class SX592).

a compound (L-2) wherein $A^1$ represents a nitrogen atom, G represents —O-$G^2$, $G^2$ represents 12G, and T Table 6 (hereinafter, referred to as Compound Class SX593).

a compound (L-2) wherein $A^1$ represents a nitrogen atom, G represents —O-$G^2$, $G^2$ represents 13G, and T represents any one of substituents indicated in Table 1 to Table 6 (hereinafter, referred to as Compound Class SX594).

a compound (L-2) wherein $A^1$ represents a nitrogen atom, G represents —O-$G^2$, $G^2$ represents 14G, and T represents any one of substituents indicated in Table 1 to Table 6 (hereinafter, referred to as Compound Class SX595).

a compound (L-2) wherein $A^1$ represents a nitrogen atom, G represents —O-$G^2$, $G^2$ represents 15G, and T represents any one of substituents indicated in Table 1 to Table 6 (hereinafter, referred to as Compound Class SX596).

a compound (L-2) wherein $A^1$ represents a nitrogen atom, G represents —O-$G^2$, $G^2$ represents 16G, and T represents any one of substituents indicated in Table 1 to Table 6 (hereinafter, referred to as Compound Class SX597).

a compound (L-2) wherein $A^1$ represents a nitrogen atom, G represents —O-$G^2$, $G^2$ represents 17G, and T represents any one of substituents indicated in Table 1 to Table 6 (hereinafter, referred to as Compound Class SX598).

a compound (L-2) wherein $A^1$ represents a nitrogen atom, G represents —O-$G^2$, $G^2$ represents 18G, and T represents any one of substituents indicated in Table 1 to Table 6 (hereinafter, referred to as Compound Class SX599).

a compound (L-2) wherein $A^1$ represents a nitrogen atom, G represents —O-$G^2$, $G^2$ represents 19G, and T represents any one of substituents indicated in Table 1 to Table 6 (hereinafter, referred to as Compound Class SX600).

a compound (L-2) wherein $A^1$ represents a nitrogen atom, G represents —O-$G^2$, $G^2$ represents 20G, and T represents any one of substituents indicated in Table 1 to Table 6 (hereinafter, referred to as Compound Class SX601).

a compound (L-2) wherein $A^1$ represents a nitrogen atom, G represents —O-$G^2$, $G^2$ represents 21G, and T represents any one of substituents indicated in Table 1 to Table 6 (hereinafter, referred to as Compound Class SX602).

a compound (L-2) wherein $A^1$ represents a nitrogen atom, G represents —O-$G^2$, $G^2$ represents 22G, and T represents any one of substituents indicated in Table 1 to Table 6 (hereinafter, referred to as Compound Class SX603).

a compound (L-2) wherein $A^1$ represents a nitrogen atom, G represents —O-$G^2$, $G^2$ represents 23G, and T represents any one of substituents indicated in Table 1 to Table 6 (hereinafter, referred to as Compound Class SX604).

a compound (L-2) wherein $A^1$ represents a nitrogen atom, G represents —O-$G^2$, $G^2$ represents 24G, and T represents any one of substituents indicated in Table 1 to Table 6 (hereinafter, referred to as Compound Class SX605).

a compound (L-2) wherein $A^1$ represents a nitrogen atom, G represents —O-$G^2$, $G^2$ represents 25G, and T represents any one of substituents indicated in Table 1 to Table 6 (hereinafter, referred to as Compound Class SX606).

a compound (L-2) wherein $A^1$ represents a nitrogen atom, G represents —O-$G^2$, $G^2$ represents 26G, and T represents any one of substituents indicated in Table 1 to Table 6 (hereinafter, referred to as Compound Class SX607).

a compound (L-2) wherein $A^1$ represents a nitrogen atom, G represents —O-$G^2$, $G^2$ represents 27G, and T represents any one of substituents indicated in Table 1 to Table 6 (hereinafter, referred to as Compound Class SX608).

a compound (L-2) wherein $A^1$ represents a nitrogen atom, G represents —O-$G^2$, $G^2$ represents 28G, and T represents any one of substituents indicated in Table 1 to Table 6 (hereinafter, referred to as Compound Class SX609).

a compound (L-2) wherein $A^1$ represents a nitrogen atom, G represents —O-$G^2$, $G^2$ represents 29G, and T represents any one of substituents indicated in Table 1 to Table 6 (hereinafter, referred to as Compound Class SX610).

a compound (L-2) wherein $A^1$ represents a nitrogen atom, G represents —O-$G^2$, $G^2$ represents 30G, and T represents any one of substituents indicated in Table 1 to Table 6 (hereinafter, referred to as Compound Class SX611).

a compound (L-2) wherein $A^1$ represents a nitrogen atom, G represents —O-$G^2$, $G^2$ represents 31G, and T represents any one of substituents indicated in Table 1 to Table 6 (hereinafter, referred to as Compound Class SX612).

a compound (L-2) wherein $A^1$ represents a nitrogen atom, G represents —O-$G^2$, $G^2$ represents 32G, and T represents any one of substituents indicated in Table 1 to Table 6 (hereinafter, referred to as Compound Class SX613).

a compound (L-2) wherein $A^1$ represents a nitrogen atom, G represents —O-$G^2$, $G^2$ represents 33G, and T represents any one of substituents indicated in Table 1 to Table 6 (hereinafter, referred to as Compound Class SX614).

a compound (L-2) wherein $A^1$ represents a nitrogen atom, G represents —O-$G^2$, $G^2$ represents 34G, and T represents any one of substituents indicated in Table 1 to Table 6 (hereinafter, referred to as Compound Class SX615).

a compound (L-2) wherein $A^1$ represents a nitrogen atom, G represents —O-$G^2$, $G^2$ represents 35G, and T represents any one of substituents indicated in Table 1 to Table 6 (hereinafter, referred to as Compound Class SX616).

a compound (L-2) wherein $A^1$ represents a nitrogen atom, G represents —O-$G^2$, $G^2$ represents 36G, and T represents any one of substituents indicated in Table 1 to Table 6 (hereinafter, referred to as Compound Class SX617).

a compound (L-2) wherein $A^1$ represents a nitrogen atom, G represents —O-$G^2$, $G^2$ represents 37G, and T Table 6 (hereinafter, referred to as Compound Class SX618).

a compound (L-2) wherein $A^1$ represents a nitrogen atom, G represents —O-$G^2$, $G^2$ represents 38G, and T represents any one of substituents indicated in Table 1 to Table 6 (hereinafter, referred to as Compound Class SX619).

a compound (L-2) wherein $A^1$ represents a nitrogen atom, G represents —O-$G^2$, $G^2$ represents 39G, and T represents any one of substituents indicated in Table 1 to Table 6 (hereinafter, referred to as Compound Class SX620).

a compound (L-3) wherein $A^1$ represents a nitrogen atom, G represents —O-$G^2$, $G^2$ represents 1G, and T represents any one of substituents indicated in Table 1 to Table 6 (hereinafter, referred to as Compound Class SX62L).

a compound (L-3) wherein $A^1$ represents a nitrogen atom, G represents —O-$G^2$, $G^2$ represents 2G, and T represents any one of substituents indicated in Table 1 to Table 6 (hereinafter, referred to as Compound Class SX622).

a compound (L-3) wherein $A^1$ represents a nitrogen atom, G represents —O-$G^2$, $G^2$ represents 3G, and T represents any one of substituents indicated in Table 1 to Table 6 (hereinafter, referred to as Compound Class SX623).

a compound (L-3) wherein $A^1$ represents a nitrogen atom, G represents —O-$G^2$, $G^2$ represents 4G, and T Table 6 (hereinafter, referred to as Compound Class SX624).

a compound (L-3) wherein $A^1$ represents a nitrogen atom, G represents —O-$G^2$, $G^2$ represents 5G, and T represents any one of substituents indicated in Table 1 to Table 6 (hereinafter, referred to as Compound Class SX625).

a compound (L-3) wherein $A^1$ represents a nitrogen atom, G represents —O-$G^2$, $G^2$ represents 6G, and T represents any one of substituents indicated in Table 1 to Table 6 (hereinafter, referred to as Compound Class SX626).

a compound (L-3) wherein $A^1$ represents a nitrogen atom, G represents —O-$G^2$, $G^2$ represents 7G, and T represents any one of substituents indicated in Table 1 to Table 6 (hereinafter, referred to as Compound Class SX627).

a compound (L-3) wherein $A^1$ represents a nitrogen atom, G represents —O-$G^2$, $G^2$ represents 8G, and T represents any one of substituents indicated in Table 1 to Table 6 (hereinafter, referred to as Compound Class SX628).

a compound (L-3) wherein $A^1$ represents a nitrogen atom, G represents —O-$G^2$, $G^2$ represents 9G, and T represents any one of substituents indicated in Table 1 to Table 6 (hereinafter, referred to as Compound Class SX629).

a compound (L-3) wherein $A^1$ represents a nitrogen atom, G represents —O-$G^2$, $G^2$ represents 10G, and T represents any one of substituents indicated in Table 1 to Table 6 (hereinafter, referred to as Compound Class SX630).

a compound (L-3) wherein $A^1$ represents a nitrogen atom, G represents —O-$G^2$, $G^2$ represents 11G, and T represents any one of substituents indicated in Table 1 to Table 6 (hereinafter, referred to as Compound Class SX631).

a compound (L-3) wherein $A^1$ represents a nitrogen atom, G represents —O-$G^2$, $G^2$ represents 12G, and T represents any one of substituents indicated in Table 1 to Table 6 (hereinafter, referred to as Compound Class SX632).

a compound (L-3) wherein $A^1$ represents a nitrogen atom, G represents —O-$G^2$, $G^2$ represents 13G, and T represents any one of substituents indicated in Table 1 to Table 6 (hereinafter, referred to as Compound Class SX633).

a compound (L-3) wherein $A^1$ represents a nitrogen atom, G represents —O-$G^2$, $G^2$ represents 14G, and T represents any one of substituents indicated in Table 1 to Table 6 (hereinafter, referred to as Compound Class SX634).

a compound (L-3) wherein $A^1$ represents a nitrogen atom, G represents —O-$G^2$, $G^2$ represents 15G, and T represents any one of substituents indicated in Table 1 to Table 6 (hereinafter, referred to as Compound Class SX451).

a compound (L-3) wherein $A^1$ represents a nitrogen atom, G represents —O-$G^2$, $G^2$ represents 16G, and T represents any one of substituents indicated in Table 1 to Table 6 (hereinafter, referred to as Compound Class SX452).

a compound (L-3) wherein $A^1$ represents a nitrogen atom, G represents —O-$G^2$, $G^2$ represents 17G, and T represents any one of substituents indicated in Table 1 to Table 6 (hereinafter, referred to as Compound Class SX490).

a compound (L-3) wherein $A^1$ represents a nitrogen atom, G represents —O-$G^2$, $G^2$ represents 18G, and T represents any one of substituents indicated in Table 1 to Table 6 (hereinafter, referred to as Compound Class SX491).

a compound (L-3) wherein $A^1$ represents a nitrogen atom, G represents —O-$G^2$, $G^2$ represents 19G, and T represents any one of substituents indicated in Table 1 to Table 6 (hereinafter, referred to as Compound Class SX494).

a compound (L-3) wherein $A^1$ represents a nitrogen atom, G represents —O-$G^2$, $G^2$ represents 20G, and T represents any one of substituents indicated in Table 1 to Table 6 (hereinafter, referred to as Compound Class SX495).

a compound (L-3) wherein $A^1$ represents a nitrogen atom, G represents —O-$G^2$, $G^2$ represents 21G, and T represents any one of substituents indicated in Table 1 to Table 6 (hereinafter, referred to as Compound Class SX498).

a compound (L-3) wherein $A^1$ represents a nitrogen atom, G represents —O-$G^2$, $G^2$ represents 22G, and T represents any one of substituents indicated in Table 1 to Table 6 (hereinafter, referred to as Compound Class SX499).

a compound (L-3) wherein $A^1$ represents a nitrogen atom, G represents —O-$G^2$, $G^2$ represents 23G, and T represents any one of substituents indicated in Table 1 to Table 6 (hereinafter, referred to as Compound Class SX502).

a compound (L-3) wherein $A^1$ represents a nitrogen atom, G represents —O-$G^2$, $G^2$ represents 24G, and T represents any one of substituents indicated in Table 1 to Table 6 (hereinafter, referred to as Compound Class SX503).

a compound (L-3) wherein $A^1$ represents a nitrogen atom, G represents —O-$G^2$, $G^2$ represents 25G, and T represents any one of substituents indicated in Table 1 to Table 6 (hereinafter, referred to as Compound Class SX134).

a compound (L-3) wherein $A^1$ represents a nitrogen atom, G represents —O-$G^2$, $G^2$ represents 26G, and T represents any one of substituents indicated in Table 1 to Table 6 (hereinafter, referred to as Compound Class SX135).

a compound (L-3) wherein $A^1$ represents a nitrogen atom, G represents —O-$G^2$, $G^2$ represents 27G, and T represents any one of substituents indicated in Table 1 to Table 6 (hereinafter, referred to as Compound Class SX138).

a compound (L-3) wherein $A^1$ represents a nitrogen atom, G represents —O-$G^2$, $G^2$ represents 28G, and T represents any one of substituents indicated in Table 1 to Table 6 (hereinafter, referred to as Compound Class SX139).

a compound (L-3) wherein $A^1$ represents a nitrogen atom, G represents —O-$G^2$, $G^2$ represents 29G, and T Table 6 (hereinafter, referred to as Compound Class SX142).

a compound (L-3) wherein $A^1$ represents a nitrogen atom, G represents —O-$G^2$, $G^2$ represents 30G, and T represents any one of substituents indicated in Table 1 to Table 6 (hereinafter, referred to as Compound Class SX143).

a compound (L-3) wherein $A^1$ represents a nitrogen atom, G represents —O-$G^2$, $G^2$ represents 31G, and T represents any one of substituents indicated in Table 1 to Table 6 (hereinafter, referred to as Compound Class SX146).

a compound (L-3) wherein $A^1$ represents a nitrogen atom, G represents —O-$G^2$, $G^2$ represents 32G, and T represents any one of substituents indicated in Table 1 to Table 6 (hereinafter, referred to as Compound Class SX147).

a compound (L-3) wherein $A^1$ represents a nitrogen atom, G represents —O-$G^2$, $G^2$ represents 33G, and T represents any one of substituents indicated in Table 1 to Table 6 (hereinafter, referred to as Compound Class SX185).

a compound (L-3) wherein $A^1$ represents a nitrogen atom, G represents —O-$G^2$, $G^2$ represents 34G, and T represents any one of substituents indicated in Table 1 to Table 6 (hereinafter, referred to as Compound Class SX186).

a compound (L-3) wherein $A^1$ represents a nitrogen atom, G represents —O-$G^2$, $G^2$ represents 35G, and T represents any one of substituents indicated in Table 1 to Table 6 (hereinafter, referred to as Compound Class SX189).

a compound (L-3) wherein $A^1$ represents a nitrogen atom, G represents —O-$G^2$, $G^2$ represents 36G, and T represents any one of substituents indicated in Table 1 to Table 6 (hereinafter, referred to as Compound Class SX190).

a compound (L-3) wherein $A^1$ represents a nitrogen atom, G represents —O-$G^2$, $G^2$ represents 37G, and T represents any one of substituents indicated in Table 1 to Table 6 (hereinafter, referred to as Compound Class SX193).

a compound (L-3) wherein $A^1$ represents a nitrogen atom, G represents —O-$G^2$, $G^2$ represents 38G, and T represents any one of substituents indicated in Table 1 to Table 6 (hereinafter, referred to as Compound Class SX194).

a compound (L-3) wherein $A^1$ represents a nitrogen atom, G represents —O-$G^2$, $G^2$ represents 39G, and T represents any one of substituents indicated in Table 1 to Table 6 (hereinafter, referred to as Compound Class SX197).

a compound (L-4) wherein $A^1$ represents a nitrogen atom, G represents —O-$G^2$, $G^2$ represents 1G, and T represents any one of substituents indicated in Table 1 to Table 6 (hereinafter, referred to as Compound Class SX198).

a compound (L-4) wherein $A^1$ represents a nitrogen atom, G represents —O-$G^2$, $G^2$ represents 2G, and T represents any one of substituents indicated in Table 1 to Table 6 (hereinafter, referred to as Compound Class SX236).

a compound (L-4) wherein $A^1$ represents a nitrogen atom, G represents —O-$G^2$, $G^2$ represents 3G, and T represents any one of substituents indicated in Table 1 to Table 6 (hereinafter, referred to as Compound Class SX237).

a compound (L-4) wherein $A^1$ represents a nitrogen atom, G represents —O-$G^2$, $G^2$ represents 4G, and T represents any one of substituents indicated in Table 1 to Table 6 (hereinafter, referred to as Compound Class SX240).

a compound (L-4) wherein $A^1$ represents a nitrogen atom, G represents —O-$G^2$, $G^2$ represents 5G, and T represents any one of substituents indicated in Table 1 to Table 6 (hereinafter, referred to as Compound Class SX241).

a compound (L-4) wherein $A^1$ represents a nitrogen atom, G represents —O-$G^2$, $G^2$ represents 6G, and T represents any one of substituents indicated in Table 1 to Table 6 (hereinafter, referred to as Compound Class SX244).

a compound (L-4) wherein $A^1$ represents a nitrogen atom, G represents —O-$G^2$, $G^2$ represents 7G, and T represents any one of substituents indicated in Table 1 to Table 6 (hereinafter, referred to as Compound Class SX245).

a compound (L-4) wherein $A^1$ represents a nitrogen atom, G represents —O-$G^2$, $G^2$ represents 8G, and T represents any one of substituents indicated in Table 1 to Table 6 (hereinafter, referred to as Compound Class SX248).

a compound (L-4) wherein $A^1$ represents a nitrogen atom, G represents —O-$G^2$, $G^2$ represents 9G, and T represents any one of substituents indicated in Table 1 to Table 6 (hereinafter, referred to as Compound Class SX249).

a compound (L-4) wherein $A^1$ represents a nitrogen atom, G represents —O-$G^2$, $G^2$ represents 10G, and T represents any one of substituents indicated in Table 1 to Table 6 (hereinafter, referred to as Compound Class SX287).

a compound (L-4) wherein $A^1$ represents a nitrogen atom, G represents —O-$G^2$, $G^2$ represents 11G, and T represents any one of substituents indicated in Table 1 to Table 6 (hereinafter, referred to as Compound Class SX288).

a compound (L-4) wherein $A^1$ represents a nitrogen atom, G represents —O-$G^2$, $G^2$ represents 12G, and T represents any one of substituents indicated in Table 1 to Table 6 (hereinafter, referred to as Compound Class SX291).

a compound (L-4) wherein $A^1$ represents a nitrogen atom, G represents —O-$G^2$, $G^2$ represents 13G, and T represents any one of substituents indicated in Table 1 to Table 6 (hereinafter, referred to as Compound Class SX292).

a compound (L-4) wherein $A^1$ represents a nitrogen atom, G represents —O-$G^2$, $G^2$ represents 14G, and T represents any one of substituents indicated in Table 1 to Table 6 (hereinafter, referred to as Compound Class SX295).

a compound (L-4) wherein $A^1$ represents a nitrogen atom, G represents —O-$G^2$, $G^2$ represents 15G, and T represents any one of substituents indicated in Table 1 to Table 6 (hereinafter, referred to as Compound Class SX296).

a compound (L-4) wherein $A^1$ represents a nitrogen atom, G represents —O-$G^2$, $G^2$ represents 16G, and T represents any one of substituents indicated in Table 1 to Table 6 (hereinafter, referred to as Compound Class SX299).

a compound (L-4) wherein $A^1$ represents a nitrogen atom, G represents —O-$G^2$, $G^2$ represents 17G, and T represents any one of substituents indicated in Table 1 to Table 6 (hereinafter, referred to as Compound Class SX300).

a compound (L-4) wherein $A^1$ represents a nitrogen atom, G represents —O-$G^2$, $G^2$ represents 18G, and T represents any one of substituents indicated in Table 1 to Table 6 (hereinafter, referred to as Compound Class SX337).

a compound (L-4) wherein $A^1$ represents a nitrogen atom, G represents —O-$G^2$, $G^2$ represents 19G, and T represents any one of substituents indicated in Table 1 to Table 6 (hereinafter, referred to as Compound Class SX338).

a compound (L-4) wherein $A^1$ represents a nitrogen atom, G represents —O-$G^2$, $G^2$ represents 20G, and T represents any one of substituents indicated in Table 1 to Table 6 (hereinafter, referred to as Compound Class SX341).

a compound (L-4) wherein $A^1$ represents a nitrogen atom, G represents —O-$G^2$, $G^2$ represents 21G, and T Table 6 (hereinafter, referred to as Compound Class SX342).

a compound (L-4) wherein $A^1$ represents a nitrogen atom, G represents —O-$G^2$, $G^2$ represents 22G, and T represents any one of substituents indicated in Table 1 to Table 6 (hereinafter, referred to as Compound Class SX345).

a compound (L-4) wherein $A^1$ represents a nitrogen atom, G represents —O-$G^2$, $G^2$ represents 23G, and T represents any one of substituents indicated in Table 1 to Table 6 (hereinafter, referred to as Compound Class SX346).

a compound (L-4) wherein $A^1$ represents a nitrogen atom, G represents —O-$G^2$, $G^2$ represents 24G, and T represents any one of substituents indicated in Table 1 to Table 6 (hereinafter, referred to as Compound Class SX349).

a compound (L-4) wherein $A^1$ represents a nitrogen atom, G represents —O-$G^2$, $G^2$ represents 25G, and T represents any one of substituents indicated in Table 1 to Table 6 (hereinafter, referred to as Compound Class SX350).

a compound (L-4) wherein $A^1$ represents a nitrogen atom, G represents —O-$G^2$, $G^2$ represents 26G, and T represents any one of substituents indicated in Table 1 to Table 6 (hereinafter, referred to as Compound Class SX388).

a compound (L-4) wherein $A^1$ represents a nitrogen atom, G represents —O-$G^2$, $G^2$ represents 27G, and T represents any one of substituents indicated in Table 1 to Table 6 (hereinafter, referred to as Compound Class SX389).

a compound (L-4) wherein $A^1$ represents a nitrogen atom, G represents —O-$G^2$, $G^2$ represents 28G, and T represents any one of substituents indicated in Table 1 to Table 6 (hereinafter, referred to as Compound Class SX392).

a compound (L-4) wherein $A^1$ represents a nitrogen atom, G represents —O-$G^2$, $G^2$ represents 29G, and T represents any one of substituents indicated in Table 1 to Table 6 (hereinafter, referred to as Compound Class SX393).

a compound (L-4) wherein $A^1$ represents a nitrogen atom, G represents —O-$G^2$, $G^2$ represents 30G, and T represents any one of substituents indicated in Table 1 to Table 6 (hereinafter, referred to as Compound Class SX396).

a compound (L-4) wherein $A^1$ represents a nitrogen atom, G represents —O-$G^2$, $G^2$ represents 31G, and T represents any one of substituents indicated in Table 1 to Table 6 (hereinafter, referred to as Compound Class SX397).

a compound (L-4) wherein $A^1$ represents a nitrogen atom, G represents —O-$G^2$, $G^2$ represents 32G, and T represents any one of substituents indicated in Table 1 to Table 6 (hereinafter, referred to as Compound Class SX400).

a compound (L-4) wherein $A^1$ represents a nitrogen atom, G represents —O-$G^2$, $G^2$ represents 33G, and T represents any one of substituents indicated in Table 1 to Table 6 (hereinafter, referred to as Compound Class SX401).

a compound (L-4) wherein $A^1$ represents a nitrogen atom, G represents —O-$G^2$, $G^2$ represents 34G, and T represents any one of substituents indicated in Table 1 to Table 6 (hereinafter, referred to as Compound Class SX439).

a compound (L-4) wherein $A^1$ represents a nitrogen atom, G represents —O-$G^2$, $G^2$ represents 35G, and T represents any one of substituents indicated in Table 1 to Table 6 (hereinafter, referred to as Compound Class SX440).

a compound (L-4) wherein $A^1$ represents a nitrogen atom, G represents —O-$G^2$, $G^2$ represents 36G, and T represents any one of substituents indicated in Table 1 to Table 6 (hereinafter, referred to as Compound Class SX443).

a compound (L-4) wherein $A^1$ represents a nitrogen atom, G represents —O-$G^2$, $G^2$ represents 37G, and T represents any one of substituents indicated in Table 1 to Table 6 (hereinafter, referred to as Compound Class SX444).

a compound (L-4) wherein $A^1$ represents a nitrogen atom, G represents —O-$G^2$, $G^2$ represents 38G, and T represents any one of substituents indicated in Table 1 to Table 6 (hereinafter, referred to as Compound Class SX447).

a compound (L-4) wherein $A^1$ represents a nitrogen atom, G represents —O-$G^2$, $G^2$ represents 39G, and T represents any one of substituents indicated in Table 1 to Table 6 (hereinafter, referred to as Compound Class SX448).

The compound of the present invention may be mixed or combined with one or more ingredients selected from a group consisting of the following Group (a), Group (b), Group (c), Group (d), and Group (e) (hereinafter, referred to as "Present ingredient").

The above-mentioned mixing or combining represents a use of the Present compound and the Present ingredient at same time, separately or at certain intervals.

When the Present compound and the present ingredient are used at the same time, the Present compound and the Present ingredient may be contained in separate formulations respectively, or may be contained in the same one formulation.

One aspect of the present invention is a composition comprising one or more ingredients selected from Group (a), Group (b), Group (c), Group (d) and Group (e) (that is, Present ingredient) as well as the Present compound.

Group (a) represents an insecticidal ingredient group, a miticidal ingredient group, or a nematicidal ingredient group, which is selected from the group consisting of the following sub group a-1 to sub group a-10.

Sub group a-1: Carbamate acetylcholinesterase (AChE) inhibitors

Sub group a-2: Organophosphorus acetylcholinesterase (AChE) inhibitors

Sub group a-3: GABA-gated chloride channel blockers

Sub group a-4: GABA-gated chloride channel allosteric modulators

Sub group a-5: Sodium channel modulators

Sub group a-6: Nicotinic acetylcholine receptor (nAChR) competitive modulators

Sub group a-7: Ryanodine receptor modulators

Sub group a-8: Microbial materials

Sub group a-9: Nematicidal ingredients

Sub group a-10: The other group as insecticidal active ingredients and miticidal active ingredients Group (b) represents a fungicidal active ingredient group selected from the group consisting of the following sub group b-1 to sub group b-18.

Sub group b-1: PA fungicides (Phenyl amide)
Sub group b-2: NBC fungicides (methyl benzimidazole carbamate)
Sub group b-3: Thiazole carboxamides
Sub group b-4: SDHI (Succinate dehydrogenase inhibitors)
Sub group b-5: QoI fungicides (Qo Inhibitors)
Sub group b-6: QiI fungicides (Qi Inhibitors)
Sub group b-7: Thiophene carboxamides
Sub group b-8: AP fungicides (Anilinopyrimidine)
Sub group b-9: PP fungicides (Phenylpyrrole)
Sub group b-10: AH fungicides (Aromatic hydrocarbons)
Sub group b-11: DMI fungicides (Demethylation inhibitors)
Sub group b-12: CCA fungicides (Carboxylic acid amide)
Sub group b-13: Piperidinyl thiazole isoxazoline
Sub group b-14: Tetrazolyl oxime
Sub group b-15: Dithiocarbamate
Sub group b-16: Phthalimide
Sub group b-17: Microbial fungicides
Sub group b-18: Other fungicides Group (c) represents a plant growth modulating ingredients group selected from the group consisting of the following sub group c-1, sub group c-2, and sub group c-3.
Sub group c-1: Plant growth modulating compounds
Sub group c-2: Mycorrhizal fungi group
Sub group c-3: Root nodule bacteria group Group (d) represents a phytotoxicity-reducing ingredient group which reduce a phytotoxicity of a crop when it is used by mixing the other agents.

Group (e) represents a synergist group which strengthen an efficacy of the other agent when it is used by mixing with the agent.

The composition comprising the above-mentioned present ingredient and the present compound can exert an effect of the composition depending on the content(s) or the content ratio of the above-mentioned present ingredient(s) or the above-mentioned present compound in the above-mentioned composition. Accordingly, the use of the above-mentioned composition may be decided depending on the effect that is produced by the above-mentioned composition. The above-mentioned composition may have one or two or more applied use.

One embodiment of the above-mentioned composition is an agrochemical composition.

Also, another embodiment of the above-mentioned composition is an insecticidal, miticidal or nematicidal composition.

Also, another embodiment of the above-mentioned composition is a fungicidal composition.

Also, another embodiment of the above-mentioned composition is a plant growth modulating composition.

Also, another embodiment of the above-mentioned composition is a phytotoxicity-reducing composition.

Examples of the combination of the Present ingredient and the Present compound are described below. For example, alanycarb+SX means a combination of alanycarb and SX.

The symbol of "SX" represents any one of the present compound selected from the Compound Class $SX_1$ to the Compound Class $SX_{634}$. Also, all of the below-mentioned present ingredient are known ingredients, and are commercially available or can be produced by a known method. If the present ingredient is a bacteria, it is available from the bacterial authority depository. The numerical number in bracket represents a CAS register number.

Examples of the combination of the Present ingredient of the above sub group a-1 and the Present compound:
alanycarb+SX, aldicarb+SX, bendiocarb+SX, benfuracarb+SX, butocarboxim+SX, butoxycarboxim+SX, carbaryl: MAC+SX, carbofuran+SX, carbosulfan+SX, ethiofencarb+SX, fenobucarb: BPMC+SX, formetanate+SX, furathiocarb+SX, isoprocarb: HIPC+SX, methiocarb+SX, methomyl+SX, metolcarb+SX, oxamyl+SX, pirimicarb+SX, propoxur: PHC+SX, thiodicarb+SX, thiofanox+SX, triazamate+SX, trimethacarb+SX, XNC+SX, xylylcarb+SX.

Examples of the combination of the Present ingredient of the above sub group a-2 and the Present compound:
acephate+SX, azamethiphos+SX, azinphos-ethyl+SX, azinphos-methyl+SX, cadusafos+SX, chlorethoxyfos+SX, chlorfenvinphos+SX, chlormephos+SX, chlorpyrifos+SX, chlorpyrifos-methyl+SX, coumaphos+SX, cyanophos: CYAP+SX, demeton-S-methyl+SX, diazinon+SX, dichlorvos: DDVP+SX, dicrotophos+SX, dimethoate+SX, dimethylvinphos+SX, disulfoton+SX, EPN+SX, ethion+SX, ethoprophos+SX, famphur+SX, fenamiphos+SX, fenitrothion: MEP+SX, fenthion: MPP+SX, fosthiazate+SX, heptenophos+SX, imicyafos+SX, isofenphos+SX, isopropyl-O-(methoxyaminothiophosphoryl)salicylate+SX, isoxathion+SX, malathion+SX, mecarbam+SX, methamidophos+SX, methidathion: DMTP+SX, mevinphos+SX, monocrotophos+SX, naled: BRP+SX, omethoate+SX, oxydemeton-methyl+SX, parathion+SX, parathion-methyl+SX, phenthoate: PAP+SX, phorate+SX, phosalone+SX, phosmet: PMP+SX, phosphamidon+SX, phoxim+SX, pirimiphos-methyl+SX, profenofos+SX, propetamphos+SX, prothiofos+SX, pyraclofos+SX, pyridaphenthion+SX, quinalphos+SX, sulfotep+SX, tebupirimfos+SX, temephos+SX, terbufos+SX, tetrachlorvinphos+SX, thiometon+SX, triazophos+SX, trichlorfon: DEP+SX, vamidothion+SX.

Examples of the combination of the Present ingredient of the above sub group a-3 and the Present compound:
ethiprole+SX, fipronil+SX, flufiprole+SX, chlordane+SX, endosulfan+SX, alpha-endosulfan+SX.

Examples of the combination of the Present ingredient of the above sub group a-4 and the Present compound:
afoxolaner+SX, fluralaner+SX, broflanilide+SX, fluxametamide+SX.

Examples of the combination of the Present ingredient of the above sub group a-5 and the Present compound:
acrinathrin+SX, allethrin+SX, bifenthrin+SX, kappa-bifenthrin+SX, bioallethrin+SX, bioresmethrin+SX, cyclopzothrin+SX, cyfluthrin+SX, beta-cyfluthrin+SX, cyhalothrin+SX, gamma-cyhalothrin+SX, lambda-cyhalothrin+SX, cypermethrin+SX, alpha-cypermethrin+SX, beta-cypermethrin+SX, theta-cypermethrin+SX, zeta-cypermethrin+SX, cyphenothrin+SX, deltamethrin+SX, empenthrin+SX, esfenvalerate+SX, etofenprox+SX, fenpropathrin+SX, fenvalerate+SX, flucythrinate+SX, flumethrin+SX, fluvalinate+SX, tau-fluvalinate+SX, halfenprox+SX, heptafluthrin+SX, imiprothrin+SX, kadethrin+SX, meperfluthrin+SX, momfluorothrin+SX, permethrin+SX, phenothrin+SX, prallethrin+SX, pyrethrins+SX, resmethrin+SX, silafluofen+SX, tefluthrin+SX, kappa-tefluthrin+SX, tetramethrin+SX, tetramethylfluthrin+SX, tralomethrin+SX, transfluthrin+SX, benfluthrin+SX, flutenoprox+SX, flumethrin+SX, sigma-cypermethrin+SX, furamethrin+SX, metofluthrin+SX, profluthrin+SX, dimefluthrin+SX, epsilon-metofluthrin+SX, epsilon-momfluorothrin+SX, methoxychlor+SX.

Examples of the combination of the Present ingredient of the above sub group a-6 and the Present compound:

acetamiprid+SX, clothianidin+SX, dinotefuran+SX, imidacloprid+SX, nitenpyram+SX, thiacloprid+SX, thiamethoxam+SX, sulfoxaflor+SX, flupyradifurone+SX, triflumezopyrim+SX, dicloromezotiaz+SX, cycloxaprid+SX, (E)-N-(1-[(6-chloropyridin-3-yl)methyl]pyridine-2(1H)-ylidene)-2,2,2-trifluoroacetamide (1689566-03-7)+SX.

Examples of the combination of the Present ingredient of the above sub group a-7 and the Present compound:

chlorantraniliprole+SX, cyantraniliprole+SX, cycloniliprole+SX, flubendiamide+SX, tetraniliprole+SX, cyhalodiamide+SX, 3-bromo-N-[2,4-dichloro-6-(methylcarbamoyl)phenyl]-1-(35-dichloropyridin-2-yl)-1H-pyrazole-5-carboxamide (1104384-14-6)+SX.

Examples of the combination of the Present ingredient of the above sub group a-8 and the Present compound:

*Beauveria bassiana*+SX, *Beauveria brongniartii*+SX, *Paecilomyces fumosoroseus*+SX, *Paecilomyces lilacinus*+SX, *Paeciloeyces tenuipes*+SX, *Verticillium lecani*+SX, *Arthrobotrys dactyloides*+SX, *Bacillus thuringiensis*+SX, *Bacillus firmus*+SX, *Bacillus megaterium*+SX, *Hirsutella rhossiliensis*+SX, *Hirsutella minnesotensis*+SX, *Monacrosporium phymatopagus*+SX, *Pasteuria nishizawse*+SX, *Pasteuria penetrans*+SX, *Pasteuria usgae*+SX, *Verticillium chlamydosporium*+SX.

Examples of the combination of the Present ingredient of the above sub group a-9 and the Present compound:

abamectin+SX, fluazaindolizine+SX, fluensulfone+SX, fluopyra+SX, tioxazafen+SK.

Examples of the combination of the Present ingredient of the above sub group a-10 and the Present compound:

spinetoram+SX, spinosad+SX, emamectin-benzoate+SX, lepimectin+SX, milbemectin+SX, hydroprene+SX, kinoprene+SX, methoprene+SX, fenoxycarb+SX, pyriproxyfen+SX, methyl bromide+SX, chloropicrin+SX, sulfuryl fluoride+SX, sodium aluminium fluoride or chiolite+SX, borax+SX, boric acid+SX, disodium octaborate+SX, sodium borate+SX, sodium metaborate+SX, tartar emetic+SX, dazomet+SX, metam+SX, pymetrozine+SX, pyrifluquinazone+SX, clofentezine+SX, hexythiazox+SX, diflovidazin+SX, etoxazole+SX, diafenthiuron+SX, azocyclotin+SX, cyhexatin+SX, fenbutatin oxide+SX, propargite+SX, tetraditon+SX, chlorfenapyr+SX, DNOC+SX, sulfluramid+SX, bensultap+SX, cartap+SX, cartap hydrochloride+SX, thiocyclam+SX, thiosultap-disodium+SX, thiosultap-monosodium+SX, bistrifluron+SX, chlorfluazuron+SX, diflubenzuron+SX, fluazuron+SX, flucycloxuron+SX, flufenoxuron+SX, hexaflumuron+SX, lufenuron+SX, novaluron+SX, noviflumuron+SX, teflubenzuron+SX, triflumuron+SX, buprofezin+SX, cyromazine+SX, chromatenozide+SX, halofenozide+SX, methoxyfenozide+SX, tebufenozide+SX, amitraz+SX, hydramethylnon+SX, acequinocyl+SX, fluacrypyrim+SX, bifenazate+SX, fenazaquin+SX, fenpyroximate+SX, pyridaben+SX, pyrimidifen+SX, tebufenpyrad+SX, tolfenpyrad+SX, rotenone+SX, indoxacarb+SX, metaflumizone+SX, spirodiclofen+SX, spiromesifen+SX, spirotetramat+SX, aluminium phosphide+SX, calcium phosphide+SX, phosphine+SX, zinc phosphide+SX, calcium cyanide+SX, potassium cyanide+SX, sodium cyanide+SX, cyenopyrafen+SX, cyflumetofen+SX, pyflubumide+SX, flonicamid+SX, azadirachtin+SX, benzoximate+SX, bromopropylate+SX, chinomethionat+SX, dicofol+SX, pyridalyl+SX, lime sulfur+SX, sulfur+SX, machine oil+SX, nicotine+SX, nicotine-sulfate+SX, afidopyropen+SX, flometoquin+SX, metoxadiazone+SX, pyriminostrobin+SX, N-[3-chloro-1-(pyridin-3-yl)-1H-pyrazol-4-yl]-N-ethyl-3-(3,3,3-trifluoropropylsulfanyl)propanamide (1477919-27-9)+SX, N-[3-chloro-1-(pyridin-3-yl)-1H-pyrazol-4-yl]-N-ethyl-3-(3,3,3-trifluoropropanesulftinyl)propanamide (1477923-37-7)+SX, 5-(1,3-dioxan-2-yl)-4-[4-(trifluoromethyl)benzyloxy]pyridine (1449021-97-9)+SX, 2-[3-(ethanesulfonyl)pyridin-2-yl]-5-(trifluoromethanesulfinyl)benzoxazole (1616678-31-9)+SX, 2-(3-(ethanesulfonyl)pyridin-2-yl)-5-(trifluoromethanesulfonyl)benzoxazole (1616678-32-0)+SX, a compound represented by the following formula:

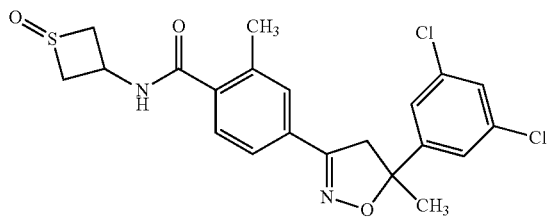 [SMILES: Cc1cc(C2=NOC(C)(c3cc(Cl)cc(Cl)c3)C2)ccc1C(=O)NC1CS(=O)C1]

(1241050-20-3)+SX, a compound represented by the following formula:

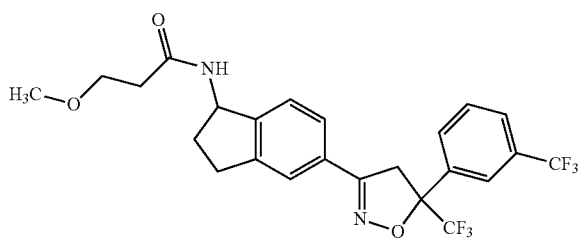 [SMILES: COCCC(=O)NC1CCc2cc(C3=NOC(c4cccc(C(F)(F)F)c4)(C(F)(F)F)C3)ccc21]

(1118626-57-5)+SX, a compound represented by the following formula:

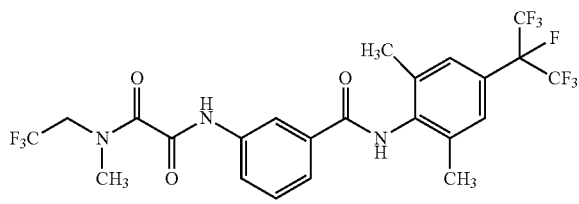 [SMILES: Cc1cc(C(F)(C(F)(F)F)C(F)(F)F)cc(C)c1NC(=O)c1cccc(NC(=O)C(=O)N(C)CC(F)(F)F)c1]

(1239276-34-6)+SX, a compound represented by the following formula:

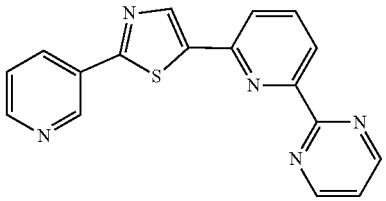 [SMILES: c1cnc(-c2cccc(-c3cnc(-c4cccnc4)s3)n2)nc1]

(1204608-98-9)+SX, a compound represented by the following formula:

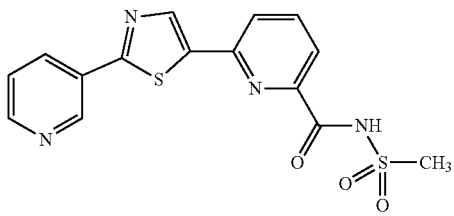 [SMILES: CS(=O)(=O)NC(=O)c1cccc(-c2cnc(-c3cccnc3)s2)n1]

(1353559-47-3)+SX, a compound represented by the following formula:

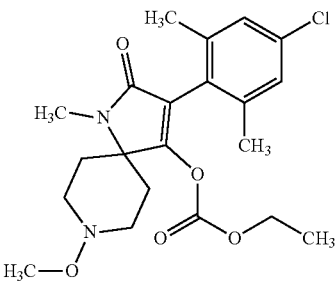 [SMILES: CCOC(=O)OC1=C(c2c(C)cc(Cl)cc2C)C(=O)N(C)C12CCN(OC)CC2]

(1229023-00-0)+SX, a compound represented by the following formula:

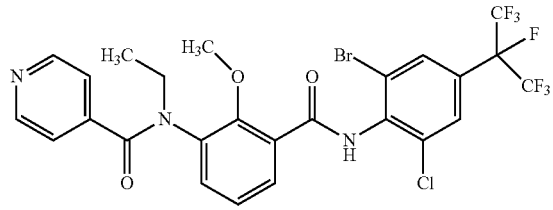 [SMILES: CCN(C(=O)c1ccncc1)c1cccc(C(=O)Nc2c(Cl)cc(C(F)(C(F)(F)F)C(F)(F)F)cc2Br)c1OC]

(1429513-53-0)+SX, a compound represented by the following formula:

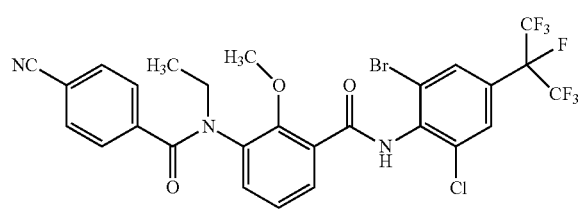 [SMILES: CCN(C(=O)c1ccc(C#N)cc1)c1cccc(C(=O)Nc2c(Cl)cc(C(F)(C(F)(F)F)C(F)(F)F)cc2Br)c1OC]

(1609007-65-9)+SX, a compound represented by the following formula:

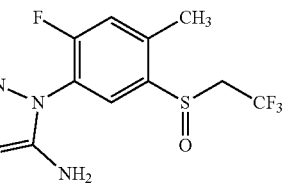

(885026-50-6)+SX, a compound represented by the following formula:

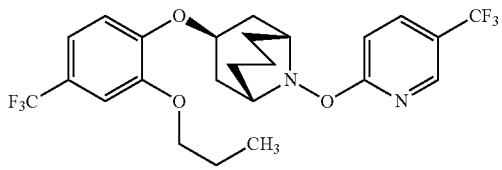 [SMILES: CCCOc1cc(C(F)(F)F)ccc1O[C@H]1C[C@H]2CCC[C@@H](C1)N2Oc1ccc(C(F)(F)F)cn1]

(1332838-17-1)+SX,

Examples of the combination of the Present active ingredient of the above sub group b-1 and the Present compound:
benalaxyl+SX, benalaxyl-M+SX, furalaxyl+SX, metalaxyl+SX, metalaxyl-M+SX, oxadixyl+SX, ofurace+SX.

Examples of the combination of the Present active ingredient of the above sub group b-2 and the Present compound:
benomyl+SX, carbendazim+SX, fuberidazole+SX, thiabendazole+SX, thiophanate+SX, thiophanate-methyl+SX.

Examples of the combination of the Present active ingredient of the above sub group b-3 and the Present compound:
ethaboxam+SX.

Examples of the combination of the Present active ingredient of the above nub group b-4 and the Present compound:
benodanil+SX, flutolanil+SX, mepronil+SX, isofetamid+SX, fenfuram+SX, carboxin+SX, oxycarboxin+SX, thifluzamide+SX, benzovindiflupyr+SX, bixafen+SX, fluxapyroxad+SX, furametpyr+SX, isopyrazam+SX, penf lufen+SX, penthiopyrad+SX, sedaxane+SX, pydiflumetofen+SX, boscalid+SX, pyraziflumid+SX,
3-difluoromethyl-N-methoxy-1-methyl-N-[((1R)-1-methyl-2-(2,4,6-trichlorophenyl)ethyl)pyrazol-4-carboxamide (1639015-48-7)+SX,
3-difluoromethyl-N-methoxy-1-methyl-N-((1S)-1-methyl-2-(2,4,6-trichlorophenyl)ethyl]pyrazol-4-carboxamide (1639015-49-8)+SX,
N-cyclopropyl-3-(difluoromethyl)-5-fluoro-N-(5-chloro-2-isopropylbenzyl)-1-methyl-1H-pyrazole-4-carboxamide (1255734-28-1)+SX,
3-difluoromethyl-1-methyl-N-(1,1,3-trimethylindan-4-yl) pyrazole-4-carboxamide (141573-94-6)+SX,
3-difluoromethyl-1-methyl-N-[(3R)-1,1,3-trimethylindan-4-yl)pyrazole-4-carboxamide (1352994-67-2)+SX,
3-difluoromethyl-N-(7-fluoro-1,1,3-trimethylindan-4-yl)-1-methylpyrazole-4-carboxamide (1383809-87-7)+SX,
3-difluoromethyl-N4-[(3R)-7-fluoro-1,1,3-trimethylindan-4-yl)-1-methylpyrazole-4-carboxamide (1513466-73-3)+SX.

Examples of the combination of the Present active ingredient of the above sub group b-5 and the Present compound:
azoxystrobin+SX, coumoxystrobin+SX, enoxastrobin+SX, flufenoxystrobin+SX, picoxystrobin+SX, pyraoxystrobin+SX, mandestrobin+SX, pyraclostrobin+SX, pyrametostrobin+SX, triclopyricarb+SX, kresoxim-methyl+SX, trifloxystrobin+SX, dimoxystrobin+SX, fenaminstrobin+

SX, metominostrobin+SX, orysastrobin+SX, famoxadone+SX, fluoxastrobin+SX, fenamidone+SX, pyribencarb+SX.

Examples of the combination of the Present active ingredient of the above sub group b-6 and the Present compound:
cyazofamid+SX, amisulbrom+SX, binapacryl+SX, meptyldinocap+SX, dinocap+SX, fluazinam+SX.

Examples of the combination of the Present active ingredient of the above sub group b-7 and the Present compound:
silthiofam+SX.

Examples of the combination of the Present active ingredient of the above sub group b-8 and the Present compound:
cyprodinil+SX, mepanipyrim+SX, pyrimethanil+SX.

Examples of the combination of the Present active ingredient of the above sub group b-9 and the Present compound:
fenpiclonil+SX, fludioxonil+SX.

Examples of the combination of the Present active ingredient of the above sub group b-10 and the Present compound:
biphenyl+SX, chloroneb+SX, dicloran+SX, quintozene+SX, tecnazene+SX, tolclofos-methyl+SXK.

Examples of the combination of the Present active ingredient of the above sub group b-11 and the Present compound:
azaconazole+SX, bitertanol+SX, bromuconazole+SX, cyproconazole+SX, difenoconazole+SX, diniconazole+SX, diniconazole+SX, epoxiconazole+SX, etaconazole+SX, fenbuconazole+SX, fluquinconazole+SX, flusilazole+SX, flutriafol+SX, hexaconazole+SX, imibenconazole+SX, ipconazole+SX, ipfentrifluconazole+SX, mefentrifluconazole+SX, metconazole+SX, myclobutanil+SX, penconazole+SX, propiconazole+SX, simeconazole+SX, tebuconazole+SX, tetraconazole+SX, triadimefon+SX, triadimenol+SX, triticonazole+SX, prothioconazole+SX, triforine+SX, pyrifenox+SX, pyrisoxazole+SX, fenarimol+SX, nuarimol+SX, imazalil+SX, oxpoconazole+SXK, oxpoconazole fumarate+SX, pefurazoate+SX, prochloraz+SX, triflumizole+SX.

Examples of the combination of the Present active ingredient of the above sub group b-12 and the Present compound:
dimethomorph+SX, flumorph+SX, pyrimorph+SX, benthiavalicarb+SX, benthivalicarb-isopropyl+SX, iprovalicarb+SX, valifenalate+SX, mandipropamid+SX.

Examples of the combination of the Present active ingredient of the above sub group b-13 and the Present compound:
oxathiapiprolin+SX.

Examples of the combination of the Present active ingredient of the above sub group b-14 and the Present compound:
picarbutrazox+SX.

Examples of the combination of the Present active ingredient of the above sub group b-15 and the Present compound:
ferbam+SX, mancozeb+SX, maneb+SX, metiram+SX, propineb+SX, thiram+SX, zineb+SX, ziram+SX.

Examples of the combination of the Present active ingredient of the above sub group b-16 and the Present compound:
captan+SX, captafol+SX, folpet+SX.

Examples of the combination of the Present active ingredient of the above sub group b-17 and the Present compound:
*Agrobacterium radiobactor* strains (such as its 84 strain)+SX, *Bacillus amyloliquefaciens*+SX, *Bacillus amyloliquefaciens* strain QST713+SX, *Bacillus amyloliquefaciens* strain FZB24+SX, *Bacillus amyloliquefaciens* strain MBI600+SX, *Bacillus amyloliquefaciens* strain D747+SX, *Bacillus amyloliquefaciens* strain AT332+SX, *Bacillus amyloliquefaciens* strain PTA4838+SX, *Bacillus pumilus*+SX, *Bacillus simplex* CGF2856 strains (such as its CGF2856 strain)+SX, *Bacillus subtilis*+SX, *Bacillus subtilis* strain QST713+SX, *Bacillus subtilis* strain HAI0404+SX, *Bacillus subtilis* strain Y1336+SX, *Variovorax paradoxus* strains (such as its CGF4526 strain)+SX, *Erwinia carotovora* strains (such as its CGE234M403 strain)+SX, *Pseudomonas fluorescens* strains (such as its G7090 strain)+SX, *Talaroamyces flavus* strains (such as its SAY-Y-94-01 strain)+SX, *Trichoderma atroviride* strains (such as its SKT-1 strain), *Trichoderma harzianum* strains+SX, Harpin protein+SX.

Examples of the combination of the Present active ingredient of the above sub group b-18 and the Present compound:
bupirimate+SX, dimethirimol+SX, ethirimol+SX, hymexazole+SX, octhilinone+SX, oxolinic acid+SX, diethofencarb+SX, zoxamide+SX, pencycuron+SX, fluopicolide+SX, phenamacril+SX, ditlumetorim+SX, tolfenpyrad+SX, fentin acetate+SX, fentin chloride+SX, fentin hydroxide+SX, ametoctradin+SX, blasticidin-S+SX, kasugamycin+SX, streptomycin+SX, oxytetracycline+SX, quinoxyfen+SX, proquinazid+SX, chlozolinate+SX, dimethachlone+SX, iprodione+SX, procymidone+SX, vinclozolin+SX, edifenphos+SX, iprobenfos+SX, pyrazophos+SX, isoprothiolane+SX, etridiazole+SX, iodocarb+SX, propamocarb+SX, prothiocarb+SX, aldimorph+SX, dodemorph+SX, fenpropidin+SX, fenpropimorph+SX, piperalina+SX, spiroxamine+SX, tridemorph+SX, fenhexamid+SX, fenpyrazamine+SX, pyributicarb+SX, naftifine+SX, terbinaf ine+SX, polyoxins+SX, phthalid+SX, pyroquilon+SX, tricyclazole+SX, carpropamid+SX, diclocymet+SX, fenoxanil+SX, tolprocarb+SX, acibenzolar-S-methyl+SX, probenazole+SX, tiadinil+SX, isotianil+SX, laminarin+SX, cynoxanil+SX, fosetyl+SX, teclofthalam+SX, triazoxide+SX, flusulfamuide+SX, diclomezine+SX, methasulfocarb+SX, cyflufenamid+SX, metrafenone+SX, pyriofenone+SX, dodine+SX, flutianil+SX, ferimzone+SX, tebufloquin+SX, validamycin+SX, basic copper chloride+SX, copper (II) hydroxide+SX, basic copper sulphate+SX, Dodecylbenzenesulphonic acid bisethylenediamine copper [II] salt (DBEDC)+SX, organocopper+SX, sulfur+SX, chlorothalonil+SX, dichiofluanid+SX, tolyifluanid+SX, guazatine+SX, iminoctadine+SX, anilazine+SX, dithianon+SX, chinomnethionat+SX, fluozoidide+SX, dipymetitrone+SX, quinofumuelin+SX, dichlobentiazox+SX,
3-chloro-5-phenyl-6-methyl-4-(2,6-difluorophenyl) pyridazine (1358061-55-8)+SX,
fenpicoxamid+SX,
N'-(4-((3-[(4-chlorophenyl)methyl-1,2,4-thiadiazol-5-yl) oxy-2,5-dimethylphenyl)-N-ethyl-N-methylmethaneimidamide (1202781-91-6)+SX,
2-(3-(2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl)-3-chlorophenyl-methanesulfonate (1360819-11-9) 4 SX,
4-(2-bromo-4-fluorophenyl)-N-(2-chloro-6-fluorophenyl)-1,3-dimethyl-1H-pyrazole-5-amine (1362477-26-6)+SX,
2,2-dimethyl-9-fluoro-5-(quinolin-3-yl)-2,3-dihydrobenzo [f][1,4]oxazepine (1207749-50-5) 4 SX,
2-[6-(3-fluoro-4-methoxyphenyl)-5-methylpyridini-2-yl] quinazoline (1257056-97-5)+SX,
5-fluoro-2-[(4-methylphenyl)methoxy]-4-pyrimidineamine (1174376-25-0)+SX,
5-fluoro-4-imino-3-methyl-1-tosyl-3,4-dihydropyrimidine-2(1H)-one (1616664-98-2)+SX, N'-(2,5-dimethyl-4-phenoxyphenyl)-N-ethyl-N-methyl-methanimidamide (1052688-31-9) 4 SX,
N'-{4-[(4,5-dichlorothiazol-2-yl)oxy]-2,5-dimethylphenyl}-N-ethyl-N-methyl-methanimidamide (929908-57-6)+SX,
ethyl (2Z)-3-amino-2-cyano-3-phenylacrylate (39491-78-6)+SX,
N-((2-chlorothiazol-5-yl)methyl)-N-ethyl-6-methoxy-3-nitropyridine-2-amine (1446247-98-8)+SX,
1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX.

Examples of the combination of the Present active ingredient of the above sub group c-1 and the Present compound:
ethephon+SX, chlormequat+SX, chlormequat-chloride+SX, mepiquat+SX, mepiquat-chloride+SX, Gibberellin A3+SX, abscisic acid+SX, Kinetin+SX, benzyladenine+SX, forchlorfenuron+SX, thidiazuron+SX.

Examples of the combination of the Present active ingredient of the above sub group c-2 and the Present compound:
Glomus spp.+SX, Glomus intraradices+SX, Glomus mosseae+SX, Glomus aggregatum+SX, Glomus etunicatum+SX.

Examples of the combination of the Present active ingredient of the above sub group c-3 and the Present compound:
Bradyrhizobium elkani+SX, Bradyrhizobium japonicum+SX, Bradyrhizobium lupini+SX, Rhizobium leguminosarum bv. trifolii+SX, Rhizobium leguminosarum bv. phaseoli+SX, Rhizobium leguminosarum bv. viciae+SX, Sinorhizobium meliloti+SX, Rhizobium spp.+SX.

Examples of the combination of the Present active ingredient of the above sub group d and the Present compound:
benoxacor+SX, cloquintocet-mexyl+SX, cyometrinil+SX, dichlormid+SX, fenchlorazole-ethyl+SX, fenclorm+SX, flurazole+SX, furilazole+SX, mefenpyr-diethyl+SX, MG191 (2-(dichloromethyl)-2-methyl-1,3-dioxolane)+SX, oxabetrinil+SX, allidochlor+SX, isoxadifen-ethyl+SX, cyprosulfamide+SX, fluxofenim+SX, 1,8-naphthalic anhydride+SX, AD-67 (4-(dichloroacetyl)-1-oxa-4-azaspiro[4.5]decane)+SX.

Examples of the combination of the Present active ingredient of the above sub group e and the Present compound:
piperonyl butoxide+SX.

Examples of the harmful arthropods on which the compound of the present invention has efficacies include harmful insects and harmful mites. Specific examples of harmful arthropods include the followings.

Hemiptera Pests:

Delphacidae (for example, *Laodelphax striatellus*, *Nilaparvata lugens*, *Sogatella furcifera*, *Peregrinus maidis*, *Javesella pellucida*, *Perkinsiella saccharicida*, or *Tagosodes orizicolus*);

Cicadellidae (for example, *Nephotettix cincticeps*, *Nephotettix vireacens*, *Nephotettix nigropictus*, *Recilia dorsalis*, *Empoasca onukii*, *Empoasca fabae*, *Dalbulus maidis*, or *Cofana spectra*);

Cercopidae (for example, *Mahanarva posticata*, or *Mahanarva fimbriolata*);

Aphididae (for example, *Aphis fabae*, *Aphis glycinea*, *Aphis goasypii*, *Aphis poal*, *Aphis spiraecola*, *Myzus pericae*, *Brachycaudus helichrysi*, *Brevicoryne brassicae*, Rosy apple aphid (*Dysaphis plantaginea*), *Lipaphis erysimi*, *Macrosiphum euphorbiae*, *Aulacorthum solani*, *Nasonovia ribisnigri*, *Rhopalosiphum padi*, *Rhopalosiphum maidis*, *Toxoptera citricidus*, *Hyalopterus pruni*, *Melanaphis sacchari*, *Tetraneura nigriabdominalis*, *Ceratovacuna lanigera*, or *Eriosoua lanigerum*);

Phylloxeridae (for example, *Daktulosphaira vitifoliae*, Pecan *phylloxera* (*Phylloxera devastatrix*), Pecan leaf *phylloxera* (*Phylloxera notabilis*), or Southern pecan leaf *phylloxera* (*Phylloxera russellae*));

Adelgidae (for example, *Adelges tsugae*, *Adelges piceae*, or *Aphrastasia pectinatae*);

Pentatomidae (for example, *Scotinophara lurida*, Malayan rice black bug (*Scotinophara coarctata*), *Nezara antennata*, *Eysarcoris aeneus*, *Eysarcoris lewisi*, *Eysarcoris venttralis*, *Eysarcoris annamita*, *Halyomorpha halys*, *Nezara viridula*, Brown stink bug (*Euschistus heros*), Red banded stink bug (*Piezodorus guildinii*), *Oebalus pugnax*, *Dichelops melacanthus*);

Cydnidae (for example, Burrower brown bug (*Scaptocoris castanea*));

Alydidae (for example, *Riptortus pedestris*, *Leptocorisa chinensis*, or *Leptocorisa acuta*);

Coreidae (for example, *Cletus punctiger*, or *Leptoglossus australis*);

Lygaeidae (for example, *Caverelius saccharivorus*, *Togo hemipterus*, or *Blissus leucopterus*);

Miridae (for example, *Trigonotylus caelestialium*, *Stenotus rubrovittatus*, *Stenodema calcarata*, or *Lygus lineolaris*);

Aleyrodidae (for example, *Trialeurodes vaporariorum*, *Bemisia tabaci*, *Dialeurodes citri*, *Aleurocanthus spiniferus*, *Aleurocanthus camelliae*, or *Peaelus euryae*);

Diaspididae (for example, *Abgrallaspis cyanophylli*, *Aonidiella aurantii*, *Diaspidioatus perniciosus*, *Pseudaulacaspis pentagona*, *Unaspis yanonensis*, or *Unaspis citri*);

Coccidae (for example, *Ceroplastes rubens*);

Kargarodidae (for example, *Icerya purchasi*, or *Icerya seychellarum*);

Pseudococcidae (for example, *Phenacoccus solani*, *Phenacoccus solenopsis*, *Planococcus kraunhiae*, *Planococcus comstocki*, *Planococcus citri*, *Pseudococcus calceolariae*, *Pseudococcus longispinus*, or *Brevennia rehi*);

Psyllidae (for example, *Deaphorina citri*, *Trioza erytreae*, *Cacopsylla pyrisuga*, *Cacopsylla chinensis*, *Bactericera cockerelli*, or Pear psylla (*Cacopsylla pyricola*));

Tingidae (for example, *Corythucha ciliata*, *Corythucha marmorata*, *Stephanitis nashi*, or *Stephanitis pyrioides*);

Cimicidae (for example, *Cimex lectularius*); and

Cicadidae (for example, Giant Cicada (*Quesada gigas*)).

Lepidoptera

Crambidae (for example, *Chilo suppressalis*, Darkheaded stem borer (*Chilo polychrysus*), White stem borer (*Scirpophaga innotata*), *Scirpophaga incertulas*, *Rupela albina*, *Cnaphalocrocis medinalis*, *Marasmia patnalis*, *Marasmia exigus*, *Notarcha derogata*, *Ostrinia furnacalis*, European corn borer (*Ostrinia nubilalis*), *Hellula undalis*, *Herpetoagramma luctuosale*, *Pediasia teterrellus*, *Nymphula depunctalis*, Sugarcane borer (*Diatraea saccharalis*));

Pyralidae (for example, *Elasmopalpus lignosellus* or *Plodia interpunctella*);

Noctuidae (for example, *Spodoptera litura*, *Spodoptera exigua*, *Mythimna separata*, *Mamestria brassicae*, *Sesamia inferens*, *Spodoptera mauritia*, *Naranga aenescens*, *Spodoptera frugiperda*, *Spodoptera exempta*, *Agrotis ipsilon*, *Autographa nigrisigna*, *Plusia festucae*, Soybean looper (*Chrysodeixis includens*), *Trichopluala* spp., *Heliothis* spp. (for example, *Heliothis virescena*), *Helicoverpa armigera*,

*Helicoverpa* spp. (for example, *Helicoverpa zea*), Velvetbean caterpillar (*Anticarsia gemmatalis*), Cotton leafworm (*Alabama argillacea*), Hop vine borer (*Hydraecia immanis*)), Pieridae (for example, *Pieris rapae*);

Tortricidae (for example, *Grapholita molesta, Grapholita dimorpha, Leguminivora glycinivorella, Matsumuraeses azukivora, Adoxophyes orana fasciata, Adoxophyes honmai, Homona magnanima, Archips fuscocupreanus, Cydia pomonella, Tetramoera schistaceana*, Bean Shoot Borer (*Epinotia aporema*), or Citrus fruit borer (*Ecdytolopha aurantiana*));

Gracillariidae (for example, *Caloptilla theivora*, or *Phyllonorycter ringoniella*);

Carposinidae (for example, *Carposina sasakii*);

Lyonetiidae (for example, Coffee Leaf miner (*Leucoptera coffeela*), *Lyonetia clerkella*, or *Lyonetia prunifolifella*);

Lymantriidae (for example, *Lymantria* spp. (for example, *Lymantria dispar*), or *Euproctis* spp. (for example, *Euproctis pseudoconspersa*));

Pluteliidae (for example, *Plutella xylostella*);

Gelechiidae (for example, *Anarsia lineatella, Helcystogramma triannulellum, Pectinophora gossypiella, Phthorimaea operculella*, or *Tuta absolut*);

Arctiidae (for example, *Hypantria cunea*);

Catniidae (for example, Giant Sugarcane borer (*Telchln licus*));

Cossidae (for example, *Cosus insularis*);

Geometridae (for example, *Ascotis selenaria*);

Limacodidae (for example, *Parasa lepida*);

Stathmopodidae (for example, *Stathmopoda masinisaa*);

Sphingidae (for example, *Acherontia lachesis*);

Sesiidae (for example, *Nokona feralis*);

Heaperiidae (for example, *Parnara guttata*).

Thysanoptera

Thripidae (for example, *Frankliniella occidentalis, Thrips palmi, Scirtothrips dorsalis, Thrips tabaci, Frankliniella intonsa, Stenchaetothrips bifomis*, or *Echinothrips americanus*);

Phlaeothripidae (for example, *Haplothrips aculeatus*).

Diptera

Anthomyiidae (for example, *Delia platura* or *Delia antiqua*);

Ulidiidae (for example, *Tetanops myopaeformis*);

Agromyzidae (for example, *Agromyza oryzae, Liriomyza sativae, Liriomyza trifolli*, or *Chromatoyia horticola*);

Chloropidae (for example, *Chlorops oryzae*);

Tephritidae (for example, *Bactrocera cucurbitae, Bactrocera dorsalis, Bactrocera latifrons, Bactrocera oleae, Bactrocera tryoni*, or *Ceratitis capitata*);

Ephydridae (for example, *Hydrellia griseola, Hydrallia philippina*, or *Hydrellia sasakii*);

Drosophilidae (for example, *Drosophila suzukii*);

Phoridee (for example, *Megaselia spiracularis*);

Psychodidae (for example, *Clogmia albipunctata*);

Sciaridae (for example, *Bradysia difformis*);

Cecidomyiidae (for example, *Mayetiola destructor*, or *Orseolia oryzae*);

Diopsidae (for example, *Diopsis macrophthalma*);

Tipulidae (for example, *Tipula aino*, Common cranefly (*Tipula oleracea*), or European cranefly (*Tipula paludosa*)).

Coleoptera

Chrysomelidae (for example, *Diabrotica virgifera virgifera, Diabrotica undecimpunctata howardi, Diabrotica barberi, Diabrotica virgifera zeae, Diabrotica balteata*, Cucurbit Beetle (*Diabrotica speciosa*), *Cerotoma trifurcata, Oulema melanopus, Aulacophora feaoralis, Phyllotreta striolata*, Cabbage flea beetle (*Phyllotreta cruciferae*), Western black flea beetle (*Phyllotreta pusilla*), Cabbage stem flea beetle (*Psylliodes chrysocephala*), *Leptinotarsa decealineata, Oulema oryzae, Colaspis brunnea, Chaetocnema pulicaria, Chaetocnema confinis, Epitrix cucumeris, Dicladispa armigera*, Grape *Colaspis* (*Colaspis brunnea*), southern corn leaf beetle (*Myochrous denticollis*), *Laccoptera quadrimacu*, or *Epitrix hirtipennis*);

Carabidae (for example, Seedcorn beetle (*Stenolophus lecontei*), or Slender seedcorn beetle (*Clivina impressifrons*));

Scarabaeidae (for example, *Anomala cuprea, Anomala rufocuprea, Anomala albopilosa, Popillia japonica, Heptophylla picea*, European Chafer (*Rhizotrogus majalis*), *Tomarus gibbosus, Holotrichia* spp., or *Phyllophaga* spp. (for example, *Phyllophaga crinita*)), *Diloboderus* spp. (for example, *Diloboderus abderus*));

Curculionidae (*Aracanthus* spp. (for example, *Araecerus coffeae, Cylas formicarius, Euscepes postfasciatus, Hypera postica, Sitophilus zeamais, Echinocnemus squameus, Lissorhoptrus oryzophilus, Rhabdoscelus lineatocollis, Anthonomus grandis, Sphenophorus venatus*, Southern Corn Billbug (*Sphenophorus callosus*), Soybean stalk weevil (*Sternechus subsignatus*), Sugarcane wiivil (*Sphenophorus levis*), *Scepticus griseus, Scepticus uniformis, Zabrotes subfasciatus, Tomicus piniperda*, Coffee Berry Borer (*Hypothenemus hampei*), or *Aracanthus mourei*) or cotton root borer (*Eutinobothrus brasiliensis*);

Tenebrionidae (for example, *Tribolium castaneum*, or *Tribolium confusum*);

Coccinellidae (for example, *Epilachna vigintioctopunctata*);

Bostrychidae (for example, *Lyctus brunneus*);

Ptinidae;

Cerambycidae (for example, *Anoplophora malasiaca*, or *Migdolus fryanus*);

Elateridae (for example, *Melanotus okinawensis, Agriotes fuscicollis, Melanotus legatus, Anchastus* spp., *Conoderus* spp., *Ctenicera* spp., *Limonius* spp., *Aeolus* spp.);

Staphylinidae (for example, *Paederus fuscipes*).

Orthoptera

Acrididae (for example, *Locusta migratoria, Dociostaurus maroccanus, Chortoicetes cerminifera, Nomadacris septemfasciata*, Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearvinged grasshopper (*Camnula pellucida*), *Schistocerca gregaria*, Yellow-winged locust (*Gastrimargus musicus*), Spur-throated locust (*Austracris guttulosaa*), *Oxya yezoensia, Oxya japonica*, or *Patanga succincta*);

Gryllotalpidae (for example, *Gryllotalpa orientalis*);

Gryllidae (for example, *Acheta domesticus*, or *Teleogryllus emma*);

Tettigoniidae (for example, Mormon cricket (*Anabrus simplex*).

Hymenoptera

Tenthredinidae (for example, *Athalia rosae*, or *Athalia japonica*);

*Solenopsis* spp.;

Formicidae (for example, Brown leaf-cutting ant (*Atta capiguara*)).

Blattodea

Blattellidae (for example, *Blattella germanica*);

Blattidae (for example, *Periplaneta fuliginosa, Periplaneta americana, Periplaneta brunnea*, or *Blatta orientalis*), Termitidae (for example, *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticultermes kanmonensis, Nasutitermes takaagoensis, Pericapritermes nitobel, Sinocapritermes mushae,* or *Cornitermes cumulans*).

Acari

Tetranychidae (for example, *Tetranychus urticae, Tetranychus kansawai, Tetranychus evansi, Panonychus citri, Panonychus ulmi,* or *Oligonychus* spp.);

Eriophyidae (for example, *Aculops pelekassi, Phyllocoptruta citri, Aculops lycopersici, Calacarus carinatus, Acaphylla theavagrans, Eriophyes chibaensis, Aculus schlechtendali, Aceria diospyri, Aceria tosichella,* or *Shevtchenkella* sp.);

Tarsonemidae (for example, *Polyphagotarsonemus latus*),

Tenuipalpidae (for exmaple, *Brevipalpus phoenicis*);

Tuckerellidae;

Ixodidae (for example, *Haemaphysalis longicornis, Haemaphysalis flava, Dermacentor taiwaenensis, Dermacentor variabilis, Ixodes ovatus, Zxodes persulcatus, Ixodes scapularis, Amblyomma americanum, Boophilus aicroplus,* or *Rhipicephalus sanguineus*);

Acaridae (for example, *Tyrophagus putrescentiae,* or *Tyrophagus similis*);

Pyroglyphidae (for example, *Dermatophagoides farinae,* or *Dermatophagoides pteronyssinus*);

Cheyletidae (for example, *Cheyletus eruditus, Cheyletus malaccensis, Cheyletus moorei,* or *Cheyletiella yasguri*);

Sarcoptidae (for example, *Otodectes cynotis,* or *Sarcoptes scabiei*);

Demodicidae (for example, *Demodex cania*);

Listrophoridae;

Haplochthoniidae;

Macronyasidae (for example, *Ornithonyssus bacoti,* or *Ornithonyssus sylviarum*);

Dermanyssidae (for example, *Dermanyssus gallinae*);

Trombiculidae (for example, *Leptotrombidium akamushi*).

The composition for controlling harmful arthropods of the present invention comprises the compound of the present invention and an inert active carrier. The composition for controlling harmful arthropods of the present invention is usually prepared by mixing the compound of the present invention with an inert active carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment.

The composition for controlling harmful arthropods of the present invention comprises usually 0.01 to 95% by weight of the compound of the present invention based on the total weights of the composition for controlling harmful arthropods.

Examples of the solid carrier to be used in the formulation include fine powders or granules of clays (for example, kaolin clay, diatomaceous earth, bentonite, Fubasami clay, or acid white clay), dry silica, wet silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea or ammonium chloride) and the others; as well as synthetic resins (for example, polyester resins such as polypropylene, polyacrylonitrile, polymethylmethacrylate and polyethylene terephthalate; nylon resins (for example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for example, acetonitrile or isobutyronitrile); ethers (for example, diisopropyl ether, 1,4-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, DMF or dimethylacetamide); sulfoxides (for example, DMSO); propylene carbonate; and vegetable oils (for example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters: and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture with a usually kneader, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

The method for controlling harmful arthropods of the present invention is conducted by applying an effective amount of the compound of the present invention to a harmful arthropod directly and/or a habitat thereof (for example, plant bodies, soil, an interior of a house, animal bodies). In the method for controlling harmful arthropods of the present invention, the Present compound is usually used in the form of a harmful arthropod controlling composition.

When a composition for controlling harmful arthropods of the present invention is used for controlling harmful arthropods in an agricultural field, the application dose as an amount of the compound of the present invention is usually within a range from 1 to 10,000 g per 10,000 m$^2$. When a composition for controlling harmful arthropods of the present invention is formulated into an emulsifiable concentrate, a wettable powder, or a flowable formulation etc., the composition is usually applied by diluting it with water in such a way that a concentration of the compound of the present invention is within a range from 0.01 to 10,000 pm. The granular formulation, or the dust formulation etc., is usually applied as itself without diluting it.

These formulations or an aqueous dilution thereof can be spared directly to harmful arthropods or plants (such as crops) to be protected from harmful arthropods, and also may be applied to the soil of crop land in order to control harmful arthropods which live there.

Also, the resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the composition for controlling harmful arthropods of the present invention is used to control harmful arthropods that live inside a house, the application dose as an amount of the present compound is usually within a range from 0.01 to 1,000 mg per 1 m$^2$ of an area to be treated, in the case of using it on a planar area. In the case of using it spatially, the application dose as an amount of the present compound is usually within a range from 0.01 to 500 mg per 1 m$^3$ of the space to be treated. When the composition for controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the composition for controlling harmful arthropods of the present invention is used for controlling external parasites of livestock such as cows, horses, pigs, sheep, goats and chickens and small animals such as dogs, cats, rats and mice, the composition of the present invention can be applied to the animals by a known method in the veterinary field. Specifically, when systemic control is intended, the control composition of the present invention is administered to the animals as a tablet, a mixture with feed or a suppository, or by injection (including intramuscular, subcutaneous, intravenous and intraperitoneal injections). On the other hand, when non-systemic control is intended, the composition of the present invention is applied to the animals by means of spraying of the oil solution or aqueous solution, pour-on or spot-on treatment, or washing the animal with a shampoo formulation, or by putting a collar or ear tag made of the resin formulations to the animal. In the case of administering to an animal body, the dose of the Present compound is usually within a range from 0.1 to 1,000 mg per 1 kg of an animal body weight.

EXAMPLES

Hereinafter, the present invention is explained in more detail by using Preparation example, Formulation example, and Test example, however, the present invention should not be limited to these examples.

Firstly, the preparation example of the compound of the present invention is shown.

Preparation Example 1

An intermediate compound represented by the following formula was prepared by using the present compound 94 which was described in WO 2016/121969, according to the method described in Synthetic Communications, 2011, 41, 1852-1857.

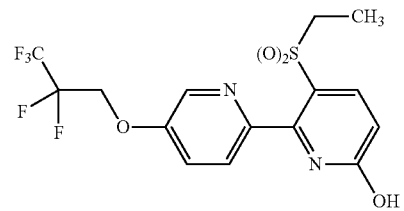

Intermediate Compound 1

$^1$H-NMR (CDCl$_3$) δ: 8.44 (1H, d), 7.99 (1H, d), 7.84 (1H, d), 7.42 (1H, dd), 6.58 (1H, d), 4.56 (2H, t), 3.34 (2H, q), 1.29 (3H, t).

Preparation Example 2

A mixture of the intermediate compound 1 (30 g), acetic acid 60 mL, and N-bromosuccinimide 14 g was stirred at 70° C. for 3 hours. To the resulting mixture were added successively a 12N (normal) sodium hydroxide aqueous solution 20 mL and a saturated sodium hydrogen sulfite aqueous solution 20 mL. The precipitated out solids were filtered, and the obtained solids were washed with water, and dried under reduced pressure to obtain the intermediate compound 2 represented by the following formula 35 g.

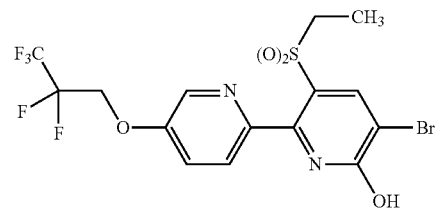

Intermediate Compound 2

¹H-NMR (CDCl₃) δ: 8.46 (1H, d), 8.40 (1H, s), 8.01 (1H, d), 7.42 (1H, dd), 4.56 (2H, dd), 3.33-3.23 (2H, br m), 1.29 (3H, t).

Preparation Example 3

A mixture of the intermediate compound 2 35 g and phosphorus oxychloride 60 mL was stirred at 100° C. for 9 hours. The resulting mixture was concentrated under reduced pressure, and to the resulting residue was added a saturated sodium hydrogen carbonate aqueous solution, and the mixture was extracted with ethyl acetate. The resulting organic layers were dried over anhydrous sodium sulfate, and concentrated under reduced pressure to obtain as a crude product the intermediate compound 3 represented by the following formula 35 g.

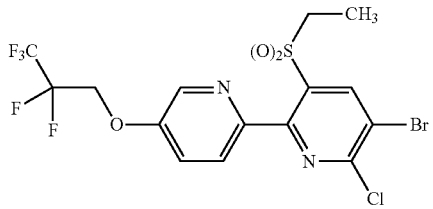

Intermediate Compound 3

¹H-NMR (CDCl₃) δ: 8.68 (1H, s), 8.37 (1H, d), 7.93 (1H, d), 7.42 (1H, dd), 4.54 (2H, t), 3.96 (2H, q), 1.41 (3H, t).

Preparation Example 4

A mixture of the intermediate compound 3 as a crude product 35 g which was obtained by the preparation example 3, hydrazine monohydrate 17.5 g, diisopropylethylamine 25 mL, and THF 300 mL was stirred at 50° C. for 8 hours. The resulting mixture was concentrated under reduced pressure. To the resulting residue was added water, and the mixture was extracted with ethyl acetate. The resulting organic layers were dried over anhydrous sodium sulfate, and concentrated under reduced pressure to obtain as a crude product the intermediate compound 4 represented by the following formula 33 g.

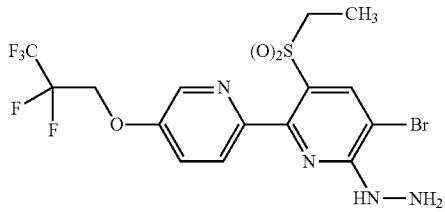

Intermediate Compound 4

¹H-NMR (CDCl₃) δ: 8.34 (1H, d), 8.34 (1H, s), 7.78 (1H, d), 7.39 (2H, dd), 6.77 (1H, s), 4.57-4.51 (2H, m), 3.76 (2H, q), 1.36 (3H, t).

Preparation Example 5

A mixture of the intermediate compound 4 as a crude product 33 g which was obtained by the preparation example 4, p-toluenesulfonic acid chloride 17 g, pyridine 7.0 mL, and acetonitrile 300 mL was stirred at room temperature for 12 hours. The resulting mixture was concentrated, and to the resulting residue was added ethylene glycol 72 mL. To the mixture was added an 8N (normal) sodium hydroxide aqueous solution 40 mL, and the mixture was stirred at 80° C. for 10 hours. The resulting mixture was extracted with ethyl acetate. The resulting organic layers were dried over anhydrous sodium sulfate, and concentrated under reduced pressure. The resulting residue was subjected to a silica gel column chromatography to obtain the intermediate compound 5 represented by the following formula 16 g.

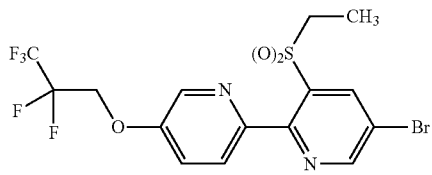

Intermediate Compound 5

¹H-NMR (CDCl₃) δ: 8.90 (1H, d), 8.62 (1H, d), 8.37 (1H, d), 7.88 (1H, d), 7.42 (1H, dd), 4.54 (2H, t), 3.94 (2H, q), 1.40 (3H, t).

Preparation Example 6

A mixture of the intermediate compound 5 300 mg, cyclopropylboronic acid 160 mg, tri-potassium phosphate, n-hydrate 550 mg, [1,1'-bis(diphenylphoshino)ferrocene]dichloropalladium (II) 23 mg, water 0.3 mL, and 1,2-dimethoxymethane 3 mL was stirred at 100° C. for 5 hours. To the resulting mixture was added water, and the resulting mixture was extracted with ethyl acetate. The resulting organic layers were dried over anhydrous sodium sulfate, and concentrated under reduced pressure. The resulting residue was subjected to a silica gel column chromatography to obtain the present compound 1 represented by the following formula 230 mg.

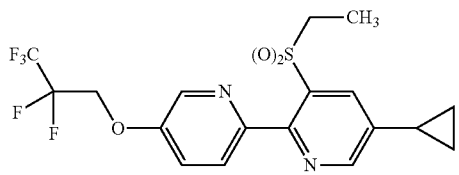

Present Compound 1

¹H-NMR (CDCl₃) δ: 8.63 (1H, d), 8.35 (1H, d), 8.05 (1H, d), 7.81 (1H, d), 7.40 (1H, dd), 4.53 (2H, t), 3.86 (2H, q), 2.10-2.01 (1H, m), 1.36 (3H, t), 1.21-1.14 (2H, m), 0.90-0.85 (2H, m).

Preparation Example 7-1

1-(Ethanesulfonyl)propane-2-one 8.15 g was added to a mixture of magnesium chloride 5.16 g, triethylamine 9.15 g, and THF 24 g at room temperature, and the mixture was stirred for 1 hour. To the mixture were added dropwise a mixture of 5-chloropyrazine-2-carbonylchloride 8.0 g and THF 8 g over 30 minutes, and the mixture was stirred at room temperature for 3 hours. To the mixture was added 13% hydrochloric acid 25 g, and the mixture was stirred for additional 17 hours. The resulting mixture was extracted with toluene 40 g, and the organic layers were washed with water, and concentrated under reduced pressure. The resulting residue was recrystallized with toluene 8 g to obtain the intermediate compound 6 represented by the following formula 9.16 g.

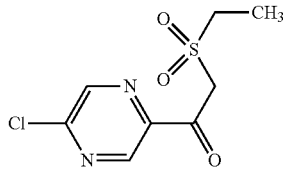

Intermediate Compound 6
$^1$H-NMR (CDCl$_3$) δ: 9.08 (1H, d), 8.70 (1H, d), 4.89 (2H, s), 3.29 (2H, q), 1.48 (3H, t)

Preparation Example 7-2

The compound which was prepared according to the method described in the preparation example 7-1, and its physical property values are shown below.

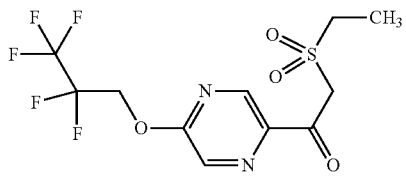 [SMILES: CCS(=O)(=O)CC(=O)c1cnc(OCC(F)(F)C(F)(F)F)cn1]

Intermediate Compound 7
$^1$H-NMR (CDCl$_3$) δ: 8.90 (1H, d), 8.40 (1H, d), 4.95 (2H, td), 4.88 (2H, s), 3.29 (2H, q), 1.47 (3H, t).

Preparation Example 8-1

A mixture of the intermediate compound 6 2.2 g, ammonium acetate 3.4 g, and methanol 10 g was stirred at 70° C. for 3 hours. The mixture was allowed to cool to room temperature, and thereto was then added water, and the mixture was extracted with ethyl acetate. The resulting organic layers were washed with water, dried over anhydrous sodium sulfate, and concentrated under reduced pressure to obtain the intermediate compound 8 represented by the following formula 1.6 g.

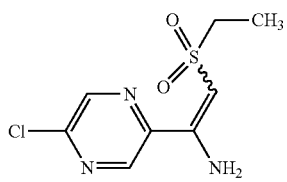

Intermediate Compound 8
$^1$H-NMR (DMSO-d$_6$) δ: 9.05 (1H, d), 8.89 (1H, d), 7.01 (2H, br), 5.67 (1H, s), 3.09 (2H, q), 1.23 (3H, t)

Preparation Example 8-2

The compound which was prepared according to the method described in the preparation example 8-1, and its physical property values are shown below.

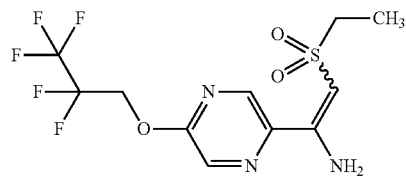

Intermediate Compound 9
$^1$H-NMR (CDCl$_3$) δ: 8.52 (1H, d), 8.35 (1H, d), 6.68 (2H, s), 5.34 (1H, s), 4.91 (2H, td), 3.11 (2H, q), 1.41 (3H, t).

Preparation Example 9

A mixture of the intermediate compound 9 500 mg, sodium hydride (60%, in oil) 110 mg, 2-chloro-1,3-bis(dimethylamino)trimethynium hexafluorophosphate 760 mg, and DMF 3 mL was stirred at 60° C. for 2 hours. To the resulting mixture was added water, and the mixture was extracted with ethyl acetate. The resulting organic layers were dried over anhydrous sodium sulfate, and concentrated under reduced pressure. The resulting residue was subjected to a silica gel column chromatography to obtain the intermediate compound 10 represented by the following formula 260 mg.

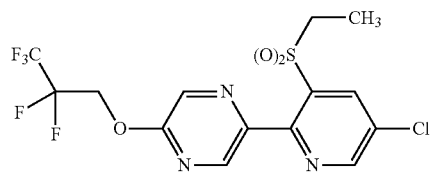

Intermediate Compound 10
$^1$H-NMR (CDCl$_3$) δ: 8.84 (1H, d), 8.66 (1H, d), 8.49 (1H, d), 8.33 (1H, d), 4.91 (2H, td), 3.87 (2H, q), 1.41 (3H, t).

Preparation Example 10

A mixture of the intermediate compound 10 250 mg, cyclopropylboronic acid 400 mg, [1,1'-bis(diphenylphoshino)ferrocene]dichloropalladium (II) dichloromethane adduct 21 mg, tri-potassium phosphate, n-hydrate 670 mg, butyl bis(1-adamantyl)phosphine 21 mg, 1,2-dimethoxyethane 2.7 mL, and water 0.3 mL was stirred at 100° C. for 8 hours. The resulting mixtures were concentrated under reduced pressure, and the resulting residue was subjected to a silica gel column chromatography to obtain the present compound 2 represented by the following formula 40 mg.

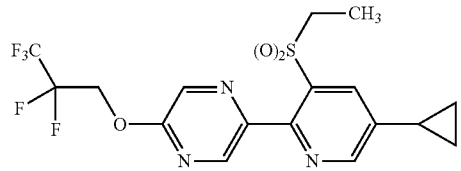

Present Compound 2
$^1$H-NMR (CDCl$_3$) δ: 8.66 (1H, d), 8.60 (1H, d), 8.31 (1H, d), 8.06 (1H, d), 4.90 (2H, t), 3.80 (2H, q), 2.12-2.01 (1H, m), 1.37 (3H, t), 1.23-1.17 (2H, m), 0.92-0.87 (2H, m).

Preparation Example 11

Triethylamine 10.6 mL was added dropwise to a mixture of 5-bromo-3-chloropyridine-2-carboxylic acid 9.02 g, 1-ethyl-3-(3-dimethylaminopropyl)carbodiimide hydrochloric acid salt 9.10 q, N,O-dimethylhydroxylamine hydrochloric acid salt 4.11 g, 4-(dimethylamino)pyridine 0.93 q, and chloroform 100 mL under ice-cooling. The mixture was allowed to rise to room temperature, and stirred for 16 hours. Thereto was then added a sodium hydrogen carbonate aqueous solution, and the mixture was extracted with chloroform. The resulting organic layers were washed with saturated brine, and dried over anhydrous sodium sulfate, and concentrated under reduced pressure. The resulting residue was subjected to a silica gel column chromatography to obtain the intermediate compound 11 represented by the following formula 9.11 g.

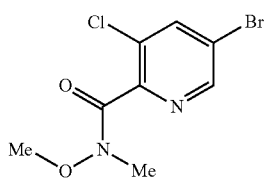

Intermediate Compound 11
$^1$H-NMR (CDCl$_3$) δ: 8.57 (1H, d), 7.94 (1H, d), 3.57 (3H, s), 3.40 (3H, s).

Preparation Example 12

Ethanethiol 0.35 mL was added dropwise to a mixture of sodium hydride (60%, in oil) 193 mg and THF 12 mL under ice-cooling, and a solution of the intermediate compound 11 1 g and THF 3 mL was then added dropwise. The mixture was stirred under ice-cooling for 1 hour, and stirred at room temperature overnight. Water was added to the resulting mixture, and the mixture was extracted with ethyl acetate. The resulting organic layers were dried over anhydrous sodium sulfate. The resulting organic layers were concentrated under reduced pressure, and the resulting residue was subjected to a silica gel column chromatography to obtain the intermediate compound 12 represented by the following formula 0.76 g.

Intermediate Compound 12
$^1$H-NMR (CDCl$_3$) δ: 8.47 (1H, d), 7.84 (1H, d), 3.57 (3H, s), 3.39 (3H, d), 2.96 (2H, q), 1.32 (3H, t).

Preparation Example 13

A 3M methyl magnesium bromide in diethylether solution 9.1 mL was added dropwise to a mixture of the intermediate compound 12 6.41 g and THF 100 mL under ice-cooling, and the mixture was stirred at room temperature for 1 hour. To the resulting mixture was a saturated ammonium chloride aqueous solution under ice-cooling, and the mixture was extracted with ethyl acetate. The resulting organic layers were washed with saturated brine, dried over anhydrous sodium sulfate, and concentrated under reduced pressure to obtain the intermediate compound 13 represented by the following formula 5.48 g.

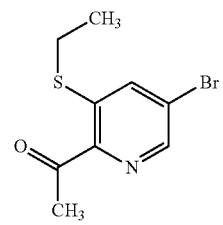

Intermediate Compound 13
$^1$H-NMR (CDCl$_3$) δ: 8.41 (1H, d), 7.77 (1H, d), 2.90 (2H, q), 2.68 (3H, s), 1.41 (3H, t).

Preparation Example 14

A 2N (normal) sodium hydroxide aqueous solution 38 mL was added dropwise to a mixture of the intermediate compound 13 4.89 g, glyoxylic acid monohydrate 3.46 g, and methanol 40 ML under ice-cooling, and the mixture was stirred at room temperature for 4 hours. The mixture was allowed to cool under ice-cooling, and thereto were added concentrated hydrochloric acid 10 mL, and hydrazine monohydrate 4 mL successively. The resulting mixture was stirred at 90° C. for 23 hours. The resulting mixture was allowed to cool to room temperature, and thereto was then added a saturated ammonium chloride aqueous solution, and the mixture was extracted with chloroform. The resulting organic layers were dried over anhydrous sodium sulfate, and concentrated under reduced pressure. The resulting residue was subjected to a silica gel column chromatography to obtain the intermediate compound 14 represented by the following formula 2.29 g.

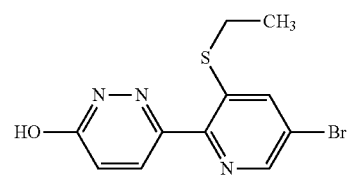 [SMILES: CCSc1cc(Br)cnc1-c1ccc(O)nn1]

Intermediate Compound 14
$^1$H-NMR (CDCl$_3$) δ: 11.18 (1H, brs), 8.44 (1H, d), 8.13 (1H, d), 7.77 (1H, dd), 7.05 (1H, d), 2.94 (2H, q), 1.38 (3H, t).

Preparation Example 15

Phosphoryl chloride 1.5 mL was added to a mixture of the intermediate compound 14 6.90 g and acetonitrile 40 mL at room temperature, and the mixture was stirred under reflux for 2 hours. The resulting mixture was allowed to cool to room temperature, and the mixture was added dropwise to a saturated sodium bicarbonate solution, and the mixture was extracted with ethyl acetate. The resulting organic layers were washed with water and saturated brine successively, and dried over anhydrous sodium sulfate, and concentrated under reduced pressure. The resulting residue was subjected to a silica gel column chromatography to obtain the intermediate compound 15 represented by the following formula 3.98 g.

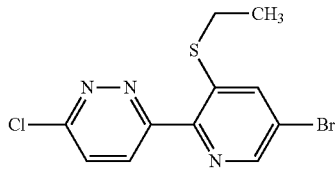 [SMILES: CCSc1cc(Br)cnc1-c1ccc(Cl)nn1]

Intermediate Compound 15
$^1$H-NMR (CDCl$_3$) δ: 8.49 (1H, d), 8.27 (1H, d), 7.87 (1H, d), 7.63 (1H, d), 2.95 (2H, q), 1.37 (3H, t).

Preparation Example 16

A mixture of the intermediate compound 15 1.1 q, 2,2,3,3,3-pentafluoro-1-propanol 0.5 mL, cesium carbonate 1.6 g, and DMF 11 mL was stirred at 60° C. for 3 hours. The resulting mixture was allowed to cool to room temperature, and thereto was then added water, and the mixture was extracted with methyl t-butyl ether. The resulting organic layers were washed with water and saturated brine successively, dried over anhydrous sodium sulfate, and concentrated under reduced pressure. The resulting residue was subjected to a silica gel column chromatography to obtain the intermediate compound 16 represented by the following formula 1.5 g.

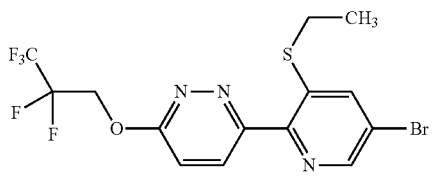 [SMILES: CCSc1cc(Br)cnc1-c1ccc(OCC(F)(F)C(F)(F)F)nn1]

Intermediate Compound 16
$^1$H-NMR (CDCl$_3$) δ: 8.48 (1H, d), 8.32 (1H, d), 7.85 (1H, d), 7.24 (1H, d), 5.12 (2H, t), 2.96 (2H, q), 1.38 (3H, t).

Preparation Example 17

75% mCPBA 1.8 g was added to a mixture of the intermediate compound 16 1.5 g and chloroform 60 mL under ice-cooling, and the mixture was stirred for 7 hours. To the resulting mixture was added a saturated sodium hydrogen carbonate aqueous solution, and the mixture was extracted with chloroform. The resulting organic layers were washed with saturated brine, dried over anhydrous sodium sulfate, and concentrated under reduced pressure to obtain the intermediate compound 17 represented by the following formula 1.7 g.

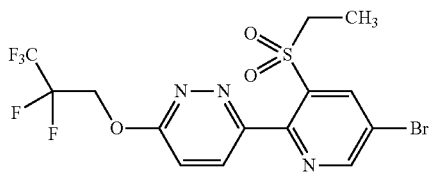

Intermediate Compound 17
$^1$H-NMR (CDCl$_3$) δ: 8.96 (1H, d), 8.66 (1H, d), 7.94 (1H, d), 7.28 (1H, d), 5.08 (2H, t), 3.91 (2H, q), 1.43 (3H, t).

Preparation Example 18

A mixture of the intermediate compound 17 1.5 g, bis(pinacolato)diboron 1.2 g, [1,1'-bis(diphenylphosphino)ferrocene]) palladium(II) dichloride 0.12 g, potassium acetate 0.95 g, and DMSO 11 mL was stirred at 90° C. under nitrogen atmosphere for 3 hours. Water was added to the resulting mixture at room temperature, and the mixture was extracted with chloroform. The resulting organic layers were washed with saturated brine, dried over anhydrous magnesium sulfate, and concentrated under reduced pressure to obtain the intermediate compound 18 represented by the following formula 1.2 g.

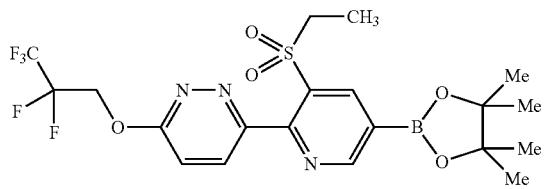 [SMILES: CCS(=O)(=O)c1cc(B2OC(C)(C)C(C)(C)O2)cnc1-c1ccc(OCC(F)(F)C(F)(F)F)nn1]

Intermediate Compound 18
$^1$H-NMR (CDCl$_3$) δ: 9.18 (1H, d), 8.85 (1H, d), 7.95 (1H, d), 7.29 (1H, d), 5.08 (2H, t), 3.85 (2H, q), 1.42 (3H, t), 1.39 (12H, s).

Preparation Example 19

A mixture of the intermediate compound 18 1.1 g, sodium acetate 1.3 g, THF 8 mL, 30% hydrogen peroxide solution 1.2 mL, and water 4 mL was stirred at 0° C. for 4 hours. To the resulting mixture was saturated sodium thiosulfate 20 mL, and the mixture was stirred for 1 hour. To the resulting mixture was added a saturated sodium hydrogen carbonate aqueous solution at room temperature, and the mixture was extracted with chloroform. The resulting organic layers were washed with saturated brine, dried over anhydrous magnesium sulfate, and concentrated under reduced pressure. The resulting residue was subjected to a silica gel column chromatography to obtain the intermediate compound 19 represented by the following formula 0.85 g.

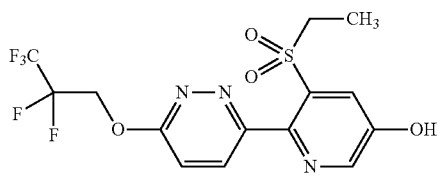

Intermediate Compound 19
$^1$H-NMR (CDCl$_3$) δ: 8.51 (1H, d), 7.98 (1H, d), 7.89 (1H, d), 7.26 (1H, d), 5.07 (2H, t), 3.88 (2H, q), 3.80-3.77 (1H, m), 1.39 (3H, t).

Preparation Example 20

A mixture of the intermediate compound 19 0.20 g, 2-iodopyridine 0.12 g, copper iodide (I) 0.018 g, 1-butyl imidazole 0.03 g, potassium carbonate 0.13 g, and toluene 2.5 mL was stirred under reflux for 6 hours. The resulting mixture was allowed to cool to room temperature, and then filtered through Celite (Registered trademark), and the filtrates were concentrated. The resulting residue was subjected to a silica gel column chromatography to obtain the present compound 3 represented by the following formula 0.17 g.

Present Compound 3
$^1$H-NMR (CDCl$_3$) δ: 8.81 (1H, d), 8.35 (1H, d), 8.19-8.18 (1H, m), 7.95 (1H, d), 7.85-7.79 (1H, m), 7.28 (1H, d), 7.16-7.10 (2H, s), 5.08 (2H, t), 3.91 (2H, q), 1.42 (3H, t).

Preparation Example 21

The compound that was prepared according to the method described in the preparation example 16, and its physical property value are shown below.

Intermediate Compound 20
$^1$H-NMR (CDCl$_3$) δ: 8.48 (1H, d), 8.31 (1H, d), 7.85 (1H, d), 7.21 (1H, d), 6.11-5.97 (1H, s), 5.05 (2H, tt), 2.96 (2H, q), 1.38 (3H, t).

Preparation Example 22

The compound that was prepared according to the method described in the preparation example 17, and its physical property value are shown below.

Intermediate Compound 21
$^1$H-NMR (CDCl$_3$) δ: 8.96 (1H, d), 8.66 (1H, d), 7.93 (1H, d), 7.26 (1H, d), 6.18-5.91 (1H, s), 5.01 (2H, t), 3.91 (2H, q), 1.43 (3H, t).

Preparation Example 23

The compound that was prepared according to the method described in the preparation example 18, and its physical property value are shown below.

Intermediate Compound 22
$^1$H-NMR (CDCl$_3$) δ: 9.17 (1H, d), 8.85 (1H, d), 7.94 (1H, d), 7.25 (1H, d), 6.09-5.99 (1H, m), 5.01 (2H, t), 3.85 (2H, q), 1.42 (3H, t), 1.39 (12H, s).

Preparation Example 24

The compound that was prepared according to the method described in the preparation example 19, and its physical property value are shown below.

Intermediate Compound 23
$^1$H-NMR (CDCl$_3$) δ: 8.51 (1H, d), 7.99 (1H, d), 7.88 (1H, d), 7.23 (1H, d), 6.09-5.99 (1H, m), 4.99 (2H, t), 3.87 (2H, q), 2.11 (1H, br s), 1.39 (3H, t).

Preparation Example 25

The compound that was prepared according to the method described in the preparation example 20, and its physical property value are shown below.

Present Compound 6
$^1$H-NMR (CDCl$_3$) δ: 8.81 (1H, d), 8.35 (1H, d), 8.19-8.18 (1H, m), 7.94 (1H, d), 7.83-7.81 (1H, m), 7.24 (1H, d), 7.16-7.10 (2H, m), 6.10-6.00 (1H, m), 5.04-4.97 (2, m), 3.91 (2H, q), 1.42 (3H, t).

Present Compound 4
$^1$H-NMR (CDCl$_3$) δ: 8.80 (1H, d), 8.65 (1H, d), 8.33-8.33 (2H, m), 8.18-8.17 (1H, m), 7.82-7.80 (1H, m), 7.15-7.10 (2H, m), 4.91 (2H, t), 3.86 (2H, q), 1.40 (3H, t).

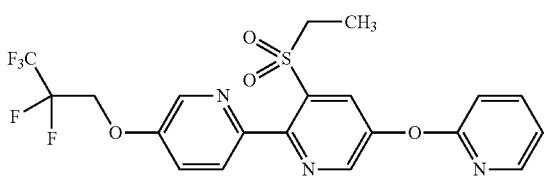 [SMILES: CCS(=O)(=O)c1cc(Oc2ccccn2)cnc1-c1ccc(OCC(F)(F)C(F)(F)F)cn1]

Present Compound 5

¹H-NMR (CDCl₃) δ: 8.76 (1H, d), 8.37-8.36 (1H, m), 8.31 (1H, d), 8.17-8.16 (1H, m), 7.87 (1H, dd), 7.81-7.79 (1H, m), 7.42 (1H, dd), 7.12-7.09 (2H, m), 4.54 (2H, t), 3.92 (2H, q), 1.40 (3H, t).

Preparation Example 26

A mixture of 2-(benzyloxy)-2-propenal 324 mg, the intermediate compound 8 248 mg, and ethanol 10 mL was heated at 90° C. with stirring for 12 hours. The resulting mixture was concentrated, and thereto were added methansulfonyl chloride 229 mg, triethylamine 405 mg, and chlorobenzene 10 mL, and the mixture was heated to 100° C., and stirred for 24 hours. The resulting mixture was concentrated under reduced pressure, and was purified with a silica gel chromatography to obtain the intermediate compound 24 represented by the following formula.

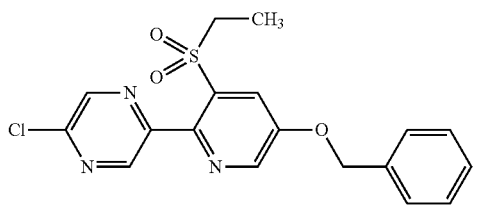 [SMILES: CCS(=O)(=O)c1cc(OCc2ccccc2)cnc1-c1cnc(Cl)cn1]

Intermediate Compound 24

¹H-NMR (CDCl₃) δ: 8.84 (1H, d), 8.63 (1H, d), 8.55 (1H, d), 9.03 (1H, d), 7.48-7.30 (5H, m), 5.27 (2H, s), 3.84-3.77 (2H, m), 1.32 (3H, t).

Preparation Example 27

A mixture of the intermediate compound 24 2.0 g, 2,2,3,3,3-hexafluoro-1-propanol 0.61 mL, cesium carbonate 2.0 q, and DMF 20 mL was stirred at 40° C. for 3 hours. The reaction mixture was added to 1N hydrochloric acid, and the mixture was extracted with ethyl acetate. The resulting organic layers were dried over anhydrous sodium sulfate, and concentrated under reduced pressure. The resulting residue was subjected to a silica gel column chromatography to obtain the intermediate compound 25 1.9 g.

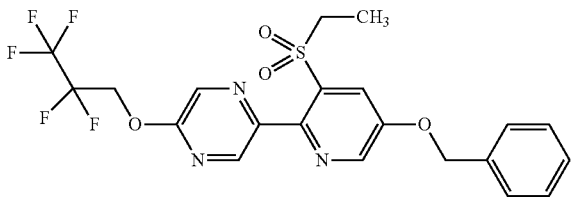 [SMILES: CCS(=O)(=O)c1cc(OCc2ccccc2)cnc1-c1cnc(OCC(F)(F)C(F)(F)F)cn1]

Intermediate Compound 25

¹H-NMR (CDCl₃) δ: 8.61 (1H, d), 8.58 (1H, d), 8.30 (1H, d), 8.03 (1H, d), 7.48-7.36 (5H, m), 5.26 (2H, s), 4.89 (2H, t), 3.80 (2H, q), 1.31 (3H, t).

Preparation Example 28

A mixture of the intermediate compound 25 as a crude product 1.9 g which was obtained by the preparation example 27, and a solution of 25% hydrogen bromide in acetic acid 4 mL was stirred at 70° C. for 2 hours. Water was added to the resulting mixture, and the mixture was extracted with ethyl acetate. The resulting organic layers were dried over anhydrous sodium sulfate, and concentrated under reduced pressure. The resulting residue was subjected to a silica gel column chromatography to obtain the intermediate compound 26 represented by the following formula 1.0 g.

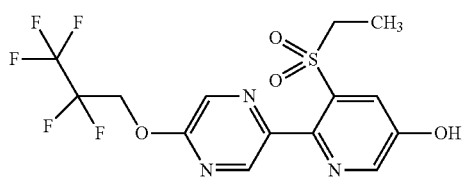 [SMILES: CCS(=O)(=O)c1cc(O)cnc1-c1cnc(OCC(F)(F)C(F)(F)F)cn1]

Intermediate Compound 26

¹H-NMR (CDCl₃) δ: 8.59 (1H, d), 8.53 (1H, d), 8.30 (1H, d), 7.99 (1H, d), 4.90 (2H, dd), 3.85 (2H, q), 1.39 (3H, t).

Preparation Example 29

The intermediate compound 28 is prepared by using the intermediate compound 27 instead of the intermediate compound 8 according to the method described in the preparation example 26.

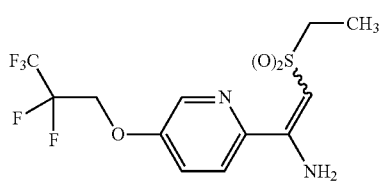

Intermediate Compound 27

¹H-NMR (CDCl₃) δ: 8.37 (1H, d), 7.69 (1H, d), 7.34 (1H, dd), 6.79 (2H, s), 5.28 (1H, s), 4.54 (2H, t), 3.10 (2H, q), 1.40 (3H, t).

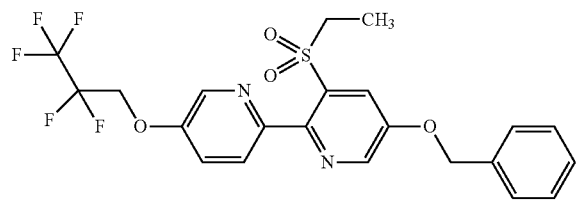 [SMILES: CCS(=O)(=O)c1cc(OCc2ccccc2)cnc1-c1ccc(OCC(F)(F)C(F)(F)F)cn1]

Intermediate Compound 28

¹H-NMR (CDCl₃) δ: 8.59 (1H, d), 8.33-8.33 (1H, m), 8.03 (1H, d), 7.80-7.78 (1H, m), 7.47-7.38 (6H, m), 5.25 (2H, s), 4.52 (2H, t), 3.86 (2H, q), 1.32 (3H, t).

Preparation Example 30

The compound that was prepared according to the method described in the preparation example 27 and its physical property values are shown below.

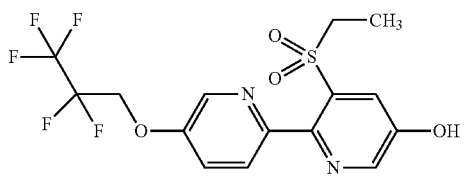

Intermediate Compound 29

$^1$H-NMR (CDCl$_3$) δ: 8.42 (1H, d), 8.34 (1H, d), 7.92 (1H, d), 7.77 (1H, d), 7.39 (1H, dd), 4.52 (2H, t), 3.83 (2H, q), 1.36 (3H, t).

Preparation Example 31

The intermediate compound 17 200 mg, cyclopropylboronic acid 134 mg, and tri-potassium phosphate 331 mg were dissolved into toluene 1.3 mL/water 0.13 mL, and thereto was added [1,1'-bis(diphenylphosphino)ferrocene]palladium(II) dichloride 20 mg under nitrogen atmosphere, and the mixture was stirred at 100° C. for 5 hours. The resulting mixture was allowed to cool to room temperature, and the mixture was extracted with ethyl acetate. The resulting organic layers were washed with saturated brine, dried over anhydrous sodium sulfate, and concentrated under reduced pressure to obtain the present compound 7 represented by the following formula 190 mg.

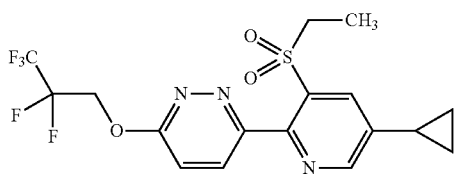 [SMILES: CCS(=O)(=O)c1cc(C2CC2)cnc1-c1ccc(OCC(F)(F)C(F)(F)F)nn1]

Present Compound 7

$^1$H-NMR (CDCl$_3$) δ: 8.67 (1H, d), 8.07 (1H, d), 7.90 (1H, d), 7.26 (1H, d), 5.07 (2H, t), 3.85 (2H, q), 2.10-2.06 (1H, m), 1.39 (3H, t), 1.25-1.20 (2H, m), 0.93-0.90 (2H, m).

Next, the formulation examples of the compound of the present invention are shown below. The "parts" represents "part by weight" unless otherwise specified.

Formulation Example 1

Into a mixture of 35 parts of xylene and 35 parts of DMF, 10 parts of any one of the present compounds 1 to 7 is dissolved, and then 14 parts of polyoxyethylene styryl phenyl ether and 6 parts of calcium dodecylbenzene sulfonate are added thereto, followed by mixing them to obtain each formulation.

Formulation Example 2

Four (4) parts of sodium lauryl sulfate, 2 parts of calcium lignin sulfonate, 20 parts of synthetic hydrated silicon oxide fine powder and 54 parts of diatomaceous earth are mixed, and further 20 parts of any one of the present compounds 1 to 7 is added, followed by mixing them to obtain each formulation.

Formulation Example 3

To 2 parts of any one of the present compounds 1 to 7, 1 part of synthetic hydrated silicon oxide fine powder, 2 parts of calcium lignin sulfonate, 30 parts of bentonite and 65 parts of kaolin clay are added, followed by mixing. An appropriate amount of water is then added to the mixture, followed by further mixing, and granulation with a granulator and forced-air drying to obtain each formulation.

Formulation Example 4

Into an appropriate amount of acetone, 1 part of any one of the present compounds 1 to 7 is mixed, and then 5 parts of synthetic hydrous silicon oxide fine powder, 0.3 parts of isopropyl acid phosphate and 93.7 parts of kaolin clay are added, followed by mixing with stirring thoroughly and removal of acetone from the mixture by evaporation to obtain each formulation.

Formulation Example 5

A mixture of 35 parts of polyoxyethylene alkyl ether sulfate ammonium salt and white carbon (weight ratio of 1:1), 20 parts of any one of the present compounds 1 to 7, and 45 parts of water are mixed thoroughly to obtain each formulation.

Formulation Example 6

Into a mixture of 5 parts of xylene and 5 parts of trichloroethane, 0.1 parts of any one of the present compounds 1 to 7 is mixed, and the resulting mixture is then mixed with 89.9 parts of kerosene to obtain each formulation.

Formulation Example 7

Into 0.5 mL of acetone, 10 mg of any one of the present compounds 1 to 7 is dissolved, and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of any one of the present compounds 1 to 7 and 49.9 parts of Neothiozole (Chuo Kasei Co., Ltd.) are placed. After mounting an aerosol valve, 25 parts of dimethylether and 25 parts of LPG are filled, followed by shaking and further mounting an actuator to obtain an oily aerosol.

Formulation Example 9

A mixture of 0.6 part of any one of the present compounds 1 to 7, 0.01 part of 2,6-di-tert-butyl-4-methylphenol, 5 parts of xylene, 3.39 parts of deodorized kerosene and 1 part of an emulsifier (Rheodol MO-60 (manufactured by Kao Corporation)) and 50 parts of distilled water are filled into an aerosol container, and a valve part is attached. Then, 40 parts

Formulation Example 10

Zero point one (0.1) g of any one of the present compounds 1 to 7 are mixed into 2 mL of propylene glycol, and the resulting solution is impregnated into a ceramic plate having a size of 4.0 cm×4.0 cm and a thickness of 1.2 cm, to obtain thermal fumigants.

of a propellant (LPG) is filled therein through the valve under pressure to obtain an aqueous aerosol.

Formulation Example 11

Five (5) parts of any one of the present compounds 1 to 7, and 95 parts of ethylene-methyl methacrylate copolymer (the ratio of the methyl methacrylate in the copolymer: 10 weight %), Acryft (Registered trademark) WD 301, manufactured by Sumitomo Chemical Co. Ltd.) are melted and kneaded with a closed type pressure kneader (manufactured by Moriyama Manufacturing Co. Ltd.), and the resulting kneaded product is extruded from an extrusion molding machine through a molding die to obtain a rod-shaped molded product having a length of 15 cm and a diameter of 3 mm.

Formulation Example 12

Five (5) parts of any one of the present compounds 1 to 7, and 95 parts of plasticized polyvinyl chloride resin are melted and kneaded with a closed type pressure kneader (manufactured by Moriyama Manufacturing Co. Ltd.), and the resulting kneaded product Is extruded from an extrusion molding machine through a molding die to obtain a rod-shaped molded product having a length of 15 cm and a diameter of 3 mm.

Formulation Example 13

One hundred (100) mg of any one of the present compounds 1 to 7, 68.75 mg of lactose, 237.5 mg of corn starch, 43.75 mg of microcrystalline cellulose, 18.75 mg of polyvinylpyrrolidone, 28.75 mg of sodium carbomethyl starch and 2.5 mg of magnesium stearate are mixed, and the resulting mixture was compressed to an appropriate size to obtain a tablet.

Formulation Example 14

Twenty five (25) mg of any one of the present compounds 1 to 7, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain capsules.

Formulation Example 15

To 100 mg of any one of the present compounds 1 to 7, 500 mg of fumaric acid, 2,000 mg of sodium chloride, 150 mg of methyl paraben, 50 mg of propyl paraben, 25,000 mg of granulated sugar, 13,000 mg of sorbitol (70% solution), 100 mg of Veegum K (manufactured by Vanderbilt Co.), 35 mg of perfume, and 500 mg of coloring agent, a distilled water is added so that a final volume is set to be 100 mL, followed by mixing them to obtain a suspension for oral administration.

Formulation Example 16

Into a mixture of 5% by weight of an emulsifier, 3% by weight of benzyl alcohol and 30% by weight of propylene glycol, 5% by weight of any one of the present compounds 1 to 7 is dissolved, and phosphate buffer is added thereto so that a pH of the solution is set to be 6.0 to 6.5, and water is added as the rest parts to obtain the solution for oral administration.

Formulation Example 17

To a mixture of 57% by weight of fractional distillated palm oil and 3% by weight of polysorbate 85, 5% by weight of aluminum distearate is added, and heated to disperse it. The resulting mixture is cooled to room temperature, and 25% by weight of saccharin is dispersed in an oil vehicle. Ten (10) % by weight of any one of the present compounds 1 to 7 is divided thereto to obtain a paste for oral administration.

Formulation Example 18

Five (5)% by weight of any one of the present compounds 1 to 7 is mixed with 95% by weight of limestone filler, followed by a wet granulation of the resulting mixture to obtain a granule for oral administration.

Formulation Example 19

Into 80 parts of diethylene glycol monomethyl ether, 5 parts of any one of the present compounds 1 to 7 is dissolved, and 15 parts of propylene carbonate is added thereto, and the resulting mixture is mixed to obtain a spot-on solution.

Formulation Example 20

Into 70 parts of diethylene glycol monomethyl ether, 10 parts of any one of the present compounds 1 to 7 is dissolved, and 20 parts of 2-octyldodecanol is added thereto, and the resulting mixture is mixed to obtain a pour-on solution.

Formulation Example 21

To 0.5 parts of any one of the present compounds 1 to 7, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain a hydrogenous solution of shampoo formulation.

Formulation Example 22

Zero point fifteen (0.15) % by weight of any one of the present compounds 1 to 7, 95% by weight of animal feed, as well as 4.85% by weight of a mixture of dibasic calcium phosphate, diatomaceous earth, aerosol and carbonate (or chalk) are mixed with stirring thoroughly to obtain a premix for animal feed.

Formulation Example 23

Seven point two (7.2) g of any one of the present compounds 1 to 7, and 92.8 g of Hosco (registered trademark) S-55 (manufactured by Maruishi Pharmaceuticals) are melted and mixed at 100° C., and the resulting mixture was poured into a suppository mold, followed by performing a cooling solidification to obtain a suppository.

Next, Test Examples are used to show an efficacy of the present compound on controlling harmful arthropods.

The following test examples were carried out at 25° C.

Test Example 1

The test compounds is made to a formulation according to the method described in the Formulation Example 5, and thereto is added water containing 0.03 v/v % of a spreader to prepare a diluted solution containing a prescribed concentration of the test compound.

Cucumber (*Cucumis sativus*) seedling (on the developmental stage of the second true leaf) is planted in a container and approximately 30 of cotton aphid (*Aphis gossypii*) (all stages of life) are released onto the leaves of the cucumber. After 1 day, the diluted solutions are sprayed into the seedling in a ratio of 10 mL/seedling. After 5 days, the number of the surviving insects is examined and the controlling value is calculated by the following equation.

Controlling value (%)=(1−($Cb \times Tai$)/($Cai \times Tb$))×100 wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where a similar treatment procedure to that of the treated group except not using the test compound is done.

The test was conducted by making the prescribed concentration 500 ppm and using the below-mentioned present compounds as a test compound according to the test example 1. As a result of the test, the below-mentioned present compounds showed 90% or greater as the controlling value.

Present Compound(s): 1, 4 and 7

The test was conducted by making the prescribed concentration 200 ppm and using the below-mentioned present compounds as a test compound according to the test example 1. As a result of the test, the below-mentioned present compounds showed 90% or greater as the controlling value.

Present Compound(s): 1, 2, 3, 4, 5, 6 and 7

Test Example 2

The test compounds are made to a formulation according to the method described in the Formulation Example 5, and thereto is added water to prepare a diluted solution containing a prescribed concentration of the test compound.

Cucumber seedling (on the developmental stage of the second true leaf) is planted in a container, and the diluted solutions in the ratio on 5 mL/seedling are irrigated into the plant foot. After 7 days, approximately 30 of cotton aphid (all stages of life) are inoculated onto the cucumber leaves. After additional 6 days, the number of the surviving insects is examined, and the controlling value is calculated by the following equation.

Controlling value (%)=(1−($Cb \times Tai$)/($Cai \times Tb$))×100 wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where a similar treatment procedure to that of the treated group except not using the test compound is done.

The test was conducted by making the prescribed concentration 200 ppm and using the below-mentioned present compounds as a test compound according to the test example 2. As a result of the test, the below-mentioned present compounds showed 90% or greater as the controlling value.

Present Compound(s): 1, 3, 5, 6 and 7

Test Example 3

The test compounds are made to a formulation according to the method described in the Formulation Example 5, and thereto was added water containing 0.03 v/v % of a spreader to prepare a diluted solution containing a prescribed concentration of the test compound.

Rice (*Oryza sativa*) seedling (on the developmental stage of the second true leaf) is planted in a container, and the diluted solutions are sprayed into the seedling in a ratio of 10 mL/seedling. Thereafter, 20 of 3rd instar larvae of brown planthopper (*Nilaparvata lugens*) are released onto the rice leaves. After 6 days, the number of the surviving insects is examined, and the mortality is calculated by the following equation.

Mortality (%)={1−the number of the surviving insects/20}×100

The test is conducted by making the prescribed concentration 500 ppm and using the below-mentioned present compounds as a test compound according to the test example 3. As a result of the test, the below-mentioned present compounds showed 90% or greater as the mortality.

Present Compound(s): 1 and 4

The test was conducted by making the prescribed concentration 200 ppm and using the below-mentioned present compounds as a test compound according to the test example 3. As a result of the test, the below-mentioned present compounds showed 90% or greater as the mortality.

Present Compound(s): 2

Test Example 4

The test compounds are made to a formulation according to the method described in the Formulation Example 5, and thereto was is water to prepare a diluted solution containing a prescribed concentration of the test compound.

In a container, 7.7 g of artificial diet (Insects LF, manufactured by NOSAN CORPORATION) is placed, and 2 mL of the diluted solution is irrigated thereto. Five (5) fourth instar larvae of tobacco cutworm (*Spodoptera litura*) are released onto the artificial diet. After 5 days, the number of the surviving insects is examined, and the mortality of insects is calculated by the following equation.

Mortality (%)={1X−the number of the surviving insects/5}×100

The test was conducted by making the prescribed concentration 500 ppm and using the below-mentioned present compounds as a test compound according to the test example 4. As a result of the test, the below-mentioned present compounds showed 80% or greater as the mortality.
Present Compound(s): 1, 4 and 7

Test Example 5

The test compounds is made to a formulation according to the method described in the Formulation Example 5, and thereto is added water containing 0.03 v/v % of a spreader to prepare a diluted solution containing a prescribed concentration of the test compound.

The diluted solutions are sprayed into the cabbage (*Brassicae oleracea*) seedling (on the developmental stage of the second to third true leaf) that is planted in a container in a ratio of 20 mL/seedling. Thereafter, the stem and leaf thereof is cut out and is then installed into the container that is covered with the filter paper. Five (5) cabbage moth (*Plutella xylostella*) at the second instar larval stages are released into the cup. After 5 days, the number of the surviving insects is counted, and the mortality of insects is calculated by the following equation.

Mortality (%)={1−the number of the surviving insects/5}×100

The test was conducted by making the prescribed concentration 500 ppm and using the below-mentioned present compounds as a test compound according to the test example 5. As a result of the test, the below-mentioned present compounds showed 80% or greater as the mortality.
Present Compound(s): 1, 4 and 7

The test was conducted by making the prescribed concentration 200 ppm and using the below-mentioned present compounds as a test compound according to the test example 5. As a result of the test, the below-mentioned present compounds showed 80% or greater as the mortality.
Present Compound(s): 1, 2, 3, 4, 5, 6 and 7

Test Example 6

The test compounds are dissolved into a mixed solution of polyoxyethylene sorbitan mono-cocoate and acetone (acetone and polyoxyethylene sorbitan mono-cocoate=5:95 (v/v ratio)) in a ratio of 50 μL of the mixed solution per 1 mg of the test compound. Thereto is added water containing 0.03% by volume of a spreader to prepare a diluted solution containing a prescribed concentration of the test compound.

Corns (*Zea mays*) are sown on a tray overlaid with damped KimWipes (Registered trademark). After corns are grown for 5 days, the entire seedling of the corn is immersed into the diluted solution for 30 seconds. Thereafter, each two grains of the seedling are installed in a plastic petri dish (90 mm radius), and 10 western corn rootworms (*Diabrotica virgifera virgifera*) at the second instar larval stages are released onto the cup. After 5 days, the number of the died insects is counted, and the mortality of insects is calculated by the following equation.

Mortality (%)={1−the number of the surviving insects/10}×100

The test was conducted by making the prescribed concentration 500 ppm and using the below-mentioned present compounds as a test compound according to the test example 6. As a result of the test, the below-mentioned present compounds showed 80% or greater as the mortality.
Present Compound(s): 1, 3, 4 and 7

The test was conducted by making the prescribed concentration 50 ppm and using the below-mentioned present compounds as a test compound according to the test example 6. As a result of the test, the below-mentioned present compounds showed 80% or greater as the mortality.
Present Compound(s): 1, 4, 6 and 7

Test Example 7

The test compounds are made to a formulation according to the method described in the Formulation Example 5, and thereto is added water to prepare a diluted solution containing a prescribed concentration of the test compound.

The container is matted with a filter paper having 5.5 cm diameter, and 30 mg sucrose is placed on the filter paper, and 0.7 mL of the diluted solution is added dropwise to the filter paper. Ten (10) female adult houseflies (*Musca domestica*) are released into the container. After 24 hours, the number of died insects is counted, and the mortality of insects is calculated by the following equation.

Mortality of insects (%)=(Number of dead insects/ Number of test insects)×100

The test was conducted by making the prescribed concentration 500 ppm and using the below-mentioned compounds as a test compound according to the test example 7. As a result of the test, the below-mentioned present compounds showed 100% as the mortality.
Present Compound(s): 1 and 4

INDUSTRIAL APPLICABILITY

The present compound shows an excellent control effect against a harmful arthropod.

The invention claimed is:
1. A compound represented by formula (I):

$$\text{(I)}$$

wherein
  $A^1$ represents a nitrogen atom or $CR^{3b}$,
  n is 0, 1 or 2,
  q is 0, 1 or 2,
  G represents a C3-C8 alicyclic hydrocarbon group optionally having one or more substituents selected from Group E, or -$L^1$-$G^2$,
  $L^1$ represents an oxygen atom or a sulfur atom,
  $G^2$ represents a five to ten membered heterocyclic group optionally having one or more substituents selected from Group D,
  $R^{3a}$ represents each independently a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, NR$^{24}$NR$^{11}$C(O)OR$^{14}$, NR$^{11}$C(O)NR$^{15}$R$^{16}$, NR$^{24}$NR$^{11}$C(O)NR$^{15}$R$^{16}$, N=CHNR$^{15}$R$^{16}$, N=S(O)$_x$R$^{15}$R$^{16}$, C(O)OR$^{17}$, a cyano group, a nitro group, or a halogen atom, R$^{3b}$ represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, OR$^{12}$, NR$^{11}$R$^{12}$, NR$^{11a}$R$^{12a}$, NR$^{24}$NR$^{11}$R$^{12}$, NR$^{24}$OR$^{11}$, NR$^{11}$C(O)R$^{13}$, NR$^{24}$NR$^{11}$C(O)R$^{13}$, NR$^{11}$C(O)OR$^{14}$, NR$^{24}$NR$^{11}$C(O)OR$^{14}$, NR$^{11}$C(O)NR$^{15}$R$^{16}$, NR$^{24}$NR$^{11}$C(O)NR$^{15}$R$^{16}$, N=CHNR$^{15}$R$^{16}$, N=S(O)$_x$R$^{15}$R$^{16}$, C(O)OR$^{17}$, a cyano group, a nitro group, a hydrogen atom, or a halogen atom, x is 0 or 1, A$^2$ represents a nitrogen atom or CR$^{4a}$, A$^3$ represents a nitrogen atom or CR$^{4b}$, A$^4$ represents a nitrogen atom or CR$^{4c}$, R$^{4a}$, R$^{4b}$ and R$^{4c}$ each independently represents a hydrogen atom, a C1-C6 chain hydrocarbon group optionally having one or more halogen atoms, a nitro group, OR$^{18}$, NR$^{18}$R$^{19}$, a cyano group, or a halogen atom, T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, OR$^1$, S(O)$_m$R$^1$, OS(O)$_2$R$^1$, CH$_2$OR$^1$, NR$^1$R$^{29}$, C(O)R$^1$, C(O)NR$^1$R$^{29}$, NR$^{29}$C(O)R$^1$, N=CR$^1$R$^{30}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12, T-1
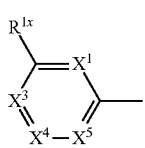

T-2
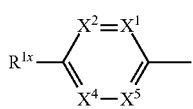

T-3
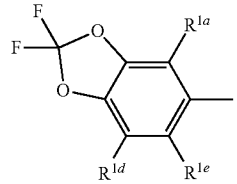

T-4
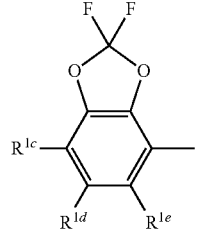

T-5
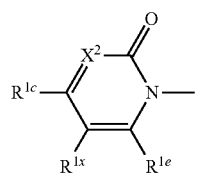

T-6
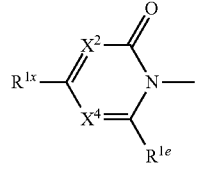

T-7
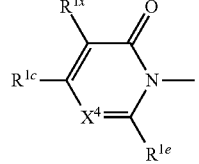

T-8
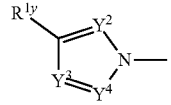

T-9
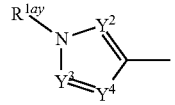

T-10
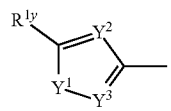

T-11
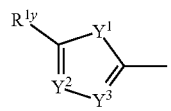

T-12
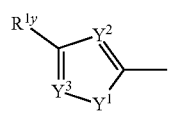

$X^1$ represents a nitrogen atom, or $CR^{1a}$,
$X^2$ represents a nitrogen atom, or $CR^{1b}$,
$X^3$ represents a nitrogen atom, or $CR^{1c}$,
$X^4$ represents a nitrogen atom, or $CR^{1d}$,
$X^5$ represents a nitrogen atom, or $CR^{1e}$,
$R^{1a}$, $R^{1b}$, $R^{1c}$, $R^{1d}$ and $R^{1e}$ each independently represents a hydrogen atom, a C1-C6 chain hydrocarbon group optionally having one or more halogen atoms, a C3-C7 cycloalkyl group optionally having one or more halogen atoms, or a halogen atom,
$R^{1x}$ represents $OR^7$, $OS(O)_2R^7$, $S(O)_mR^7$, $NR^1R^{29}$, $NR^8S(O)_2R^7$, a C1-C5 chain hydrocarbon group having one or more halogen atoms, a cyano group, or a halogen atom,
$Y^1$ represents $NR^{25}$, an oxygen atom, or a sulfur atom,
$Y^2$ represents a nitrogen atom, or $CR^{26}$,
$Y^3$ represents a nitrogen atom, or $CR^{27}$,
$Y^4$ represents a nitrogen atom, or $CR^{28}$,
$R^{25}$ represents a hydrogen atom, a C1-C6 chain hydrocarbon group optionally having one or more halogen atoms, a C1-C6 alkoxy group optionally having one or more halogen atoms, a C3-C7 cycloalkyl group optionally having one or more halogen atoms, or a (C3-C7 cycloalkyl)C1-C6 alkyl group optionally having one or more halogen atoms,
$R^{26}$, $R^{27}$, and $R^{28}$ each independently represents a hydrogen atom, a C1-C6 chain hydrocarbon group optionally having one or more halogen atoms, a C3-C7 cycloalkyl group optionally having one or more halogen atoms, or a halogen atom,
$R^{1y}$ represents $OR^7$, $OS(O)_2R^7$, $S(O)_mR^7$, $NR^8S(O)_2R^7$, a cyano group, a C1-C5 chain hydrocarbon group having one or more halogen atoms, or a halogen atom,
$R^{1ay}$ and $R^7$ each independently represents a C1-C6 chain hydrocarbon group having one or more halogen atoms,
$R^8$ represents a hydrogen atom, or a C1-C6 chain hydrocarbon group optionally having one or more halogen atoms,
m is 0, 1, or 2,
$R^1$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G,
$R^2$ represents a cyclopropyl group, a cyclopropylmethyl group, or a C1-C6 alkyl group optionally having one or more halogen atoms,
$R^{11}$, $R^{17}$, $R^{19}$, $R^{24}$ and $R^{29}$ each independently represents a hydrogen atom, or a C1-C6 chain hydrocarbon group optionally having one or more halogen atoms,
$R^{30}$ represents a hydrogen atom, a halogen atom, $OR^{31}$, $NR^{32}R^{33}$, or a C1-C6 chain hydrocarbon group optionally having one or more halogen atoms,
$R^{18}$ and $R^{31}$ each independently represents a hydrogen atom, or a C1-C6 chain hydrocarbon group optionally having one or more halogen atoms,
$R^{32}$ and $R^{33}$ each independently represents a hydrogen atom, or a C1-C6 chain hydrocarbon group optionally having one or more halogen atoms,
$R^{12}$ represents a hydrogen atom, $S(O)_2R^{23}$, a C1-C6 chain hydrocarbon group optionally having one or more halogen atoms, or a C1-C6 alkyl group having one or more substituents selected from Group F,
$R^{23}$ represents a C1-C6 chain hydrocarbon group optionally having one or more halogen atoms, or a phenyl group optionally having one or more substituents selected from Group D,
$R^{11a}$ and $R^{12a}$, and the nitrogen atom to which they are attached are taken together to form a three to seven membered nonaromatic heterocyclic group optionally having one or more substituents selected from Group E,
$R^{13}$ represents a hydrogen atom, a C1-C6 chain hydrocarbon group optionally having one or more halogen atoms, a C3-C7 cycloalkyl group optionally having one or more halogen atoms, a (C3-C7 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D,
$R^{14}$ represents a C1-C6 chain hydrocarbon group optionally having one or more halogen atoms, a C3-C7 cycloalkyl group optionally having one or more halogen atoms, a (C3-C7 cycloalkyl)C1-C3 alkyl group optionally having one or more halogen atoms, or a phenyl C1-C3 alkyl group, wherein the phenyl moiety in the phenyl C1-C3 alkyl group optionally has one or more substituents selected from Group D,
$R^{15}$ and $R^{16}$ each independently represents a C1-C6 alkyl group optionally having one or more halogen atoms,
Group B is selected from the group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C7 cycloalkyl group optionally having one or more halogen atoms, a cyano group, a hydroxy group, and a halogen atom;
Group D is selected from the group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, wherein $R^{21}$ and $R^{22}$ each independently represents a C1-C6 alkyl group optionally having one or more halogen atoms;

Group E is selected from the group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, an amino group, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a C3-C7 cycloalkyl group optionally having one or more halogen atoms, a phenyl group optionally having one or more substituents selected from Group H, a five or six membered aromatic heterocyclic group optionally having one or more substituents selected from Group H, a halogen atom, an oxo group, a thioxo group, a hydroxy group, a cyano group, and a nitro group, wherein $R^9$ represents a C1-C6 alkyl group optionally having one or more halogen atoms, or a C3-C7 cycloalkyl group optionally having one or more halogen atoms, and $R^{10}$ represents a hydrogen atom, a C1-C6 alkyl group optionally having one or more halogen atoms, or a C3-C7 cycloalkyl group optionally having one or more halogen atoms;

Group F is selected from the group consisting of a C1-C6 alkoxy group optionally having one or more halogen atoms, an amino group, $NHR^{21}$, $NR^{21}R^{22}$, a cyano group, a phenyl group optionally having one or more substituents selected from Group D, a five or six membered aromatic heterocyclic group optionally having one or more substituents selected from Group D, a C3-C7 cycloalkyl group optionally having one or more halogen atoms, and a three to seven nonaromatic heterocyclic group optionally having one or more substituents selected from Group C, wherein the $R^{21}$ and $R^{22}$ each independently represents a C1-C6 alkyl group optionally having one or more halogen atoms;

Group C is selected from the group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group G is selected from the group consisting of a halogen atom, and a C1-C6 haloalkyl group;

Group H is selected from the group consisting of a halogen atom, a nitro group, a cyano group, an amino group, a five or six membered aromatic heterocyclic group optionally having one or more halogen atoms, a C1-C6 alkyl group optionally having one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, and $C(O)OR^{10}$, wherein the $R^9$ represents a C1-C6 alkyl group optionally having one or more halogen atoms, or a C3-C7 cycloalkyl group optionally having one or more halogen atoms, and $R^{10}$ represents a hydrogen atom, a C1-C6 alkyl group optionally having one or more halogen atoms, or a C3-C7 cycloalkyl group optionally having one or more halogen atoms.

2. The compound according to claim 1 wherein $L^1$ represents an oxygen atom.

3. The compound according to claim 1 wherein $G^2$ represents a pyridyl group, a pyrimidinyl group, a pyrazinyl group, a pyridazinyl group, a pyrazolyl group, an imidazolyl group, a triazolyl group, an oxazolyl group, a thiazolyl group, a thiadiazolyl group, or an isoxazolyl group, wherein the pyridyl group, the pyrimidinyl group, the pyrazinyl group, the pyridazinyl group, the pyrazolyl group, the imidazolyl group, the triazolyl group, the oxazolyl group, the thiazolyl group, the thiadiazolyl group, or the isoxazolyl group each independently and optionally has one or more substituents selected from Group D.

4. The compound according to claim 1 wherein G represents a C3-C8 alicyclic hydrocarbon group optionally having one or more substituents selected from Group E.

5. The compound according to claim 1 wherein $A^3$ represents $CR^{4b}$ and $A^4$ represents $CR^{4c}$.

6. The compound according to claim 1 wherein $A^2$ represents $CR^{4a}$, $A^3$ represents a nitrogen atom and $A^4$ represents $CR^{4c}$, alternatively, $A^2$ represents $CR^{4a}$, $A^3$ represents $CR^{4b}$ and $A^4$ represents a nitrogen atom.

7. The compound according to claim 1 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G, $OR^1$, $S(O)_mR^1$, $OS(O)_2R^1$ or $NR^1R^{29}$.

8. The compound according to claim 1 wherein T represents $OR^1$ and $R^1$ represents a C1-C5 alkyl group having three or more fluorine atoms.

9. The compound according to claim 1 wherein $R^{3a}$ represents a C1-C6 alkyl group optionally having one or more halogen atoms, a phenyl group, a pyridyl group, a pyrimidinyl group, a pyrazolyl group, or a triazolyl group, wherein the phenyl group, the pyridyl group, the pyrimidinyl group, the pyrazolyl group, and the triazolyl group each independently and optionally has one or more substituents selected from Group H, $OR^{12}$, $NR^{11}R^{12}$, $NR^{11}C(O)R^{13}$, or a halogen atom.

10. The compound according to claim 1 wherein $R^2$ represents an ethyl group.

11. A composition for controlling a harmful arthropod comprising the compound according to claim 1 and an inert carrier.

12. A method for controlling a harmful arthropod which comprises applying an effective amount of the compound according to claim 1 to a harmful arthropod or a habitat where a harmful arthropod lives.

13. A composition comprising the compound according to claim 1, and one or more ingredients selected from the group consisting of the following Group (a), Group (b), Group (c), Group (d) and Group (e), wherein:

Group (a) is selected from the group consisting of insecticidal ingredients, miticidal ingredients, and nematicidal ingredients;

Group (b) is selected from fungicidal ingredients;

Group (c) is selected from plant growth modulating ingredients;

Group (d) is selected from phytotoxicity-reducing ingredients; and

Group (e) is selected from synergist ingredients.

* * * * *